(12) United States Patent
Jaworski et al.

(10) Patent No.: US 6,713,664 B2
(45) Date of Patent: Mar. 30, 2004

(54) FATTY ACID ELONGASE 3-KETOACYL COA SYNTHASE POLYPEPTIDES

(75) Inventors: Jan G. Jaworski, Oxford, OH (US); Brenda J. Blacklock, Oxford, OH (US)

(73) Assignee: Miami University, Oxford, OH (US)

( * ) Notice: Subject to any disclaimer, the term of this patent is extended or adjusted under 35 U.S.C. 154(b) by 10 days.

(21) Appl. No.: 09/877,476

(22) Filed: Jun. 8, 2001

(65) Prior Publication Data

US 2002/0049994 A1 Apr. 25, 2002

Related U.S. Application Data

(60) Provisional application No. 60/210,326, filed on Jun. 8, 2000.

(51) Int. Cl.$^7$ .............................. A01H 5/00; C12N 5/04; C12N 15/82

(52) U.S. Cl. ..................... 800/298; 800/281; 435/419; 435/254.2; 536/23.6

(58) Field of Search .................... 536/23.6; 435/419, 435/254.2; 800/281, 298

(56) References Cited

U.S. PATENT DOCUMENTS

| | | |
|---|---|---|
| 6,051,756 A | 4/2000 | Chen et al. |
| 6,124,524 A | 9/2000 | James, Jr. et al. |

FOREIGN PATENT DOCUMENTS

| | | |
|---|---|---|
| WO | WO 95/15387 | 6/1995 |
| WO | WO 96/13582 | 5/1996 |
| WO | WO 98/46766 | 10/1998 |
| WO | WO 98/54954 | 12/1998 |
| WO | WO 01/29238 | 4/2001 |

OTHER PUBLICATIONS

Broun et al. Science 282:131–133, Nov. 13, 1998.*
Van de Loo et al. Proc. Natl. Acad. Sci, USA 92: 6743–6747, Jul. 1995.*
Clemens et al., "Brassica napus 3–ketoacyl–CoA synthase (fae1) mRNA, complete cds," GenBank Accession No. AF009563, XP002191552, Oct. 7, 1997.
James et al., "*Arabidopsis thaliana* fatty acid elongase 1 (Fae 1) gene, complete cds," GenBank Accession No. U29142, XP–002191553, Jul. 21, 1995.
GenBank Accession No. U29142, Jul. 21, 1995.
GenBank Accession No. U50771, Apr. 4, 1996.
GenBank Accession No. AF009563, Oct. 7, 1997.
GenBank Accession No. AAA70154, Jun. 28, 1995.
GenBank Accession No. AAA96054, Apr. 4, 1996.
GenBank Accession No. AAB72178, Oct. 6, 1997.
GenBank Accession No. AAD22309, Apr. 5, 2000.
GenBank Accession No. CAA71898, Mar. 19, 1998.
GenBank Accession No. CAB36702, Mar. 10, 2000.
Blacklock et al "1999 Biochemistry and Molecular Biology of Plant Fatty Acids and Glycerolipids Symposium," *National Plant Lipid Cooperative*, Jun. 9–13, 1999, South Lake Tahoe, California, P12.
Barret et al., "A rapeseed FAE1 gene is linked to the E1 locus associated with variation in the content of erucic acid," *Theor. Appl. Genet.*, 1998, 96:177–186.
Clemens and Kunst, "Isolation of a *Brassica napus* cDNA (Accession No. AF009563) Encoding 3–Ketoacyl–CoA Synthase, a Condensing Enzyme Involved in the Biosynthesis of Very Long Chain Fatty Acids in Seeds," *Plant Physiol.*, 1997, 115:313–314.
Domergue et al., "Purification of the Acyl–CoA Elongase Complex from Developing Rapeseed and Characterization of the 3–Ketoacyl–CoA Synthase and the 3–Hydroxyacyl–CoA Dehydratase," *Lipids*, 2000, 35(5):487–494.
Fiebig et al., "Alterations in CER6, a Gene Identical to CUT1, Differentially Affect Long–Chain Lipid Content on the Surface of Pollen and Stems," Plant Cell, 2000, 12:2001–2008.
Fourmann et al., "The two genes hologous to *Arabidopsis FAE1* co–segregate with the two loci governing erucic acid content in *Brassica napus*," *Theor. Appl. Genet.*, 1998, 96:852–858.
Ghanevati and Jaworski, "Active–site residues of a plant membrane–bound fatty acid elongase β–ketoacyl–CoA synthase, FAE1 KCS," *Biochim. Biophys. Acta*, 2001, 1530:77–85.
Ghanevati, "Engineering and Mechanistic Studies of Fatty Acid Elongase1 β–Ketoacyl–CoA Synthase, FAE1 KCS," A Dissertation, submitted to the Faculty of Miami University, Oxford, Ohio, 2000.
Han, "β–Ketoacyl–CoA Synthase Gene from *Brassica napus* L.: Functional Characterization and Promoter Analysis," A Dissertation, submitted to the University of Hamburg, Hamburg, 1999.
Han et al., "Functional characterizaton of β–ketoacyl–CoA synthase genes from *Brassica napus* L.," *Plant Mol. Bio.*, 2001, 46:229–239.
James, Jr., et al., "Directed Tagging of the Arabidopsis *Fatty Acid Elongation1* (*FAE1*) Gene with the Maize Transposon*Activator,*" *Plant Cell*, 1995, 7:309–319.
Kunst et al., "Fatty acid elongation in developing seeds of *Arabidopsis thaliana*," *Plant Physiol. Biochem.*, 1992, 30(4):425–434.
Lassner et al., "A Jojoba β–Ketoacyl–CoA Synthase cDNA Complements the Canola Fatty Acid Elongation Mutation in Transgenic Plants," *Plant Cell*, 1996, 8:281–292.

(List continued on next page.)

Primary Examiner—Elizabeth F. McElwain
(74) *Attorney, Agent, or Firm*—Fish & Richardson P.C., P.A.

(57) ABSTRACT

Elongase KCS polypeptides with altered substrate specificity and/or catalytic activity are disclosed. Such elongase KCS polypeptides are effective for producing very long chain fatty acids (VLCFA) fatty acids. Also disclosed are nucleic acids encoding elongase KCS polypeptides, and yeast and plants expressing these polypeptides.

10 Claims, 28 Drawing Sheets

OTHER PUBLICATIONS

Millar and Kunst, "Very–long–chain fatty acid biosynthesis is controlled through the expression and specificity of the condensing enzyme," *Plant J.,* 1997, 12(1):121–131.

Millar et al., "Accumulation of Very–Long–Chain Fatty Acids in Membrane Glycerolipids Is Associated with Dramatic Alterations in Plant Morphology," *Plant Cell,* 1998, 11:1889–1902.

Millar and Kunst, "The natural genetic variation of the fatty–acyl composition of seed oils in different ecotypes of *Arabidopsis thaliana,*" *Phytochemistry,* 1999, 52:1029–1033.

Millar et al., "*CUT1*, and Arabidopsis Gene Required for Cuticular Wax Biosynthesis and Pollen Fertility, Encodes a Very–Long–Chain Fatty Acid Condensing Enzyme" *Plant Cell,* 1999, 11:825–838.

Pruitt et al., "FIDDLEHEAD, a gene required to suppress epidermal cell interactions in *Arabidopsis*, encodes a putative lipid biosynthetic enyme," *Proc. Natl. Acad. Sci. USA,* 97(3):1311–1316.

Roscoe et al., "Mutations in the *fatty acid elongation 1* gene are associated with a loss of β–ketoacyl–CoA synthase activity in low erucic acid rapeseed," *FEBS Letters,* 2001, 492:107–111.

Todd et al., "*KCS1* encodes a fatty acid elongase 3–ketoacyl–CoA synthase affecting wax biosynthesis in *Arabidopsis thaliana,*" *Plant J.,* 1999, 17(2):119–130.

Venkateswari et al., "Molecular Cloning and Characterization on *Fatty Acid Elongation1* (*BjFAE1*) Gene of *Brassica juncea,*" *J. Plant Biochem. Biotech.,* 1999, 8:53–55.

Yephremov et al., "Characterization of the FIDDLEHEAD Gene of Arabidopsis Reveals a Link between Adhesion Response and Cell Differentiation in the Epidermis," *Plant Cell,* 1999, 11:2187–2201.

Domergue et al., "Les acyl–CoA élongases des graines: l'autre système de synthèse d'acides gras," *Ocl–Oleagineux Corps Gras Lipides,* 1999, 6(1):101–106.

Post–Beittenmiller, "Biochemistry and Molecular Biology of Wax Production of Wax Production in Plants," *Annu. Rev. Plant Physiol. Plant Mol. Biol.,* 1996, 47:405–430.

* cited by examiner

*Arabidopsis thaliana* FAE1 (SEQ ID NO:2)

MTSVNVKLLY RYVLTNFFNL CLFPLTAFLA GKASRLTIND LHNFLSYLQH
NLITVTLLFA FTVFGLVLYI VTRPNPVYLV DYSCYLPPPH LKVSVSKVMD
IFYQIRKADT SSRNVACDDP SSLDFLRKIQ ERSGLGDETY SPEGLIHVPP
RKTFAASREE TEKVIIGALE NLFENTKVNP REIGILVVNS SMFNPTPSLS
AMVVNTFKLR SNIKSFNLGG MGCSAGVIAI DLAKDLLHVH KNTYALVVST
ENITQGIYAG ENRSMMVSNC LFRVGGAAIL LSNKSGDRRR SKYKLVHTVR
THTGADDKSF RCVQQEDDES GKIGVCLSKD ITNVAGTTLT KNIATLGPLI
LPLSEKFLFF ATFVAKKLLK DKIKHYYVPD FKLAVDHFCI HAGGRAVIDE
LEKNLGLSPI DVEASRSTLH RFGNTSSSSI WYELAYIEAK GRMKKGNKAW
QIALGSGFKC NSAVWVALRN VKASANSPWQ HCIDRYPVKI DSDLSKSKTH
VQNGRS

*Brassica napus* elongase KCS (SEQ ID NO:4)

MTSINVKLLY HYVITNLFNL CFFPLTAIVA GKAYRLTIDD LHHLYYSYLQ
HNLITIAPLF AFTVFGSVLY IATRPKPVYL VEYSCYLPPT HCRSSISKVM
DIFYQVRKAD PSRNGTCDDS SWLDFLRKIQ ERSGLGDETH GPEGLLQVPP
RKTFAAAREE TEQVIIGALE NLFKNTNVNP KDIGILVVNS SMFNPTPSLS
AMVVNTFKLR SNVRSFNLGG MGCSAGVIAI DLAKDLLHVH KNTYALVVST
ENITYNIYAG DNRSMMVSNC LFRVGGAAIL LSNKPGDRRR SKYELVHTVR
THTGADGKSF RCVQQGDDEN GKIGVSLSKD ITDVAGRTVK KNIATLGPLI
LPLSEKLLFF VTFMGKKLFK DKIKHYYVPD FKLAIDHFCI HAGGRAVIDV
LEKNLALAPI DVEASRSTLH RFGNTSSSSI WYELAYIEAK GRMKKGNKVW
QIALGSGFKC NSAVWVALNN VKASTNSPWE HCIDRYPVKI DSDSGKSETR
VQNGRS

*B. napus* elongase KCS (SEQ ID NO:6)

MTSINVKLLY HYVITNLFNL CFFPLTAIVA GKAYLTIDDL HHLYYSYLQH
NLITIAPLLA FTVFGSVLYI ATRPKPVYLV EYSCYLPPTH CRSSISKVMD
IFFQVRKADP SRNGTCDDSS WLDFLRKIQE RSGLGDETHG PEGLLQVPPR
KTFARAREET EQVIIGALEN LFKNTVNPK DIGILVVNSS MFNPTPSLSA
MVVNTFKLRS NVRSFNLGGM GCSAGVIAID LAKDLLHVHK NTYALVVSTE
NITYNIYAGD NRSMMVSNCL FRVGGAAILL SNKPRDRRRS KYELVHTVRT
HTGADDKSFR CVQQGDDENG QTGVSLSKDI TDVAGRTVKK NIATLGPLIL
PLSEKLLFFV TFMGKKLFKD EIKHYYVPDF KLAIDHFCIH AGGKAVIDVL
EKNLGLAPID VEASRSTLHR FGNTSSSSIW YELAYIEPKG RMKKGNKVWQ
IALGSGFKCN SAVWVALNNV KASTNSPWEH CIDRYPVKID SDSGKSETRV
PNGRS

FIGURE 1-1

At114 (SEQ ID NO:8)

MTSVNVKLLY RYVLTNFFNL CLFPLTAFLA GKASRLTIND LHNFLSYLQH
NLITVTLLFA FTVFGLVLYI VTRPNPVYLV DYSCYLPPPH LKVSVSKVMD
IFYQIRKADT SSRNGTCDDS SWLDFLRKIQ ERSGLGDETH GPEGLLQVPP
RKTFAAAREE TEQVIIGALE NLFKNTNVNP KDIGILVVNS SMFNPTPSLS
AMVVNTFKLR SNVRSFNLGG MGCSAGVIAI DLAKDLLHVH KNTYALVVST
ENITYNIYAG DNRSMMVSNC LFRVGGAAIL LSNKPGDRRR SKYELVHTVR
THTGADGKSF RCVQQGDDEN GKIGVSLSKD ITDVAGRTVK KNIATLGPLI
LPLSEKLLFF VTFMGKKLFK DKIKHYYVPD FKLAIDHFCI HAGGRAVIDV
LEKNLALAPI DVEASRSTLH RFGNTSSSSI WYELAYIEAK GRMKKGNKVW
QIALGSGFKC NSAVWVALNN VKASTNSPWE HCIDRYPVKI DSDSGKSETR
VPNGRS

At74 (SEQ ID NO:10)

MTSVNVKLLY RYVLTNFFNL CLFPLTAFLA GKASRLTIND LHNFLSYLQH
NLITVTLLFA FTVFGLVLYI VTRPKPVYLV EYSCYLPPTH CRSSISKVMD
IFYQVRKADP SRNGTCDDSS WLDFLRKIQE RSGLGDETHG PEGLLQVPPR
KTFAAAREET EQVIIGALEN LFKNTNVNPK DIGILVVNSS MFNPTPSLSA
MVVNTFKLRS NVRSFNLGGM GCSAGVIAID LAKDLLHVHK NTYALVVSTE
NITYNIYAGD NRSMMVSNCL FRVGGAAILL SNKPGDRRRS KYELVHTVRT
HTGADGKSFR CVQQGDDENG KIGVSLSKDI TDVAGRTVKK NIATLGPLIL
PLSEKLLFFV TFMGKKLFKD KIKHYYVPDF KLAIDHFCIH AGGRAVIDVL
EKNLALAPID VEASRSTLHR FGNTSSSSIW YELAYIEAKG RMKKGNKVWQ
IALGSGFKCN SAVWVALNNV KASTNSPWEH CIDRYPVKID SDSGKSETRV
QNGRS

At114 L91C K92R (SEQ ID NO:12)

MTSVNVKLLY RYVLTNFFNL CLFPLTAFLA GKASRLTIND LHNFLSYLQH
NLITVTLLFA FTVFGLVLYI VTRPNPVYLV DYSCYLPPPH CRVSVSKVMD
IFYQIRKADT SSRNGTCDNS SWLDFLRKIQ ERSGLGDETH GPEGLLQVPP
RKTFAAAREE TEQVIIGALE NLFKNTNVNP KDIGILVVNS SMFNPTPSLS
AMVVNTFKLR SNVRSFNLGG MGCSAGVIAI DLAKDLLHVH KNTYALVVST
ENITYNIYAG DNRSMMVSNC LFRVGGAAIL LSNKPGDRRR SKYELVHTVR
THTGADGKSF RCVQQGDDEN GKIGVSLSKD ITDVAGRTVK KNIATLGPLI
LPLSEKLLFF VTFMGKKLFK DKIKHYYVPD FKLAIDHFCI HAGGRAVIDV
LEKNLALAPI DVEASRSTLH RFGNTSSSSI WYELAYIEAK GRMKKGNKVW
QIALGSGFKC NSAVWVALNN VKASTNSPWE HCIDRYPVKI DSDSGKSETR
VPNGRS

FIGURE 1-2

At114 K92R (SEQ ID NO:14)

```
MTSVNVKLLY RYVLTNFFNL CLFPLTAFLA GKASRLTIND LHNFLSYLQH
NLITVTLLFA FTVFGLVLYI VTRPNPVYLV DYSCYLPPPH LRVSVSKVMD
IFYQIRKADT SSRNGTCDDS SWLDFLRKIQ ERSGLGDETH GPEGLLQVPP
RKTFAAAREE TEQVIIGALE NLFKNTNVNP KDIGILVVNS SMFNPTPSLS
AMVVNTFKLR SNVRSFNLGG MGCSAGVIAI DLAKDLLHVH KNTYALVVST
ENITYNIYAG DNRSMMVSNC LFRVGGAAIL LSNKPGDRRR SKYELVHTVR
THTGADGKSF RCVQQGDDEN GKIGVSLSKD ITDVAGRTVK KNIATLGPLI
LPLSEKLLFF VTFMGKKLFK DKIKHYYVPD FKLAIDHFCI HAGGRAVIDV
LEKNLALAPI DVEASRSTLH RFGNTSSSSI WYELAYIEAK GRMKKGNKVW
QIALGSGFKC NSAVWVALNN VKASTNSPWE HCIDRYPVKI DSDSGKSETR
VPNGRS
```

At114 G307D (SEQ ID NO:16)

```
MTSVNVKLLY RYVLTNFFNL CLFPLTAFLA GKASRLTIND LHNFLSYLQH
NLITVTLLFA FTVFGLVLYI VTRPNPVYLV DYSCYLPPPH LKVSVSKVMD
IFYQIRKADT SSRNGTCDDS SWLDFLRKIQ ERSGLGDETH GPEGLLQVPP
RKTFAAAREE TEQVIIGALE NLFKNTNVNP KDIGILVVNS SMFNPTPSLS
AMVVNTFKLR SNVRSFNLGG MGCSAGVIAI DLAKDLLHVH KNTYALVVST
ENITYNIYAG DNRSMMVSNC LFRVGGAAIL LSNKPGDRRR SKYELVHTVR
THTGADDKSF RCVQQGDDEN GKIGVSLSKD ITDVAGRTVK KNIATLGPLI
LPLSEKLLFF VTFMGKKLFK DKIKHYYVPD FKLAIDHFCI HAGGRAVIDV
LEKNLALAPI DVEASRSTLH RFGNTSSSSI WYELAYIEAK GRMKKGNKVW
QIALGSGFKC NSAVWVALNN VKASTNSPWE HCIDRYPVKI DSDSGKSETR
VQNGRS
```

At74 G306D (SEQ ID NO:18)

```
MTSVNVKLLY RYVLTNFFNL CLFPLTAFLA GKASRLTIND LHNFLSYLQH
NLITVTLLFA FTVFGLVLYI VTRPKPVYLV EYSCYLPPTH CRSSISKVMD
IFYQVRKADP SRNGTCDDSS WLDFLRKIQE RSGLGDETHG PEGLLQVPPR
KTFAAAREET EQVIIGALEN LFKNTNVNPK DIGILVVNSS MFNPTPSLSA
MVVNTFKLRS NVRSFNLGGM GCSAGVIAID LAKDLLHVHK NTYALVVSTE
NITYNIYAGD NRSMMVSNCL FRVGGAAILL SNKPGDRRRS KYELVHTVRT
HTGADDKSFR CVQQGDDENG KIGVSLSKDI TDVAGRTVKK NIATLGPLIL
PLSEKLLFFV TFMGKKLFKD KIKHYYVPDF KLAIDHFCIH AGGRAVIDVL
EKNLALAPID VEASRSTLHR FGNTSSSSIW YELAYIEAKG RMKKGNKVWQ
IALGSGFKCN SAVWVALNNV KASTNSPWEH CIDRYPVKID SDSGKSETRV
QNGRS
```

FIGURE 1-3

At114 L91C K92R G307D (SEQ ID NO:20)

```
MTSVNVKLLY RYVLTNFFNL CLFPLTAFLA GKASRLTIND LHNFLSYLQH
NLITVTLLFA FTVFGLVLYI VTRPNPVYLV DYSCYLPPPH CRVSVSKVMD
IFYQIRKADT SSRNGTCDNS SWLDFLRKIQ ERSGLGDETH GPEGLLQVPP
RKTFAAAREE TEQVIIGALE NLFKNTNVNP KDIGILVVNS SMFNPTPSLS
AMVVNTFKLR SNVRSFNLGG MGCSAGVIAI DLAKDLLHVH KNTYALVVST
ENITYNIYAG DNRSMMVSNC LFRVGGAAIL LSNKPGDRRR SKYELVHTVR
THTGADDKSF RCVQQGDDEN GKIGVSLSKD ITDVAGRTVK KNIATLGPLI
LPLSEKLLFF VTFMGKKLFK DKIKHYYVPD FKLAIDHFCI HAGGRAVIDV
LEKNLALAPI DVEASRSTLH RFGNTSSSSI WYELAYIEAK GRMKKGNKVW
QIALGSGFKC NSAVWVALNN VKASTNSPWE HCIDRYPVKI DSDSGKSETR
VQNGRS
```

At114 K92R G307D (SEQ ID NO:22)

```
MTSVNVKLLY RYVLTNFFNL CLFPLTAFLA GKASRLTIND LHNFLSYLQH
NLITVTLLFA FTVFGLVLYI VTRPNPVYLV DYSCYLPPPH LRVSVSKVMD
IFYQIRKADT SSRNGTCDDS SWLDFLRKIQ ERSGLGDETH GPEGLLQVPP
RKTFAAAREE TEQVIIGALE NLFKNTNVNP KDIGILVVNS SMFNPTPSLS
AMVVNTFKLR SNVRSFNLGG MGCSAGVIAI DLAKDLLHVH KNTYALVVST
ENITYNIYAG DNRSMMVSNC LFRVGGAAIL LSNKPGDRRR SKYELVHTVR
THTGADDKSF RCVQQGDDEN GKIGVSLSKD ITDVAGRTVK KNIATLGPLI
LPLSEKLLFF VTFMGKKLFK DKIKHYYVPD FKLAIDHFCI HAGGRAVIDV
LEKNLALAPI DVEASRSTLH RFGNTSSSSI WYELAYIEAK GRMKKGNKVW
QIALGSGFKC NSAVWVALNN VKASTNSPWE HCIDRYPVKI DSDSGKSETR
VQNGRS
```

At254 (SEQ ID NO:24)

```
MTSVNVKLLY RYVLTNFFNL CLFPLTAFLA GKASRLTIND LHNLLSYLQH
NLITVTLLFA FTVFGLVLYI VTRPNPVYLV DYSCYLPPPH LKVSVSKVMD
IFYQIRKADT SSRNVACDDP SSLDFLRKIQ ERSGLGDETY SPEGLIHVPP
RKTFAASREE TEKVIIGALE NLFENTKVNP REIGILVVNS SMFNPTPSLS
AMVVNTFKLR SNIKSFNLGG MGCSAGVIAI DLAKDLLHVH KNTYALVVST
ENITYNIYAG DNRSMMVSNC LFRVGGAAIL LSNKPGDRRR SKYELVHTVR
THTGADGKSF RCVQQGDDEN GKIGVSLSKD ITDVAGRTVK KNIATLGPLI
LPLSEKLLFF VTFMGKKLFK DKIKHYYVPD FKLAIDHFCI HAGGRAVIDV
LEKNLALAPI DVEASRSTLH RFGNTSSSSI WYELAYIEAK GRMKKGNKVW
QIALGSGFKC NSAVWVALNN VKASTNSPWE HCIDRYPVKI DSDSGKSETR
VPNGRS
```

FIGURE 1-4

At173 (SEQ ID NO:26)

```
MTSVNVKLLY RYVLTNFFNL CLFPLTAFLA GKASRLTIND LHNFLSYLQH
NLITVTLLFA FTVFGLVLYI VTRPNPVYLV DYSCYLPPPH LKVSVSKVMD
IFYQIRKADT SSRNVACDDP SSLDFLRKIQ ERSGLGDETY SPEGLIHVPP
RKTFAASREE TEKVIIGALE NLFKNTNVNP KDIGILVVNS SMFNPTPSLS
AMVVNTFKLR SNVRSFNLGG MGCSAGVIAI DLAKDLLHVH KNTYALVVST
ENITYNIYAG DNRSMMVSNC LFRVGGAAIL LSNKPGDRRR SKYELVHTVR
THTGADGKSF RCVQQGDDEN GKIGVSLSKD ITDVAGRTVK KNIATLGPLI
LPLSEKLLFF VTFMGKKLFK DKIKHYYVPD FKLAIDHFCI HAGGRAVIDV
LEKNLALAPI DVEASRSTLH RFGNTSSSSI WYELAYIEAK GRMKKGNKVW
QIALGSGFKC NSAVWVALNN VKASTNSPWE HCIDRYPVKI DSDSGKSETR
VQNGRS
```

Bn176 (SEQ ID NO:28)

```
MTSINVKLLY HYVITNLFNL CFFPLTAIVA GKAYRLTIDD LHHLYYSYLQ
HNLITIAPLF AFTVFGSVLY IATRPKPVYL VEYSCYLPPT HCRSSISKVM
DIFYQVRKAD PSRNGTCDDS SWLDFLRKIQ ERSGLGDETH GPEGLLQVPP
RKTFAAAREE TEQVIIGALE NLFKNTKVNP REIGILVVNS SMFNPTPSLS
AMVVNTFKLR SNIKSFNLGG MGCSAGVIAI DLAKDLLHVH KNTYALVVST
ENITQGIYAG ENRSMMVSNC LFRVGGAAIL LSNKSGDRRR SKYKLVHTVR
THTGADDKSF RCVQQEDDES GKIGVCLSKD ITNVAGTTLT KNIATLGPLI
LPLSEKFLFF ATFVAKKLLK DKIKHYYVPD FKLAVDHFCI HAGGRAVIDE
LEKNLGLSPI DVEASRSTLH RFGNTSSSSI WYELAYIEAK GRMKKGNKAW
QIALGSGFKC NSAVWVALRN VKASANSPWQ HCIDRYPVKI DSDLSKSKTH
VQNGRS
```

At399 (SEQ ID NO:30)

```
MTSVNVKLLY RYVLTNFFNL CLFPLTAFLA GKASRLTIND LHNFLSYLQH
NLITVTLLFA FTVFGLVLYI VTRPNPVYLV DYSCYLPPPH LKVSVSKVMD
IFYQIRKADT SSRNVACDDP SSLDFLRKIQ ERSGLGDETY SPEGLIHVPP
RKTFAASREE TEKVIIGALE NLFENTKVNP REIGILVVNS SMFNPTPSLS
AMVVNTFKLR SNIKSFNLGG MGCSAGVIAI DLAKDLLHVH KNTYALVVST
ENITQGIYAG ENRSMMVSNC LFRVGGAAIL LSNKSGDRRR SKYKLVHTVR
THTGADDKSF RCVQQEDDES GKIGVCLSKD ITNVAGTTLT KNIATLGPLI
LPLSEKFLFF ATFVAKKLLK DKIKHYYVPD FKLAVDHFCI HAGGRAVIDV
LEKNLALAPI DVEASRSTLH RFGNTSSSSI WYELAYIEAK GRMKKGNKVW
QIALGSGFKC NSAVWVALNN VKASTNSPWE HCIDRYPVKI DSDSGKSETR
VQNGRS
```

FIGURE 1-5

Bn399 (SEQ ID NO:32)

```
MTSINVKLLY HYVITNLFNL CFFPLTAIVA GKAYRLTIDD LHHLYYSYLQ
HNLITIAPLF AFTVFGSVLY IATRPKPVYL VEYSCYLPPT HCRSSISKVM
DIFYQVRKAD PSRNGTCDDS SWLDFLRKIQ ERSGLGDETH GPEGLLQVPP
RKTFAAAREE TEQVIIGALE NLFKNTNVNP KDIGILVVNS SMFNPTPSLS
AMVVNTFKLR SNVRSFNLGG MGCSAGVIAI DLAKDLLHVH KNTYALVVST
ENITYNIYAG DNRSMMVSNC LFRVGGAAIL LSNKPGDRRR SKYELVHTVR
THTGADGKSF RCVQQGDDEN GKIGVSLSKD ITDVAGRTVK KNIATLGPLI
LPLSEKLLFF VTFMGKKLFK DKIKHYYVPD FKLAIDHFCI HAGGRAVIDE
LEKNLGLSPI DVEASRSTLH RFGNTSSSSI WYELAYIEAK GRMKKGNKAW
QIALGSGFKC NSAVWVALRN VKASANSPWQ HCIDRYPVKI DSDLSKSKTH
VQNGRS
```

Bn G307D (SEQ ID NO:34)

```
MTSINVKLLY HYVITNLFNL CFFPLTAIVA GKAYRLTIDD LHHLYYSYLQ
HNLITIAPLF AFTVFGSVLY IATRPKPVYL VEYSCYLPPT HCRSSISKVM
DIFYQVRKAD PSRNGTCDDS SWLDFLRKIQ ERSGLGDETH GPEGLLQVPP
RKTFAAAREE TEQVIIGALE NLFKNTNVNP KDIGILVVNS SMFNPTPSLS
AMVVNTFKLR SNVRSFNLGG MGCSAGVIAI DLAKDLLHVH KNTYALVVST
ENITYNIYAG DNRSMMVSNC LFRVGGAAIL LSNKPGDRRR SKYELVHTVR
THTGADDKSF RCVQQGDDEN GKIGVSLSKD ITDVAGRTVK KNIATLGPLI
LPLSEKLLFF VTFMGKKLFK DKIKHYYVPD FKLAIDHFCI HAGGRAVIDV
LEKNLALAPI DVEASRSTLH RFGNTSSSSI WYELAYIEAK GRMKKGNKVW
QIALGSGFKC NSAVWVALNN VKASTNSPWE HCIDRYPVKI DSDSGKSETR
VQNGRS
```

At K92R (SEQ ID NO:36)

```
MTSVNVKLLY RYVLTNFFNL CLFPLTAFLA GKASRLTIND LHNFLSYLQH
NLITVLLFA FTVFGLVLYI VTRPNPVYLV DYSCYLPPPH LRVSVSKVMD
IFYQIRKADT SSRNVACDDP SSLDFLRKIQ ERSGLGDETY SPEGLIHVPP
RKTFAASREE TEKVIIGALE NLFENTKVNP REIGILVVNS SMFNPTPSLS
AMVVNTFKLR SNIKSFNLGG MGCSAGVIAI DLAKDLLHVH KNTYALVVST
ENITQGIYAG ENRSMMVSNC LFRVGGAAIL LSNKSGDRRR SKYKLVHTVR
THTGADDKSF RCVQQEDDES GKIGVCLSKD ITNVAGTTLT KNIATLGPLI
LPLSEKFLFF ATFVAKKLLK DKIKHYYVPD FKLAVDHFCI HAGGRAVIDE
LEKNLGLSPI DVEASRSTLH RFGNTSSSSI WYELAYIEAK GRMKKGNKAW
QIALGSGFKC NSAVWVALRN VKASANSPWQ HCIDRYPVKI DSDLSKSKTH
VQNGRS
```

FIGURE 1-6

At254 G307D (SEQ ID NO:38)

```
MTSVNVKLLY RYVLTNFFNL CLFPLTAFLA GKASRLTIND LHNFLSYLQH
NLITVTLLFA FTVFGLVLYI VTRPNPVYLV DYSCYLPPPH LKVSVSKVMD
IFYQIRKADT SSRNVACDDP SSLDFLRKIQ ERSGLGDETY SPEGLIHVPP
RKTFAASREE TEKVIIGALE NLFENTKVNP REIGILVVNS SMFNPTPSLS
AMVVNTFKLR SNIKSFNLGG MGCSAGVIAI DLAKDLLHVH KNTYALVVST
ENITYNIYAG DNRSMMVSNC LFRVGGAAIL LSNKPGDRRR SKYELVHTVR
THTGADDKSF RCVQQGDDEN GKIGVSLSKD ITDVAGRTVK KNIATLGPLI
LPLSEKLLFF VTFMGKKLFK DKIKHYYVPD FKLAIDHFCI HAGGRAVIDV
LEKNLALAPI DVEASRSTLH RFGNTSSSSI WYELAYIEAK GRMKKGNKVW
QIALGSGFKC NSAVWVALNN VKASTNSPWE HCIDRYPVKI DSDSGKSETR
VQNGRS
```

At173 G307D (SEQ ID NO:40)

```
MTSVNVKLLY RYVLTNFFNL CLFPLTAFLA GKASRLTIND LHNFLSYLQH
NLITVTLLFA FTVFGLVLYI VTRPNPVYLV DYSCYLPPPH LKVSVSKVMD
IFYQIRKADT SSRNVACDDP SSLDFLRKIQ ERSGLGDETY SPEGLIHVPP
RKTFAASREE TEKVIIGALE NLFKNTVNP KDIGILVVNS SMFNPTPSLS
AMVVNTFKLR SNVRSFNLGG MGCSAGVIAI DLAKDLLHVH KNTYALVVST
ENITYNIYAG DNRSMMVSNC LFRVGGAAIL LSNKPGDRRR SKYELVHTVR
THTGADDKSF RCVQQGDDEN GKIGVSLSKD ITDVAGRTVK KNIATLGPLI
LPLSEKLLFF VTFMGKKLFK DKIKHYYVPD FKLAIDHFCI HAGGRAVIDV
LEKNLALAPI DVEASRSTLH RFGNTSSSSI WYELAYIEAK GRMKKGNKVW
QIALGSGFKC NSAVWVALNN VKASTNSPWE HCIDRYPVKI DSDSGKSETR
VQNGRS
```

Bn399 G307D (SEQ ID NO:42)

```
MTSINVKLLY HYVITNLFNL CFFPLTAIVA GKAYRLTIDD LHHLYYSYLQ
HNLITIAPLF AFTVFGSVLY IATRPKPVYL VEYSCYLPPT HCRSSISKVM
DIFYQVRKAD PSRNGTCDDS SWLDFLRKIQ ERSGLGDETH GPEGLLQVPP
RKTFAAAREE TEQVIIGALE NLFKNTNVNP KDIGILVVNS SMFNPTPSLS
AMVVNTFKLR SNVRSFNLGG MGCSAGVIAI DLAKDLLHVH KNTYALVVST
ENITYNIYAG DNRSMMVSNC LFRVGGAAIL LSNKPGDRRR SKYELVHTVR
THTGADDKSF RCVQQGDDEN GKIGVSLSKD ITDVAGRTVK KNIATLGPLI
LPLSEKLLFF VTFMGKKLFK DKIKHYYVPD FKLAIDHFCI HAGGRAVIDE
LEKNLGLSPI DVEASRSTLH RFGNTSSSSI WYELAYIEAK GRMKKGNKAW
QIALGSGFKC NSAVWVALRN VKASANSPWQ HCIDRYPVKI DSDLSKSKTH
VQNGRS
```

FIGURE 1-7

*Arabidopsis thaliana* FAE1 (SEQ ID NO:1)

```
atgacgtccg ttaacgttaa gctcctttac cgttacgtct taaccaactt
tttcaacctc tgtttgttcc cgttaacggc gttcctcgcc ggaaaagcct
ctcggcttac cataaacgat ctccacaact tcctttccta tctccaacac
aaccttataa cagtaacttt actctttgct ttcactgttt tcggtttggt
tctctacatc gtaacccgac ccaatccggt tatctcgtt gactactcgt
gttaccttcc accaccgcat ctcaaagtta gtgtctctaa agtcatggat
attttctacc aaataagaaa agctgatact tcttcacgga acgtggcatg
tgatgatccg tcctcgctcg atttcctgag gaagattcaa gagcgttcag
gtctaggtga tgagacgtac agtcctgagg gactcattca cgtaccaccg
cggaagactt ttgcagcgtc acgtgaagag acagagaagg ttatcatcgg
tgcgctcgaa aatctattcg agaaccaa agttaaccct agagagattg
gtatacttgt ggtgaactca agcatgttta atccaactcc ttcgctatcc
gctatggtcg ttaatacttt caagctccga agcaacatca aaagctttaa
tctaggagga atgggttgta gtgctggtgt tattgccatt gatttggcta
aagacttgtt gcatgttcat aaaaacactt atgctcttgt ggtgagcact
gagaacatca cacaggcat ttatgctgga gaaaatagat caatgatggt
tagcaattgc ttgtttcgtg ttggtggggc cgcgattttg ctctctaaca
agtcgggaga ccggagacgg tccaagtaca agctagttca cacggtccga
acgcatactg gagctgatga caagtctttt cgatgtgtgc aacaagaaga
cgatgagagc ggcaaaatcg gagtttgtct gtcaaggac ataaccaatg
ttgcggggac aacacttacg aaaaatatag caacattggg tccgttgatt
cttcctttaa gcgaaaagtt tcttttttc gctaccttcg tcgccaagaa
acttctaaag gataaaatca agcattacta tgttccggat ttcaagcttg
ctgttgacca tttctgtatt catgccggag gcagagccgt gatcgatgag
ctagagaaga acttaggact atcgccgatc gatgtggagg catctagatc
aacgttacat agatttggga atacttcatc tagctcaatt ggtatgaat
tagcatacat agaggcaaag ggaagaatga agaaagggaa taaagcttgg
cagattgctt taggatcagg gtttaagtgt aatagtgcgg tttgggtggc
tctacgcaat gtcaaggcat cggcaaatag tccttggcaa cattgcatcg
atagatatcc ggttaaaatt gattctgatt tgtcaaagtc aaagactcat
gtccaaaacg gtcggtccta atttgatgta tctgagtgcc aacgtttact
ttgtctttcc tttctttat tggttatgaa ttagatgttt actaatgttc
ctctcttttt cgttataaat aaagaagttc aattcttcct atagtttcaa
acgcgatttt aagcgtttct atttaggttt acatgaattt cttttacaaa
ccatcttttt
```

FIGURE 2-1

*Brassica napus* elongase KCS (SEQ ID NO:3)

```
atgacgtcca ttaacgtaaa gctcctttac cattacgtca taaccaacct
tttcaacctt tgcttctttc cgttaacggc gatcgtcgcc ggaaaagcct
atcggcttac catagacgat cttcaccact tatactattc ctatctccaa
cacaacctca taaccatcgc tccactcttt gccttaccg ttttcggttc
ggttctctac atcgcaaccc ggcccaaacc ggtttacctc gttgagtact
catgctacct tccaccaacg cattgtagat caagtatctc caaggtcatg
gatatctttt atcaagtaag aaaagctgat ccttctcgga acggacgtg
cgatgactcg tcgtggcttg acttcttgag gaagattcaa gaacgttcag
gtctaggcga tgaaactcac gggcccgagg ggctgcttca ggtccctccc
cggaagactt ttgcggcggc gcgtgaagag acggagcaag ttatcattgg
tgcgctagaa aatctattca agaacaccaa cgttaaccct aaagatatag
gtatacttgt ggtgaactca agcatgttta atccaactcc atcgctctcc
gcgatggtcg ttaacacttt caagctccga agcaacgtaa gaagctttaa
ccttggtggc atgggttgta gtgccggcgt tatagccatt gatctagcaa
aggacttgtt gcatgtccat aaaaatacgt atgctcttgt ggtgagcaca
gagaacatca cttataacat ttacgctggt gataataggt ccatgatggt
ttcaaattgc ttgttccgtg ttggtggggc cgctatttg ctctccaaca
agcctggaga tcgtagacgg tccaagtacg agctagttca cacggttcga
acgcataccg gagctgacgg caagtctttt cgttgcgtgc aacaaggaga
cgatgagaac ggcaaaatcg gagtgagttt gtccaaggac ataaccgatg
ttgctggtcg aacggttaag aaaaacatag caacgttggg tccgttgatt
cttccgttaa gcgagaaact tcttttttc gttaccttca tgggcaagaa
acttttcaaa gataaaatca aacattacta cgtcccggat ttcaaacttg
ctattgacca ttttgtata catgccggag gcagagccgt gattgatgtg
ctagagaaga acctagccct agcaccgatc gatgtagagg catcaagatc
aacgttacat agatttggaa acacttcatc tagctcaata tggtatgagt
tggcatacat agaagcaaaa ggaaggatga agaaaggtaa taaagtttgg
cagattgctt tagggtcagg ctttaagtgt aacagtgcag tttgggtggc
tctaaacaat gtcaaagctt cgacaaatag tccttgggaa cactgcatcg
acagataccc ggtcaaaatt gattctgatt caggtaagtc agagactcgt
gtccaaaacg gtcggtccta ataa
```

FIGURE 2-2

*B. napus* elongase KCS (SEQ ID NO:5)

```
tagagcgtaa cggaccacaa aagaggatcc atacaaatac atctcatcgc
ttccattact attctccgac acacactg agcaatgacg tccattaacg
taaagctcct ttaccattac gtcataacca accttttcaa cctttgtttc
tttccattaa cggcgatcgt cgccggaaaa gcctatctta ccatagacga
tcttcaccac ttatactatt cctatctcca acacaacctc ataaccattg
ctccactctt ggccttcacc gttttcggtt cggttctcta catcgcaacc
cggcccaaac cggtttacct cgtggagtac tcatgctacc ttccaccaac
gcattgtaga tcaagtatct ccaaggtcat ggatatcttt ttccaagtaa
gaaaagctga tccttctcgg aacggcacgt gcgatgactc gtcctggctt
gacttcttga ggaagattca agaacgttca ggtctaggcg atgaaaccca
cgggcccgag gggctgcttc aggtccctcc ccggaagact tttgcgcgcg
cgcgtgaaga gacggagcaa gttatcattg gtgcgctaga aaatctattc
aagaacacca atgttaaccc taaagatata ggtatacttg tggtgaactc
aagcatgttt aatccaactc cttcgctctc cgcgatggtc gttaacactt
tcaagctccg aagcaacgta agaagcttta accttggtgg catgggttgt
agtgccggcg ttatagccat tgatctagca aaggacttgt tgcatgtcca
taaaaatacg tatgctcttg tggtgagcac agagaacatc acttataaca
tttacgctgg tgataatagg tccatgatgg tttcaaattg cttgttccgt
gttggtgggg ccgctatttt gctctccaac aagcctagag atcgtagacg
gtccaagtac gagctagttc acacggttcg aacgcatacc ggagctgacg
acaagtcttt tcgttgcgtg caacaaggag acgatgagaa cggccaaacc
ggagtgagtt tgtccaagga cataaccgat gttgctggtc gaacggttaa
gaaaaacata gcaacgctgg gtccgttgat tcttccgtta agcgagaaac
ttctttttt cgttaccttc atgggcaaga aacttttcaa agacgaaatc
aaacattatt acgtcccgga cttcaagctt gctatcgacc atttttgtat
acatgccgga ggcaaagccg tgattgatgt gctagagaag aacctaggcc
tagcaccgat cgatgtagag gcatcaagat caacgttaca tagatttgga
aacacttcat ctagctcaat atggtatgag ttggcataca tagaacccaa
aggaaggatg aagaaaggta ataaagtttg gcagattgct ttagggtcag
gctttaagtg taacagtgca gtttgggtgg ctctaaacaa tgtcaaagct
tcaacaaata gtccttggga acactgcatc gacagatacc cggttaaaat
tgattctgat tcaggtaagt cagagactcg tgtcccaaac ggtcggtcct
aataaatgat gtttgctctc tttcgtttct ttttattggt tataataatt
tgatggccac gatgtttctc ttgtttgtta tgaataaaga atcccacggt
gttctagtaa aaaaaaaaaa aaaaaaaaa aaaaaa
```

FIGURE 2-3

At114 (SEQ ID NO:7)

```
atgacgtccg ttaacgttaa gctcctttac cgttatgtct taaccaactt
tttcaacctc tgtttgttcc cgttaacggc gttcctcgcc ggaaaagcct
ctcggcttac cataaacgat ctccacaact tcctttccta tctccaacac
aaccttataa cagtaacttt actctttgct ttcactgttt tcggtttggt
tctctacatc gtaacccgac ccaatccggt ttatctcgtt gactactcgt
gttaccttcc gccaccgcat ctcaaagtta gtgtctctaa agtcatggat
attttctacc aaataagaaa agctgatact tcttcacgga acggcacgtg
tgatgattcg tcgtggcttg acttcttgag gaagattcaa gaacgttcag
gtctaggcga tgaaactcac gggcccgagg ggctgcttca ggtccctccc
cggaagactt ttgcggcggc gcgtgaagag acggagcaag ttatcattgg
tgcgctagaa aatctattca agaacaccaa cgttaaccct aaagatatag
gtatacttgt ggtgaactca agcatgttta atccaactcc atcgctctcc
gcgatggtcg ttaacacttt caagctccga agcaacgtaa gaagctttaa
ccttggtggc atgggttgta gtgccggcgt tatagccatt gatctagcaa
aggacttgtt gcatgtccat aaaaatacgt atgctcttgt ggtgagcaca
gagaacatca cttataacat ttacgctggt gataataggt ccatgatggt
ttcaaattgc ttgttccgtg ttggtggggc cgctattttg ctctccaaca
agcctggaga tcgtagacgg tccaagtacg agctagttca cacggttcga
acgcataccg gagctgacgg caagtctttt cgttgcgtgc aacaaggaga
cgatgagaac ggcaaaatcg gagtgagttt gtccaaggac ataaccgatg
ttgctggtcg aacggttaag aaaaacatag caacgttggg tccgttgatt
cttccgttaa gcgagaaact tcttttttc gttaccttca tgggcaagaa
acttttcaaa gataaaatca aacattacta cgtcccggat ttcaaacttg
ctattgacca tttttgtata catgccggag gcagagccgt gattgatgtg
ctagagaaga acctagccct agcaccgatc gatgtagagg catcaagatc
aacgttacat agatttggaa acacttcatc tagctcaata tggtatgagt
tggcatacat agaagcaaaa ggaaggatga agaaaggtaa taaagtttgg
cagattgctt tagggtcagg ctttaagtgt aacagtgcag tttgggtggc
tctaaacaat gtcaaagctt cgacaaatag tccttgggaa cactgcatcg
acagataccc ggtcaaaatt gattctgatt caggtaagtc agagactcgt
gtcccaaacg gtcggtccta a
```

FIGURE 2-4

At74 (SEQ ID NO:9)

```
atgacgtccg ttaacgttaa gctcctttac cgttacgtct taaccaactt
tttcaacctc tgtttgttcc cgttaacggc gttcctcgcc ggaaaagcct
ctcggcttac cataaacgat ctccacaact tcctttccta tctccaacac
aaccttataa cagtaacttt actctttgct ttcactgttt tcggtttggt
tctctacatc gtaacccgac ccaaaccggt ttacctcgtt gagtactcat
gctaccttcc accaacgcat tgtagatcaa gtatctccaa ggtcatggat
atcttttatc aagtaagaaa agctgatcct tctcggaacg gcacgtgcga
tgactcgtcg tggcttgact tcttgaggaa gattcaagaa cgttcaggtc
taggcgatga aactcacggg cccgaggggc tgcttcaggt ccctccccgg
aagactttttg cggcggcgcg tgaagagacg gagcaagtta tcattggtgc
gctagaaaat ctattcaaga acaccaacgt taaccctaaa gatataggta
tacttgtggt gaactcaagc atgtttaatc caactccatc gctctccgcg
atggtcgtta acactttcaa gctccgaagc aacgtaagaa gctttaacct
tggtggcatg ggttgtagtg ccggcgttat agccattgat ctagcaaagg
acttgttgca tgtccataaa aatacgtatg ctcttgtggt gagcacagag
aacatcactt ataacattta cgctggtgat aataggtcca tgatggtttc
aaattgcttg ttccgtgttg gtggggccgc tatttttgctc tccaacaagc
ctggagatcg tagacggtcc aagtacgagc tagttcacac ggttcgaacg
cataccggag ctgacggcaa gtcttttcgt tgcgtgcaac aaggagacga
tgagaacggc aaaatcggag tgagtttgtc caaggacata accgatgttg
ctggtcgaac ggttaagaaa aacatagcaa cgttgggtcc gttgattctt
ccgttaagcg agaaacttct ttttttcgtt accttcatgg gcaagaaact
tttcaaagat aaaatcaaac attactacgt cccggatttc aaacttgcta
ttgaccattt ttgtatacat gccggaggca gagccgtgat tgatgtgcta
gagaagaacc tagccctagc accgatcgat gtagaggcat caagatcaac
gttacataga tttggaaaca cttcatctag ctcaatatgg tatgagttgg
catacataga agcaaaagga aggatgaaga aaggtaataa agtttggcag
attgctttag ggtcaggctt taagtgtaac agtgcagttt gggtggctct
aaacaatgtc aaagcttcga caaatagtcc ttgggaacac tgcatcgaca
gatacccggt caaaattgat tctgattcag gtaagtcaga gactcgtgtc
caaaacggtc ggtcctaa
```

FIGURE 2-5

At114 L91C K92R (SEQ ID NO:11)

```
atgacgtccg ttaacgttaa gctcctttac cgttatgtct taaccaactt
tttcaacctc tgtttgttcc cgttaacggc gttcctcgcc ggaaaagcct
ctcggcttac cataaacgat ctccacaact tcctttccta tctccaacac
aaccttataa cagtaacttt actctttgct ttcactgttt tcggtttggt
tctctacatc gtaacccgac ccaatccggt ttatctcgtt gactactcgt
gttaccttcc gccaccgcat tgcagagtta gtgtctctaa agtcatggat
attttctacc aaataagaaa agctgatact tcttcacgga acggcacgtg
tgataattcg tcgtggcttg acttcttgag gaagattcaa gaacgttcag
gtctaggcga tgaaactcac gggcccgagg ggctgcttca ggtccctccc
cggaagactt ttgcggcggc gcgtgaagag acggagcaag ttatcattgg
tgcgctagaa aatctattca agaacaccaa cgttaaccct aaagatatag
gtatacttgt ggtgaactca agcatgttta atccaactcc atcgctctcc
gcgatggtcg ttaacacttt caagctccga agcaacgtaa gaagctttaa
ccttggtggc atgggttgta gtgccggcgt tatagccatt gatctagcaa
aggacttgtt gcatgtccat aaaaatacgt atgctcttgt ggtgagcaca
gagaacatca cttataacat ttacgctggt gataataggt ccatgatggt
ttcaaattgc ttgttccgtg ttggtggggc cgctattttg ctctccaaca
agcctggaga tcgtagacgg tccaagtacg agctagttca cacggttcga
acgcataccg gagctgacgg caagtctttt cgttgcgtgc aacaaggaga
cgatgagaac ggcaaaatcg gagtgagttt gtccaaggac ataaccgatg
ttgctggtcg aacggttaag aaaaacatag caacgttggg tccgttgatt
cttccgttaa gcgagaaact tctttttttc gttaccttca tgggcaagaa
acttttcaaa gataaaatca aacattacta cgtcccggat ttcaaacttg
ctattgacca tttttgtata catgccggag gcagagccgt gattgatgtg
ctagagaaga acctagccct agcaccgatc gatgtagagg catcaagatc
aacgttacat agatttggaa acacttcatc tagctcaata tggtatgagt
tggcatacat agaagcaaaa ggaaggatga agaaggtaa taaagtttgg
cagattgctt tagggtcagg ctttaagtgt aacagtgcag tttgggtggc
tctaaacaat gtcaaagctt cgacaaatag tccttgggaa cactgcatcg
acagataccc ggtcaaaatt gattctgatt caggtaagtc agagactcgt
gtcccaaacg gtcggtccta a
```

FIGURE 2-6

At114 K92R (SEQ ID NO:13)

```
atgacgtccg ttaacgttaa gctcctttac cgttatgtct taaccaactt
tttcaacctc tgtttgttcc cgttaacggc gttcctcgcc ggaaaagcct
ctcggcttac cataaacgat ctccacaact tcctttccta tctccaacac
aaccttataa cagtaacttt actctttgct ttcactgttt tcggtttggt
tctctacatc gtaacccgac ccaatccggt ttatctcgtt gactactcgt
gttaccttcc gccaccgcat ctcagagtta gtgtctctaa agtcatggat
attttctacc aaataagaaa agctgatact tcttcacgga acggcacgtg
tgatgattcg tcgtggcttg acttcttgag gaagattcaa gaacgttcag
gtctaggcga tgaaactcac gggcccgagg ggctgcttca ggtccctccc
cggaagactt ttgcggcggc gcgtgaagag acggagcaag ttatcattgg
tgcgctagaa aatctattca agaacaccaa cgttaaccct aaagatatag
gtatacttgt ggtgaactca agcatgttta atccaactcc atcgctctcc
gcgatggtcg ttaacacttt caagctccga agcaacgtaa gaagctttaa
ccttggtggc atgggttgta gtgccggcgt tatagccatt gatctagcaa
aggacttgtt gcatgtccat aaaaatacgt atgctcttgt ggtgagcaca
gagaacatca cttataacat ttacgctggt gataataggt ccatgatggt
ttcaaattgc ttgttccgtg ttggtggggc cgctattttg ctctccaaca
agcctggaga tcgtagacgg tccaagtacg agctagttca cacggttcga
acgcataccg gagctgacgg caagtctttt cgttgcgtgc aacaaggaga
cgatgagaac ggcaaaatcg gagtgagttt gtccaaggac ataaccgatg
ttgctggtcg aacggttaag aaaaacatag caacgttggg tccgttgatt
cttccgttaa gcgagaaact tcttttttc gttaccttca tgggcaagaa
acttttcaaa gataaaatca aacattacta cgtcccggat ttcaaacttg
ctattgacca tttttgtata catgccggag gcagagccgt gattgatgtg
ctagagaaga acctagccct agcaccgatc gatgtagagg catcaagatc
aacgttacat agatttggaa acacttcatc tagctcaata tggtatgagt
tggcatacat agaagcaaaa ggaaggatga agaaaggtaa taaagtttgg
cagattgctt tagggtcagg ctttaagtgt aacagtgcag tttggggtggc
tctaaacaat gtcaaagctt cgacaaatag tccttgggaa cactgcatcg
acagataccc ggtcaaaatt gattctgatt caggtaagtc agagactcgt
gtcccaaacg gtcggtccta a
```

FIGURE 2-7

At114 G307D (SEQ ID NO:15)

```
atgacgtccg ttaacgttaa gctcctttac cgttatgtct taaccaactt
tttcaacctc tgtttgttcc cgttaacggc gttcctcgcc ggaaaagcct
ctcggcttac cataaacgat ctccacaact tcctttccta tctccaacac
aaccttataa cagtaacttt actctttgct ttcactgttt tcggtttggt
tctctacatc gtaacccgac ccaatccggt ttatctcgtt gactactcgt
gttaccttcc gccaccgcat ctcaaagtta gtgtctctaa agtcatggat
attttctacc aaataagaaa agctgatact tcttcacgga acggcacgtg
tgatgattcg tcgtggcttg acttcttgag gaagattcaa gaacgttcag
gtctaggcga tgaaactcac gggcccgagg ggctgcttca ggtccctccc
cggaagactt ttgcggcggc gcgtgaagag acggagcaag ttatcattgg
tgcgctagaa aatctattca agaacaccaa cgttaaccct aaagatatag
gtatacttgt ggtgaactca agcatgttta atccaactcc atcgctctcc
gcgatggtcg ttaacacttt caagctccga agcaacgtaa gaagctttaa
ccttggtggc atgggttgta gtgccggcgt tatagccatt gatctagcaa
aggacttgtt gcatgtccat aaaaatacgt atgctcttgt ggtgagcaca
gagaacatca cttataacat ttacgctggt gataataggt ccatgatggt
ttcaaattgc ttgttccgtg ttggtggggc cgctattttg ctctccaaca
agcctggaga tcgtagacgg tccaagtacg agctagttca cacggttcga
acgcataccg gagctgacga caagtctttt cgttgcgtgc aacaaggaga
cgatgagaac ggcaaaatcg gagtgagttt gtccaaggac ataaccgatg
ttgctggtcg aacggttaag aaaaacatag caacgttggg tccgttgatt
cttccgttaa gcgagaaact tcttttttc gttaccttca tgggcaagaa
acttttcaaa gataaaatca aacattacta cgtcccggat ttcaaacttg
ctattgacca tttttgtata catgccggag gcagagccgt gattgatgtg
ctagagaaga acctagccct agcaccgatc gatgtagagg catcaagatc
aacgttacat agatttggaa acacttcatc tagctcaata tggtatgagt
tggcatacat agaagcaaaa ggaaggatga agaaaggtaa taaagtttgg
cagattgctt tagggtcagg ctttaagtgt aacagtgcag tttgggtggc
tctaaacaat gtcaaagctt cgacaaatag tccttgggaa cactgcatcg
acagataccc ggtcaaaatt gattctgatt caggtaagtc agagactcgt
gtccaaaacg gtcggtccta a
```

FIGURE 2-8

At74 G306D (SEQ ID NO:17)

```
atgacgtccg ttaacgttaa gctcctttac cgttacgtct taaccaactt
tttcaacctc tgtttgttcc cgttaacggc gttcctcgcc ggaaaagcct
ctcggcttac cataaacgat ctccacaact tcctttccta tctccaacac
aaccttataa cagtaacttt actctttgct ttcactgttt tcggtttggt
tctctacatc gtaacccgac ccaaaccggt ttacctcgtt gagtactcat
gctaccttcc accaacgcat tgtagatcaa gtatctccaa ggtcatggat
atcttttatc aagtaagaaa agctgatcct tctcggaacg gcacgtgcga
tgactcgtcg tggcttgact tcttgaggaa gattcaagaa cgttcaggtc
taggcgatga aactcacggg cccgaggggc tgcttcaggt ccctccccgg
aagactttg cggcggcgcg tgaagagacg gagcaagtta tcattggtgc
gctagaaaat ctattcaaga acaccaacgt taaccctaaa gatataggta
tacttgtggt gaactcaagc atgtttaatc caactccatc gctctccgcg
atggtcgtta acactttcaa gctccgaagc aacgtaagaa gctttaacct
tggtggcatg ggttgtagtg ccggcgttat agccattgat ctagcaaagg
acttgttgca tgtccataaa aatacgtatg ctcttgtggt gagcacagag
aacatcactt ataacattta cgctggtgat aataggtcca tgatggtttc
aaattgcttg ttccgtgttg gtggggccgc tatttgctc tccaacaagc
ctggagatcg tagacggtcc aagtacgagc tagttcacac ggttcgaacg
cataccggag ctgacgacaa gtcttttcgt tgcgtgcaac aaggagacga
tgagaacggc aaaatcggag tgagtttgtc caaggacata accgatgttg
ctggtcgaac ggttaagaaa aacatagcaa cgttgggtcc gttgattctt
ccgttaagcg agaaacttct tttttcgtt accttcatgg gcaagaaact
tttcaaagat aaaatcaaac attactacgt cccggatttc aaacttgcta
ttgaccattt ttgtatacat gccggaggca gagccgtgat tgatgtgcta
gagaagaacc tagccctagc accgatcgat gtagaggcat caagatcaac
gttacataga tttggaaaca cttcatctag ctcaatatgg tatgagttgg
catacataga agcaaaagga aggatgaaga aaggtaataa agtttggcag
attgctttag ggtcaggctt taagtgtaac agtgcagttt gggtggctct
aaacaatgtc aaagcttcga caaatagtcc ttgggaacac tgcatcgaca
gatacccggt caaaattgat tctgattcag gtaagtcaga gactcgtgtc
caaaacggtc ggtcctaa
```

FIGURE 2-9

At114 L91C K92R G307D (SEQ ID NO:19)

```
atgacgtccg ttaacgttaa gctcctttac cgttatgtct taaccaactt
tttcaacctc tgtttgttcc cgttaacggc gttcctcgcc ggaaaagcct
ctcggcttac cataaacgat ctccacaact tcctttccta tctccaacac
aaccttataa cagtaacttt actctttgct ttcactgttt tcggtttggt
tctctacatc gtaacccgac ccaatccggt ttatctcgtt gactactcgt
gttaccttcc gccaccgcat tgcagagtta gtgtctctaa agtcatggat
attttctacc aaataagaaa agctgatact tcttcacgga acggcacgtg
tgataattcg tcgtggcttg acttcttgag gaagattcaa gaacgttcag
gtctaggcga tgaaactcac gggcccgagg ggctgcttca ggtccctccc
cggaagactt ttgcggcggc gcgtgaagag acggagcaag ttatcattgg
tgcgctagaa aatctattca agaacaccaa cgttaaccct aaagatatag
gtatacttgt ggtgaactca agcatgttta atccaactcc atcgctctcc
gcgatggtcg ttaacacttt caagctccga agcaacgtaa gaagctttaa
ccttggtggc atgggttgta gtgccggcgt tatagccatt gatctagcaa
aggacttgtt gcatgtccat aaaaatacgt atgctcttgt ggtgagcaca
gagaacatca cttataacat ttacgctggt gataataggt ccatgatggt
ttcaaattgc ttgttccgtg ttggtggggc cgctatttg ctctccaaca
agcctggaga tcgtagacgg tccaagtacg agctagttca cacggttcga
acgcataccg gagctgacga caagtctttt cgttcgtgc aacaaggaga
cgatgagaac ggcaaaatcg gagtgagttt gtccaaggac ataaccgatg
ttgctggtcg aacggttaag aaaacatag caacgttggg tccgttgatt
cttccgttaa gcgagaaact tcttttttc gttaccttca tgggcaagaa
acttttcaaa gataaaatca aacattacta cgtcccggat ttcaaacttg
ctattgacca tttttgtata catgccggag gcagagccgt gattgatgtg
ctagagaaga acctagccct agcaccgatc gatgtagagg catcaagatc
aacgttacat agatttggaa acacttcatc tagctcaata tggtatgagt
tggcatacat agaagcaaaa ggaaggatga agaaggtaa taaagtttgg
cagattgctt tagggtcagg ctttaagtgt aacagtgcag tttgggtggc
tctaaacaat gtcaaagctt cgacaaatag tccttgggaa cactgcatcg
acagataccc ggtcaaaatt gattctgatt caggtaagtc agagactcgt
gtccaaaacg gtcggtccta a
```

FIGURE 2-10

At114 K92R G307D (SEQ ID NO:21)

```
atgacgtccg ttaacgttaa gctcctttac cgttatgtct taaccaactt
tttcaacctc tgtttgttcc cgttaacggc gttcctcgcc ggaaaagcct
ctcggcttac cataaacgat ctccacaact tcctttccta tctccaacac
aaccttataa cagtaacttt actctttgct ttcactgttt tcggtttggt
tctctacatc gtaacccgac ccaatccggt ttatctcgtt gactactcgt
gttaccttcc gccaccgcat ctcagagtta gtgtctctaa agtcatggat
attttctacc aaataagaaa agctgatact tcttcacgga acggacgtg
tgatgattcg tcgtggcttg acttcttgag gaagattcaa gaacgttcag
gtctaggcga tgaaactcac gggcccgagg ggctgcttca ggtccctccc
cggaagactt ttgcggcggc gcgtgaagag acggagcaag ttatcattgg
tgcgctagaa aatctattca agaacaccaa cgttaaccct aaagatatag
gtatacttgt ggtgaactca agcatgttta tccaactcc atcgctctcc
gcgatggtcg ttaacacttt caagctccga agcaacgtaa gaagctttaa
ccttggtggc atgggttgta gtgccggcgt tatagccatt gatctagcaa
aggacttgtt gcatgtccat aaaaatacgt atgctcttgt ggtgagcaca
gagaacatca cttataacat ttacgctggt gataataggt ccatgatggt
ttcaaattgc ttgttccgtg ttggtggggc cgctattttg ctctccaaca
agcctggaga tcgtagacgg tccaagtacg agctagttca cacggttcga
acgcataccg gagctgacga caagtctttt cgttgcgtgc aacaaggaga
cgatgagaac ggcaaaatcg gagtgagttt gtccaaggac ataaccgatg
ttgctggtcg aacggttaag aaaacatag caacgttggg tccgttgatt
cttccgttaa gcgagaaact tcttttttc gttaccttca tgggcaagaa
acttttcaaa gataaaatca aacattacta cgtcccggat ttcaaacttg
ctattgacca tttttgtata catgccggag gcagagccgt gattgatgtg
ctagagaaga acctagccct agcaccgatc gatgtagagg catcaagatc
aacgttacat agatttggaa acacttcatc tagctcaata tggtatgagt
tggcatacat agaagcaaaa ggaaggatga agaaaggtaa taaagtttgg
cagattgctt tagggtcagg ctttaagtgt aacagtgcag tttgggtggc
tctaaacaat gtcaaagctt cgacaaatag tccttgggaa cactgcatcg
acagataccc ggtcaaaatt gattctgatt caggtaagtc agagactcgt
gtccaaaacg gtcggtccta a
```

FIGURE 2-11

At254 (SEQ ID NO:23)

```
atgacgtccg ttaacgttaa gctcctttac cgttacgtct taaccaactt
tttcaacctc tgtttgttcc cgttaacggc gttcctcgcc ggaaaagcct
ctcggcttac cataaacgat ctccacaacc tcctttccta tctccaacac
aaccttataa cagtaacttt actctttgct ttcactgttt tcggtttggt
tctctacatc gtaacccgac ccaatccggt ttatctcgtt gactactcgt
gttaccttcc accaccgcat ctcaaagtta gtgtctctaa agtcatggat
attttctacc aaataagaaa agctgatact tcttcacgga acgtggcatg
tgatgatccg tcctcgctcg atttcctgag gaagattcaa gagcgttcag
gtctaggtga tgagacgtac agtcctgagg gactcattca cgtaccaccg
cggaagactt ttgcagcgtc acgtgaagag acagagaagg ttatcatcgg
tgcgctcgaa aatctattcg agaacaccaa agttaaccct agagagattg
gtatacttgt ggtgaactca agcatgttta atccaactcc ttcgctatcc
gctatggtcg ttaatacttt caagctccga agcaacatca aaagctttaa
tctaggagga atgggttgta gtgctggtgt tattgccatt gatttggcta
aagacttgtt gcatgttcat aaaaacactt atgctctcgt ggtgagcaca
gagaacatca cttataacat ttacgctggt gataataggt ccatgatggt
ttcaaattgc ttgttccgtg ttggtggggc cgctattttg ctctccaaca
agcctggaga tcgtagacgg tccaagtacg agctagttca cacggttcga
acgcataccg gagctgacgg caagtctttt cgttgcgtgc aacaaggaga
cgatgagaac ggcaaaatcg gagtgagttt gtccaaggac ataaccgatg
ttgctggtcg aacggttaag aaaaacatag caacgttggg tccgttgatt
cttccgttaa gcgagaaact tcttttttc gttaccttca tgggcaagaa
acttttcaaa gataaaatca aacattacta cgtcccggat ttcaaacttg
ctattgacca tttttgtata catgccggag gcagagccgt gattgatgtg
ctagagaaga acctagccct agcaccgatc gatgtagagg catcaagatc
aacgttacat agatttggaa acacttcatc tagctcaata tggtatgagt
tggcatacat agaagcaaaa ggaaggatga agaaaggtaa taaagtttgg
cagattgctt tagggtcagg ctttaagtgt aacagtgcag tttgggtggc
tctaaacaat gtcaaagctt cgacaaatag tccttgggaa cactgcatcg
acagataccc ggtcaaaatt gattctgatt caggtaagtc agagactcgt
gtcccaaacg gtcggtccta a
```

FIGURE 2-12

At173 (SEQ ID NO:25)

```
atgacgtccg ttaacgttaa gctcctttac cgttacgtct taaccaactt
tttcaacctc tgtttgttcc cgttaacggc gttcctcgcc ggaaaagcct
ctcggcttac cataaacgat ctccacaact tcctttccta tctccaacac
aaccttataa cagtaacttt actctttgct ttcactgttt tcggtttggt
tctctacatc gtaacccgac ccaatccggt ttatctcgtt gactactcgt
gttaccttcc accaccgcat ctcaaagtta gtgtctctaa agtcatggat
attttctacc aaataagaaa agctgatact tcttcacgga acgtggcatg
tgatgatccg tcctcgctcg atttcctgag gaagattcaa gagcgttcag
gtctaggtga tgagacgtac agtcctgagg gactcattca cgtaccaccg
cggaagactt ttgcagcgtc acgtgaagag acagagaagg ttatcatcgg
tgcgctcgaa aatctattca agaacaccaa cgttaaccct aaagatatag
gtatacttgt ggtgaactca agcatgttta atccaactcc atcgctctcc
gcgatggtcg ttaacacttt caagctccga agcaacgtaa gaagctttaa
ccttggtggc atgggttgta gtgccggcgt tatagccatt gatctagcaa
aggacttgtt gcatgtccat aaaaatacgt atgctcttgt ggtgagcaca
gagaacatca cttataacat ttacgctggt gataataggt ccatgatggt
ttcaaattgc ttgttccgtg ttggtggggc cgctattttg ctctccaaca
agcctggaga tcgtagacgg tccaagtacg agctagttca cacggttcga
acgcataccg gagctgacgg caagtctttt cgttgcgtgc aacaaggaga
cgatgagaac ggcaaaatcg gagtgagttt gtccaaggac ataaccgatg
ttgctggtcg aacggttaag aaaaacatag caacgttggg tccgttgatt
cttccgttaa gcgagaaact tctttttttc gttaccttca tgggcaagaa
acttttcaaa gataaaatca aacattacta cgtcccggat ttcaaacttg
ctattgacca tttttgtata catgccggag gcagagccgt gattgatgtg
ctagagaaga acctagccct agcaccgatc gatgtagagg catcaagatc
aacgttacat agatttggaa acacttcatc tagctcaata tggtatgagt
tggcatacat agaagcaaaa ggaaggatga agaaaggtaa taaagtttgg
cagattgctt tagggtcagg ctttaagtgt aacagtgcag tttgggtggc
tctaaacaat gtcaaagctt cgacaaatag tccttgggaa cactgcatcg
acagataccc ggtcaaaatt gattctgatt caggtaagtc agagactcgt
gtccaaaacg gtcggtccta a
```

FIGURE 2-13

Bn176 (SEQ ID NO:27)

```
atgacgtcca ttaacgtaaa gctcctttac cattacgtca taaccaacct
tttcaacctt tgcttctttc cgttaacggc gatcgtcgcc ggaaaagcct
atcggcttac catagacgat cttcaccact tatactattc ctatctccaa
cacaacctca taaccatcgc tccactcttt gccttcaccg ttttcggttc
ggttctctac atcgcaaccc ggcccaaacc ggtttacctc gttgagtact
catgctacct tccaccaacg cattgtagat caagtatctc caaggtcatg
gatatctttt atcaagtaag aaaagctgat ccttctcgga acggcacgtg
cgatgactcg tcgtggcttg acttcttgag gaagattcaa gaacgttcag
gtctaggcga tgaaactcac gggcccgagg ggctgcttca ggtccctccc
cggaagactt tgcggcggc gcgtgaagag acggagcaag ttatcattgg
tgcgctagaa aatctattca agaacaccaa agttaaccct agagagattg
gtatacttgt ggtgaactca agcatgttta atccaactcc ttcgctatcc
gctatggtcg ttaatacttt caagctccga agcaacatca aaagctttaa
tctaggagga atgggttgta gtgctggtgt tattgccatt gatttggcta
aagacttgtt gcatgttcat aaaaacactt atgctcttgt ggtgagcact
gagaacatca cacaaggcat ttatgctgga gaaaatagat caatgatggt
tagcaattgc ttgtttcgtg ttggtgggc cgcgattttg ctctctaaca
agtcgggaga ccggagacgg tccaagtaca agctagttca cacggtccga
acgcatactg gagctgatga caagtctttt cgatgtgtgc aacaagaaga
tgatgagagc ggcaaaatcg gagtttgtct gtcaaaggac ataaccaatg
ttgcggggac aacacttacg aaaatatag caacattggg tccgttgatt
cttcctttaa gcgaaaagtt tcttttttc gctaccttcg tcgccaagaa
acttctaaag gataaaatca agcattacta tgttccggat ttcaagcttg
ctgttgacca tttctgtatt catgccggag gcagagccgt gatcgatgag
ctagagaaga acttaggact atcgccgatc gatgtggagg catctagatc
aacgttacat agatttggga atacttcatc tagctcaatt tggtatgaat
tagcatacat agaggcaaag ggaagaatga agaaagggaa taaagcttgg
cagattgctt taggatcagg gtttaagtgt aatagtgcgg tttgggtggc
tctacgcaat gtcaaggcat cggcaaatag tccttggcaa cattgcatcg
atagatatcc ggttaaaatt gattctgatt tgtcaaagtc aaagactcat
gtccaaaacg gtcggtccta a
```

FIGURE 2-14

At399 (SEQ ID NO:29)

```
atgacgtccg ttaacgttaa gctcctttac cgttacgtct taaccaactt
tttcaacctc tgtttgttcc cgttaacggc gttcctcgcc ggaaaagcct
ctcggcttac cataaacgat ctccacaact tcctttccta tctccaacac
aaccttataa cagtaacttt actctttgct ttcactgttt tcggtttggt
tctctacatc gtaacccgac ccaatccggt ttatctcgtt gactactcgt
gttaccttcc accaccgcat ctcaaagtta gtgtctctaa agtcatggat
attttctacc aaataagaaa agctgatact tcttcacgga acgtggcatg
tgatgatccg tcctcgctcg atttcctgag gaagattcaa gagcgttcag
gtctaggtga tgagacgtac agtcctgagg gactcattca cgtaccaccg
cggaagactt ttgcagcgtc acgtgaagag acagagaagg ttatcatcgg
tgcgctcgaa aatctattcg agaacaccaa agttaaccct agagagattg
gtatacttgt ggtgaactca agcatgttta atccaactcc ttcgctatcc
gctatggtcg ttaatacttt caagctccga agcaacatca aaagctttaa
tctaggagga atgggttgta gtgctggtgt tattgccatt gatttggcta
aagacttgtt gcatgttcat aaaaacactt atgctcttgt ggtgagcact
gagaacatca cacaaggcat ttatgctgga gaaaatagat caatgatggt
tagcaattgc ttgtttcgtg ttggtggggc cgcgatttg ctctctaaca
agtcgggaga ccggagacgg tccaagtaca agctagttca cacggtccga
acgcatactg gagctgatga caagtctttt cgatgtgtgc aacaagaaga
cgatgagagc ggcaaaatcg gagtttgtct gtcaaaggac ataaccaatg
ttgcggggac aacacttacg aaaaatatag caacattggg tccgttgatt
cttcctttaa gcgaaaagtt tcttttttc gctaccttcg tcgccaagaa
acttctaaag gataaaatca agcattacta tgttccggat ttcaagcttg
ctgttgacca tttctgtatt catgccggag gcagagccgt gatcgatgtg
ctagagaaga acctagccct agcaccgatc gatgtagagg catcaagatc
aacgttacat agatttggaa acacttcatc tagctcaata tggtatgagt
tggcatacat agaagcaaaa ggaaggatga agaaaggtaa taaagtttgg
cagattgctt tagggtcagg ctttaagtgt aacagtgcag tttgggtggc
tctaaacaat gtcaaagctt cgacaaatag tccttgggaa cactgcatcg
acagataccc ggtcaaaatt gattctgatt caggtaagtc agagactcgt
gtccaaaacg gtcggtccta a
```

FIGURE 2-15

Bn399 (SEQ ID NO:31)

```
atgacgtcca ttaacgttaa gctcctttac cattacgtca taaccaacct
tttcaacctt tgcttctttc cgttaacggc gatcgtcgcc ggaaaagcct
atcggcttac catagacgat cttcaccact tatactattc ctatctccaa
cacaacctca taaccatcgc tccactcttt gccttaccg ttttcggttc
ggttctctac atcgcaaccc ggcccaaacc ggtttacctc gttgagtact
catgctacct tccaccaacg cattgtagat caagtatctc caaggtcatg
gatatctttt atcaagtaag aaaagctgat ccttctcgga acggcacgtg
cgatgactcg tcgtggcttg acttcttgag gaagattcaa gaacgttcag
gtctaggcga tgaaactcac gggcccgagg ggctgcttca ggtccctccc
cggaagactt ttgcggcggc gcgtgaagag acggagcaag ttatcattgg
tgcgctagaa aatctattca agaacaccaa cgttaaccct aaagatatag
gtatacttgt ggtgaactca agcatgttta atccaactcc atcgctctcc
gcgatggtcg ttaacacttt caagctccga agcaacgtaa gaagctttaa
ccttggtggc atgggttgta gtgccggcgt tatagccatt gatctagcaa
aggacttgtt gcatgtccat aaaaatacgt atgctcttgt ggtgagcaca
gagaacatca cttataacat ttacgctggt gataataggt ccatgatggt
ttcaaattgc ttgttccgtg ttggtggggc cgctattttg ctctccaaca
agcctggaga tcgtagacgg tccaagtacg agctagttca cacggttcga
acgcataccg gagctgacgg caagtctttt cgttgcgtgc aacaaggaga
cgatgagaac ggcaaaatcg gagtgagttt gtccaaggac ataaccgatg
ttgctggtcg aacggttaag aaaaacatag caacgttggg tccgttgatt
cttccgttaa gcgagaaact tctttttttc gttaccttca tgggcaagaa
acttttcaaa gataaaatca aacattacta cgtcccggat ttcaaacttg
ctattgacca tttttgtata catgccggag gcagagccgt gatcgatgag
ctagagaaga acttaggact atcgccgatc gatgtggagg catctagatc
aacgttacat agatttggga atacttcatc tagctcaatt tggtatgaat
tagcatacat agaggcaaag ggaagaatga agaaagggaa taaagcttgg
cagattgctt taggatcagg gtttaagtgt aatagtgcgg tttgggtggc
tctacgcaat gtcaaggcat cggcaaatag tccttggcaa cattgcatcg
atagatatcc ggttaaaatt gattctgatt tgtcaaagtc aaagactcat
gtccaaaacg gtcggtccta a
```

FIGURE 2-16

Bn G307D (SEQ ID NO:33)

```
atgacgtcca ttaacgtaaa gctcctttac cattacgtca taaccaacct
tttcaacctt tgcttctttc cgttaacggc gatcgtcgcc ggaaaagcct
atcggcttac catagacgat cttcaccact tatactattc ctatctccaa
cacaacctca taaccatcgc tccactcttt gccttcaccg ttttcggttc
ggttctctac atcgcaaccc ggcccaaacc ggtttacctc gttgagtact
catgctacct tccaccaacg cattgtagat caagtatctc caaggtcatg
gatatctttt atcaagtaag aaaagctgat ccttctcgga acggcacgtg
cgatgactcg tcgtggcttg acttcttgag gaagattcaa gaacgttcag
gtctaggcga tgaaactcac gggcccgagg ggctgcttca ggtccctccc
cggaagactt ttgcggcggc gcgtgaagag acggagcaag ttatcattgg
tgcgctagaa aatctattca agaacaccaa cgttaaccct aaagatatag
gtatacttgt ggtgaactca agcatgttta atccaactcc atcgctctcc
gcgatggtcg ttaacacttt caagctccga agcaacgtaa gaagctttaa
ccttggtggc atgggttgta gtgccggcgt tatagccatt gatctagcaa
aggacttgtt gcatgtccat aaaaatacgt atgctcttgt ggtgagcaca
gagaacatca cttataacat ttacgctggt gataataggt ccatgatggt
ttcaaattgc ttgttccgtg ttggtggggc cgctattttg ctctccaaca
agcctggaga tcgtagacgg tccaagtacg agctagttca cacggttcga
acgcataccg gagctgacga caagtctttt cgttgcgtgc aacaaggaga
cgatgagaac ggcaaaatcg gagtgagttt gtccaaggac ataaccgatg
ttgctggtcg aacggttaag aaaaacatag caacgttggg tccgttgatt
cttccgttaa gcgagaaact tcttttttc gttaccttca tgggcaagaa
acttttcaaa gataaaatca aacattacta cgtcccggat ttcaaacttg
ctattgacca ttttgtata catgccggag gcagagccgt gattgatgtg
ctagagaaga acctagccct agcaccgatc gatgtagagg catcaagatc
aacgttacat agatttggaa acacttcatc tagctcaata tggtatgagt
tggcatacat agaagcaaaa ggaaggatga agaaggtaa taaagtttgg
cagattgctt tagggtcagg ctttaagtgt aacagtgcag tttgggtggc
tctaaacaat gtcaaagctt cgacaaatag tccttgggaa cactgcatcg
acagataccc ggtcaaaatt gattctgatt caggtaagtc agagactcgt
gtccaaaacg gtcggtccta ataa
```

FIGURE 2-17

At K92R (SEQ ID NO:35)

```
atgacgtccg ttaacgttaa gctcctttac cgttacgtct taaccaactt
tttcaacctc tgtttgttcc cgttaacggc gttcctcgcc ggaaaagcct
ctcggcttac cataaacgat ctccacaact tcctttccta tctccaacac
aaccttataa cagtaacttt actctttgct ttcactgttt tcggtttggt
tctctacatc gtaacccgac ccaatccggt ttatctcgtt gactactcgt
gttaccttcc accaccgcat ctcagagtta gtgtctctaa agtcatggat
attttctacc aaataagaaa agctgatact tcttcacgga acgtggcatg
tgatgatccg tcctcgctcg atttcctgag gaagattcaa gagcgttcag
gtctaggtga tgagcgtac agtcctgagg gactcattca cgtaccaccg
cggaagactt ttgcagcgtc acgtgaagag acagagaagg ttatcatcgg
tgcgctcgaa aatctattcg agaacaccaa agttaaccct agagagattg
gtatacttgt ggtgaactca agcatgttta atccaactcc ttcgctatcc
gctatggtcg ttaatacttt caagctccga agcaacatca aaagctttaa
tctaggagga atgggttgta gtgctggtgt tattgccatt gatttggcta
aagacttgtt gcatgttcat aaaaacactt atgctcttgt ggtgagcact
gagaacatca cacaaggcat ttatgctgga gaaaatagat caatgatggt
tagcaattgc ttgtttcgtg ttggtggggc cgcgattttg ctctctaaca
agtcgggaga ccggagacgg tccaagtaca agctagttca cacggtccga
acgcatactg gagctgatga caagtctttt cgatgtgtgc aacaagaaga
cgatgagagc ggcaaaatcg gagtttgtct gtcaaggac ataaccaatg
ttgcggggac aacacttacg aaaaatatag caacattggg tccgttgatt
cttcctttaa gcgaaagtt tcttttttc gctaccttcg tcgccaagaa
acttctaaag gataaaatca agcattacta tgttccggat ttcaagcttg
ctgttgacca tttctgtatt catgccggag gcagagccgt gatcgatgag
ctagagaaga acttaggact atcgccgatc gatgtggagg catctagatc
aacgttacat agatttggga atacttcatc tagctcaatt tggtatgaat
tagcatacat agaggcaaag ggaagaatga agaaagggaa taaagcttgg
cagattgctt taggatcagg gtttaagtgt aatagtgcgg tttgggtggc
tctacgcaat gtcaaggcat cggcaaatag tccttggcaa cattgcatcg
atagatatcc ggttaaaatt gattctgatt tgtcaaagtc aaagactcat
gtccaaaacg gtcggtccta atttgatgta tctgagtgcc aacgtttact
ttgtctttcc tttctttat tggttatgaa ttagatgttt actaatgttc
ctctcttttt cgttataaat aaagaagttc aattcttcct atagtttcaa
acgcgatttt aagcgtttct atttaggttt acatgaattt cttttacaaa
ccatctttt
```

FIGURE 2-18

At254 G307D (SEQ ID NO:37)

```
atgacgtccg ttaacgttaa gctcctttac cgttacgtct taaccaactt
tttcaacctc tgtttgttcc cgttaacggc gttcctcgcc ggaaaagcct
ctcggcttac cataaacgat ctccacaact tcctttccta tctccaacac
aaccttataa cagtaacttt actctttgct ttcactgttt tcggtttggt
tctctacatc gtaacccgac ccaatccggt ttatctcgtt gactactcgt
gttaccttcc accaccgcat ctcaaagtta gtgtctctaa agtcatggat
attttctacc aaataagaaa agctgatact tcttcacgga acgtggcatg
tgatgatccg tcctcgctcg atttcctgag gaagattcaa gagcgttcag
gtctaggtga tgagacgtac agtcctgagg gactcattca cgtaccaccg
cggaagactt ttgcagcgtc acgtgaagag acagagaagg ttatcatcgg
tgcgctcgaa aatctattcg agaacaccaa agttaaccct agagagattg
gtatacttgt ggtgaactca agcatgttta atccaactcc ttcgctatcc
gctatggtcg ttaatacttt caagctccga agcaacatca aaagctttaa
tctaggagga atgggttgta gtgctggtgt tattgccatt gatttggcta
aagacttgtt gcatgttcat aaaaacactt atgctctcgt ggtgagcaca
gagaacatca cttataacat ttacgctggt gataataggt ccatgatggt
ttcaaattgc ttgttccgtg ttggtggggc cgctattttg ctctccaaca
agcctggaga tcgtagacgg tccaagtacg agctagttca cacggttcga
acgcataccg gagctgacga caagtctttt cgttgcgtgc aacaaggaga
cgatgagaac ggcaaaatcg gagtgagttt gtccaaggac ataaccgatg
ttgctggtcg aacggttaag aaaaacatag caacgttggg tccgttgatt
cttccgttaa gcgagaaact tcttttttc gttaccttca tgggcaagaa
acttttcaaa gataaaatca aacattacta cgtcccggat ttcaaacttg
ctattgacca ttttgtata catgccggag gcagagccgt gattgatgtg
ctagagaaga acctagccct agcaccgatc gatgtagagg catcaagatc
aacgttacat agatttggaa acacttcatc tagctcaata tggtatgagt
tggcatacat agaagcaaaa ggaaggatga agaaaggtaa taaagtttgg
cagattgctt tagggtcagg ctttaagtgt aacagtgcag tttgggtggc
tctaaacaat gtcaaagctt cgacaaatag tccttgggaa cactgcatcg
acagataccc ggtcaaaatt gattctgatt caggtaagtc agagactcgt
gtccaaaacg gtcggtccta a
```

FIGURE 2-19

At173 G307D (SEQ ID NO:39)

```
atgacgtccg ttaacgttaa gctcctttac cgttacgtct taaccaactt
tttcaacctc tgtttgttcc cgttaacggc gttcctcgcc ggaaaagcct
ctcggcttac cataaacgat ctccacaact tcctttccta tctccaacac
aaccttataa cagtaacttt actctttgct ttcactgttt tcggtttggt
tctctacatc gtaacccgac ccaatccggt ttatctcgtt gactactcgt
gttaccttcc accaccgcat ctcaaagtta gtgtctctaa agtcatggat
attttctacc aaataagaaa agctgatact tcttcacgga acgtggcatg
tgatgatccg tcctcgctcg atttcctgag gaagattcaa gagcgttcag
gtctaggtga tgagacgtac agtcctgagg gactcattca cgtaccaccg
cggaagactt ttgcagcgtc acgtgaagag acagagaagg ttatcatcgg
tgcgctcgaa aatctattca agaacaccaa cgttaaccct aaagatatag
gtatacttgt ggtgaactca agcatgttta atccaactcc atcgctctcc
gcgatggtcg ttaacacttt caagctccga agcaacgtaa gaagctttaa
ccttggtggc atgggttgta gtgccggcgt tatagccatt gatctagcaa
aggacttgtt gcatgtccat aaaaatacgt atgctcttgt ggtgagcaca
gagaacatca cttataacat ttacgctggt gataataggt ccatgatggt
ttcaaattgc ttgttccgtg ttggtggggc cgctattttg ctctccaaca
agcctggaga tcgtagacgg tccaagtacg agctagttca cacggttcga
acgcataccg gagctgacga caagtctttt cgttgcgtgc aacaaggaga
cgatgagaac ggcaaaatcg gagtgagttt gtccaaggac ataaccgatg
ttgctggtcg aacggttaag aaaaacatag caacgttggg tccgttgatt
cttccgttaa gcgagaaact tctttttttc gttaccttca tgggcaagaa
acttttcaaa gataaaatca aacattacta cgtcccggat ttcaaacttg
ctattgacca ttttttgtata catgccggag gcagagccgt gattgatgtg
ctagagaaga acctagccct agcaccgatc gatgtagagg catcaagatc
aacgttacat agatttggaa acacttcatc tagctcaata tggtatgagt
tggcatacat agaagcaaaa ggaaggatga agaaaggtaa taaagtttgg
cagattgctt tagggtcagg ctttaagtgt aacagtgcag tttgggtggc
tctaaacaat gtcaaagctt cgacaaatag tccttgggaa cactgcatcg
acagataccc ggtcaaaatt gattctgatt caggtaagtc agagactcgt
gtccaaaacg gtcggtccta a
```

FIGURE 2-20

Bn399 G307D (SEQ ID NO:41)

```
atgacgtcca ttaacgttaa gctcctttac cattacgtca taaccaacct
tttcaacctt tgcttctttc cgttaacggc gatcgtcgcc ggaaaagcct
atcggcttac catagacgat cttcaccact tatactattc ctatctccaa
cacaacctca taaccatcgc tccactcttt gccttcaccg ttttcggttc
ggttctctac atcgcaaccc ggcccaaacc ggtttacctc gttgagtact
catgctacct tccaccaacg cattgtagat caagtatctc caaggtcatg
gatatctttt atcaagtaag aaaagctgat ccttctcgga acggcacgtg
cgatgactcg tcgtggcttg acttcttgag gaagattcaa gaacgttcag
gtctaggcga tgaaactcac gggcccgagg ggctgcttca ggtccctccc
cggaagactt ttgcggcggc gcgtgaagag acggagcaag ttatcattgg
tgcgctagaa aatctattca agaacaccaa cgttaaccct aaagatatag
gtatacttgt ggtgaactca agcatgttta atccaactcc atcgctctcc
gcgatggtcg ttaacacttt caagctccga agcaacgtaa gaagctttaa
ccttggtggc atgggttgta gtgccggcgt tatagccatt gatctagcaa
aggacttgtt gcatgtccat aaaaatacgt atgctcttgt ggtgagcaca
gagaacatca cttataacat ttacgctggt gataataggt ccatgatggt
ttcaaattgc ttgttccgtg ttggtggggc cgctattttg ctctccaaca
agcctggaga tcgtagacgg tccaagtacg agctagttca cacggttcga
acgcataccg gagctgacga caagtctttt cgttgcgtgc aacaaggaga
cgatgagaac ggcaaaatcg gagtgagttt gtccaaggac ataaccgatg
ttgctggtcg aacggttaag aaaacatag caacgttggg tccgttgatt
cttccgttaa gcgagaaact tctttttttc gttaccttca tgggcaagaa
acttttcaaa gataaaatca aacattacta cgtcccggat ttcaaacttg
ctattgacca tttttgtata catgccggag gcagagccgt gatcgatgag
ctagagaaga acttaggact atcgccgatc gatgtggagg catctagatc
aacgttacat agatttggga atacttcatc tagctcaatt tggtatgaat
tagcatacat agaggcaaag ggaagaatga agaaagggaa taaagcttgg
cagattgctt taggatcagg gttaagtgt aatagtgcgg tttgggtggc
tctacgcaat gtcaaggcat cggcaaatag tccttggcaa cattgcatcg
atagatatcc ggttaaaatt gattctgatt tgtcaaagtc aaagactcat
gtccaaaacg gtcggtccta a
```

FATTY ACID ELONGASE 3-KETOACYL COA SYNTHASE POLYPEPTIDES

CROSS REFERENCE TO RELATED APPLICATIONS

This application claims priority under 35 U.S.C. §119(e) of U.S. provisional application Serial No. 60/210,326, filed Jun. 8, 2000.

TECHNICAL FIELD

This invention relates to enzymes involved in very long chain fatty acid (VLCFA) synthesis, and more particularly to chimeras and mutants of nucleic acid sequences encoding fatty acid elongase 3-ketoacyl CoA synthase polypeptides.

BACKGROUND

Plant seeds accumulate primarily 16- and 18-carbon fatty acids (FA). Plants also synthesize very long chain fatty acids (VLCFA). VLCFAs are saturated or unsaturated monocarboxylic acids with an unbranched even-numbered carbon chain that is greater than 18 carbons in length. Very long chain fatty acids are key components of many biologically important compounds in animals, plants, and microorganisms. For example, in animals, the VLCFA arachidonic acid is a precursor to many prostaglandins. In plants, VLCFAs are major constituents of triacylglycerols in many seed oils, are essential precursors for cuticular wax production, and are utilized in the synthesis of glycosylceramides, a component of the plasma membrane. Important VLCFAs include arachidic acid (C20:0; i.e., a 20 carbon chain with no double bonds), behenic acid (C22:0), erucic acid (C22:1), and lignoceric acid (C24:1).

VLCFAs are not desirable in edible oils. Oilseeds of the Crucifereae (e.g., rapeseed) and a few other plants, however, accumulate C20 and C22 fatty acids. Although plant breeders have developed rapeseed lines that have low levels of VLCFAs for edible oil purposes, even lower levels would be desirable. On the other hand, vegetable oils having elevated levels of VLCFAs are desirable for certain industrial uses, including uses as lubricants, fuels and as a feedstock for plastics, pharmaceuticals and cosmetics.

The biosynthesis in plants of saturated fatty acids up to an 18-carbon chain occurs in the chloroplast. C2 units from acyl thioesters are linked sequentially, beginning with the condensation of acetyl Co-enzyme A (CoA) and malonyl-acyl carrier protein (malonyl-ACP) to form a C4 acyl fatty acid. This condensation reaction is catalyzed by a 3-ketoacyl synthase III (KASIII). The enzyme 3-ketoacyl synthase I (KASI) catalyzes the stepwise condensation of a fatty acyl moiety (C4 to C14) with C2 groups and malonyl-ACP to produce a 3-ketoacyl-ACP product that is 2 carbons longer than the original substrate (C6 to C16). The last condensation reaction in the chloroplast, converting C16 to C18, is catalyzed by 3-ketoacyl synthase II (KASII). 3-ketoacyl moieties are also referred to as β-ketoacyl moieties.

Each elongation cycle involves three additional enzymatic steps in addition to the condensation reaction discussed above. Briefly, the 3-ketoacyl condensation product is reduced to 3-hydroxyacyl-ACP, dehydrated to the enoyl-ACP, and reduced to an acyl-ACP. The fully reduced fatty acyl-ACP reaction product then serves as the substrate for the next cycle of elongation.

The C18:0 saturated fatty acid (stearic acid) can be desaturated to produce a C18:1 fatty acid (oleic acid), which can be transported out of the chloroplast and converted to a C18:2 fatty acid (linoleic acid) or a C18:3 fatty acid (α-linolenic acid). Stearic acid and oleic acid can also be elongated outside the chloroplast to form VLCFAs. The formation of fatty acids longer than 18 carbons depends on the activity of a fatty acid elongase complex to carry out four reactions similar to those described above for fatty acid synthesis in the chloroplast. The initial reaction is catalyzed by an elongase 3-ketoacyl CoA synthase (elongase KCS) and involves the condensation of a two carbon group from malonyl CoA with a C18:0 or C18:1 fatty acyl CoA substrate. A gene encoding an elongase KCS from *Arabidopsis thaliana* has been identified and designated FAE1. See, e.g., U.S. Pat. No. 6,124,524. The gene product catalyzes the condensation of oleoyl CoA and malonyl CoA, leading to the conversion of the C18 substrate to a C20:1 product, eicosenoyl CoA. Mutations have been identified in the *A. thaliana* FAE1 gene (see WO 96/13582). *A. thaliana* plants carrying a mutation in FAE1 have significant decreases in the levels of VLCFAs in seeds.

SUMMARY

Despite 85% sequence identity at the amino acid level between the *Arabidopsis thaliana* FAE1 polypeptide and the *Brassica napus* polypeptide of GenBank Accession No. AAB72178, the composition of the oil from *A. thaliana* and *B. napus* seeds suggests that the enzymes may have different substrate specificities and/or catalytic activity. VLCFAs constitute about 22% of the seed oil of *A. thaliana*, whereas VLCFAs constitute about 62% of the seed oil in rape. *A. thaliana* seed oil is primarily eicosenoic acid (about 18%), with a small amount of erucic acid and longer-chain monunusaturated fatty acids (about 2%). In contrast, rapeseed oil has a relatively small amount of eicosenoic acid (about 10%) and relatively larger amounts of erucic acid and longer-chain monunsaturates (about 52%).

The present invention provides novel polypeptides with altered elongase KCS substrate specificity and/or catalytic activity. One such novel polypeptide comprises three polypeptide segments. The amino-terminal first polypeptide segment has membrane-anchoring properties. It is joined to a second polypeptide segment whose amino acid sequence is residues 75–114 of SEQ ID NO:12 or residues 75–114 of SEQ ID NO:14, followed by a third polypeptide segment having at least 40% sequence identity to the C-terminal 392 amino acids of SEQ ID NO:4. Examples of such polypeptides have the amino acid sequences shown in SEQ ID NOS:12 and 14. The third polypeptide segment can have an aspartic acid residue at the position corresponding to amino acid 307 of SEQ ID NO:4. Examples of such polypeptides have the amino acid sequences shown in SEQ ID NOS:20, 22, 34 and 36.

Such polypeptides can catalyze the condensation of a C18 fatty acyl substrate and malonyl CoA, leading to the synthesis of a C20 fatty acyl CoA. The fatty acid substrate can be oleic acid (C18:1), in which case the product formed is eicosenoic acid (C20:1). In some instances, the fatty acid substrate is stearic acid (C18:0) and the product formed therefrom is arachidic acid (C20:0). Such polypeptides often can further catalyze the condensation of malonyl CoA and a C20 fatty acyl substrate, leading to the synthesis of a C22 fatty acyl CoA. The substrate often is eicosenoic acid (C20:1) and the product is erucic acid (C22:1). The ratio of the C22 fatty acid product to the C20 fatty acid product (C22:1/C20:1) resulting from the activity of such polypeptides can be about 0.20 or greater, about 0.30 or greater, about 0.40 or greater, or about 0.50 or greater as measured in a yeast microsome assay.

The invention also features a polypeptide comprising in the amino-terminal to carboxy-terminal direction: a first polypeptide segment that has membrane anchoring properties, joined to a second polypeptide segment that has residues 75–114 of SEQ ID NO:2, which is in turn joined to a third polypeptide segment that has at least 90% sequence identity to residues 115–506 of SEQ ID NO:4. An example of such a polypeptide has the amino acid sequence of SEQ ID NO:8. Also featured is a polypeptide comprising in the amino-terminal to carboxy-terminal direction: a first polypeptide segment having at least 80% sequence identity to residues 1–74 of SEQ ID NO:2, joined to a second polypeptide segment having residues 76–114 of SEQ ID NO:4, joined to a third polypeptide segment having at least 40% sequence identity to residues 115–506 of SEQ ID NO:4. An example of such a polypeptide has the amino acid sequence of SEQ ID NO:10. In some embodiments of these polypeptides, the third segment has an aspartic acid at the position corresponding to amino acid 307 of said SEQ ID NO:4. Examples of such polypeptides have the amino acid sequences of SEQ ID NO:16 and SEQ ID NO:18.

A plant is also disclosed, comprising at least one exogenous nucleic acid encoding one or more of the novel polypeptides disclosed herein, as well as seeds having such nucleic acids.

Nucleic acid constructs of the invention comprise at least one regulatory element operably linked to the nucleic acid coding sequence for a novel polypeptide. Host cells containing such nucleic acid constructs are disclosed. Such host cells include bacterial cells, fungal cells, insect cells, plant cells and animal cells.

A method of altering very long chain fatty acids in an organism is disclosed. The method comprises introducing an exogenous nucleic acid into the organism. The nucleic acid encodes one or more of the polypeptides described herein. The nucleic acid is expressed in the organism to produce the polypeptide(s), and the very long chain fatty acid content of the organism is increased compared to the very long chain fatty acid content of a corresponding organism that lacks the exogenous nucleic acid or does not express the exogenous nucleic acid. Suitable organisms include fungi (e.g., yeast), plants, animals, insects and bacteria. Such organisms can produce a higher level of erucic acid than a corresponding organism that lacks or does not express the exogenous nucleic acid.

Unless otherwise defined, all technical and scientific terms used herein have the same meaning as commonly understood by one of ordinary skill in the art to which this invention belongs. For example, the one letter and three letter abbreviations for amino acids and the one-letter abbreviations for nucleotides are commonly understood. Although methods and materials similar or equivalent to those described herein can be used in the practice or testing of the present invention, suitable methods and materials are described below. In addition, the materials, methods and examples are illustrative only and not intended to be limiting. All publications, patent applications, patents, and other references mentioned herein are incorporated by reference in their entirety. In case of conflict, the present specification, including definitions, will control.

The details of one or more embodiments of the invention are set forth in the accompanying drawings and the description below. Other features, objects, and advantages of the invention will be apparent from the drawings and detailed description, and from the claims.

BRIEF DESCRIPTION OF SEQUENCES

SEQ ID NO:1 is the nucleotide sequence of the *Arabidopsis thaliana* FAE1 gene (GenBank Accession No. U29142).

SEQ ID NO:2 is the amino acid sequence of the polypeptide encoded by SEQ ID NO:1 (GenBank Accession No. AAA70154).

SEQ ID NO:3 is the nucleotide sequence of a *Brassica napus* fatty acid elongase KCS (GenBank Accession No. AF009563).

SEQ ID NO:4 is the amino acid sequence of the *B. napus* polypeptide encoded by SEQ ID NO:3 (GenBank Accession No. AAB72178).

SEQ ID NO:5 is the nucleotide sequence of a *B. napus* fatty acid elongase KCS (GenBank Accession No. U50771).

SEQ ID NO:6 is the amino acid sequence of the *B. napus* polypeptide encoded by SEQ ID NO:5 (GenBank Accession No. AAA96054).

SEQ ID NO:7 is a nucleotide sequence encoding a polypeptide designated At114.

SEQ ID NO:8 is the amino acid sequence of the polypeptide encoded by SEQ ID NO:7.

SEQ ID NO:9 is a nucleotide sequence encoding a polypeptide designated At74.

SEQ ID NO:10 is the amino acid sequence of the polypeptide encoded by SEQ ID NO:9.

SEQ ID NO:11 is a nucleotide sequence encoding a polypeptide designated At114 L91C K92R.

SEQ ID NO:12 is the amino acid sequence of the polypeptide encoded by SEQ ID NO:11.

SEQ ID NO:13 is a nucleotide sequence encoding a polypeptide designated At114 K92R.

SEQ ID NO:14 is the amino acid sequence of the polypeptide encoded by SEQ ID NO:13.

SEQ ID NO:15 is a nucleotide sequence encoding a polypeptide designated At114 G307D.

SEQ ID NO:16 is the amino acid sequence of the polypeptide encoded by SEQ ID NO:15.

SEQ ID NO:17 is a nucleotide sequence encoding a polypeptide designated At74 G306D.

SEQ ID NO:18 is the amino acid sequence of the polypeptide encoded by SEQ ID NO:17.

SEQ ID NO:19 is a nucleotide sequence encoding a polypeptide designated At114 L91C K92R G307D.

SEQ ID NO:20 is the amino acid sequence of the polypeptide encoded by SEQ ID NO:19.

SEQ ID NO:21 is a nucleotide sequence encoding a polypeptide designated At114 K92R G307D.

SEQ ID NO:22 is the amino acid sequence of the polypeptide encoded by SEQ ID NO:21.

SEQ ID NO:23 is a nucleotide sequence encoding a polypeptide designated At254.

SEQ ID NO:24 is the amino acid sequence of the polypeptide encoded by SEQ ID NO:23.

SEQ ID NO:25 is a nucleotide sequence encoding a polypeptide designated At173.

SEQ ID NO:26 is the amino acid sequence of the polypeptide encoded by SEQ ID NO:25.

SEQ ID NO:27 is a nucleotide sequence encoding a polypeptide designated Bn176.

SEQ ID NO:28 is the amino acid sequence of the polypeptide encoded by SEQ ID NO:27.

SEQ ID NO:29 is a nucleotide sequence encoding a polypeptide designated At399.

SEQ ID NO:30 is the amino acid sequence of the polypeptide encoded by SEQ ID NO:29.

SEQ ID NO:31 is a nucleotide sequence encoding a polypeptide designated Bn399.

SEQ ID NO:32 is the amino acid sequence of the polypeptide encoded by SEQ ID NO:31.

SEQ ID NO:33 is a nucleotide sequence encoding a polypeptide designated Bn G307D.

SEQ ID NO:34 is the amino acid sequence of the polypeptide encoded by SEQ ID NO:33.

SEQ ID NO:35 is a nucleotide sequence encoding a polypeptide designated At K92R.

SEQ ID NO:36 is the amino acid sequence of the polypeptide encoded by SEQ ID NO:35.

SEQ ID NO:37 is a nucleotide sequence encoding a polypeptide designated At254 G307D.

SEQ ID NO:38 is the amino acid sequence of the polypeptide encoded by SEQ ID NO:37.

SEQ ID NO:39 is a nucleotide sequence encoding a polypeptide designated At173 G307D.

SEQ ID NO:40 is the amino acid sequence of the polypeptide encoded by SEQ ID NO:39.

SEQ ID NO:41 is a nucleotide sequence encoding a polypeptide designated Bn399 G307D.

SEQ ID NO:42 is the amino acid sequence of the polypeptide encoded by SEQ ID NO:41.

SEQ ID NO:43 is the 3' chimera-specific primer used in the generation of At173.

SEQ ID NO:44 is the 5' chimera-specific primer used in the generation of At173.

SEQ ID NO:45 is the 3' chimera-specific primer used in the generation of At114.

SEQ ID NO:46 is the 5' chimera-specific primer used in the generation of At114.

SEQ ID NO:47 is the 3' chimera-specific primer used in the generation of At74.

SEQ ID NO:48 is the 5' chimera-specific primer used in the generation of At74.

SEQ ID NO:49 is the 3' chimera-specific primer used in the generation of At114 L91C K92R.

SEQ ID NO:50 is the 5' chimera-specific primer used in the generation of At114 L91C K92R.

SEQ ID NO:51 is the 3' chimera-specific primer used in the generation of At114 K92R.

SEQ ID NO:52 is the 5' chimera-specific primer used in the generation of At114 K92R.

SEQ ID NO:53 is the 5' universal primer used in the generation of At-Bn chimeras.

SEQ ID NO:54 is the 3' universal primer used in the generation of At-Bn chimeras.

SEQ ID NO:55 is the 5' universal primer used in the generation of Bn-At chimeras.

SEQ ID NO:56 is the 3' universal primer used in the generation of Bn-At chimeras.

DESCRIPTION OF DRAWINGS

FIG. 1 shows amino acid sequences of *Brassica napus* (Bn) elongase KCS polypeptides, *Arabidopsis thaliana* FAE1 (At) and novel chimeric polypeptides and novel chimeric polypeptides containing site-directed modifications. Sequences corresponding to those derived from At FAE1 are underlined. Site-directed modifications are indicated in bold. One of the Bn elongase KCS sequences shown corresponds to GenBank Accession No. AAB72178; the other *B. napus* sequence shown corresponds to a second *B. napus* elongase KCS having GenBank Accession No. AAA96054.

FIG. 2 shows nucleotide sequences of Bn elongase KCS, At FAE1 and novel chimeric nucleic acids and novel chimeric nucleic acids containing site-directed modifications. Sequences corresponding to those derived from At FAE1 are underlined. Site-directed modifications are indicated in bold. The two Bn elongase KCS nucleic acid sequences shown encode the two Bn polypeptides shown in FIG. 1. The GenBank Accession Numbers are AF009563 and U50771, respectively.

Like reference symbols in the various drawings indicate like elements.

DETAILED DESCRIPTION

Fatty Acid Elongase KCS Polypeptides

In one aspect, the invention provides a polypeptide containing the following segments in the amino-terminal to carboxy-terminal direction: a first polypeptide segment having membrane anchoring properties, joined to a second polypeptide segment having the amino acid sequence of residues of 75–114 of SEQ ID NO:12 or SEQ ID NO:14, joined to a third polypeptide segment having at least 40% sequence identity to the C-terminal approximately 392 amino acids of the *Brassica napus* elongase KCS polypeptide shown in SEQ ID NO:4. For example, polypeptides designated At114 L91C K92R (SEQ ID NO:12) and At114 K92R (SEQ ID NO:14) are provided by the present invention. The primary sequence of the novel polypeptides of the invention are identified by the source and number of amino-terminal residues (e.g., At74 polypeptides have 74 amino-terminal residues from *Arabidopsis thaliana*), and site-directed modifications are indicated by the original amino acid residue, the position of the modification and the new residue (e.g., polypeptides containing a K92R site-directed modification had a K at amino acid position 92 which was modified by site-directed mutagenesis of the nucleic acid to encode an R residue).

The above-described polypeptides include a first polypeptide segment that can serve as a membrane anchor. Such a segment has properties that result in the elongase KCS polypeptide being anchored to a membrane, such as a lipid bilayer, detergent bilayer, micelle, or cell membrane. Possession of membrane anchoring properties may be the result of the primary structure, secondary structure and/or tertiary structure of the segment. For example, the segment may contain one or more transmembrane domain(s). Alternatively, a post-translational modification of an amino acid residue within the segment can result in the polypeptide being anchored to a membrane. Suitable modifications include, but are not limited to, covalent attachment of a lipid (e.g., a glycosyl phosphatidylinositol anchor) or a carbohydrate (e.g., an oligosaccharide). See, Alberts et al., *The Cell*, 2$^{nd}$ Edition, Garland Publishing, New York, pp 284–298 and Lodish et al., *Molecular Cell Biology*, 3$^{rd}$ Edition, Scientific American Books, p. 604 and pp. 688–692. The ability of a segment to serve as a membrane anchor can be demonstrated by observing whether a polypeptide having such a segment co-purifies with a membrane fraction. Alternatively, a segment can be a membrane-anchor if, after fusing it to the second and third segments, it is shown that the polypeptide possesses elongase KCS activity in an in vitro yeast microsome assay, since elongase KCS polypeptides are active when anchored to a membrane. As another alternative, computer algorithms, such as Predict Protein or META Predict Protein, can be used to predict the presence of a transmembrane domain within a segment, and hence, the ability of that polypeptide segment to serve as a membrane anchor.

Examples of polypeptide segments that can be membrane anchors include, but are not limited to, amino acids 1–74 of *A. thaliana* FAE1 (SEQ ID NO:2), and amino acid sequences having 40% or greater sequence identity to residues 1–74 of SEQ ID NO:2. For example, amino acids 1–75 of an elongase KCS from *B. napus* (GenBank Accession No. AAB72178), amino acids 1–75 of *B. juncea* protein (EMBL Accession No. CAA71898), amino acids 1–75 of an elongase KCS from *B. napus* (GenBank Accession No. AAA96054), amino acids 29–105 of a putative β-ketoacyl-CoA synthase from *A. thaliana* (GenBank Accession No. AAD22309) and amino acids 8–76 of a fatty acid elongase-like protein from *A. thaliana* (EMBL Accession No. CAB36702) have at least 40% sequence identity to SEQ ID NO:2. In some embodiments, the first polypeptide segment has at least 80% sequence identity, 90% sequence identity, at least 95% sequence identity, or at least 99% sequence identity to amino acids 1–74 of SEQ ID NO:2.

A percent identity for any subject nucleic acid or amino acid sequence (e.g., any of the fatty acid elongase chimeras described herein) relative to another "target" nucleic acid or amino acid sequence can be determined as follows. First, a target nucleic acid or amino acid sequence of the invention can be compared and aligned to a subject nucleic acid or amino acid sequence, preferably using the BLAST 2 Sequences (Bl2seq) program from the stand-alone version of BLASTZ containing BLASTN and BLASTP (e.g., version 2.0.14). The stand-alone version of BLASTZ can be obtained at Fish & Richardson's website or the National Center for Biotechnology Information (NCBI) website. Instructions explaining how to use BLASTZ, and specifically the Bl2seq program, can be found in the 'readme' file accompanying BLASTZ. The programs also are described in detail by Karlin et al. (*Proc. Natl. Acad. Sci. USA*, 87:2264 (1990) and 90:5873 (1993)) and Altschul et al. (*Nucl. Acids Res.*, 25:3389 (1997)).

Bl2seq performs a comparison between the subject sequence and a target sequence using either the BLASTN (used to compare nucleic acid sequences) or BLASTP (used to compare amino acid sequences) algorithm. Typically, the default parameters of a BLOSUM62 scoring matrix, gap existence cost of 11, a per residue cost of 1 and a lambda ratio of 0.85 are used when performing amino acid sequence alignments. The output file contains aligned regions of homology between the target sequence and the subject sequence. Once aligned, a length is determined by counting the number of consecutive nucleotides or amino acid residues (i.e., excluding gaps) from the target sequence that align with sequence from the subject sequence starting with any matched position and ending with any other matched position. A matched position is any position where an identical nucleotide or amino acid residue is present in both the target and subject sequence. Gaps of one or more residues can be inserted into a target or subject sequence to maximize sequence alignments between structurally conserved domains (e.g., α-helices, β-sheets, and loops).

The percent identity over a particular length is determined by counting the number of matched positions over that particular length, dividing that number by the length and multiplying the resulting value by 100. For example, if (i) a 1000 nucleotide target sequence is compared to a subject nucleic acid sequence (e.g., SEQ ID NO:21), (ii) the Bl2seq program presents 200 nucleotides from the target sequence aligned with a region of the subject sequence where the first and last nucleotides of that 200 nucleotide region are matches, and (iii) the number of matches over those 200 aligned nucleotides is 180, then the 1000 nucleotide target sequence contains a length of 200 and a percent identity over that length of 90 (i.e., 180÷200×100=90).

It will be appreciated that a nucleic acid or amino acid target sequence that aligns with a subject sequence can result in many different lengths with each length having its own percent identity. It is noted that the percent identity value can be rounded to the nearest tenth. For example, 78.11, 78.12, 78.13, and 78.14 is rounded down to 78.1, while 78.15, 78.16, 78.17, 78.18, and 78.19 is rounded up to 78.2. It is also noted that the length value will always be an integer.

Polypeptides of the invention have a second segment which contains amino acid residues, in particular, the amino acid residue corresponding to position 92 in SEQ ID NO:2, that affect elongase KCS substrate specificity. If the residue at position 92 is an arginine residue, the ratio of the C22:1 product to the C20:1 product is higher than the corresponding ratio observed when the residue is a lysine. Accordingly, the second segment (residues 75–114) of At114 L91C K92R and At114 K92R both possess an R at position 92. Another example of such a polypeptide has the amino acid sequence of SEQ ID NO:2, except that the lysine at amino acid residue 92 is replaced with an arginine. This polypeptide, designated At K92R, has the amino acid sequence shown in SEQ ID NO:36.

Some polypeptides of the invention have a third segment that has at least 40% sequence identity to residues 115–506 of SEQ ID NO:4, which are the carboxy-terminal 392 amino acids of the *B. napus* polypeptide. In some embodiments, the third polypeptide segment has at least 50% sequence identity, at least 60% sequence identity, at least 70%, 80%, 90%, 95% or 99% sequence identity to the carboxy-terminal 392 amino acids of SEQ ID NO:4.

In some embodiments, the third segment has an aspartic acid residue at the position corresponding to amino acid residue 307 of SEQ ID NO:4. An aspartic acid residue at this position is useful for increasing the catalytic activity of an elongase KCS, compared to the catalytic activity of an otherwise similar polypeptide that has a glycine at this position. For example, polypeptides designated At114 G307D, At74 G306D, At114 L91C K92R G307D, At114 K92R G307D, At254 G307D, At173 G307D, Bn G307D and Bn399 G307D have an aspartic acid residue at the position corresponding to residue 307 of SEQ ID NO:4. These polypeptides have SEQ ID NOS: 16, 18, 20, 22, 38, 40, 34 and 42, respectively.

In some embodiments, the third segment contains one or more of the following groups of residues: GNTSSSS at positions corresponding to residues 423–429 of SEQ ID NO:4, HAGG(R/K)A at positions corresponding to residues 391–396 of SEQ ID NO:4, or MGCSAG at positions corresponding to residues 221–226 of SEQ ID NO:4. These groups of residues are among those that are conserved among elongase KCS polypeptides and are thus found in preferred embodiments.

Segments of a polypeptide are joined to one another by covalent bonds, typically peptide bonds. The segments can be joined directly, without any intervening residues between two segments. Alternatively, one segment can be joined indirectly to an adjacent segment by amino acid residues that are situated between the two adjacent segments and are themselves covalently joined to the adjacent segments. In some embodiments, there are one, two or three intervening amino acid residues. In other embodiments, there are four, five, six, seven, eight, nine or ten intervening residues.

A polypeptide of the invention optionally can possess additional amino acid residues at the amino-terminus or the carboxy-terminus. For example, six His-tag or FLAG™ residues may be linked to a polypeptide at the amino-terminus. See, e.g., U.S. Pat. Nos. 4,851,341 and 5,001,912. A reporter polypeptide, such as green fluorescent protein, may be fused to the carboxy-terminus. See, for example, U.S. Pat. No. 5,491,084. With respect to polypeptides, "isolated" refers to a polypeptide that constitutes the major component in a mixture of components, e.g., 30% or more, 40% or more, 50% or more, 60% or more, 70% or more, 80% or more, 90% or more, or 95% or more by weight. Isolated polypeptides typically are obtained by purification from an organism that makes the polypeptide, although chemical synthesis is also feasible. As used herein, "enriched" refers to a polypeptide that constitutes 20–30% (by weight) of a mixture of components. Methods of polypeptide purification include, for example, chromatography or immunoaffinity techniques.

A polypeptide of the invention may be detected by sodium dodecyl sulphate (SDS)-polyacrylamide gel electrophoresis followed by Coomassie Blue-staining or Western blot analysis using monoclonal or polyclonal antibodies that have binding affinity for the polypeptide to be detected.

The presence of a polypeptide of the invention may often be detected by measuring elongase KCS activity. An elongase KCS can catalyze the condensation of a C18 fatty acyl substrate and malonyl CoA, leading to the formation of a C20 fatty acyl product. C18 fatty acids include C18:0 (e.g., stearic acid), C18:1 (e.g., oleic acid), C18:2 (e.g., linoleic acid), and C18:3 (e.g., α-linolenic acid). In some embodiments, an elongase KCS can catalyze the conversion of a C20 fatty acyl substrate to a C22 fatty acyl product. An example of a C20:1 fatty acyl substrate is an eicosenoyl substrate. Such a substrate can be converted to a C22:1 fatty acyl product, e.g., an erucyl product.

Some polypeptides may result in an elongase KCS that does not form reaction product(s) at a desired rate. Such elongases and their genes are useful as controls in analyses of product formation by enzymatically active elongase KCS polypeptides. Such inactive elongase KCS polypeptides and their genes can also be useful in studying the regulation (e.g., transcription, translation, and post-translational events) of genes encoding enzymatically active elongase KCS polypeptides. Such elongase KCS polypeptides can be attached to Sepharose beads and used for affinity purification of fatty acyl substrates from crude preparations. In addition, such elongase KCS polypeptides and their genes can also be useful to develop reagents for various purposes, e.g., immunological reagents to monitor expression of a elongase KCS polypeptides or nucleic acid probes or primers to monitor inheritance of a elongase KCS gene in a plant breeding program.

Products formed in plants by elongase reactions involving an elongase KCS can be subsequently used to form fatty acyl triacylglycerides (TAGs) during seed development. Alternatively, such products can be further elongated to form cuticular lipids, such as waxes.

In yet another aspect, the invention provides a polypeptide containing the following segments in the amino-terminal to carboxy-terminal direction: a first polypeptide segment having at least 80% sequence identity to the first 74 amino acids of the *A. thaliana* FAE1 gene product (SEQ ID NO:2), joined to a second polypeptide segment having amino acids 76–114 of SEQ ID NO:4, joined to a third polypeptide segment having at least 40% sequence identity to the C-terminal 392 amino acids of a *B. napus* elongase KCS (SEQ ID NO:4). An example of such a polypeptide is At74 (SEQ ID NO:10). This polypeptide possesses an R residue at position 92. Another example is At74 G306D (SEQ ID NO:18), which has a D residue at position 306.

Another novel polypeptide disclosed herein contains the following segments in the amino-terminal to carboxy-terminal direction: a first polypeptide segment having membrane anchoring properties, joined to a second polypeptide segment corresponding to amino acids 75–114 of SEQ ID NO:2, joined to a third polypeptide segment having at least 90% sequence identity to the C-terminal 392 amino acids of SEQ ID NO:4. An example of such a polypeptide is At114 (SEQ ID NO:8).

The invention also features the following polypeptide, comprising in the amino-terminal to carboxy-terminal direction: (a) a first polypeptide segment having at least 90% sequence identity to residues 1–254 of SEQ ID NO:2, joined to (b) a second polypeptide segment having the amino acid sequence of residues 255–506 of SEQ ID NO:4. An example of such a polypeptide is designated At254 and the amino acid sequence is shown in FIG. 1 and SEQ ID NO:24.

Another novel polypeptide comprises (a) a first polypeptide segment having at least 85% sequence identity to residues 1–173 of SEQ ID NO:2, joined to (b) a second polypeptide segment having the amino acid sequence of residues 174–506 of SEQ ID NO:4. An example of such a polypeptide is designated At173 and the amino acid sequence is shown in FIG. 1 and SEQ ID NO:26.

Another novel polypeptide comprises: (a) a first polypeptide segment having at least 90% sequence identity to residues 1–399 of SEQ ID NO:2, joined to (b) a second polypeptide segment having amino acid residues 400–506 of SEQ ID NO:4. An example of such a polypeptide is designated At399 and the amino acid sequence is shown in FIG. 1 and SEQ ID NO:30. Such a polypeptide can exhibit a product ratio and catalytic activity resembling that of wild-type At FAE1.

The invention also features the following polypeptide, comprising in the amino-terminal to carboxy-terminal direction: (a) a first polypeptide segment having amino acid residues 1–176 of SEQ ID NO:4, joined to (b) a second polypeptide segment having at least 95% sequence identity to residues 177–506 of SEQ ID NO:2. An example of such a polypeptide is designated Bn176 and the amino acid sequence is shown in FIG. 1 and SEQ ID NO:28. In yeast microsome assays, the Bn176 polypeptide exhibits detectable elongase KCS catalytic activity and a C21:1/C20:1 product ratio of about 0.51.

The invention also features the following polypeptide, comprising in the amino-terminal to carboxy-terminal direction: (a) a first polypeptide segment having amino acid residues 1–399 of SEQ ID NO:4, joined to (b) a second polypeptide segment having at least 95% sequence identity to residues 400–506 of SEQ ID NO:2. An example of such a polypeptide is designated Bn399 and the amino acid sequence is shown in FIG. 1 and SEQ ID NO:32. In yeast microsome assays, the Bn399 polypeptide exhibits detectable elongase KCS catalytic activity and a C21:1/C20:1 product ratio of about 0.35.

Elongase KCS Nucleic Acids and Constructs

The present invention also includes nucleic acids encoding the above-described polypeptides. As used herein, nucleic acid refers to RNA or DNA, including cDNA, synthetic DNA or genomic DNA. The nucleic acids may be single- or double-stranded, and if single-stranded, may be either the coding or non-coding strand. As used herein with respect to nucleic acids, "isolated" refers to (i) a naturally-occurring nucleic acid encoding part or all of a polypeptide of the invention, but free of sequences, i.e., coding sequences, that normally flank one or both sides of the nucleic acid encoding polypeptide in a genome; (ii) a nucleic acid incorporated into a vector or into the genomic DNA of an organism such that the resulting molecule is not identical to any naturally-occurring vector or genomic DNA; or (iii) a cDNA, a genomic nucleic acid fragment, a fragment produced by polymerase chain reaction (PCR) or a restriction fragment. Specifically excluded from this definition are nucleic acids present in mixtures of nucleic acid molecules or cells.

Examples of such nucleic acids include those encoding polypeptides designated At114, At74, At114 L91C K92R, At114 K92R, At114 G307D, At74 G306D, At114 L91C K92R G307D, At114 K92R G307D, At254, At173, Bn176, At399, Bn399 and At K92R. These nucleic acids have SEQ ID NOS: 7, 9, 11, 13, 15, 17, 19, 21, 23, 25, 27, 29, 31 and 35, respectively. It should be appreciated that nucleic acids having a nucleotide sequence other than the specific nucleotide sequences disclosed can still encode a polypeptide having the exemplified amino acid sequence. The degeneracy of the genetic code is well known to the art; i.e., for many amino acids, there is more than one nucleotide triplet that serves as the codon for the amino acid.

Further provided are nucleic acid constructs comprising the above-described nucleic acid coding sequences. Such constructs may be incorporated into a cloning vector. Cloning vectors suitable for use in the present invention are commercially available and used routinely by those of ordinary skill. Nucleic acid constructs of the invention may additionally comprise one or more regulatory elements operably linked to a nucleic acid coding sequence. Such regulatory elements may include promoter sequences, enhancer sequences, response elements or inducible elements that modulate expression of a nucleic acid sequence. As used herein, "operably linked" refers to positioning of a regulatory element in a construct relative to a nucleic acid coding sequence in such a way as to permit or facilitate expression of the encoded polypeptide. The choice of element(s) that may be included depends upon several factors, including, but not limited to, replication efficiency, selectability, inducibility, targeting, the level of expression desired, ease of recovery and the ability of the host to perform post-translational modifications.

The term "host" or "host cell" includes not only prokaryotes, such as *E. coli*, but also eukaryotes, such as fungal, insect, plant and animal cells. Animal cells include, for example, COS cells and HeLa cells. Fungal cells include yeast cells, such as *Saccharomyces cereviseae* cells. A host cell can be transformed or transfected with a DNA molecule (e.g., a vector) using techniques known to those of ordinary skill in this art, such as calcium phosphate or lithium acetate precipitation, electroporation, lipofection and particle bombardment. Host cells containing a vector of the present invention may be used for such purposes as propagating the vector, producing a nucleic acid (e.g., DNA, RNA, antisense RNA) or expressing a polypeptide or fragments thereof.

A nucleic acid encoding a novel polypeptide of the invention may be obtained using standard molecular biology techniques, for example, molecular cloning, DNA synthesis, and the polymerase chain reaction (PCR). PCR refers to a procedure or technique in which target nucleic acids are amplified. PCR can be used to amplify specific sequences from DNA as well as RNA, including sequences from total genomic DNA or total cellular RNA. Various PCR methods are described, for example, in *PCR Primer: A Laboratory Manual*, Dieffenbach, C. & Dveksler, G., Eds., Cold Spring Harbor Laboratory Press, 1995. Generally, sequence information from the ends of the region of interest or beyond is employed to design oligonucleotide primers that are identical or similar in sequence to opposite strands of the template to be amplified. Various PCR strategies are available by which site-specific nucleotide sequence modifications can be introduced into a template nucleic acid.

Nucleic acids of the present invention may be detected by methods such as ethidium bromide staining of agarose gels, Southern or Northern blot hybridization, PCR or in situ hybridizations. Hybridization typically involves Southern or Northern blotting (see, for example, sections 9.37–9.52 of Sambrook et al., 1989, *"Molecular Cloning, A Laboratory Manual"*, $2^{nd}$ Edition, Cold Spring Harbor Press, Plainview; N.Y.). Probes should hybridize under high stringency conditions to a nucleic acid or the complement thereof. High stringency conditions can include the use of low ionic strength and high temperature washes, for example 0.015 M NaCl/0.0015 M sodium citrate (0.1×SSC), 0.1% sodium dodecyl sulfate (SDS) at 65° C. In addition, denaturing agents, such as formamide, can be employed during high stringency hybridization, e.g., 50% formamide with 0.1% bovine serum albumin/0.1% Ficoll/0.1% polyvinylpyrrolidone/50 mM sodium phosphate buffer at pH 6.5 with 750 mM NaCl, 75 mM sodium citrate at 42° C.

Transgenic Plants

The invention provides a plant containing an exogenous nucleic acid that encodes a polypeptide of the invention, e.g., nucleic acids encoding a polypeptide having an amino acid sequence as shown in SEQ ID NOS:8, 10, 12, 14, 16, 18, 20, 22, 24, 26, 28, 30, 32, 34, or 36.

Accordingly, a method according to the invention comprises introducing a nucleic acid construct into a plant cell and producing a plant (and progeny of such a plant) from the transformed cell. Techniques for introducing exogenous nucleic acids into monocotyledonous and dicotyledonous plants are known in the art, and include, without limitation, Agrobacterium-mediated transformation, viral vector-mediated transformation, electroporation and particle gun transformation, e.g., U.S. Pat. Nos. 5,204,253 and 6,013,863. If cell or tissue cultures are used as the recipient tissue for transformation, plants can be regenerated from transformed cultures by techniques known to those skilled in the art. Transgenic plants may be entered into a breeding program, e.g., to introduce a nucleic acid encoding a polypeptide into other lines, to transfer the nucleic acid to other species or for further selection of other desirable traits. Alternatively, transgenic plants may be propagated vegetatively for those species amenable to such techniques. Progeny includes descendants of a particular plant or plant line. Progeny of an instant plant include seeds formed on $F_1$, $F_2$, $F_3$, and subsequent generation plants, or seeds formed on $BC_1$, $BC_2$, $BC_3$, and subsequent generation plants. Seeds produced by a transgenic plant can be grown and then selfed (or outcrossed and selfed) to obtain seeds homozygous for the nucleic acid encoding a novel polypeptide.

In another aspect, the invention provides a method of altering very long chain fatty acids in an organism. The method involves introducing an exogenous nucleic acid into the organism. The organism may be, for example, a yeast or a plant. A nucleic acid construct of the invention can alter the levels of very long chain fatty acids in plant tissues expressing the novel polypeptide, compared to VLCFA levels in corresponding tissues from a plant that does not contain or does not express the polypeptide. A comparison can be made, for example, between a transgenic plant of a plant line and a plant of the same line that lacks the nucleic acid construct or does not express the nucleic acid construct in that tissue. Plants having an altered VLCFA composition may be identified by techniques known to the skilled artisan, e.g., thin layer chromatographic or gas-liquid chromatographic (GLC) analysis of the appropriate plant tissue. Novel polypeptides can catalyze the conversion of oleic acid (18:1) to eicosenoic acid (20:1), and the conversion of eicosenoic acid to erucic acid (22:1). In some embodiments, the ratio of erucic acid to eicosenoic acid (22:1/20:1) is greater than or equal to 0.20, as measured in the yeast microsome assay described below.

A suitable group of plants with which to practice the invention include dicots, such as alfalfa, soybean, rapeseed (high erucic and canola), safflower, or sunflower, and monocots, such as corn, wheat, rye, barley, rice, or sorghum. Suitable rapeseed species include *B. napus, B. rapa, B. juncea*, and *B. hirta*. Additional plant species suitable for use in the present invention include *Sinapsis alba, Crambe abyssinica, Limnanthes douglasii* and *L. alba*.

Suitable tissues in which to express polynucleotides and/ or polypeptides of the invention include, without limitation, seeds, stems and leaves. Seeds expressing a novel coding sequence can be used to extract an oil having elevated levels of eicosenoic acid and/or erucic acid. Leaf tissues in which a novel coding sequence can be expressed include cells and tissues of the epidermis, e.g., cells that are involved in forming trichomes. Also of interest are epidermal cells involved in forming the cuticular layer. The cuticular layer comprises various very long chain fatty acids and VLCFA derivatives such as alkanes, esters, alcohols and aldehydes. Increasing the amount of VLCFAs in epidermal cells and tissues may enhance defense mechanisms and drought tolerance of plants.

The invention will be further described in the following examples, which do not limit the scope of the invention described in the claims.

EXAMPLES

Example 1
Construction and Cloning of Nucleic Acids

Nucleic acids encoding chimeric polypeptides were generated by an overlap polymerase chain reaction (PCR) strategy. Horton et al. (1989), *Gene,* 77:61–68 and see FIG. 1 of Ho et al. (1989), *Gene,* 77:51–59. Briefly, a first round of PCR products were generated in separate reactions using *Arabidopsis thaliana* FAE1 and *Brassica napus* elongase KCS nucleic acid as template. Nucleic acid sequences of the *A. thaliana* FAE1 and *B. napus* elongase KCS templates are shown in SEQ ID NO:1 and 3, respectively. The portion of each template that was amplified corresponded to the segment to be combined in a desired chimera. The amino-terminal fragment of a given chimera was amplified using a 5' universal primer (sense) and a 3' chimera-specific primer (anti-sense). The carboxy-terminal fragment of a given chimera was amplified with a 5' chimera-specific primer (sense) and a 3' universal primer (anti-sense). Universal primer sequences are shown in Table 1 and SED ID NOS: 53–56. Chimera-specific primer sequences are shown in Table 2 and SEQ ID NOS:43–52. The 5' and 3' universal primers anneal to the 5' and 3' ends of the template nucleic acid, respectively, and contain BamHI and EcoRI restriction sites, respectively, for ease in subcloning into an expression vector. The 5' chimera-specific primers are antisense to the amino-terminal template and the 3' chimera-specific primers are antisense to the carboxy-terminal template. The 5' and 3' chimera-specific primers each contain an internal complementary sequence where a switch occurs from the At to Bn sequence, or alternatively, from Bn to At.

The products produced by the first round of PCR were purified, and a second round of PCR was conducted using a mixture of the products from the first round of PCR as template nucleic acid. The appropriate 5' and 3' universal primers were used to generate the chimeric nucleic acid product in the second round PCR. The amplified product was then digested with BamHI and EcoRI, ligated into pYES2 (Invitrogen, Carlsbad, Calif.) and transformed into *E. coli*. pYES2 is a yeast centromere-containing, episomal plasmid that is stably propagated in both *E. coli* and in yeast. Each nucleic acid was inserted downstream of the GAL1 promoter in pYES2. The GAL1 promoter is induced in yeast when galactose is present in the medium and repressed when glucose is present in the growth medium.

Nucleic acids encoding polypeptides with site-directed alterations in the coding sequence were also prepared by overlap PCR, using 5' and 3' chimera-specific primers in which the internal complementary region contained the desired sequence modification.

TABLE 1

| Chimera type | | | |
|---|---|---|---|
| 5' portion | 3' portion | 5' universal primer | 3' universal primer |
| At | Bn | 5'-ggggatccatgacgtccgttaacgttaagctcc-3' (SEQ ID NO:53) | 5'-ccgaattcttaggaccgaccgttttggacac-3' (SEQ ID NO:54) |
| Bn | At | 5'-ggggatccatgacgtccattaacgtaaagctcc-3 (SEQ ID NO:55) | 5'-ccgaattcttaggaccgaccgttttggacatgagtctt-3' (SEQ ID NO:56) |

TABLE 2

| Chimera | 3' chimera-specific primers | 5' chimera-specific primers |
|---|---|---|
| At173 | 5'-gcgctcgaaaatctattcaagaaca-3' (SEQ ID NO:43) | 5'-gttcttgaatagattttcgagcgcaccgatgat-3' (SEQ ID NO:44) |
| At114 | 5'-cggaacggcacgtgtgatgattcgtcct-3' (SEQ ID NO:45) | 5'-aggacggatcatcacagcgacgttccg-3' (SEQ ID NO:46) |
| At74 | 5'-cccaaaccggtttacctcgttga-3' (SEQ ID NO:47) | 5'-tcaacgaggtaaaccggattggg-3' (SEQ ID NO:48) |

TABLE 2-continued

| Chimera | 3'chimera-specific primers | 5'chimera-specific primers |
| --- | --- | --- |
| At114 L91C K92R | 5'-ccgcattgcagagttagtgtctctaaa-3' (SEQ ID NO:49) | 5'-tttagagacactaactctgcaatgcgg-3' (SEQ ID NO:50) |
| At114 K92R | 5'-ccaccgcatctcagagttagtgtctct-3' (SEQ ID NO:51) | 5'-agagacactaactctgagatgcggtgg-3' (SEQ ID NO:52) |

Due to a degeneracy in the primer used to generate the nucleic acids encoding carboxy-terminal sequences from *B. napus*, the amino acid residue at the fifth to last position from the carboxy-terminus in the polypeptides designated At114, At114 L91C K92R, At114 K92R and At254 is a P and the polypeptide designated At74 is a Q at that position as indicated in FIG. 1. The polypeptides designated At173 and At399 may have a P or a Q at this position and are shown as Q in FIG. 1. A Q is found in the wild-type Bn polypeptide sequence at this position. In addition, due to PCR infidelity in the preparation of the nucleic acid encoding At114, the amino acid residue at position 439 of SEQ ID NO:8 may be an A or a T, with an A being found in the wild-type Bn sequence. In addition, PCR infidelity in the preparation of the nucleic acid encoding At114 L91C K92R resulted in the residue at position 119 being an N. Position 119 in the wild-type Bn amino acid sequence is a D. Based on the data presented below, this residue can be either a D or an N without any apparent effect on activity.

Mutagenesis was confirmed by automated DNA sequencing, and each construct was used to transform *S. cerevisiae* strain InvScl (Invitrogen) using a lithium-acetate procedure (Gietz, R. and Woods, R., in *Molecular Genetics of Yeast: Practical Approaches*, Oxford Press, pp. 121–134 (1994)).

Example 2
Fatty Acid Elongase KCS Activity in Yeast Microsomes

Elongase KCS enzymatic activity was analyzed by preparing microsomes from transformed yeast cells and assaying these microsomes in vitro for elongase KCS activity. Transformed yeast cells were grown overnight in YPD media at 30° C. with vigorous shaking. Complete minimal uracil dropout media (cm-ura) supplemented with galactose (2% weight/volume in 40 ml) was inoculated to an $OD_{600}$ of 0.002 to 0.01. Cultures were grown at 30° C. to an $OD_{600}$ of approximately 1.5 to 2.0. Cells were harvested by centrifugation at 5000×g for 10 min and washed with 10 ml ice cold isolation buffer (IB), which contains 80 mM Hepes-KOH (pH 7.2), 5 mM EGTA, 5 mM EDTA, 10 mM KCl, 320 mM sucrose and 2 mM DTT). Cells were then resuspended in enough IB to fill a 1.7 ml tube containing 700 µl of 0.5 µm glass beads and yeast microsomes were isolated from the cells essentially as described in Tillman, T. & Bell, R., *J. Biol. Chem.* 261:9144–9149 (1986). The microsomal membrane pellet was recovered by centrifugation at 252,000×g for 60 min. Microsomal pellets were resuspended in a minimal volume of IB, and the protein concentration adjusted to 2.5 µg µl$^{-1}$ by addition of IB containing 15% glycerol. Microsomes were frozen on dry ice and stored at −80° C. The protein concentration in microsomes was determined by the Bradford method (Bradford, Anal. Biochem., 72:248–54, 1976).

Elongase KCS activity was measured essentially as described in Hlousek-Radojcic, et al., *Plant J.* 8:803–809 (1995). Briefly, the standard elongation reaction mix contained 80 mM Hepes-KOH (pH 7.2), 20 mM $MgCl_2$, 500 µM NADPH, 100 µM malonyl-CoA, 10 µM CoA-SH and 15 µM [$^{14}$C]18:1-CoA (50 µCi µmol$^{-1}$). The reaction was initiated by the addition of yeast microsomes (6 µg protein) and the mixture was incubated at 30° C., in a final reaction volume of 25 µl. Reaction time was 10 min unless indicated otherwise.

Methyl esters of the acyl-CoA elongase products were prepared by incubation with 500 µl 2% $H_2SO_4$/MeOH at 80° C. for 2 h. Extracted methyl esters were separated on reverse phase silica gel TLC plates (Analtech, Newark, Del.), quantified by phosphorimaging, and analyzed by ImageQuant software (Molecular Dynamics, Inc., Sunnyvale, Calif.). The detection limit for each product is about 0.001 nmoles/min/mg microsomal protein, depending on the phosphorimage exposure time.

Example 3
Elongase KCS Substrate Specificity

Table 3 is a summary of elongase activity and product ratios of *B. napus* (Bn) and *A. thaliana* (At) elongase KCS nucleic acid sequences expressed in yeast and assayed as described in Example 2. Microsomes prepared from galactose-induced yeast expressing the indicated nucleic acid were assayed after 10 min for conversion of labeled oleoyl substrate to eicosenoyl product, erucyl product, and lignoceryl product. For convenience, fatty acyl substrates and products are oftentimes referred to as the acid rather than as the acyl or acyl CoA. The ratio of 22:1 product to 20:1 product is also shown. Experiments were performed on 17 individual yeast transformants for each construct.

TABLE 3[1]

| | 18:1 (± sd) | 20:1 (± sd) | 22:1 (± sd) | 20:1 + 22:1 (± sd) | 22:1/20:1 (± sd) |
| --- | --- | --- | --- | --- | --- |
| *B. napus* elongase KCS (SEQ ID NO:4) | 45 ± 4 | 3.3 ± 0.4 | 1.4 ± 0.5 | 4.8 ± 0.2 | 0.43 ± 0.11 |
| *A. thaliana* FAE1 (SEQ ID NO:2) | 29 ± 9 | 6 ± 0.8 | 1.2 ± 0.2 | 7.1 ± 0.9 | 0.20 ± 0.04 |

[1]Amounts of oleic acid (18:1), eicosenoic acid (20:1), erucic acid (22:1), and the sum of 20:1 and 22:1, are expressed as nmol/mg microsomal protein; ± sd = standard deviation.

Table 4 shows the ratio of 22:1/20:1 products produced by Bn, At, and various chimeric polypeptides after incubation of the microsomes with the labeled 18:1 substrate for 5, 10 or 20 min. The results shown in Table 4 represent 4 different microsome preparations from a single yeast transformant with each construct and 2–3 assays of each microsomal preparation. The At FAE1 (SEQ ID NO:2) produces about 5 times more eicosenoic acid than erucic acid. In contrast, the Bn elongase KCS (SEQ ID NO:4) produces about 2–3 times more eicosenoic acid than erucic acid. See also Table 3.

The At254, At173 and At114 polypeptides have a 22:1/20:1 product ratio that is similar to that of wild-type At FAE1, whereas the At74 polypeptide has a product ratio that is similar to that of wild-type Bn (Table 4). These results indicate that amino acids affecting product specificity are present between residues 75 and 114 of the wild-type At elongase KCS. The At74 gene product possesses the amino acid sequence of the Bn elongase KCS of SEQ ID NO:4 at positions 75 to 114, indicating that amino acids of the Bn elongase KCS that differ from the at FAE1 in this region contribute to the difference in C22:1/C20:1 product ratio.

TABLE 4

| | Polypeptide Assayed[1] | | | | | | |
|---|---|---|---|---|---|---|---|
| Time (min) | Bn (SEQ ID NO:4) | At (SEQ ID NO:2) | At254 (SEQ ID NO:24) | At173 (SEQ ID NO:26) | At114 (SEQ ID NO:8) | At74 (SEQ ID NO:10) | At114 L91C K92R (SEQ ID NO:12) |
| 5 | 0.35 ± 0.07 | 0.18 ± 0.04 | 0.14 ± 0.03 | 0.11 ± 0.07 | 0.17 ± 0.04 | 0.42 ± 0.07 | 0.22 ± 0.02 |
| 10 | 0.33 ± 0.10 | 0.13 ± 0.01 | 0.11 ± 0.03 | 0.08 ± 0.01 | 0.15 ± 0.03 | 0.36 ± 0.06 | 0.20 ± 0.02 |
| 20 | 0.35 ± 0.13 | 0.13 ± 0.02 | 0.12 ± 0.03 | 0.11 ± 0.05 | 0.16 ± 0.04 | 0.29 ± 0.05 | 0.20 ± 0.04 |

[1]The data are the C22:1/C20:1 ratio ± standard deviation

Site-directed modifications were made to the At114 or At74 nucleic acid sequence within the region corresponding to residues 75 to 114 in order to determine which amino acids contributed to the altered product ratio. The modified nucleic acids were made according to the overlap PCR strategy described in Example 1 and the constructs were introduced into yeast. Elongase KCS activity was measured as described in Example 2. The results showed that changing the At114 amino acid sequence from alanine to serine and glutamine to lysine at positions 157 and 163, respectively, resulted in undetectable elongase activity. Likewise, changing serine and isoleucine at positions 93 and 95 within At74 to valine in both positions also resulted in undetectable elongase activity.

However, when the leucine and lysine residues at positions 91 and 92 within the At114 polypeptide were changed to cysteine and arginine, respectively, the C22:1/C20:1 product ratio of the resulting polypeptide, At114 L91C K92R, was shifted to more closely resemble that of the wild-type Bn polypeptide (Table 4).

Site-directed modifications were made to the At114 nucleic acid sequence to generate coding sequences for two new polypeptides, one bearing the leucine to cysteine modification and one bearing the lysine to arginine modification. These polypeptides were designated At114 L91C and At114 K92R. The nucleotide sequence of the nucleic acid encoding At114 K92R is shown in SEQ ID NO:13 and the amino acid sequence of the polypeptide is shown in SEQ ID NO:14. The two nucleic acids were introduced into yeast and the activity of each polypeptide was analyzed in yeast microsome assays. The results showed that the L to C-modified polypeptide, At114 L91C, had low but detectable catalytic activity. The K to R-modified polypeptide, At114 K92R, had a higher 22:1/20:1 ratio that approached that of wild-type Bn (Table 5). Results presented are the mean of 1 to 3 individual assays each of at least 7 separate microsomal preparations.

TABLE 5

| | 20:1 + 22:1[1] | (22:1/20:1) |
|---|---|---|
| At (SEQ ID NO:2) | 16.0 +/− 2.7 | 0.15 +/− 0.04 |
| Bn (SEQ ID NO:4) | 9.8 +/− 3.2 | 0.32 +/− 0.07 |
| At114 K92R (SEQ ID NO:14) | 5.8 +/− 3.1 | 0.32 +/− 0.09 |

[1]The sum of the amounts of eicosenoic acid (20:1) and erucic acid (22:1) is expressed as nmole/mg microsomal protein.

Example 4

Elongase KCS Catalytic Activity

Table 6 shows the results of yeast microsome assays of Bn elongase KCS, At FAE1, and various chimeric polypeptides for various incubation times. The data in Table 6 show the sum of C20:1 and C22:1 in nmole/mg protein from microsome preparations assayed 2 to 3 times each.

The results indicate that the amount of elongase KCS activity of the wild-type At FAE1 is about 1.5 to 2 times higher than that of wild-type Bn elongase KCS. The At114 polypeptide has an activity that is intermediate between the wild-type At and wild-type Bn, while the At74 polypeptide has an activity that is lower than that of wild-type Bn enzymes. These results indicate that modifying amino acid residues in the region from position 74 to 114 affects elongase activity.

The activity of the At114 L91C K92R gene product was measured in yeast microsomes and is shown in Table 6. The elongase activity of this polypeptide was higher than that of At114.

TABLE 6[1]

| Time (min) | pYES2 | Bn (SEQ ID NO:2) | At (SEQ ID NO:4) | At114 (SEQ ID NO:8) | At74 (SEQ ID NO:10) | At114 L91C K92R (SEQ ID NO:12) |
|---|---|---|---|---|---|---|
| 0 | −2.4 ± 2.4 | 2.7 ± 1.8 | 2.4 ± 1.8 | 1.4 ± 1.0 | 2.2 ± 0.84 | 2.3 ± 1.08 |
| 5 | 0.24 ± 0.6 | 5.1 ± 1.6 | 8.7 ± 1.2 | 5.9 ± 0.6 | 3.2 ± 1.1 | 6.5 ± 1.0 |
| 10 | 0.78 ± 0.6 | 7.4 ± 1.8 | 12.1 ± 0.6 | 8.8 ± 0.5 | 4.1 ± 0.8 | 9.6 ± 1.2 |
| 20 | 0.96 ± 0.6 | 7.8 ± 2.1 | 13.7 ± 1.8 | 10.1 ± 1.2 | 4.4 ± 0.8 | 11.5 ± 1.1 |
| 45 | 1.32 ± 0.6 | 8.1 ± 2.2 | 14.0 ± 0.6 | 10.2 ± 1.2 | 4.6 ± 0.5 | 12.1 ± 0.9 |

[1]The data are the sum of the C20:1 and C22:1 elongase products (nmole/mg microsomal protein) ± standard deviation.

The elongase activity of the At114 L91C and At114 K92R polypeptides were also assayed in yeast microsomes. The results indicated that the catalytic activity of the At114 L91C polypeptide was about 15–30% of the activity of At114, whereas the activity of At114 K92R was approximately the same as that of At114.

A yeast microsome assay was carried out to compare the Bn elongase KCS shown in SEQ ID NO:4 and another naturally-occurring elongase KCS from the *B. napus* cultivar Askari. The elongase KCS from Askari has the same sequence as that shown in SEQ ID NO:4, except for a valine at position 4 and an aspartic acid at position 307. The results indicated that the Askari elongase KCS had a higher elongase activity and a higher C22:1/C20:1 ratio that did the Bn elongase KCS of SEQ ID NO:4.

Site-directed modifications to SEQ ID NO:3 were made by the techniques described in Example 2 to generate nucleic acids encoding polypeptides Bn I4V, Bn G307D and Bn I4V G307D. The latter polypeptide has the same amino acid sequence as the naturally occurring Askari elongase KCS. After cloning and transforming of each construct into yeast as described in Example 2, microsome assays were performed. Table 7 presents the results from a single experiment in which elongase activity and product ratios for the elongase KCS constructs were measured. Assays were performed as described in Example 2. The results indicate that changing the residue at position 4 from isoleucine to valine had little or no effect on the elongase activity or the C22:1/C20:1 ratio. On the other hand, the Bn G307D polypeptide had a higher elongase activity and produced more C22:1 product than did the unmodified wild-type Bn polypeptide. The amino acid sequence of Bn G307D is shown in SEQ ID NO:34.

TABLE 7[1]

|  | 18:1 | 20:1 | 22:1 | 24:1 | 22:1/20:1 | 20:1 + 22:1 |
|---|---|---|---|---|---|---|
| Bn | 47.9 | 5.5 | 1.9 | 0.3 | 0.35 | 7.7 |
| Bn I4V | 48.4 | 5.5 | 2.0 | 0.4 | 0.37 | 7.8 |
| Bn G307D | 37.2 | 6.7 | 5.4 | 0.7 | 0.80 | 12.7 |
| Bn I4V G307D | 41.9 | 6.5 | 4.5 | 0.5 | 0.68 | 11.6 |
| *B. napus* (Ask) | 37.6 | 7.7 | 6.7 | 0.8 | 0.86 | 15.2 |

[1]Amounts of oleic acid (18:1), eicosenoic acid (20:1), erucic acid (22:1), lignoceric acid (24:1), and the sum of 20:1 and 22:1, are expressed as nmol/mg microsomal protein.

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. An isolated nucleic acid encoding a polypeptide, said polypeptide comprising in the amino-terminal to carboxy-terminal direction:

(a) a first polypeptide segment, wherein said first polypeptide segment has membrane anchoring properties; joined to
   (b) a second polypeptide segment having a sequence selected from the group consisting of residues 75–114 of SEQ ID NO:12 and residues 75–114 of SEQ ID NO:14; joined to
   (c) a third polypeptide segment having at least 40% sequence identity to residues 115–506 of SEQ ID NO:4.

2. The nucleic acid of claim 1, wherein said third polypeptide segment has at least 50% sequence identity to residues 115–506 of SEQ ID NO:4.

3. Host cells containing the nucleic acid of claims 1.

4. Host cells containing the nucleic acid of claim 2.

5. The host cells of claim 3, wherein said host cells are yeast cells.

6. The host cells of claim 3, wherein said host cells are plant cells.

7. A plant containing the nucleic acid of claim 1.

8. A plant containing the nucleic acid of claim 2.

9. The plant of claim 7, wherein said plant is *Brassica napus*.

10. The plant of claim 8, wherein said plant is *Brassica napus*.

* * * * *

UNITED STATES PATENT AND TRADEMARK OFFICE
CERTIFICATE OF CORRECTION

PATENT NO. : 6,713,664 B2
DATED : March 30, 3004
INVENTOR(S) : Jan G. Jaworski and Brenda J. Blacklock It is certified that error appears in the above-identified patent and that said Letters Patent is hereby corrected as shown below:

Title page,
Item [75], Inventors, "Brenda J. Blacklock", please delete "US" and insert -- Canada -- therefor;
Item [56], References Cited, OTHER PUBLICATIONS,
"Fourmann et al." reference, please delete "hologous" and insert -- homologous -- therefor;
"Pruitt et al." reference, please delete "enyme" and insert -- enzyme -- therefor.

Column 158,
Line 32, please delete "claims" and insert -- claim -- therefor.

Signed and Sealed this

Seventh Day of December, 2004

JON W. DUDAS
*Director of the United States Patent and Trademark Office*

SEQUENCE LISTING

<160> NUMBER OF SEQ ID NOS: 56

<210> SEQ ID NO 1
<211> LENGTH: 1709
<212> TYPE: DNA
<213> ORGANISM: Arabidopsis thaliana
<220> FEATURE:
<221> NAME/KEY: CDS
<222> LOCATION: (1)...(1518)

<400> SEQUENCE: 1

```
atg acg tcc gtt aac gtt aag ctc ctt tac cgt tac gtc tta acc aac      48
Met Thr Ser Val Asn Val Lys Leu Leu Tyr Arg Tyr Val Leu Thr Asn
 1               5                  10                  15 ttt ttc aac ctc tgt ttg ttc ccg tta acg gcg ttc ctc gcc gga aaa      96
Phe Phe Asn Leu Cys Leu Phe Pro Leu Thr Ala Phe Leu Ala Gly Lys
             20                  25                  30 gcc tct cgg ctt acc ata aac gat ctc cac aac ttc ctt tcc tat ctc     144
Ala Ser Arg Leu Thr Ile Asn Asp Leu His Asn Phe Leu Ser Tyr Leu
         35                  40                  45 caa cac aac ctt ata aca gta act tta ctc ttt gct ttc act gtt ttc     192
Gln His Asn Leu Ile Thr Val Thr Leu Leu Phe Ala Phe Thr Val Phe
     50                  55                  60 ggt ttg gtt ctc tac atc gta acc cga ccc aat ccg gtt tat ctc gtt     240
Gly Leu Val Leu Tyr Ile Val Thr Arg Pro Asn Pro Val Tyr Leu Val
 65                  70                  75                  80 gac tac tcg tgt tac ctt cca cca ccg cat ctc aaa gtt agt gtc tct     288
Asp Tyr Ser Cys Tyr Leu Pro Pro Pro His Leu Lys Val Ser Val Ser
                 85                  90                  95 aaa gtc atg gat att ttc tac caa ata aga aaa gct gat act tct tca     336
Lys Val Met Asp Ile Phe Tyr Gln Ile Arg Lys Ala Asp Thr Ser Ser
            100                 105                 110 cgg aac gtg gca tgt gat gat ccg tcc tcg ctc gat ttc ctg agg aag     384
Arg Asn Val Ala Cys Asp Asp Pro Ser Ser Leu Asp Phe Leu Arg Lys
        115                 120                 125 att caa gag cgt tca ggt cta ggt gat gag acg tac agt cct gag gga     432
Ile Gln Glu Arg Ser Gly Leu Gly Asp Glu Thr Tyr Ser Pro Glu Gly
```

```
            130                 135                 140
ctc att cac gta cca ccg cgg aag act ttt gca gcg tca cgt gaa gag    480
Leu Ile His Val Pro Pro Arg Lys Thr Phe Ala Ala Ser Arg Glu Glu
145                 150                 155                 160 aca gag aag gtt atc atc ggt gcg ctc gaa aat cta ttc gag aac acc    528
Thr Glu Lys Val Ile Ile Gly Ala Leu Glu Asn Leu Phe Glu Asn Thr
                165                 170                 175 aaa gtt aac cct aga gag att ggt ata ctt gtg gtg aac tca agc atg    576
Lys Val Asn Pro Arg Glu Ile Gly Ile Leu Val Val Asn Ser Ser Met
            180                 185                 190 ttt aat cca act cct tcg cta tcc gct atg gtc gtt aat act ttc aag    624
Phe Asn Pro Thr Pro Ser Leu Ser Ala Met Val Val Asn Thr Phe Lys
        195                 200                 205 ctc cga agc aac atc aaa agc ttt aat cta gga gga atg ggt tgt agt    672
Leu Arg Ser Asn Ile Lys Ser Phe Asn Leu Gly Gly Met Gly Cys Ser
    210                 215                 220 gct ggt gtt att gcc att gat ttg gct aaa gac ttg ttg cat gtt cat    720
Ala Gly Val Ile Ala Ile Asp Leu Ala Lys Asp Leu Leu His Val His
225                 230                 235                 240 aaa aac act tat gct ctt gtg gtg agc act gag aac atc aca caa ggc    768
Lys Asn Thr Tyr Ala Leu Val Val Ser Thr Glu Asn Ile Thr Gln Gly
                245                 250                 255 att tat gct gga gaa aat aga tca atg atg gtt agc aat tgc ttg ttt    816
Ile Tyr Ala Gly Glu Asn Arg Ser Met Met Val Ser Asn Cys Leu Phe
            260                 265                 270 cgt gtt ggt ggg gcc gcg att ttg ctc tct aac aag tcg gga gac cgg    864
Arg Val Gly Gly Ala Ala Ile Leu Leu Ser Asn Lys Ser Gly Asp Arg
        275                 280                 285 aga cgg tcc aag tac aag cta gtt cac acg gtc cga acg cat act gga    912
Arg Arg Ser Lys Tyr Lys Leu Val His Thr Val Arg Thr His Thr Gly
    290                 295                 300 gct gat gac aag tct ttt cga tgt gtg caa caa gaa gac gat gag agc    960
Ala Asp Asp Lys Ser Phe Arg Cys Val Gln Gln Glu Asp Asp Glu Ser
305                 310                 315                 320 ggc aaa atc gga gtt tgt ctg tca aag gac ata acc aat gtt gcg ggg   1008
Gly Lys Ile Gly Val Cys Leu Ser Lys Asp Ile Thr Asn Val Ala Gly
                325                 330                 335 aca aca ctt acg aaa aat ata gca aca ttg ggt ccg ttg att ctt cct   1056
Thr Thr Leu Thr Lys Asn Ile Ala Thr Leu Gly Pro Leu Ile Leu Pro
            340                 345                 350 tta agc gaa aag ttt ctt ttt ttc gct acc ttc gtc gcc aag aaa ctt   1104
Leu Ser Glu Lys Phe Leu Phe Phe Ala Thr Phe Val Ala Lys Lys Leu
        355                 360                 365 cta aag gat aaa atc aag cat tac tat gtt ccg gat ttc aag ctt gct   1152
Leu Lys Asp Lys Ile Lys His Tyr Tyr Val Pro Asp Phe Lys Leu Ala
    370                 375                 380 gtt gac cat ttc tgt att cat gcc gga ggc aga gcc gtg atc gat gag   1200
Val Asp His Phe Cys Ile His Ala Gly Gly Arg Ala Val Ile Asp Glu
385                 390                 395                 400 cta gag aag aac tta gga cta tcg ccg atc gat gtg gag gca tct aga   1248
Leu Glu Lys Asn Leu Gly Leu Ser Pro Ile Asp Val Glu Ala Ser Arg
                405                 410                 415 tca acg tta cat aga ttt ggg aat act tca tct agc tca att tgg tat   1296
Ser Thr Leu His Arg Phe Gly Asn Thr Ser Ser Ser Ser Ile Trp Tyr
            420                 425                 430 gaa tta gca tac ata gag gca aag gga aga atg aag aaa ggg aat aaa   1344
Glu Leu Ala Tyr Ile Glu Ala Lys Gly Arg Met Lys Lys Gly Asn Lys
        435                 440                 445 gct tgg cag att gct tta gga tca ggg ttt aag tgt aat agt gcg gtt   1392
```

```
Ala Trp Gln Ile Ala Leu Gly Ser Gly Phe Lys Cys Asn Ser Ala Val
        450                 455                 460 tgg gtg gct cta cgc aat gtc aag gca tcg gca aat agt cct tgg caa      1440
Trp Val Ala Leu Arg Asn Val Lys Ala Ser Ala Asn Ser Pro Trp Gln
465                 470                 475                 480 cat tgc atc gat aga tat ccg gtt aaa att gat tct gat ttg tca aag      1488
His Cys Ile Asp Arg Tyr Pro Val Lys Ile Asp Ser Asp Leu Ser Lys
                485                 490                 495 tca aag act cat gtc caa aac ggt cgg tcc taatttgatg tatctgagtg        1538
Ser Lys Thr His Val Gln Asn Gly Arg Ser
                500                 505 ccaacgttta ctttgtcttt cctttctttt attggttatg aattagatgt ttactaatgt    1598
tcctctcttt ttcgttataa ataaagaagt tcaattcttc ctatagtttc aaacgcgatt    1658
ttaagcgttt ctatttaggt ttacatgaat ttcttttaca aaccatcttt t             1709

<210> SEQ ID NO 2
<211> LENGTH: 506
<212> TYPE: PRT
<213> ORGANISM: Arabidopsis thaliana

<400> SEQUENCE: 2

Met Thr Ser Val Asn Val Lys Leu Leu Tyr Arg Tyr Val Leu Thr Asn
1               5                   10                  15

Phe Phe Asn Leu Cys Leu Phe Pro Leu Thr Ala Phe Leu Ala Gly Lys
            20                  25                  30

Ala Ser Arg Leu Thr Ile Asn Asp Leu His Asn Phe Leu Ser Tyr Leu
        35                  40                  45

Gln His Asn Leu Ile Thr Val Thr Leu Leu Phe Ala Phe Thr Val Phe
    50                  55                  60

Gly Leu Val Leu Tyr Ile Val Thr Arg Pro Asn Pro Val Tyr Leu Val
65                  70                  75                  80

Asp Tyr Ser Cys Tyr Leu Pro Pro His Leu Lys Val Ser Val Ser
                85                  90                  95

Lys Val Met Asp Ile Phe Tyr Gln Ile Arg Lys Ala Asp Thr Ser Ser
            100                 105                 110

Arg Asn Val Ala Cys Asp Asp Pro Ser Ser Leu Asp Phe Leu Arg Lys
        115                 120                 125

Ile Gln Glu Arg Ser Gly Leu Gly Asp Glu Thr Tyr Ser Pro Glu Gly
    130                 135                 140

Leu Ile His Val Pro Pro Arg Lys Thr Phe Ala Ala Ser Arg Glu Glu
145                 150                 155                 160

Thr Glu Lys Val Ile Ile Gly Ala Leu Glu Asn Leu Phe Glu Asn Thr
                165                 170                 175

Lys Val Asn Pro Arg Glu Ile Gly Ile Leu Val Val Asn Ser Ser Met
            180                 185                 190

Phe Asn Pro Thr Pro Ser Leu Ser Ala Met Val Val Asn Thr Phe Lys
        195                 200                 205

Leu Arg Ser Asn Ile Lys Ser Phe Asn Leu Gly Gly Met Gly Cys Ser
    210                 215                 220

Ala Gly Val Ile Ala Ile Asp Leu Ala Lys Asp Leu Leu His Val His
225                 230                 235                 240

Lys Asn Thr Tyr Ala Leu Val Val Ser Thr Glu Asn Ile Thr Gln Gly
                245                 250                 255

Ile Tyr Ala Gly Glu Asn Arg Ser Met Met Val Ser Asn Cys Leu Phe
            260                 265                 270
```

```
Arg Val Gly Gly Ala Ala Ile Leu Leu Ser Asn Lys Ser Gly Asp Arg
            275                 280                 285

Arg Arg Ser Lys Tyr Lys Leu Val His Thr Val Arg Thr His Thr Gly
        290                 295                 300

Ala Asp Asp Lys Ser Phe Arg Cys Val Gln Gln Glu Asp Asp Glu Ser
305                 310                 315                 320

Gly Lys Ile Gly Val Cys Leu Ser Lys Asp Ile Thr Asn Val Ala Gly
                325                 330                 335

Thr Thr Leu Thr Lys Asn Ile Ala Thr Leu Gly Pro Leu Ile Leu Pro
            340                 345                 350

Leu Ser Glu Lys Phe Leu Phe Phe Ala Thr Phe Val Ala Lys Lys Leu
        355                 360                 365

Leu Lys Asp Lys Ile Lys His Tyr Tyr Val Pro Asp Phe Lys Leu Ala
370                 375                 380

Val Asp His Phe Cys Ile His Ala Gly Arg Ala Val Ile Asp Glu
385                 390                 395                 400

Leu Glu Lys Asn Leu Gly Leu Ser Pro Ile Asp Val Glu Ala Ser Arg
            405                 410                 415

Ser Thr Leu His Arg Phe Gly Asn Thr Ser Ser Ser Ile Trp Tyr
        420                 425                 430

Glu Leu Ala Tyr Ile Glu Ala Lys Gly Arg Met Lys Lys Gly Asn Lys
    435                 440                 445

Ala Trp Gln Ile Ala Leu Gly Ser Gly Phe Lys Cys Asn Ser Ala Val
        450                 455                 460

Trp Val Ala Leu Arg Asn Val Lys Ala Ser Ala Asn Ser Pro Trp Gln
465                 470                 475                 480

His Cys Ile Asp Arg Tyr Pro Val Lys Ile Asp Ser Asp Leu Ser Lys
                485                 490                 495

Ser Lys Thr His Val Gln Asn Gly Arg Ser
            500                 505

<210> SEQ ID NO 3
<211> LENGTH: 1524
<212> TYPE: DNA
<213> ORGANISM: Brassica napus
<220> FEATURE:
<221> NAME/KEY: CDS
<222> LOCATION: (1)...(1521)

<400> SEQUENCE: 3 atg acg tcc att aac gta aag ctc ctt tac cat tac gtc ata acc aac      48
Met Thr Ser Ile Asn Val Lys Leu Leu Tyr His Tyr Val Ile Thr Asn
1               5                   10                  15 ctt ttc aac ctt tgc ttc ttt ccg tta acg gcg atc gtc gcc gga aaa      96
Leu Phe Asn Leu Cys Phe Phe Pro Leu Thr Ala Ile Val Ala Gly Lys
            20                  25                  30 gcc tat cgg ctt acc ata gac gat ctt cac cac tta tac tat tcc tat     144
Ala Tyr Arg Leu Thr Ile Asp Asp Leu His His Leu Tyr Tyr Ser Tyr
        35                  40                  45 ctc caa cac aac ctc ata acc atc gct cca ctc ttt gcc ttc acc gtt     192
Leu Gln His Asn Leu Ile Thr Ile Ala Pro Leu Phe Ala Phe Thr Val
    50                  55                  60 ttc ggt tcg gtt ctc tac atc gca acc cgg ccc aaa ccg gtt tac ctc     240
Phe Gly Ser Val Leu Tyr Ile Ala Thr Arg Pro Lys Pro Val Tyr Leu
65                  70                  75                  80 gtt gag tac tca tgc tac ctt cca cca acg cat tgt aga tca agt atc     288
Val Glu Tyr Ser Cys Tyr Leu Pro Pro Thr His Cys Arg Ser Ser Ile
```

-continued

```
               85                    90                    95
tcc aag gtc atg gat atc ttt tat caa gta aga aaa gct gat cct tct    336
Ser Lys Val Met Asp Ile Phe Tyr Gln Val Arg Lys Ala Asp Pro Ser
            100                   105                   110 cgg aac ggc acg tgc gat gac tcg tcg tgg ctt gac ttc ttg agg aag    384
Arg Asn Gly Thr Cys Asp Asp Ser Ser Trp Leu Asp Phe Leu Arg Lys
            115                   120                   125 att caa gaa cgt tca ggt cta ggc gat gaa act cac ggg ccc gag ggg    432
Ile Gln Glu Arg Ser Gly Leu Gly Asp Glu Thr His Gly Pro Glu Gly
130                   135                   140 ctg ctt cag gtc cct ccc cgg aag act ttt gcg gcg gcg cgt gaa gag    480
Leu Leu Gln Val Pro Pro Arg Lys Thr Phe Ala Ala Ala Arg Glu Glu
145                   150                   155                   160 acg gag caa gtt atc att ggt gcg cta gaa aat cta ttc aag aac acc    528
Thr Glu Gln Val Ile Ile Gly Ala Leu Glu Asn Leu Phe Lys Asn Thr
                165                   170                   175 aac gtt aac cct aaa gat ata ggt ata ctt gtg gtg aac tca agc atg    576
Asn Val Asn Pro Lys Asp Ile Gly Ile Leu Val Val Asn Ser Ser Met
            180                   185                   190 ttt aat cca act cca tcg ctc tcc gcg atg gtc gtt aac act ttc aag    624
Phe Asn Pro Thr Pro Ser Leu Ser Ala Met Val Val Asn Thr Phe Lys
            195                   200                   205 ctc cga agc aac gta aga agc ttt aac ctt ggt ggc atg ggt tgt agt    672
Leu Arg Ser Asn Val Arg Ser Phe Asn Leu Gly Gly Met Gly Cys Ser
210                   215                   220 gcc ggc gtt ata gcc att gat cta gca aag gac ttg ttg cat gtc cat    720
Ala Gly Val Ile Ala Ile Asp Leu Ala Lys Asp Leu Leu His Val His
225                   230                   235                   240 aaa aat acg tat gct ctt gtg gtg agc aca gag aac atc act tat aac    768
Lys Asn Thr Tyr Ala Leu Val Val Ser Thr Glu Asn Ile Thr Tyr Asn
                245                   250                   255 att tac gct ggt gat aat agg tcc atg atg gtt tca aat tgc ttg ttc    816
Ile Tyr Ala Gly Asp Asn Arg Ser Met Met Val Ser Asn Cys Leu Phe
            260                   265                   270 cgt gtt ggt ggg gcc gct att ttg ctc tcc aac aag cct gga gat cgt    864
Arg Val Gly Gly Ala Ala Ile Leu Leu Ser Asn Lys Pro Gly Asp Arg
            275                   280                   285 aga cgg tcc aag tac gag cta gtt cac acg gtt cga acg cat acc gga    912
Arg Arg Ser Lys Tyr Glu Leu Val His Thr Val Arg Thr His Thr Gly
            290                   295                   300 gct gac ggc aag tct ttt cgt tgc gtg caa caa gga gac gat gag aac    960
Ala Asp Gly Lys Ser Phe Arg Cys Val Gln Gln Gly Asp Asp Glu Asn
305                   310                   315                   320 ggc aaa atc gga gtg agt ttg tcc aag gac ata acc gat gtt gct ggt    1008
Gly Lys Ile Gly Val Ser Leu Ser Lys Asp Ile Thr Asp Val Ala Gly
                325                   330                   335 cga acg gtt aag aaa aac ata gca acg ttg ggt ccg ttg att ctt ccg    1056
Arg Thr Val Lys Lys Asn Ile Ala Thr Leu Gly Pro Leu Ile Leu Pro
            340                   345                   350 tta agc gag aaa ctt ctt ttt ttc gtt acc ttc atg ggc aag aaa ctt    1104
Leu Ser Glu Lys Leu Leu Phe Phe Val Thr Phe Met Gly Lys Lys Leu
            355                   360                   365 ttc aaa gat aaa atc aaa cat tac tac gtc ccg gat ttc aaa ctt gct    1152
Phe Lys Asp Lys Ile Lys His Tyr Tyr Val Pro Asp Phe Lys Leu Ala
370                   375                   380 att gac cat ttt tgt ata cat gcc gga ggc aga gcc gtg att gat gtg    1200
Ile Asp His Phe Cys Ile His Ala Gly Gly Arg Ala Val Ile Asp Val
385                   390                   395                   400 cta gag aag aac cta gcc cta gca ccg atc gat gta gag gca tca aga    1248
```

```
Leu Glu Lys Asn Leu Ala Leu Ala Pro Ile Asp Val Glu Ala Ser Arg
                405                 410                 415 tca acg tta cat aga ttt gga aac act tca tct agc tca ata tgg tat         1296
Ser Thr Leu His Arg Phe Gly Asn Thr Ser Ser Ser Ser Ile Trp Tyr
                420                 425                 430 gag ttg gca tac ata gaa gca aaa gga agg atg aag aaa ggt aat aaa         1344
Glu Leu Ala Tyr Ile Glu Ala Lys Gly Arg Met Lys Lys Gly Asn Lys
                435                 440                 445 gtt tgg cag att gct tta ggg tca ggc ttt aag tgt aac agt gca gtt         1392
Val Trp Gln Ile Ala Leu Gly Ser Gly Phe Lys Cys Asn Ser Ala Val
450                 455                 460 tgg gtg gct cta aac aat gtc aaa gct tcg aca aat agt cct tgg gaa         1440
Trp Val Ala Leu Asn Asn Val Lys Ala Ser Thr Asn Ser Pro Trp Glu
465                 470                 475                 480 cac tgc atc gac aga tac ccg gtc aaa att gat tct gat tca ggt aag         1488
His Cys Ile Asp Arg Tyr Pro Val Lys Ile Asp Ser Asp Ser Gly Lys
                485                 490                 495 tca gag act cgt gtc caa aac ggt cgg tcc taa taa                         1524
Ser Glu Thr Arg Val Gln Asn Gly Arg Ser *
                500                 505

<210> SEQ ID NO 4
<211> LENGTH: 506
<212> TYPE: PRT
<213> ORGANISM: Brassica napus

<400> SEQUENCE: 4

Met Thr Ser Ile Asn Val Lys Leu Leu Tyr His Tyr Val Ile Thr Asn
1               5                   10                  15

Leu Phe Asn Leu Cys Phe Phe Pro Leu Thr Ala Ile Val Ala Gly Lys
                20                  25                  30

Ala Tyr Arg Leu Thr Ile Asp Asp Leu His His Leu Tyr Tyr Ser Tyr
            35                  40                  45

Leu Gln His Asn Leu Ile Thr Ile Ala Pro Leu Phe Ala Phe Thr Val
        50                  55                  60

Phe Gly Ser Val Leu Tyr Ile Ala Thr Arg Pro Lys Pro Val Tyr Leu
65                  70                  75                  80

Val Glu Tyr Ser Cys Tyr Leu Pro Pro Thr His Cys Arg Ser Ser Ile
                85                  90                  95

Ser Lys Val Met Asp Ile Phe Tyr Gln Val Arg Lys Ala Asp Pro Ser
                100                 105                 110

Arg Asn Gly Thr Cys Asp Asp Ser Ser Trp Leu Asp Phe Leu Arg Lys
            115                 120                 125

Ile Gln Glu Arg Ser Gly Leu Gly Asp Glu Thr His Gly Pro Glu Gly
        130                 135                 140

Leu Leu Gln Val Pro Pro Arg Lys Thr Phe Ala Ala Arg Glu Glu
145                 150                 155                 160

Thr Glu Gln Val Ile Ile Gly Ala Leu Glu Asn Leu Phe Lys Asn Thr
                165                 170                 175

Asn Val Asn Pro Lys Asp Ile Gly Ile Leu Val Val Asn Ser Ser Met
                180                 185                 190

Phe Asn Pro Thr Pro Ser Leu Ser Ala Met Val Val Asn Thr Phe Lys
            195                 200                 205

Leu Arg Ser Asn Val Arg Ser Phe Asn Leu Gly Gly Met Gly Cys Ser
        210                 215                 220

Ala Gly Val Ile Ala Ile Asp Leu Ala Lys Asp Leu Leu His Val His
225                 230                 235                 240
```

```
Lys Asn Thr Tyr Ala Leu Val Ser Thr Glu Asn Ile Thr Tyr Asn
                245                 250                 255

Ile Tyr Ala Gly Asp Asn Arg Ser Met Met Val Ser Asn Cys Leu Phe
            260                 265                 270

Arg Val Gly Gly Ala Ala Ile Leu Leu Ser Asn Lys Pro Gly Asp Arg
        275                 280                 285

Arg Arg Ser Lys Tyr Glu Leu Val His Thr Val Arg Thr His Thr Gly
    290                 295                 300

Ala Asp Gly Lys Ser Phe Arg Cys Val Gln Gln Gly Asp Asp Glu Asn
305                 310                 315                 320

Gly Lys Ile Gly Val Ser Leu Ser Lys Asp Ile Thr Asp Val Ala Gly
                325                 330                 335

Arg Thr Val Lys Lys Asn Ile Ala Thr Leu Gly Pro Leu Ile Leu Pro
            340                 345                 350

Leu Ser Glu Lys Leu Leu Phe Phe Val Thr Phe Met Gly Lys Lys Leu
        355                 360                 365

Phe Lys Asp Lys Ile Lys His Tyr Tyr Val Pro Asp Phe Lys Leu Ala
    370                 375                 380

Ile Asp His Phe Cys Ile His Ala Gly Gly Arg Ala Val Ile Asp Val
385                 390                 395                 400

Leu Glu Lys Asn Leu Ala Leu Ala Pro Ile Asp Val Glu Ala Ser Arg
                405                 410                 415

Ser Thr Leu His Arg Phe Gly Asn Thr Ser Ser Ser Ile Trp Tyr
            420                 425                 430

Glu Leu Ala Tyr Ile Glu Ala Lys Gly Arg Met Lys Lys Gly Asn Lys
        435                 440                 445

Val Trp Gln Ile Ala Leu Gly Ser Gly Phe Lys Cys Asn Ser Ala Val
    450                 455                 460

Trp Val Ala Leu Asn Asn Val Lys Ala Ser Thr Asn Ser Pro Trp Glu
465                 470                 475                 480

His Cys Ile Asp Arg Tyr Pro Val Lys Ile Asp Ser Asp Ser Gly Lys
                485                 490                 495

Ser Glu Thr Arg Val Gln Asn Gly Arg Ser
            500                 505

<210> SEQ ID NO 5
<211> LENGTH: 1736
<212> TYPE: DNA
<213> ORGANISM: Brassica napus
<220> FEATURE:
<221> NAME/KEY: CDS
<222> LOCATION: (85)...(1599)

<400> SEQUENCE: 5
tagagcgtaa cggaccacaa aagaggatcc atacaaatac atctcatcgc ttccattact      60
attctccgac acacacactg agca atg acg tcc att aac gta aag ctc ctt      111
                          Met Thr Ser Ile Asn Val Lys Leu Leu
                            1               5 tac cat tac gtc ata acc aac ctt ttc aac ctt tgt ttc ttt cca tta      159
Tyr His Tyr Val Ile Thr Asn Leu Phe Asn Leu Cys Phe Phe Pro Leu
 10                  15                  20                  25 acg gcg atc gtc gcc gga aaa gcc tat ctt acc ata gac gat ctt cac      207
Thr Ala Ile Val Ala Gly Lys Ala Tyr Leu Thr Ile Asp Asp Leu His
                 30                  35                  40 cac tta tac tat tcc tat ctc caa cac aac ctc ata acc att gct cca      255
His Leu Tyr Tyr Ser Tyr Leu Gln His Asn Leu Ile Thr Ile Ala Pro
```

-continued

|  |  |  |  |  |  | 45 |  |  |  | 50 |  |  |  | 55 |  |  |
|---|---|---|---|---|---|---|---|---|---|---|---|---|---|---|---|---|
| ctc | ttg | gcc | ttc | acc | gtt | ttc | ggt | tcg | gtt | ctc | tac | atc | gca | acc | cgg | 303 |
| Leu | Leu | Ala | Phe | Thr | Val | Phe | Gly | Ser | Val | Leu | Tyr | Ile | Ala | Thr | Arg |  |
|  |  |  |  | 60 |  |  |  |  | 65 |  |  |  |  | 70 |  |  |

| ccc | aaa | ccg | gtt | tac | ctc | gtg | gag | tac | tca | tgc | tac | ctt | cca | cca | acg | 351 |
|---|---|---|---|---|---|---|---|---|---|---|---|---|---|---|---|---|
| Pro | Lys | Pro | Val | Tyr | Leu | Val | Glu | Tyr | Ser | Cys | Tyr | Leu | Pro | Pro | Thr |  |
|  | 75 |  |  |  |  | 80 |  |  |  |  | 85 |  |  |  |  |  |

| cat | tgt | aga | tca | agt | atc | tcc | aag | gtc | atg | gat | atc | ttt | ttc | caa | gta | 399 |
|---|---|---|---|---|---|---|---|---|---|---|---|---|---|---|---|---|
| His | Cys | Arg | Ser | Ser | Ile | Ser | Lys | Val | Met | Asp | Ile | Phe | Phe | Gln | Val |  |
| 90 |  |  |  |  | 95 |  |  |  |  | 100 |  |  |  |  | 105 |  |

| aga | aaa | gct | gat | cct | tct | cgg | aac | ggc | acg | tgc | gat | gac | tcg | tcc | tgg | 447 |
|---|---|---|---|---|---|---|---|---|---|---|---|---|---|---|---|---|
| Arg | Lys | Ala | Asp | Pro | Ser | Arg | Asn | Gly | Thr | Cys | Asp | Asp | Ser | Ser | Trp |  |
|  |  |  |  | 110 |  |  |  |  | 115 |  |  |  |  | 120 |  |  |

| ctt | gac | ttc | ttg | agg | aag | att | caa | gaa | cgt | tca | ggt | cta | ggc | gat | gaa | 495 |
|---|---|---|---|---|---|---|---|---|---|---|---|---|---|---|---|---|
| Leu | Asp | Phe | Leu | Arg | Lys | Ile | Gln | Glu | Arg | Ser | Gly | Leu | Gly | Asp | Glu |  |
|  |  |  | 125 |  |  |  |  | 130 |  |  |  |  | 135 |  |  |  |

| acc | cac | ggg | ccc | gag | ggg | ctg | ctt | cag | gtc | cct | ccc | cgg | aag | act | ttt | 543 |
|---|---|---|---|---|---|---|---|---|---|---|---|---|---|---|---|---|
| Thr | His | Gly | Pro | Glu | Gly | Leu | Leu | Gln | Val | Pro | Pro | Arg | Lys | Thr | Phe |  |
|  |  | 140 |  |  |  |  | 145 |  |  |  |  | 150 |  |  |  |  |

| gcg | cgc | gcg | cgt | gaa | gag | acg | gag | caa | gtt | atc | att | ggt | gcg | cta | gaa | 591 |
|---|---|---|---|---|---|---|---|---|---|---|---|---|---|---|---|---|
| Ala | Arg | Ala | Arg | Glu | Glu | Thr | Glu | Gln | Val | Ile | Ile | Gly | Ala | Leu | Glu |  |
|  | 155 |  |  |  |  | 160 |  |  |  |  | 165 |  |  |  |  |  |

| aat | cta | ttc | aag | aac | acc | aat | gtt | aac | cct | aaa | gat | ata | ggt | ata | ctt | 639 |
|---|---|---|---|---|---|---|---|---|---|---|---|---|---|---|---|---|
| Asn | Leu | Phe | Lys | Asn | Thr | Asn | Val | Asn | Pro | Lys | Asp | Ile | Gly | Ile | Leu |  |
| 170 |  |  |  |  | 175 |  |  |  |  | 180 |  |  |  |  | 185 |  |

| gtg | gtg | aac | tca | agc | atg | ttt | aat | cca | act | cct | tcg | ctc | tcc | gcg | atg | 687 |
|---|---|---|---|---|---|---|---|---|---|---|---|---|---|---|---|---|
| Val | Val | Asn | Ser | Ser | Met | Phe | Asn | Pro | Thr | Pro | Ser | Leu | Ser | Ala | Met |  |
|  |  |  | 190 |  |  |  |  | 195 |  |  |  |  | 200 |  |  |  |

| gtc | gtt | aac | act | ttc | aag | ctc | cga | agc | aac | gta | aga | agc | ttt | aac | ctt | 735 |
|---|---|---|---|---|---|---|---|---|---|---|---|---|---|---|---|---|
| Val | Val | Asn | Thr | Phe | Lys | Leu | Arg | Ser | Asn | Val | Arg | Ser | Phe | Asn | Leu |  |
|  |  |  | 205 |  |  |  |  | 210 |  |  |  |  | 215 |  |  |  |

| ggt | ggc | atg | ggt | tgt | agt | gcc | ggc | gtt | ata | gcc | att | gat | cta | gca | aag | 783 |
|---|---|---|---|---|---|---|---|---|---|---|---|---|---|---|---|---|
| Gly | Gly | Met | Gly | Cys | Ser | Ala | Gly | Val | Ile | Ala | Ile | Asp | Leu | Ala | Lys |  |
|  |  | 220 |  |  |  |  | 225 |  |  |  |  | 230 |  |  |  |  |

| gac | ttg | ttg | cat | gtc | cat | aaa | aat | acg | tat | gct | ctt | gtg | gtg | agc | aca | 831 |
|---|---|---|---|---|---|---|---|---|---|---|---|---|---|---|---|---|
| Asp | Leu | Leu | His | Val | His | Lys | Asn | Thr | Tyr | Ala | Leu | Val | Val | Ser | Thr |  |
|  | 235 |  |  |  |  | 240 |  |  |  |  | 245 |  |  |  |  |  |

| gag | aac | atc | act | tat | aac | att | tac | gct | ggt | gat | aat | agg | tcc | atg | atg | 879 |
|---|---|---|---|---|---|---|---|---|---|---|---|---|---|---|---|---|
| Glu | Asn | Ile | Thr | Tyr | Asn | Ile | Tyr | Ala | Gly | Asp | Asn | Arg | Ser | Met | Met |  |
| 250 |  |  |  |  | 255 |  |  |  |  | 260 |  |  |  |  | 265 |  |

| gtt | tca | aat | tgc | ttg | ttc | cgt | gtt | ggt | ggg | gcc | gct | att | ttg | ctc | tcc | 927 |
|---|---|---|---|---|---|---|---|---|---|---|---|---|---|---|---|---|
| Val | Ser | Asn | Cys | Leu | Phe | Arg | Val | Gly | Gly | Ala | Ala | Ile | Leu | Leu | Ser |  |
|  |  |  | 270 |  |  |  |  | 275 |  |  |  |  | 280 |  |  |  |

| aac | aag | cct | aga | gat | cgt | aga | cgg | tcc | aag | tac | gag | cta | gtt | cac | acg | 975 |
|---|---|---|---|---|---|---|---|---|---|---|---|---|---|---|---|---|
| Asn | Lys | Pro | Arg | Asp | Arg | Arg | Arg | Ser | Lys | Tyr | Glu | Leu | Val | His | Thr |  |
|  |  |  | 285 |  |  |  |  | 290 |  |  |  |  | 295 |  |  |  |

| gtt | cga | acg | cat | acc | gga | gct | gac | gac | aag | tct | ttt | cgt | tgc | gtg | caa | 1023 |
|---|---|---|---|---|---|---|---|---|---|---|---|---|---|---|---|---|
| Val | Arg | Thr | His | Thr | Gly | Ala | Asp | Asp | Lys | Ser | Phe | Arg | Cys | Val | Gln |  |
|  |  | 300 |  |  |  |  | 305 |  |  |  |  | 310 |  |  |  |  |

| caa | gga | gac | gat | gag | aac | ggc | caa | acc | gga | gtg | agt | ttg | tcc | aag | gac | 1071 |
|---|---|---|---|---|---|---|---|---|---|---|---|---|---|---|---|---|
| Gln | Gly | Asp | Asp | Glu | Asn | Gly | Gln | Thr | Gly | Val | Ser | Leu | Ser | Lys | Asp |  |
|  | 315 |  |  |  |  | 320 |  |  |  |  | 325 |  |  |  |  |  |

| ata | acc | gat | gtt | gct | ggt | cga | acg | gtt | aag | aaa | aac | ata | gca | acg | ctg | 1119 |
|---|---|---|---|---|---|---|---|---|---|---|---|---|---|---|---|---|
| Ile | Thr | Asp | Val | Ala | Gly | Arg | Thr | Val | Lys | Lys | Asn | Ile | Ala | Thr | Leu |  |
| 330 |  |  |  |  | 335 |  |  |  |  | 340 |  |  |  |  | 345 |  |

| ggt | ccg | ttg | att | ctt | ccg | tta | agc | gag | aaa | ctt | ctt | ttt | ttc | gtt | acc | 1167 |
|---|---|---|---|---|---|---|---|---|---|---|---|---|---|---|---|---|
| Gly | Pro | Leu | Ile | Leu | Pro | Leu | Ser | Glu | Lys | Leu | Leu | Phe | Phe | Val | Thr |  |
|  |  |  | 350 |  |  |  |  | 355 |  |  |  |  | 360 |  |  |  |

| ttc | atg | ggc | aag | aaa | ctt | ttc | aaa | gac | gaa | atc | aaa | cat | tat | tac | gtc | 1215 |

```
ccg gac ttc aag ctt gct atc gac cat ttt tgt ata cat gcc gga ggc      1263
Pro Asp Phe Lys Leu Ala Ile Asp His Phe Cys Ile His Ala Gly Gly
        380                 385                 390 aaa gcc gtg att gat gtg cta gag aag aac cta ggc cta gca ccg atc      1311
Lys Ala Val Ile Asp Val Leu Glu Lys Asn Leu Gly Leu Ala Pro Ile
395                 400                 405 gat gta gag gca tca aga tca acg tta cat aga ttt gga aac act tca      1359
Asp Val Glu Ala Ser Arg Ser Thr Leu His Arg Phe Gly Asn Thr Ser
410                 415                 420                 425 tct agc tca ata tgg tat gag ttg gca tac ata gaa ccc aaa gga agg      1407
Ser Ser Ser Ile Trp Tyr Glu Leu Ala Tyr Ile Glu Pro Lys Gly Arg
            430                 435                 440 atg aag aaa ggt aat aaa gtt tgg cag att gct tta ggg tca ggc ttt      1455
Met Lys Lys Gly Asn Lys Val Trp Gln Ile Ala Leu Gly Ser Gly Phe
                445                 450                 455 aag tgt aac agt gca gtt tgg gtg gct cta aac aat gtc aaa gct tca      1503
Lys Cys Asn Ser Ala Val Trp Val Ala Leu Asn Asn Val Lys Ala Ser
            460                 465                 470 aca aat agt cct tgg gaa cac tgc atc gac aga tac ccg gtt aaa att      1551
Thr Asn Ser Pro Trp Glu His Cys Ile Asp Arg Tyr Pro Val Lys Ile
        475                 480                 485 gat tct gat tca ggt aag tca gag act cgt gtc cca aac ggt cgg tcc      1599
Asp Ser Asp Ser Gly Lys Ser Glu Thr Arg Val Pro Asn Gly Arg Ser
490                 495                 500                 505 taataaatga tgtttgctct ctttcgtttc tttttattgg ttataataat ttgatggcca    1659
cgatgtttct cttgtttgtt atgaataaag aatcccacgg tgttctagta aaaaaaaaa    1719 aaaaaaaaaa aaaaaaa                                                  1736

<210> SEQ ID NO 6
<211> LENGTH: 505
<212> TYPE: PRT
<213> ORGANISM: Brassica napus

<400> SEQUENCE: 6

Met Thr Ser Ile Asn Val Lys Leu Leu Tyr His Tyr Val Ile Thr Asn
1               5                   10                  15

Leu Phe Asn Leu Cys Phe Phe Pro Leu Thr Ala Ile Val Ala Gly Lys
            20                  25                  30

Ala Tyr Leu Thr Ile Asp Asp Leu His His Leu Tyr Tyr Ser Tyr Leu
        35                  40                  45

Gln His Asn Leu Ile Thr Ile Ala Pro Leu Leu Ala Phe Thr Val Phe
    50                  55                  60

Gly Ser Val Leu Tyr Ile Ala Thr Arg Pro Lys Pro Val Tyr Leu Val
65                  70                  75                  80

Glu Tyr Ser Cys Tyr Leu Pro Pro Thr His Cys Arg Ser Ser Ile Ser
                85                  90                  95

Lys Val Met Asp Ile Phe Phe Gln Val Arg Lys Ala Asp Pro Ser Arg
            100                 105                 110

Asn Gly Thr Cys Asp Asp Ser Ser Trp Leu Asp Phe Leu Arg Lys Ile
        115                 120                 125

Gln Glu Arg Ser Gly Leu Gly Asp Glu Thr His Gly Pro Glu Gly Leu
    130                 135                 140

Leu Gln Val Pro Pro Arg Lys Thr Phe Ala Arg Ala Arg Glu Glu Thr
145                 150                 155                 160
```

```
Glu Gln Val Ile Ile Gly Ala Leu Glu Asn Leu Phe Lys Asn Thr Asn
                165                 170                 175
Val Asn Pro Lys Asp Ile Gly Ile Leu Val Val Asn Ser Ser Met Phe
            180                 185                 190
Asn Pro Thr Pro Ser Leu Ser Ala Met Val Val Asn Thr Phe Lys Leu
        195                 200                 205
Arg Ser Asn Val Arg Ser Phe Asn Leu Gly Gly Met Gly Cys Ser Ala
    210                 215                 220
Gly Val Ile Ala Ile Asp Leu Ala Lys Asp Leu Leu His Val His Lys
225                 230                 235                 240
Asn Thr Tyr Ala Leu Val Val Ser Thr Glu Asn Ile Thr Tyr Asn Ile
                245                 250                 255
Tyr Ala Gly Asp Asn Arg Ser Met Met Val Ser Asn Cys Leu Phe Arg
            260                 265                 270
Val Gly Gly Ala Ala Ile Leu Leu Ser Asn Lys Pro Arg Asp Arg Arg
        275                 280                 285
Arg Ser Lys Tyr Glu Leu Val His Thr Val Arg Thr His Thr Gly Ala
    290                 295                 300
Asp Asp Lys Ser Phe Arg Cys Val Gln Gln Gly Asp Asp Glu Asn Gly
305                 310                 315                 320
Gln Thr Gly Val Ser Leu Ser Lys Asp Ile Thr Asp Val Ala Gly Arg
                325                 330                 335
Thr Val Lys Lys Asn Ile Ala Thr Leu Gly Pro Leu Ile Leu Pro Leu
            340                 345                 350
Ser Glu Lys Leu Leu Phe Phe Val Thr Phe Met Gly Lys Lys Leu Phe
        355                 360                 365
Lys Asp Glu Ile Lys His Tyr Tyr Val Pro Asp Phe Lys Leu Ala Ile
    370                 375                 380
Asp His Phe Cys Ile His Ala Gly Gly Lys Ala Val Ile Asp Val Leu
385                 390                 395                 400
Glu Lys Asn Leu Gly Leu Ala Pro Ile Asp Val Glu Ala Ser Arg Ser
                405                 410                 415
Thr Leu His Arg Phe Gly Asn Thr Ser Ser Ser Ile Trp Tyr Glu
            420                 425                 430
Leu Ala Tyr Ile Glu Pro Lys Gly Arg Met Lys Lys Gly Asn Lys Val
        435                 440                 445
Trp Gln Ile Ala Leu Gly Ser Gly Phe Lys Cys Asn Ser Ala Val Trp
    450                 455                 460
Val Ala Leu Asn Asn Val Lys Ala Ser Thr Asn Ser Pro Trp Glu His
465                 470                 475                 480
Cys Ile Asp Arg Tyr Pro Val Lys Ile Asp Ser Asp Ser Gly Lys Ser
                485                 490                 495
Glu Thr Arg Val Pro Asn Gly Arg Ser
            500                 505

<210> SEQ ID NO 7
<211> LENGTH: 1521
<212> TYPE: DNA
<213> ORGANISM: Artificial Sequence
<220> FEATURE:
<223> OTHER INFORMATION: 5' 342 bp from A. thaliana FAE1 (SEQ ID NO:1)
      and 3' 1179 bp from B. napus elongase KCS (SEQ ID
      NO:3); designated At114
<221> NAME/KEY: CDS
<222> LOCATION: (1)...(1518)

<400> SEQUENCE: 7
```

| | | |
|---|---|---|
| atg acg tcc gtt aac gtt aag ctc ctt tac cgt tat gtc tta acc aac<br>Met Thr Ser Val Asn Val Lys Leu Leu Tyr Arg Tyr Val Leu Thr Asn<br>1                   5                   10               15 | | 48 |
| ttt ttc aac ctc tgt ttg ttc ccg tta acg gcg ttc ctc gcc gga aaa<br>Phe Phe Asn Leu Cys Leu Phe Pro Leu Thr Ala Phe Leu Ala Gly Lys<br>                 20                   25                   30 | | 96 |
| gcc tct cgg ctt acc ata aac gat ctc cac aac ttc ctt tcc tat ctc<br>Ala Ser Arg Leu Thr Ile Asn Asp Leu His Asn Phe Leu Ser Tyr Leu<br>             35                   40                   45 | | 144 |
| caa cac aac ctt ata aca gta act tta ctc ttt gct ttc act gtt ttc<br>Gln His Asn Leu Ile Thr Val Thr Leu Leu Phe Ala Phe Thr Val Phe<br>    50                   55                   60 | | 192 |
| ggt ttg gtt ctc tac atc gta acc cga ccc aat ccg gtt tat ctc gtt<br>Gly Leu Val Leu Tyr Ile Val Thr Arg Pro Asn Pro Val Tyr Leu Val<br>65                   70                   75                   80 | | 240 |
| gac tac tcg tgt tac ctt ccg cca ccg cat ctc aaa gtt agt gtc tct<br>Asp Tyr Ser Cys Tyr Leu Pro Pro Pro His Leu Lys Val Ser Val Ser<br>                 85                   90                   95 | | 288 |
| aaa gtc atg gat att ttc tac caa ata aga aaa gct gat act tct tca<br>Lys Val Met Asp Ile Phe Tyr Gln Ile Arg Lys Ala Asp Thr Ser Ser<br>             100                 105               110 | | 336 |
| cgg aac ggc acg tgt gat gat tcg tcg tgg ctt gac ttc ttg agg aag<br>Arg Asn Gly Thr Cys Asp Asp Ser Ser Trp Leu Asp Phe Leu Arg Lys<br>             115                 120               125 | | 384 |
| att caa gaa cgt tca ggt cta ggc gat gaa act cac ggg ccc gag ggg<br>Ile Gln Glu Arg Ser Gly Leu Gly Asp Glu Thr His Gly Pro Glu Gly<br>     130                 135                 140 | | 432 |
| ctg ctt cag gtc cct ccc cgg aag act ttt gcg gcg gcg cgt gaa gag<br>Leu Leu Gln Val Pro Pro Arg Lys Thr Phe Ala Ala Ala Arg Glu Glu<br>145                  150                 155               160 | | 480 |
| acg gag caa gtt atc att ggt gcg cta gaa aat cta ttc aag aac acc<br>Thr Glu Gln Val Ile Ile Gly Ala Leu Glu Asn Leu Phe Lys Asn Thr<br>             165                 170               175 | | 528 |
| aac gtt aac cct aaa gat ata ggt ata ctt gtg gtg aac tca agc atg<br>Asn Val Asn Pro Lys Asp Ile Gly Ile Leu Val Val Asn Ser Ser Met<br>                 180                 185               190 | | 576 |
| ttt aat cca act cca tcg ctc tcc gcg atg gtc gtt aac act ttc aag<br>Phe Asn Pro Thr Pro Ser Leu Ser Ala Met Val Val Asn Thr Phe Lys<br>             195                 200               205 | | 624 |
| ctc cga agc aac gta aga agc ttt aac ctt ggt ggc atg ggt tgt agt<br>Leu Arg Ser Asn Val Arg Ser Phe Asn Leu Gly Gly Met Gly Cys Ser<br>     210                 215                 220 | | 672 |
| gcc ggc gtt ata gcc att gat cta gca aag gac ttg ttg cat gtc cat<br>Ala Gly Val Ile Ala Ile Asp Leu Ala Lys Asp Leu Leu His Val His<br>225                  230                 235               240 | | 720 |
| aaa aat acg tat gct ctt gtg gtg agc aca gag aac atc act tat aac<br>Lys Asn Thr Tyr Ala Leu Val Val Ser Thr Glu Asn Ile Thr Tyr Asn<br>             245                 250               255 | | 768 |
| att tac gct ggt gat aat agg tcc atg atg gtt tca aat tgc ttg ttc<br>Ile Tyr Ala Gly Asp Asn Arg Ser Met Met Val Ser Asn Cys Leu Phe<br>                 260                 265               270 | | 816 |
| cgt gtt ggt ggg gcc gct att ttg ctc tcc aac aag cct gga gat cgt<br>Arg Val Gly Gly Ala Ala Ile Leu Leu Ser Asn Lys Pro Gly Asp Arg<br>             275                 280               285 | | 864 |
| aga cgg tcc aag tac gag cta gtt cac acg gtt cga acg cat acc gga<br>Arg Arg Ser Lys Tyr Glu Leu Val His Thr Val Arg Thr His Thr Gly<br>     290                 295                 300 | | 912 |
| gct gac ggc aag tct ttt cgt tgc gtg caa caa gga gac gat gag aac<br>Ala Asp Gly Lys Ser Phe Arg Cys Val Gln Gln Gly Asp Asp Glu Asn | | 960 |

-continued

```
ggc aaa atc gga gtg agt ttg tcc aag gac ata acc gat gtt gct ggt       1008
Gly Lys Ile Gly Val Ser Leu Ser Lys Asp Ile Thr Asp Val Ala Gly
            325                 330                 335 cga acg gtt aag aaa aac ata gca acg ttg ggt ccg ttg att ctt ccg       1056
Arg Thr Val Lys Lys Asn Ile Ala Thr Leu Gly Pro Leu Ile Leu Pro
        340                 345                 350 tta agc gag aaa ctt ctt ttt ttc gtt acc ttc atg ggc aag aaa ctt       1104
Leu Ser Glu Lys Leu Leu Phe Phe Val Thr Phe Met Gly Lys Lys Leu
    355                 360                 365 ttc aaa gat aaa atc aaa cat tac tac gtc ccg gat ttc aaa ctt gct       1152
Phe Lys Asp Lys Ile Lys His Tyr Tyr Val Pro Asp Phe Lys Leu Ala
370                 375                 380 att gac cat ttt tgt ata cat gcc gga ggc aga gcc gtg att gat gtg       1200
Ile Asp His Phe Cys Ile His Ala Gly Gly Arg Ala Val Ile Asp Val
385                 390                 395                 400 cta gag aag aac cta gcc cta gca ccg atc gat gta gag gca tca aga       1248
Leu Glu Lys Asn Leu Ala Leu Ala Pro Ile Asp Val Glu Ala Ser Arg
            405                 410                 415 tca acg tta cat aga ttt gga aac act tca tct agc tca ata tgg tat       1296
Ser Thr Leu His Arg Phe Gly Asn Thr Ser Ser Ser Ser Ile Trp Tyr
        420                 425                 430 gag ttg gca tac ata gaa rca aaa gga agg atg aag aaa ggt aat aaa       1344
Glu Leu Ala Tyr Ile Glu Xaa Lys Gly Arg Met Lys Lys Gly Asn Lys
    435                 440                 445 gtt tgg cag att gct tta ggg tca ggc ttt aag tgt aac agt gca gtt       1392
Val Trp Gln Ile Ala Leu Gly Ser Gly Phe Lys Cys Asn Ser Ala Val
450                 455                 460 tgg gtg gct cta aac aat gtc aaa gct tcg aca aat agt cct tgg gaa       1440
Trp Val Ala Leu Asn Asn Val Lys Ala Ser Thr Asn Ser Pro Trp Glu
465                 470                 475                 480 cac tgc atc gac aga tac ccg gtc aaa att gat tct gat tca ggt aag       1488
His Cys Ile Asp Arg Tyr Pro Val Lys Ile Asp Ser Asp Ser Gly Lys
            485                 490                 495 tca gag act cgt gtc cca aac ggt cgg tcc taa                           1521
Ser Glu Thr Arg Val Pro Asn Gly Arg Ser
        500                 505
```

<210> SEQ ID NO 8
<211> LENGTH: 506
<212> TYPE: PRT
<213> ORGANISM: Artificial Sequence
<220> FEATURE:
<221> NAME/KEY: VARIANT
<222> LOCATION: (0)...(0)
<223> OTHER INFORMATION: Xaa = Ala or Thr
<223> OTHER INFORMATION: 5' 114 amino acids from A. thaliana FAE1 (SEQ
      ID NO:2) and 3' 392 amino acids from B. napus
      elongase KCS (SEQ ID NO:4); designated At114

<400> SEQUENCE: 8

```
Met Thr Ser Val Asn Val Lys Leu Leu Tyr Arg Tyr Val Leu Thr Asn
  1               5                  10                  15

Phe Phe Asn Leu Cys Leu Phe Pro Leu Thr Ala Phe Leu Ala Gly Lys
             20                  25                  30

Ala Ser Arg Leu Thr Ile Asn Asp Leu His Asn Phe Leu Ser Tyr Leu
         35                  40                  45

Gln His Asn Leu Ile Thr Val Thr Leu Leu Phe Ala Phe Thr Val Phe
     50                  55                  60

Gly Leu Val Leu Tyr Ile Val Thr Arg Pro Asn Pro Val Tyr Leu Val
 65                  70                  75                  80
```

```
Asp Tyr Ser Cys Tyr Leu Pro Pro His Leu Lys Val Ser Val Ser
                85                  90                  95
Lys Val Met Asp Ile Phe Tyr Gln Ile Arg Lys Ala Asp Thr Ser Ser
            100                 105                 110
Arg Asn Gly Thr Cys Asp Asp Ser Ser Trp Leu Asp Phe Leu Arg Lys
            115                 120                 125
Ile Gln Glu Arg Ser Gly Leu Gly Asp Glu Thr His Gly Pro Glu Gly
            130                 135                 140
Leu Leu Gln Val Pro Pro Arg Lys Thr Phe Ala Ala Ala Arg Glu Glu
145                 150                 155                 160
Thr Glu Gln Val Ile Ile Gly Ala Leu Glu Asn Leu Phe Lys Asn Thr
                165                 170                 175
Asn Val Asn Pro Lys Asp Ile Gly Ile Leu Val Val Asn Ser Ser Met
                180                 185                 190
Phe Asn Pro Thr Pro Ser Leu Ser Ala Met Val Val Asn Thr Phe Lys
            195                 200                 205
Leu Arg Ser Asn Val Arg Ser Phe Asn Leu Gly Gly Met Gly Cys Ser
            210                 215                 220
Ala Gly Val Ile Ala Ile Asp Leu Ala Lys Asp Leu Leu His Val His
225                 230                 235                 240
Lys Asn Thr Tyr Ala Leu Val Val Ser Thr Glu Asn Ile Thr Tyr Asn
                245                 250                 255
Ile Tyr Ala Gly Asp Asn Arg Ser Met Met Val Ser Asn Cys Leu Phe
            260                 265                 270
Arg Val Gly Gly Ala Ala Ile Leu Leu Ser Asn Lys Pro Gly Asp Arg
            275                 280                 285
Arg Arg Ser Lys Tyr Glu Leu Val His Thr Val Arg Thr His Thr Gly
            290                 295                 300
Ala Asp Gly Lys Ser Phe Arg Cys Val Gln Gln Gly Asp Asp Glu Asn
305                 310                 315                 320
Gly Lys Ile Gly Val Ser Leu Ser Lys Asp Ile Thr Asp Val Ala Gly
                325                 330                 335
Arg Thr Val Lys Lys Asn Ile Ala Thr Leu Gly Pro Leu Ile Leu Pro
            340                 345                 350
Leu Ser Glu Lys Leu Leu Phe Phe Val Thr Phe Met Gly Lys Lys Leu
            355                 360                 365
Phe Lys Asp Lys Ile Lys His Tyr Tyr Val Pro Asp Phe Lys Leu Ala
            370                 375                 380
Ile Asp His Phe Cys Ile His Ala Gly Gly Arg Ala Val Ile Asp Val
385                 390                 395                 400
Leu Glu Lys Asn Leu Ala Leu Ala Pro Ile Asp Val Glu Ala Ser Arg
            405                 410                 415
Ser Thr Leu His Arg Phe Gly Asn Thr Ser Ser Ser Ile Trp Tyr
            420                 425                 430
Glu Leu Ala Tyr Ile Glu Xaa Lys Gly Arg Met Lys Lys Gly Asn Lys
            435                 440                 445
Val Trp Gln Ile Ala Leu Gly Ser Gly Phe Lys Cys Asn Ser Ala Val
    450                 455                 460
Trp Val Ala Leu Asn Asn Val Lys Ala Ser Thr Asn Ser Pro Trp Glu
465                 470                 475                 480
His Cys Ile Asp Arg Tyr Pro Val Lys Ile Asp Ser Asp Ser Gly Lys
                485                 490                 495
```

-continued

```
Ser Glu Thr Arg Val Pro Asn Gly Arg Ser
            500                 505
```

<210> SEQ ID NO 9
<211> LENGTH: 1518
<212> TYPE: DNA
<213> ORGANISM: Artificial Sequence
<220> FEATURE:
<223> OTHER INFORMATION: 5' 222 bp from A. thaliana FAE1 (SEQ ID NO:1)
      and 3' 1296 bp from B. napus elongase KCS (SEQ ID
      NO:3); designated At74
<221> NAME/KEY: CDS
<222> LOCATION: (1)...(1515)

<400> SEQUENCE: 9

```
atg acg tcc gtt aac gtt aag ctc ctt tac cgt tac gtc tta acc aac      48
Met Thr Ser Val Asn Val Lys Leu Leu Tyr Arg Tyr Val Leu Thr Asn
 1               5                  10                  15 ttt ttc aac ctc tgt ttg ttc ccg tta acg gcg ttc ctc gcc gga aaa      96
Phe Phe Asn Leu Cys Leu Phe Pro Leu Thr Ala Phe Leu Ala Gly Lys
             20                  25                  30 gcc tct cgg ctt acc ata aac gat ctc cac aac ttc ctt tcc tat ctc     144
Ala Ser Arg Leu Thr Ile Asn Asp Leu His Asn Phe Leu Ser Tyr Leu
         35                  40                  45 caa cac aac ctt ata aca gta act tta ctc ttt gct ttc act gtt ttc     192
Gln His Asn Leu Ile Thr Val Thr Leu Leu Phe Ala Phe Thr Val Phe
     50                  55                  60 ggt ttg gtt ctc tac atc gta acc cga ccc aaa ccg gtt tac ctc gtt     240
Gly Leu Val Leu Tyr Ile Val Thr Arg Pro Lys Pro Val Tyr Leu Val
 65                  70                  75                  80 gag tac tca tgc tac ctt cca cca acg cat tgt aga tca agt atc tcc     288
Glu Tyr Ser Cys Tyr Leu Pro Pro Thr His Cys Arg Ser Ser Ile Ser
                 85                  90                  95 aag gtc atg gat atc ttt tat caa gta aga aaa gct gat cct tct cgg     336
Lys Val Met Asp Ile Phe Tyr Gln Val Arg Lys Ala Asp Pro Ser Arg
            100                 105                 110 aac ggc acg tgc gat gac tcg tcg tgg ctt gac ttc ttg agg aag att     384
Asn Gly Thr Cys Asp Asp Ser Ser Trp Leu Asp Phe Leu Arg Lys Ile
        115                 120                 125 caa gaa cgt tca ggt cta ggc gat gaa act cac ggg ccc gag ggg ctg     432
Gln Glu Arg Ser Gly Leu Gly Asp Glu Thr His Gly Pro Glu Gly Leu
    130                 135                 140 ctt cag gtc cct ccc cgg aag act ttt gcg gcg gcg cgt gaa gag acg     480
Leu Gln Val Pro Pro Arg Lys Thr Phe Ala Ala Ala Arg Glu Glu Thr
145                 150                 155                 160 gag caa gtt atc att ggt gcg cta gaa aat cta ttc aag aac acc aac     528
Glu Gln Val Ile Ile Gly Ala Leu Glu Asn Leu Phe Lys Asn Thr Asn
                165                 170                 175 gtt aac cct aaa gat ata ggt ata ctt gtg gtg aac tca agc atg ttt     576
Val Asn Pro Lys Asp Ile Gly Ile Leu Val Val Asn Ser Ser Met Phe
            180                 185                 190 aat cca act cca tcg ctc tcc gcg atg gtc gtt aac act ttc aag ctc     624
Asn Pro Thr Pro Ser Leu Ser Ala Met Val Val Asn Thr Phe Lys Leu
        195                 200                 205 cga agc aac gta aga agc ttt aac ctt ggt ggc atg ggt tgt agt gcc     672
Arg Ser Asn Val Arg Ser Phe Asn Leu Gly Gly Met Gly Cys Ser Ala
    210                 215                 220 ggc gtt ata gcc att gat cta gca aag gac ttg ttg cat gtc cat aaa     720
Gly Val Ile Ala Ile Asp Leu Ala Lys Asp Leu Leu His Val His Lys
225                 230                 235                 240 aat acg tat gct ctt gtg gtg agc aca gag aac atc act tat aac att     768
Asn Thr Tyr Ala Leu Val Val Ser Thr Glu Asn Ile Thr Tyr Asn Ile
```

|  |  |  |  |  |  |  |  |  |  |  |  |  |  |  |  |
|---|---|---|---|---|---|---|---|---|---|---|---|---|---|---|---|
|  |  |  | 245 |  |  |  | 250 |  |  |  | 255 |  |  |  |  |
| tac | gct | ggt | gat | aat | agg | tcc | atg | atg | gtt | tca | aat | tgc | ttg | ttc | cgt | 816 |
| Tyr | Ala | Gly | Asp | Asn | Arg | Ser | Met | Met | Val | Ser | Asn | Cys | Leu | Phe | Arg |  |
|  |  |  | 260 |  |  |  | 265 |  |  |  | 270 |  |  |  |  |
| gtt | ggt | ggg | gcc | gct | att | ttg | ctc | tcc | aac | aag | cct | gga | gat | cgt | aga | 864 |
| Val | Gly | Gly | Ala | Ala | Ile | Leu | Leu | Ser | Asn | Lys | Pro | Gly | Asp | Arg | Arg |  |
|  |  | 275 |  |  |  |  | 280 |  |  |  |  | 285 |  |  |  |  |
| cgg | tcc | aag | tac | gag | cta | gtt | cac | acg | gtt | cga | acg | cat | acc | gga | gct | 912 |
| Arg | Ser | Lys | Tyr | Glu | Leu | Val | His | Thr | Val | Arg | Thr | His | Thr | Gly | Ala |  |
|  | 290 |  |  |  |  | 295 |  |  |  |  | 300 |  |  |  |  |  |
| gac | ggc | aag | tct | ttt | cgt | tgc | gtg | caa | caa | gga | gac | gat | gag | aac | ggc | 960 |
| Asp | Gly | Lys | Ser | Phe | Arg | Cys | Val | Gln | Gln | Gly | Asp | Asp | Glu | Asn | Gly |  |
| 305 |  |  |  |  | 310 |  |  |  |  | 315 |  |  |  |  | 320 |  |
| aaa | atc | gga | gtg | agt | ttg | tcc | aag | gac | ata | acc | gat | gtt | gct | ggt | cga | 1008 |
| Lys | Ile | Gly | Val | Ser | Leu | Ser | Lys | Asp | Ile | Thr | Asp | Val | Ala | Gly | Arg |  |
|  |  |  |  | 325 |  |  |  |  | 330 |  |  |  |  | 335 |  |  |
| acg | gtt | aag | aaa | aac | ata | gca | acg | ttg | ggt | ccg | ttg | att | ctt | ccg | tta | 1056 |
| Thr | Val | Lys | Lys | Asn | Ile | Ala | Thr | Leu | Gly | Pro | Leu | Ile | Leu | Pro | Leu |  |
|  |  |  | 340 |  |  |  |  | 345 |  |  |  |  | 350 |  |  |  |
| agc | gag | aaa | ctt | ctt | ttt | ttc | gtt | acc | ttc | atg | ggc | aag | aaa | ctt | ttc | 1104 |
| Ser | Glu | Lys | Leu | Leu | Phe | Phe | Val | Thr | Phe | Met | Gly | Lys | Lys | Leu | Phe |  |
|  |  | 355 |  |  |  |  | 360 |  |  |  |  | 365 |  |  |  |  |
| aaa | gat | aaa | atc | aaa | cat | tac | tac | gtc | ccg | gat | ttc | aaa | ctt | gct | att | 1152 |
| Lys | Asp | Lys | Ile | Lys | His | Tyr | Tyr | Val | Pro | Asp | Phe | Lys | Leu | Ala | Ile |  |
|  | 370 |  |  |  |  | 375 |  |  |  |  | 380 |  |  |  |  |  |
| gac | cat | ttt | tgt | ata | cat | gcc | gga | ggc | aga | gcc | gtg | att | gat | gtg | cta | 1200 |
| Asp | His | Phe | Cys | Ile | His | Ala | Gly | Gly | Arg | Ala | Val | Ile | Asp | Val | Leu |  |
| 385 |  |  |  |  | 390 |  |  |  |  | 395 |  |  |  |  | 400 |  |
| gag | aag | aac | cta | gcc | cta | gca | ccg | atc | gat | gta | gag | gca | tca | aga | tca | 1248 |
| Glu | Lys | Asn | Leu | Ala | Leu | Ala | Pro | Ile | Asp | Val | Glu | Ala | Ser | Arg | Ser |  |
|  |  |  |  | 405 |  |  |  |  | 410 |  |  |  |  | 415 |  |  |
| acg | tta | cat | aga | ttt | gga | aac | act | tca | tct | agc | tca | ata | tgg | tat | gag | 1296 |
| Thr | Leu | His | Arg | Phe | Gly | Asn | Thr | Ser | Ser | Ser | Ser | Ile | Trp | Tyr | Glu |  |
|  |  |  | 420 |  |  |  |  | 425 |  |  |  |  | 430 |  |  |  |
| ttg | gca | tac | ata | gaa | gca | aaa | gga | agg | atg | aag | aaa | ggt | aat | aaa | gtt | 1344 |
| Leu | Ala | Tyr | Ile | Glu | Ala | Lys | Gly | Arg | Met | Lys | Lys | Gly | Asn | Lys | Val |  |
|  |  | 435 |  |  |  |  | 440 |  |  |  |  | 445 |  |  |  |  |
| tgg | cag | att | gct | tta | ggg | tca | ggc | ttt | aag | tgt | aac | agt | gca | gtt | tgg | 1392 |
| Trp | Gln | Ile | Ala | Leu | Gly | Ser | Gly | Phe | Lys | Cys | Asn | Ser | Ala | Val | Trp |  |
|  | 450 |  |  |  |  | 455 |  |  |  |  | 460 |  |  |  |  |  |
| gtg | gct | cta | aac | aat | gtc | aaa | gct | tcg | aca | aat | agt | cct | tgg | gaa | cac | 1440 |
| Val | Ala | Leu | Asn | Asn | Val | Lys | Ala | Ser | Thr | Asn | Ser | Pro | Trp | Glu | His |  |
| 465 |  |  |  |  | 470 |  |  |  |  | 475 |  |  |  |  | 480 |  |
| tgc | atc | gac | aga | tac | ccg | gtc | aaa | att | gat | tct | gat | tca | ggt | aag | tca | 1488 |
| Cys | Ile | Asp | Arg | Tyr | Pro | Val | Lys | Ile | Asp | Ser | Asp | Ser | Gly | Lys | Ser |  |
|  |  |  |  | 485 |  |  |  |  | 490 |  |  |  |  | 495 |  |  |
| gag | act | cgt | gtc | caa | aac | ggt | cgg | tcc | taa |  |  |  |  |  |  | 1518 |
| Glu | Thr | Arg | Val | Gln | Asn | Gly | Arg | Ser |  |  |  |  |  |  |  |  |
|  |  |  | 500 |  |  |  |  | 505 |  |  |  |  |  |  |  |  |

```
<210> SEQ ID NO 10
<211> LENGTH: 505
<212> TYPE: PRT
<213> ORGANISM: Artificial Sequence
<220> FEATURE:
<223> OTHER INFORMATION: 5' 74 amino acids from A. thaliana FAE1 (SEQ
      ID NO:2) and 3' 431 amino acids from B. napus
      elongase KCS (SEQ ID NO:4); designated At74

<400> SEQUENCE: 10

Met Thr Ser Val Asn Val Lys Leu Leu Tyr Arg Tyr Val Leu Thr Asn
```

-continued

```
  1               5              10              15
Phe Phe Asn Leu Cys Leu Phe Pro Leu Thr Ala Phe Leu Ala Gly Lys
                20              25              30
Ala Ser Arg Leu Thr Ile Asn Asp Leu His Asn Phe Leu Ser Tyr Leu
            35              40              45
Gln His Asn Leu Ile Thr Val Thr Leu Leu Phe Ala Phe Thr Val Phe
        50              55              60
Gly Leu Val Leu Tyr Ile Val Thr Arg Pro Lys Pro Val Tyr Leu Val
65              70              75              80
Glu Tyr Ser Cys Tyr Leu Pro Pro Thr His Cys Arg Ser Ser Ile Ser
                85              90              95
Lys Val Met Asp Ile Phe Tyr Gln Val Arg Lys Ala Asp Pro Ser Arg
            100             105             110
Asn Gly Thr Cys Asp Asp Ser Ser Trp Leu Asp Phe Leu Arg Lys Ile
        115             120             125
Gln Glu Arg Ser Gly Leu Gly Asp Glu Thr His Gly Pro Glu Gly Leu
    130             135             140
Leu Gln Val Pro Pro Arg Lys Thr Phe Ala Ala Arg Glu Glu Thr
145             150             155             160
Glu Gln Val Ile Ile Gly Ala Leu Glu Asn Leu Phe Lys Asn Thr Asn
                165             170             175
Val Asn Pro Lys Asp Ile Gly Ile Leu Val Val Asn Ser Ser Met Phe
            180             185             190
Asn Pro Thr Pro Ser Leu Ser Ala Met Val Val Asn Thr Phe Lys Leu
        195             200             205
Arg Ser Asn Val Arg Ser Phe Asn Leu Gly Gly Met Gly Cys Ser Ala
    210             215             220
Gly Val Ile Ala Ile Asp Leu Ala Lys Asp Leu Leu His Val His Lys
225             230             235             240
Asn Thr Tyr Ala Leu Val Val Ser Thr Glu Asn Ile Thr Tyr Asn Ile
            245             250             255
Tyr Ala Gly Asp Asn Arg Ser Met Met Val Ser Asn Cys Leu Phe Arg
            260             265             270
Val Gly Gly Ala Ala Ile Leu Leu Ser Asn Lys Pro Gly Asp Arg Arg
        275             280             285
Arg Ser Lys Tyr Glu Leu Val His Thr Val Arg Thr His Thr Gly Ala
    290             295             300
Asp Gly Lys Ser Phe Arg Cys Val Gln Gln Gly Asp Asp Glu Asn Gly
305             310             315             320
Lys Ile Gly Val Ser Leu Ser Lys Asp Ile Thr Asp Val Ala Gly Arg
            325             330             335
Thr Val Lys Lys Asn Ile Ala Thr Leu Gly Pro Leu Ile Leu Pro Leu
            340             345             350
Ser Glu Lys Leu Leu Phe Phe Val Thr Phe Met Gly Lys Lys Leu Phe
        355             360             365
Lys Asp Lys Ile Lys His Tyr Tyr Val Pro Asp Phe Lys Leu Ala Ile
    370             375             380
Asp His Phe Cys Ile His Ala Gly Gly Arg Ala Val Ile Asp Val Leu
385             390             395             400
Glu Lys Asn Leu Ala Leu Ala Pro Ile Asp Val Glu Ala Ser Arg Ser
            405             410             415
Thr Leu His Arg Phe Gly Asn Thr Ser Ser Ser Ile Trp Tyr Glu
        420             425             430
```

```
Leu Ala Tyr Ile Glu Ala Lys Gly Arg Met Lys Lys Gly Asn Lys Val
            435                 440                 445

Trp Gln Ile Ala Leu Gly Ser Gly Phe Lys Cys Asn Ser Ala Val Trp
    450                 455                 460

Val Ala Leu Asn Asn Val Lys Ala Ser Thr Asn Ser Pro Trp Glu His
465                 470                 475                 480

Cys Ile Asp Arg Tyr Pro Val Lys Ile Asp Ser Asp Ser Gly Lys Ser
                485                 490                 495

Glu Thr Arg Val Gln Asn Gly Arg Ser
            500                 505

<210> SEQ ID NO 11
<211> LENGTH: 1521
<212> TYPE: DNA
<213> ORGANISM: Artificial Sequence
<220> FEATURE:
<223> OTHER INFORMATION: 5' 342 bp from A. thaliana FAE1 (SEQ ID NO:1)
      and 3' 1179 bp from B. napus elongase KCS (SEQ ID
      NO:3) having mutations at positions 271, 272 and
      275; designated At114 L91C K92R
<221> NAME/KEY: CDS
<222> LOCATION: (1)...(1518)

<400> SEQUENCE: 11 atg acg tcc gtt aac gtt aag ctc ctt tac cgt tat gtc tta acc aac      48
Met Thr Ser Val Asn Val Lys Leu Leu Tyr Arg Tyr Val Leu Thr Asn
 1               5                  10                  15 ttt ttc aac ctc tgt ttg ttc ccg tta acg gcg ttc ctc gcc gga aaa      96
Phe Phe Asn Leu Cys Leu Phe Pro Leu Thr Ala Phe Leu Ala Gly Lys
             20                  25                  30 gcc tct cgg ctt acc ata aac gat ctc cac aac ttc ctt tcc tat ctc     144
Ala Ser Arg Leu Thr Ile Asn Asp Leu His Asn Phe Leu Ser Tyr Leu
         35                  40                  45 caa cac aac ctt ata aca gta act tta ctc ttt gct ttc act gtt ttc     192
Gln His Asn Leu Ile Thr Val Thr Leu Leu Phe Ala Phe Thr Val Phe
     50                  55                  60 ggt ttg gtt ctc tac atc gta acc cga ccc aat ccg gtt tat ctc gtt     240
Gly Leu Val Leu Tyr Ile Val Thr Arg Pro Asn Pro Val Tyr Leu Val
 65                  70                  75                  80 gac tac tcg tgt tac ctt ccg cca ccg cat tgc aga gtt agt gtc tct     288
Asp Tyr Ser Cys Tyr Leu Pro Pro Pro His Cys Arg Val Ser Val Ser
                 85                  90                  95 aaa gtc atg gat att ttc tac caa ata aga aaa gct gat act tct tca     336
Lys Val Met Asp Ile Phe Tyr Gln Ile Arg Lys Ala Asp Thr Ser Ser
            100                 105                 110 cgg aac ggc acg tgt gat aat tcg tcg tgg ctt gac ttc ttg agg aag     384
Arg Asn Gly Thr Cys Asp Asn Ser Ser Trp Leu Asp Phe Leu Arg Lys
        115                 120                 125 att caa gaa cgt tca ggt cta ggc gat gaa act cac ggg ccc gag ggg     432
Ile Gln Glu Arg Ser Gly Leu Gly Asp Glu Thr His Gly Pro Glu Gly
    130                 135                 140 ctg ctt cag gtc cct ccc cgg aag act ttt gcg gcg gcg cgt gaa gag     480
Leu Leu Gln Val Pro Pro Arg Lys Thr Phe Ala Ala Ala Arg Glu Glu
145                 150                 155                 160 acg gag caa gtt atc att ggt gcg cta gaa aat cta ttc aag aac acc     528
Thr Glu Gln Val Ile Ile Gly Ala Leu Glu Asn Leu Phe Lys Asn Thr
                165                 170                 175 aac gtt aac cct aaa gat ata ggt ata ctt gtg gtg aac tca agc atg     576
Asn Val Asn Pro Lys Asp Ile Gly Ile Leu Val Val Asn Ser Ser Met
            180                 185                 190
```

|  |  |
|---|---|
| ttt aat cca act cca tcg ctc tcc gcg atg gtc gtt aac act ttc aag<br>Phe Asn Pro Thr Pro Ser Leu Ser Ala Met Val Val Asn Thr Phe Lys<br>          195                    200                 205 | 624 |
| ctc cga agc aac gta aga agc ttt aac ctt ggt ggc atg ggt tgt agt<br>Leu Arg Ser Asn Val Arg Ser Phe Asn Leu Gly Gly Met Gly Cys Ser<br>    210                    215                    220 | 672 |
| gcc ggt gtt ata gcc att gat cta gca aag gac ttg ttg cat gtc cat<br>Ala Gly Val Ile Ala Ile Asp Leu Ala Lys Asp Leu Leu His Val His<br>225                  230                  235                240 | 720 |
| aaa aat acg tat gct ctt gtg gtg agc aca gag aac atc act tat aac<br>Lys Asn Thr Tyr Ala Leu Val Val Ser Thr Glu Asn Ile Thr Tyr Asn<br>          245                    250                 255 | 768 |
| att tac gct ggt gat aat agg tcc atg atg gtt tca aat tgc ttg ttc<br>Ile Tyr Ala Gly Asp Asn Arg Ser Met Met Val Ser Asn Cys Leu Phe<br>    260                    265                    270 | 816 |
| cgt gtt ggt ggg gcc gct att ttg ctc tcc aac aag cct gga gat cgt<br>Arg Val Gly Gly Ala Ala Ile Leu Leu Ser Asn Lys Pro Gly Asp Arg<br>275                  280                  285 | 864 |
| aga cgg tcc aag tac gag cta gtt cac acg gtt cga acg cat acc gga<br>Arg Arg Ser Lys Tyr Glu Leu Val His Thr Val Arg Thr His Thr Gly<br>          290                    295                300 | 912 |
| gct gac ggc aag tct ttt cgt tgc gtg caa caa gga gac gat gag aac<br>Ala Asp Gly Lys Ser Phe Arg Cys Val Gln Gln Gly Asp Asp Glu Asn<br>305                  310                  315                320 | 960 |
| ggc aaa atc gga gtg agt ttg tcc aag gac ata acc gat gtt gct ggt<br>Gly Lys Ile Gly Val Ser Leu Ser Lys Asp Ile Thr Asp Val Ala Gly<br>                325                    330                335 | 1008 |
| cga acg gtt aag aaa aac ata gca acg ttg ggt ccg ttg att ctt ccg<br>Arg Thr Val Lys Lys Asn Ile Ala Thr Leu Gly Pro Leu Ile Leu Pro<br>                340                    345                350 | 1056 |
| tta agc gag aaa ctt ctt ttt ttc gtt acc ttc atg ggc aag aaa ctt<br>Leu Ser Glu Lys Leu Leu Phe Phe Val Thr Phe Met Gly Lys Lys Leu<br>          355                    360                 365 | 1104 |
| ttc aaa gat aaa atc aaa cat tac tac gtc ccg gat ttc aaa ctt gct<br>Phe Lys Asp Lys Ile Lys His Tyr Tyr Val Pro Asp Phe Lys Leu Ala<br>370                  375                  380 | 1152 |
| att gac cat ttt tgt ata cat gcc gga ggc aga gcc gtg att gat gtg<br>Ile Asp His Phe Cys Ile His Ala Gly Gly Arg Ala Val Ile Asp Val<br>385                  390                  395                400 | 1200 |
| cta gag aag aac cta gcc cta gca ccg atc gat gta gag gca tca aga<br>Leu Glu Lys Asn Leu Ala Leu Ala Pro Ile Asp Val Glu Ala Ser Arg<br>                    405                    410                415 | 1248 |
| tca acg tta cat aga ttt gga aac act tca tct agc tca ata tgg tat<br>Ser Thr Leu His Arg Phe Gly Asn Thr Ser Ser Ser Ser Ile Trp Tyr<br>                420                    425                430 | 1296 |
| gag ttg gca tac ata gaa gca aaa gga agg atg aag aaa ggt aat aaa<br>Glu Leu Ala Tyr Ile Glu Ala Lys Gly Arg Met Lys Lys Gly Asn Lys<br>          435                    440                 445 | 1344 |
| gtt tgg cag att gct tta ggg tca ggc ttt aag tgt aac agt gca gtt<br>Val Trp Gln Ile Ala Leu Gly Ser Gly Phe Lys Cys Asn Ser Ala Val<br>450                  455                  460 | 1392 |
| tgg gtg gct cta aac aat gtc aaa gct tcg aca aat agt cct tgg gaa<br>Trp Val Ala Leu Asn Asn Val Lys Ala Ser Thr Asn Ser Pro Trp Glu<br>465                  470                  475                480 | 1440 |
| cac tgc atc gac aga tac ccg gtc aaa att gat tct gat tca ggt aag<br>His Cys Ile Asp Arg Tyr Pro Val Lys Ile Asp Ser Asp Ser Gly Lys<br>                485                    490                495 | 1488 |
| tca gag act cgt gtc cca aac ggt cgg tcc taa<br>Ser Glu Thr Arg Val Pro Asn Gly Arg Ser<br>          500                    505 | 1521 |

<210> SEQ ID NO 12
<211> LENGTH: 506
<212> TYPE: PRT
<213> ORGANISM: Artificial Sequence
<220> FEATURE:
<223> OTHER INFORMATION: 5' 114 amino acids from A. thaliana FAE1 (SEQ
      ID NO:2) and 3' 392 amino acids from B. napus
      elongase KCS (SEQ ID NO:4) having mutations at
      residues 91 and 92; designated At114 L91C K92R

<400> SEQUENCE: 12

```
Met Thr Ser Val Asn Val Lys Leu Leu Tyr Arg Tyr Val Leu Thr Asn
  1               5                  10                  15

Phe Phe Asn Leu Cys Leu Phe Pro Leu Thr Ala Phe Leu Ala Gly Lys
             20                  25                  30

Ala Ser Arg Leu Thr Ile Asn Asp Leu His Asn Phe Leu Ser Tyr Leu
         35                  40                  45

Gln His Asn Leu Ile Thr Val Thr Leu Leu Phe Ala Phe Thr Val Phe
     50                  55                  60

Gly Leu Val Leu Tyr Ile Val Thr Arg Pro Asn Pro Val Tyr Leu Val
 65                  70                  75                  80

Asp Tyr Ser Cys Tyr Leu Pro Pro His Cys Arg Val Ser Val Ser
                 85                  90                  95

Lys Val Met Asp Ile Phe Tyr Gln Ile Arg Lys Ala Asp Thr Ser Ser
                100                 105                 110

Arg Asn Gly Thr Cys Asp Asn Ser Ser Trp Leu Asp Phe Leu Arg Lys
            115                 120                 125

Ile Gln Glu Arg Ser Gly Leu Gly Asp Glu Thr His Gly Pro Glu Gly
130                 135                 140

Leu Leu Gln Val Pro Pro Arg Lys Thr Phe Ala Ala Ala Arg Glu Glu
145                 150                 155                 160

Thr Glu Gln Val Ile Ile Gly Ala Leu Glu Asn Leu Phe Lys Asn Thr
                165                 170                 175

Asn Val Asn Pro Lys Asp Ile Gly Ile Leu Val Val Asn Ser Ser Met
            180                 185                 190

Phe Asn Pro Thr Pro Ser Leu Ser Ala Met Val Val Asn Thr Phe Lys
        195                 200                 205

Leu Arg Ser Asn Val Arg Ser Phe Asn Leu Gly Gly Met Gly Cys Ser
210                 215                 220

Ala Gly Val Ile Ala Ile Asp Leu Ala Lys Asp Leu Leu His Val His
225                 230                 235                 240

Lys Asn Thr Tyr Ala Leu Val Val Ser Thr Glu Asn Ile Thr Tyr Asn
                245                 250                 255

Ile Tyr Ala Gly Asp Asn Arg Ser Met Met Val Ser Asn Cys Leu Phe
            260                 265                 270

Arg Val Gly Gly Ala Ala Ile Leu Leu Ser Asn Lys Pro Gly Asp Arg
        275                 280                 285

Arg Arg Ser Lys Tyr Glu Leu Val His Thr Val Arg Thr His Thr Gly
290                 295                 300

Ala Asp Gly Lys Ser Phe Arg Cys Val Gln Gln Gly Asp Asp Glu Asn
305                 310                 315                 320

Gly Lys Ile Gly Val Ser Leu Ser Lys Asp Ile Thr Asp Val Ala Gly
                325                 330                 335

Arg Thr Val Lys Lys Asn Ile Ala Thr Leu Gly Pro Leu Ile Leu Pro
            340                 345                 350
```

```
Leu Ser Glu Lys Leu Leu Phe Phe Val Thr Phe Met Gly Lys Lys Leu
        355                 360                 365

Phe Lys Asp Lys Ile Lys His Tyr Tyr Val Pro Asp Phe Lys Leu Ala
    370                 375                 380

Ile Asp His Phe Cys Ile His Ala Gly Gly Arg Ala Val Ile Asp Val
385                 390                 395                 400

Leu Glu Lys Asn Leu Ala Leu Ala Pro Ile Asp Val Glu Ala Ser Arg
                405                 410                 415

Ser Thr Leu His Arg Phe Gly Asn Thr Ser Ser Ser Ile Trp Tyr
            420                 425                 430

Glu Leu Ala Tyr Ile Glu Ala Lys Gly Arg Met Lys Lys Gly Asn Lys
            435                 440                 445

Val Trp Gln Ile Ala Leu Gly Ser Gly Phe Lys Cys Asn Ser Ala Val
    450                 455                 460

Trp Val Ala Leu Asn Asn Val Lys Ala Ser Thr Asn Ser Pro Trp Glu
465                 470                 475                 480

His Cys Ile Asp Arg Tyr Pro Val Lys Ile Asp Ser Asp Ser Gly Lys
                485                 490                 495

Ser Glu Thr Arg Val Pro Asn Gly Arg Ser
            500                 505

<210> SEQ ID NO 13
<211> LENGTH: 1521
<212> TYPE: DNA
<213> ORGANISM: Artificial Sequence
<220> FEATURE:
<223> OTHER INFORMATION: 5' 342 bp from A. thaliana FAE1 (SEQ ID NO:1)
      and 3' 1179 bp from B. napus elongase KCS (SEQ ID
      NO:3), having a mutation at position 275;
      designated At114 K92R
<221> NAME/KEY: CDS
<222> LOCATION: (1)...(1518)

<400> SEQUENCE: 13 atg acg tcc gtt aac gtt aag ctc ctt tac cgt tat gtc tta acc aac      48
Met Thr Ser Val Asn Val Lys Leu Leu Tyr Arg Tyr Val Leu Thr Asn
 1               5                  10                  15 ttt ttc aac ctc tgt ttg ttc ccg tta acg gcg ttc ctc gcc gga aaa      96
Phe Phe Asn Leu Cys Leu Phe Pro Leu Thr Ala Phe Leu Ala Gly Lys
                20                  25                  30 gcc tct cgg ctt acc ata aac gat ctc cac aac ttc ctt tcc tat ctc     144
Ala Ser Arg Leu Thr Ile Asn Asp Leu His Asn Phe Leu Ser Tyr Leu
            35                  40                  45 caa cac aac ctt ata aca gta act tta ctc ttt gct ttc act gtt ttc     192
Gln His Asn Leu Ile Thr Val Thr Leu Leu Phe Ala Phe Thr Val Phe
        50                  55                  60 ggt ttg gtt ctc tac atc gta acc cga ccc aat ccg gtt tat ctc gtt     240
Gly Leu Val Leu Tyr Ile Val Thr Arg Pro Asn Pro Val Tyr Leu Val
 65                  70                  75                  80 gac tac tcg tgt tac ctt ccg cca ccg cat ctc aga gtt agt gtc tct     288
Asp Tyr Ser Cys Tyr Leu Pro Pro Pro His Leu Arg Val Ser Val Ser
                85                  90                  95 aaa gtc atg gat att ttc tac caa ata aga aaa gct gat act tct tca     336
Lys Val Met Asp Ile Phe Tyr Gln Ile Arg Lys Ala Asp Thr Ser Ser
            100                 105                 110 cgg aac ggc acg tgt gat gat tcg tcg tgg ctt gac ttc ttg agg aag     384
Arg Asn Gly Thr Cys Asp Asp Ser Ser Trp Leu Asp Phe Leu Arg Lys
        115                 120                 125 att caa gaa cgt tca ggt cta ggc gat gaa act cac ggg ccc gag ggg     432
```

```
Ile Gln Glu Arg Ser Gly Leu Gly Asp Glu Thr His Gly Pro Glu Gly
    130                 135                 140 ctg ctt cag gtc cct ccc cgg aag act ttt gcg gcg gcg cgt gaa gag       480
Leu Leu Gln Val Pro Pro Arg Lys Thr Phe Ala Ala Ala Arg Glu Glu
145                 150                 155                 160 acg gag caa gtt atc att ggt gcg cta gaa aat cta ttc aag aac acc       528
Thr Glu Gln Val Ile Ile Gly Ala Leu Glu Asn Leu Phe Lys Asn Thr
                165                 170                 175 aac gtt aac cct aaa gat ata ggt ata ctt gtg gtg aac tca agc atg       576
Asn Val Asn Pro Lys Asp Ile Gly Ile Leu Val Val Asn Ser Ser Met
            180                 185                 190 ttt aat cca act cca tcg ctc tcc gcg atg gtc gtt aac act ttc aag       624
Phe Asn Pro Thr Pro Ser Leu Ser Ala Met Val Val Asn Thr Phe Lys
        195                 200                 205 ctc cga agc aac gta aga agc ttt aac ctt ggt ggc atg ggt tgt agt       672
Leu Arg Ser Asn Val Arg Ser Phe Asn Leu Gly Gly Met Gly Cys Ser
    210                 215                 220 gcc ggc gtt ata gcc att gat cta gca aag gac ttg ttg cat gtc cat       720
Ala Gly Val Ile Ala Ile Asp Leu Ala Lys Asp Leu Leu His Val His
225                 230                 235                 240 aaa aat acg tat gct ctt gtg gtg agc aca gag aac atc act tat aac       768
Lys Asn Thr Tyr Ala Leu Val Val Ser Thr Glu Asn Ile Thr Tyr Asn
                245                 250                 255 att tac gct ggt gat aat agg tcc atg atg gtt tca aat tgc ttg ttc       816
Ile Tyr Ala Gly Asp Asn Arg Ser Met Met Val Ser Asn Cys Leu Phe
            260                 265                 270 cgt gtt ggt ggg gcc gct att ttg ctc tcc aac aag cct gga gat cgt       864
Arg Val Gly Gly Ala Ala Ile Leu Leu Ser Asn Lys Pro Gly Asp Arg
        275                 280                 285 aga cgg tcc aag tac gag cta gtt cac acg gtt cga acg cat acc gga       912
Arg Arg Ser Lys Tyr Glu Leu Val His Thr Val Arg Thr His Thr Gly
    290                 295                 300 gct gac ggc aag tct ttt cgt tgc gtg caa caa gga gac gat gag aac       960
Ala Asp Gly Lys Ser Phe Arg Cys Val Gln Gln Gly Asp Asp Glu Asn
305                 310                 315                 320 ggc aaa atc gga gtg agt ttg tcc aag gac ata acc gat gtt gct ggt      1008
Gly Lys Ile Gly Val Ser Leu Ser Lys Asp Ile Thr Asp Val Ala Gly
                325                 330                 335 cga acg gtt aag aaa aac ata gca acg ttg ggt ccg ttg att ctt ccg      1056
Arg Thr Val Lys Lys Asn Ile Ala Thr Leu Gly Pro Leu Ile Leu Pro
            340                 345                 350 tta agc gag aaa ctt ctt ttt ttc gtt acc ttc atg ggc aag aaa ctt      1104
Leu Ser Glu Lys Leu Leu Phe Phe Val Thr Phe Met Gly Lys Lys Leu
        355                 360                 365 ttc aaa gat aaa atc aaa cat tac tac gtc ccg gat ttc aaa ctt gct      1152
Phe Lys Asp Lys Ile Lys His Tyr Tyr Val Pro Asp Phe Lys Leu Ala
370                 375                 380 att gac cat ttt tgt ata cat gcc gga ggc aga gcc gtg att gat gtg      1200
Ile Asp His Phe Cys Ile His Ala Gly Gly Arg Ala Val Ile Asp Val
385                 390                 395                 400 cta gag aag aac cta gcc cta gca ccg atc gat gta gag gca tca aga      1248
Leu Glu Lys Asn Leu Ala Leu Ala Pro Ile Asp Val Glu Ala Ser Arg
                405                 410                 415 tca acg tta cat aga ttt gga aac act tca tct agc tca ata tgg tat      1296
Ser Thr Leu His Arg Phe Gly Asn Thr Ser Ser Ser Ser Ile Trp Tyr
            420                 425                 430 gag ttg gca tac ata gaa gca aaa gga agg atg aag aaa ggt aat aaa      1344
Glu Leu Ala Tyr Ile Glu Ala Lys Gly Arg Met Lys Lys Gly Asn Lys
        435                 440                 445
```

```
gtt tgg cag att gct tta ggg tca ggc ttt aag tgt aac agt gca gtt    1392
Val Trp Gln Ile Ala Leu Gly Ser Gly Phe Lys Cys Asn Ser Ala Val
450                 455                 460 tgg gtg gct cta aac aat gtc aaa gct tcg aca aat agt cct tgg gaa    1440
Trp Val Ala Leu Asn Asn Val Lys Ala Ser Thr Asn Ser Pro Trp Glu
465                 470                 475                 480 cac tgc atc gac aga tac ccg gtc aaa att gat tct gat tca ggt aag    1488
His Cys Ile Asp Arg Tyr Pro Val Lys Ile Asp Ser Asp Ser Gly Lys
                485                 490                 495 tca gag act cgt gtc cca aac ggt cgg tcc taa                        1521
Ser Glu Thr Arg Val Pro Asn Gly Arg Ser
            500                 505

<210> SEQ ID NO 14
<211> LENGTH: 506
<212> TYPE: PRT
<213> ORGANISM: Artificial Sequence
<220> FEATURE:
<223> OTHER INFORMATION: 5' 114 amino acids from A. thaliana FAE1 (SEQ
      ID NO:2) and 3' 392 amino acids from B. napus
      elongase KCS (SEQ ID NO:4), having a mutation at
      position 92; designated At114 K92R

<400> SEQUENCE: 14

Met Thr Ser Val Asn Val Lys Leu Leu Tyr Arg Tyr Val Leu Thr Asn
1               5                   10                  15

Phe Phe Asn Leu Cys Leu Phe Pro Leu Thr Ala Phe Leu Ala Gly Lys
                20                  25                  30

Ala Ser Arg Leu Thr Ile Asn Asp Leu His Asn Phe Leu Ser Tyr Leu
            35                  40                  45

Gln His Asn Leu Ile Thr Val Thr Leu Leu Phe Ala Phe Thr Val Phe
        50                  55                  60

Gly Leu Val Leu Tyr Ile Val Thr Arg Pro Asn Pro Val Tyr Leu Val
65                  70                  75                  80

Asp Tyr Ser Cys Tyr Leu Pro Pro His Leu Arg Val Ser Val Ser
                85                  90                  95

Lys Val Met Asp Ile Phe Tyr Gln Ile Arg Lys Ala Asp Thr Ser Ser
                100                 105                 110

Arg Asn Gly Thr Cys Asp Asp Ser Ser Trp Leu Asp Phe Leu Arg Lys
            115                 120                 125

Ile Gln Glu Arg Ser Gly Leu Gly Asp Glu Thr His Gly Pro Glu Gly
        130                 135                 140

Leu Leu Gln Val Pro Pro Arg Lys Thr Phe Ala Ala Ala Arg Glu Glu
145                 150                 155                 160

Thr Glu Gln Val Ile Ile Gly Ala Leu Glu Asn Leu Phe Lys Asn Thr
                165                 170                 175

Asn Val Asn Pro Lys Asp Ile Gly Ile Leu Val Val Asn Ser Ser Met
            180                 185                 190

Phe Asn Pro Thr Pro Ser Leu Ser Ala Met Val Val Asn Thr Phe Lys
        195                 200                 205

Leu Arg Ser Asn Val Arg Ser Phe Asn Leu Gly Gly Met Gly Cys Ser
    210                 215                 220

Ala Gly Val Ile Ala Ile Asp Leu Ala Lys Asp Leu Leu His Val His
225                 230                 235                 240

Lys Asn Thr Tyr Ala Leu Val Val Ser Thr Glu Asn Ile Thr Tyr Asn
                245                 250                 255

Ile Tyr Ala Gly Asp Asn Arg Ser Met Met Val Ser Asn Cys Leu Phe
            260                 265                 270
```

```
Arg Val Gly Gly Ala Ala Ile Leu Leu Ser Asn Lys Pro Gly Asp Arg
            275                 280                 285

Arg Arg Ser Lys Tyr Glu Leu Val His Thr Val Arg Thr His Thr Gly
    290                 295                 300

Ala Asp Gly Lys Ser Phe Arg Cys Val Gln Gln Gly Asp Asp Glu Asn
305                 310                 315                 320

Gly Lys Ile Gly Val Ser Leu Ser Lys Asp Ile Thr Asp Val Ala Gly
                325                 330                 335

Arg Thr Val Lys Lys Asn Ile Ala Thr Leu Gly Pro Leu Ile Leu Pro
            340                 345                 350

Leu Ser Glu Lys Leu Leu Phe Phe Val Thr Phe Met Gly Lys Lys Leu
        355                 360                 365

Phe Lys Asp Lys Ile Lys His Tyr Tyr Val Pro Asp Phe Lys Leu Ala
    370                 375                 380

Ile Asp His Phe Cys Ile His Ala Gly Gly Arg Ala Val Ile Asp Val
385                 390                 395                 400

Leu Glu Lys Asn Leu Ala Leu Ala Pro Ile Asp Val Glu Ala Ser Arg
                405                 410                 415

Ser Thr Leu His Arg Phe Gly Asn Thr Ser Ser Ser Ile Trp Tyr
            420                 425                 430

Glu Leu Ala Tyr Ile Glu Ala Lys Gly Arg Met Lys Lys Gly Asn Lys
        435                 440                 445

Val Trp Gln Ile Ala Leu Gly Ser Gly Phe Lys Cys Asn Ser Ala Val
    450                 455                 460

Trp Val Ala Leu Asn Asn Val Lys Ala Ser Thr Asn Ser Pro Trp Glu
465                 470                 475                 480

His Cys Ile Asp Arg Tyr Pro Val Lys Ile Asp Ser Asp Ser Gly Lys
                485                 490                 495

Ser Glu Thr Arg Val Pro Asn Gly Arg Ser
            500                 505

<210> SEQ ID NO 15
<211> LENGTH: 1521
<212> TYPE: DNA
<213> ORGANISM: Artificial Sequence
<220> FEATURE:
<223> OTHER INFORMATION: 5' 342 bp from A. thaliana FAE1 (SEQ ID NO:1)
      and 3' 1179 bp from B. napus elongase KCS (SEQ ID
      NO:3), having a mutation at position 920;
      designated At114 G307D; hypothetical
<221> NAME/KEY: CDS
<222> LOCATION: (1)...(1518)

<400> SEQUENCE: 15 atg acg tcc gtt aac gtt aag ctc ctt tac cgt tat gtc tta acc aac    48
Met Thr Ser Val Asn Val Lys Leu Leu Tyr Arg Tyr Val Leu Thr Asn
1               5                   10                  15 ttt ttc aac ctc tgt ttg ttc ccg tta acg gcg ttc ctc gcc gga aaa    96
Phe Phe Asn Leu Cys Leu Phe Pro Leu Thr Ala Phe Leu Ala Gly Lys
            20                  25                  30 gcc tct cgg ctt acc ata aac gat ctc cac aac ttc ctt tcc tat ctc   144
Ala Ser Arg Leu Thr Ile Asn Asp Leu His Asn Phe Leu Ser Tyr Leu
        35                  40                  45 caa cac aac ctt ata aca gta act tta ctc ttt gct ttc act gtt ttc   192
Gln His Asn Leu Ile Thr Val Thr Leu Leu Phe Ala Phe Thr Val Phe
    50                  55                  60 ggt ttg gtt ctc tac atc gta acc cga ccc aat ccg gtt tat ctc gtt   240
Gly Leu Val Leu Tyr Ile Val Thr Arg Pro Asn Pro Val Tyr Leu Val
```

-continued

```
                65                  70                  75                  80
gac tac tcg tgt tac ctt ccg cca ccg cat ctc aaa gtt agt gtc tct         288
Asp Tyr Ser Cys Tyr Leu Pro Pro Pro His Leu Lys Val Ser Val Ser
                        85                  90                  95 aaa gtc atg gat att ttc tac caa ata aga aaa gct gat act tct tca         336
Lys Val Met Asp Ile Phe Tyr Gln Ile Arg Lys Ala Asp Thr Ser Ser
                100                 105                 110 cgg aac ggc acg tgt gat gat tcg tcg tgg ctt gac ttc ttg agg aag         384
Arg Asn Gly Thr Cys Asp Asp Ser Ser Trp Leu Asp Phe Leu Arg Lys
                115                 120                 125 att caa gaa cgt tca ggt cta ggc gat gaa act cac ggg ccc gag ggg         432
Ile Gln Glu Arg Ser Gly Leu Gly Asp Glu Thr His Gly Pro Glu Gly
                130                 135                 140 ctg ctt cag gtc cct ccc cgg aag act ttt gcg gcg gcg cgt gaa gag         480
Leu Leu Gln Val Pro Pro Arg Lys Thr Phe Ala Ala Ala Arg Glu Glu
145                 150                 155                 160 acg gag caa gtt atc att ggt gcg cta gaa aat cta ttc aag aac acc         528
Thr Glu Gln Val Ile Ile Gly Ala Leu Glu Asn Leu Phe Lys Asn Thr
                165                 170                 175 aac gtt aac cct aaa gat ata ggt ata ctt gtg gtg aac tca agc atg         576
Asn Val Asn Pro Lys Asp Ile Gly Ile Leu Val Val Asn Ser Ser Met
                180                 185                 190 ttt aat cca act cca tcg ctc tcc gcg atg gtc gtt aac act ttc aag         624
Phe Asn Pro Thr Pro Ser Leu Ser Ala Met Val Val Asn Thr Phe Lys
                195                 200                 205 ctc cga agc aac gta aga agc ttt aac ctt ggt ggc atg ggt tgt agt         672
Leu Arg Ser Asn Val Arg Ser Phe Asn Leu Gly Gly Met Gly Cys Ser
210                 215                 220 gcc ggc gtt ata gcc att gat cta gca aag gac ttg ttg cat gtc cat         720
Ala Gly Val Ile Ala Ile Asp Leu Ala Lys Asp Leu Leu His Val His
225                 230                 235                 240 aaa aat acg tat gct ctt gtg gtg agc aca gag aac atc act tat aac         768
Lys Asn Thr Tyr Ala Leu Val Val Ser Thr Glu Asn Ile Thr Tyr Asn
                245                 250                 255 att tac gct ggt gat aat agg tcc atg atg gtt tca aat tgc ttg ttc         816
Ile Tyr Ala Gly Asp Asn Arg Ser Met Met Val Ser Asn Cys Leu Phe
                260                 265                 270 cgt gtt ggt ggg gcc gct att ttg ctc tcc aac aag cct gga gat cgt         864
Arg Val Gly Gly Ala Ala Ile Leu Leu Ser Asn Lys Pro Gly Asp Arg
                275                 280                 285 aga cgg tcc aag tac gag cta gtt cac acg gtt cga acg cat acc gga         912
Arg Arg Ser Lys Tyr Glu Leu Val His Thr Val Arg Thr His Thr Gly
                290                 295                 300 gct gac gac aag tct ttt cgt tgc gtg caa caa gga gac gat gag aac         960
Ala Asp Asp Lys Ser Phe Arg Cys Val Gln Gln Gly Asp Asp Glu Asn
305                 310                 315                 320 ggc aaa atc gga gtg agt ttg tcc aag gac ata acc gat gtt gct ggt        1008
Gly Lys Ile Gly Val Ser Leu Ser Lys Asp Ile Thr Asp Val Ala Gly
                325                 330                 335 cga acg gtt aag aaa aac ata gca acg ttg ggt ccg ttg att ctt ccg        1056
Arg Thr Val Lys Lys Asn Ile Ala Thr Leu Gly Pro Leu Ile Leu Pro
                340                 345                 350 tta agc gag aaa ctt ctt ttt ttc gtt acc ttc atg ggc aag aaa ctt        1104
Leu Ser Glu Lys Leu Leu Phe Phe Val Thr Phe Met Gly Lys Lys Leu
                355                 360                 365 ttc aaa gat aaa atc aaa cat tac tac gtc ccg gat ttc aaa ctt gct        1152
Phe Lys Asp Lys Ile Lys His Tyr Tyr Val Pro Asp Phe Lys Leu Ala
                370                 375                 380 att gac cat ttt tgt ata cat gcc gga ggc aga gcc gtg att gat gtg        1200
```

```
Ile Asp His Phe Cys Ile His Ala Gly Gly Arg Ala Val Ile Asp Val
385                 390                 395                 400 cta gag aag aac cta gcc cta gca ccg atc gat gta gag gca tca aga      1248
Leu Glu Lys Asn Leu Ala Leu Ala Pro Ile Asp Val Glu Ala Ser Arg
                405                 410                 415 tca acg tta cat aga ttt gga aac act tca tct agc tca ata tgg tat      1296
Ser Thr Leu His Arg Phe Gly Asn Thr Ser Ser Ser Ser Ile Trp Tyr
                420                 425                 430 gag ttg gca tac ata gaa gca aaa gga agg atg aag aaa ggt aat aaa      1344
Glu Leu Ala Tyr Ile Glu Ala Lys Gly Arg Met Lys Lys Gly Asn Lys
                435                 440                 445 gtt tgg cag att gct tta ggg tca ggc ttt aag tgt aac agt gca gtt      1392
Val Trp Gln Ile Ala Leu Gly Ser Gly Phe Lys Cys Asn Ser Ala Val
        450                 455                 460 tgg gtg gct cta aac aat gtc aaa gct tcg aca aat agt cct tgg gaa      1440
Trp Val Ala Leu Asn Asn Val Lys Ala Ser Thr Asn Ser Pro Trp Glu
465                 470                 475                 480 cac tgc atc gac aga tac ccg gtc aaa att gat tct gat tca ggt aag      1488
His Cys Ile Asp Arg Tyr Pro Val Lys Ile Asp Ser Asp Ser Gly Lys
                485                 490                 495 tca gag act cgt gtc caa aac ggt cgg tcc taa                          1521
Ser Glu Thr Arg Val Gln Asn Gly Arg Ser
            500                 505

<210> SEQ ID NO 16
<211> LENGTH: 506
<212> TYPE: PRT
<213> ORGANISM: Artificial Sequence
<220> FEATURE:
<223> OTHER INFORMATION: 5' 114 amino acids from A. thaliana FAE1 (SEQ
      ID NO:2) and 3' 392 amino acids from B. napus
      elongase KCS (SEQ ID NO:4) having mutation at
      residue 307; designated At114 G307D; hypothetical

<400> SEQUENCE: 16

Met Thr Ser Val Asn Val Lys Leu Leu Tyr Arg Tyr Val Leu Thr Asn
1               5                   10                  15

Phe Phe Asn Leu Cys Leu Phe Pro Leu Thr Ala Phe Leu Ala Gly Lys
                20                  25                  30

Ala Ser Arg Leu Thr Ile Asn Asp Leu His Asn Phe Leu Ser Tyr Leu
            35                  40                  45

Gln His Asn Leu Ile Thr Val Thr Leu Leu Phe Ala Phe Thr Val Phe
        50                  55                  60

Gly Leu Val Leu Tyr Ile Val Thr Arg Pro Asn Pro Val Tyr Leu Val
65                  70                  75                  80

Asp Tyr Ser Cys Tyr Leu Pro Pro His Leu Lys Val Ser Val Ser
                85                  90                  95

Lys Val Met Asp Ile Phe Tyr Gln Ile Arg Lys Ala Asp Thr Ser Ser
                100                 105                 110

Arg Asn Gly Thr Cys Asp Asp Ser Ser Trp Leu Asp Phe Leu Arg Lys
            115                 120                 125

Ile Gln Glu Arg Ser Gly Leu Gly Asp Glu Thr His Gly Pro Glu Gly
        130                 135                 140

Leu Leu Gln Val Pro Pro Arg Lys Thr Phe Ala Ala Ala Arg Glu Glu
145                 150                 155                 160

Thr Glu Gln Val Ile Ile Gly Ala Leu Glu Asn Leu Phe Lys Asn Thr
                165                 170                 175

Asn Val Asn Pro Lys Asp Ile Gly Ile Leu Val Val Asn Ser Ser Met
            180                 185                 190
```

```
Phe Asn Pro Thr Pro Ser Leu Ser Ala Met Val Val Asn Thr Phe Lys
            195                 200                 205

Leu Arg Ser Asn Val Arg Ser Phe Asn Leu Gly Gly Met Gly Cys Ser
        210                 215                 220

Ala Gly Val Ile Ala Ile Asp Leu Ala Lys Asp Leu Leu His Val His
225                 230                 235                 240

Lys Asn Thr Tyr Ala Leu Val Val Ser Thr Glu Asn Ile Thr Tyr Asn
                245                 250                 255

Ile Tyr Ala Gly Asp Asn Arg Ser Met Met Val Ser Asn Cys Leu Phe
            260                 265                 270

Arg Val Gly Gly Ala Ala Ile Leu Leu Ser Asn Lys Pro Gly Asp Arg
        275                 280                 285

Arg Arg Ser Lys Tyr Glu Leu Val His Thr Val Arg Thr His Thr Gly
    290                 295                 300

Ala Asp Asp Lys Ser Phe Arg Cys Val Gln Gln Gly Asp Asp Glu Asn
305                 310                 315                 320

Gly Lys Ile Gly Val Ser Leu Ser Lys Asp Ile Thr Asp Val Ala Gly
                325                 330                 335

Arg Thr Val Lys Lys Asn Ile Ala Thr Leu Gly Pro Leu Ile Leu Pro
            340                 345                 350

Leu Ser Glu Lys Leu Leu Phe Phe Val Thr Phe Met Gly Lys Lys Leu
        355                 360                 365

Phe Lys Asp Lys Ile Lys His Tyr Tyr Val Pro Asp Phe Lys Leu Ala
    370                 375                 380

Ile Asp His Phe Cys Ile His Ala Gly Gly Arg Ala Val Ile Asp Val
385                 390                 395                 400

Leu Glu Lys Asn Leu Ala Leu Ala Pro Ile Asp Val Glu Ala Ser Arg
                405                 410                 415

Ser Thr Leu His Arg Phe Gly Asn Thr Ser Ser Ser Ile Trp Tyr
            420                 425                 430

Glu Leu Ala Tyr Ile Glu Ala Lys Gly Arg Met Lys Lys Gly Asn Lys
        435                 440                 445

Val Trp Gln Ile Ala Leu Gly Ser Gly Phe Lys Cys Asn Ser Ala Val
    450                 455                 460

Trp Val Ala Leu Asn Asn Val Lys Ala Ser Thr Asn Ser Pro Trp Glu
465                 470                 475                 480

His Cys Ile Asp Arg Tyr Pro Val Lys Ile Asp Ser Asp Ser Gly Lys
                485                 490                 495

Ser Glu Thr Arg Val Gln Asn Gly Arg Ser
            500                 505

<210> SEQ ID NO 17
<211> LENGTH: 1518
<212> TYPE: DNA
<213> ORGANISM: Artificial Sequence
<220> FEATURE:
<223> OTHER INFORMATION: 5' 222 bp from A. thaliana FAE1 (SEQ ID NO:1)
      and 3' 1296 bp from B. napus elongase KCS (SEQ ID
      NO:3) having a mutation at position 917;
      designated At74 G306D; hypothetical
<221> NAME/KEY: CDS
<222> LOCATION: (1)...(1515)

<400> SEQUENCE: 17 atg acg tcc gtt aac gtt aag ctc ctt tac cgt tac gtc tta acc aac    48
Met Thr Ser Val Asn Val Lys Leu Leu Tyr Arg Tyr Val Leu Thr Asn
1               5                   10                  15
```

```
ttt ttc aac ctc tgt ttg ttc ccg tta acg gcg ttc ctc gcc gga aaa        96
Phe Phe Asn Leu Cys Leu Phe Pro Leu Thr Ala Phe Leu Ala Gly Lys
             20                  25                  30 gcc tct cgg ctt acc ata aac gat ctc cac aac ttc ctt tcc tat ctc       144
Ala Ser Arg Leu Thr Ile Asn Asp Leu His Asn Phe Leu Ser Tyr Leu
         35                  40                  45 caa cac aac ctt ata aca gta act tta ctc ttt gct ttc act gtt ttc       192
Gln His Asn Leu Ile Thr Val Thr Leu Leu Phe Ala Phe Thr Val Phe
     50                  55                  60 ggt ttg gtt ctc tac atc gta acc cga ccc aaa ccg gtt tac ctc gtt       240
Gly Leu Val Leu Tyr Ile Val Thr Arg Pro Lys Pro Val Tyr Leu Val
 65                  70                  75                  80 gag tac tca tgc tac ctt cca cca acg cat tgt aga tca agt atc tcc       288
Glu Tyr Ser Cys Tyr Leu Pro Pro Thr His Cys Arg Ser Ser Ile Ser
                 85                  90                  95 aag gtc atg gat atc ttt tat caa gta aga aaa gct gat cct tct cgg       336
Lys Val Met Asp Ile Phe Tyr Gln Val Arg Lys Ala Asp Pro Ser Arg
            100                 105                 110 aac ggc acg tgc gat gac tcg tcg tgg ctt gac ttc ttg agg aag att       384
Asn Gly Thr Cys Asp Asp Ser Ser Trp Leu Asp Phe Leu Arg Lys Ile
        115                 120                 125 caa gaa cgt tca ggt cta ggc gat gaa act cac ggg ccc gag ggg ctg       432
Gln Glu Arg Ser Gly Leu Gly Asp Glu Thr His Gly Pro Glu Gly Leu
    130                 135                 140 ctt cag gtc cct ccc cgg aag act ttt gcg gcg gcg cgt gaa gag acg       480
Leu Gln Val Pro Pro Arg Lys Thr Phe Ala Ala Ala Arg Glu Glu Thr
145                 150                 155                 160 gag caa gtt atc att ggt gcg cta gaa aat cta ttc aag aac acc aac       528
Glu Gln Val Ile Ile Gly Ala Leu Glu Asn Leu Phe Lys Asn Thr Asn
                165                 170                 175 gtt aac cct aaa gat ata ggt ata ctt gtg gtg aac tca agc atg ttt       576
Val Asn Pro Lys Asp Ile Gly Ile Leu Val Val Asn Ser Ser Met Phe
            180                 185                 190 aat cca act cca tcg ctc tcc gcg atg gtc gtt aac act ttc aag ctc       624
Asn Pro Thr Pro Ser Leu Ser Ala Met Val Val Asn Thr Phe Lys Leu
        195                 200                 205 cga agc aac gta aga agc ttt aac ctt ggt ggc atg ggt tgt agt gcc       672
Arg Ser Asn Val Arg Ser Phe Asn Leu Gly Gly Met Gly Cys Ser Ala
    210                 215                 220 ggc gtt ata gcc att gat cta gca aag gac ttg ttg cat gtc cat aaa       720
Gly Val Ile Ala Ile Asp Leu Ala Lys Asp Leu Leu His Val His Lys
225                 230                 235                 240 aat acg tat gct ctt gtg gtg agc aca gag aac atc act tat aac att       768
Asn Thr Tyr Ala Leu Val Val Ser Thr Glu Asn Ile Thr Tyr Asn Ile
                245                 250                 255 tac gct ggt gat aat agg tcc atg atg gtt tca aat tgc ttg ttc cgt       816
Tyr Ala Gly Asp Asn Arg Ser Met Met Val Ser Asn Cys Leu Phe Arg
            260                 265                 270 gtt ggt ggg gcc gct att ttg ctc tcc aac aag cct gga gat cgt aga       864
Val Gly Gly Ala Ala Ile Leu Leu Ser Asn Lys Pro Gly Asp Arg Arg
        275                 280                 285 cgg tcc aag tac gag cta gtt cac acg gtt cga acg cat acc gga gct       912
Arg Ser Lys Tyr Glu Leu Val His Thr Val Arg Thr His Thr Gly Ala
    290                 295                 300 gac gac aag tct ttt cgt tgc gtg caa caa gga gac gat gag aac ggc       960
Asp Asp Lys Ser Phe Arg Cys Val Gln Gln Gly Asp Asp Glu Asn Gly
305                 310                 315                 320 aaa atc gga gtg agt ttg tcc aag gac ata acc gat gtt gct ggt cga      1008
Lys Ile Gly Val Ser Leu Ser Lys Asp Ile Thr Asp Val Ala Gly Arg
```

| | | |
|---|---|---|
| acg gtt aag aaa aac ata gca acg ttg ggt ccg ttg att ctt ccg tta | | 1056 |
| Thr Val Lys Lys Asn Ile Ala Thr Leu Gly Pro Leu Ile Leu Pro Leu | | |
| 325 330 335 | | |
| 340 | | | acg gtt aag aaa aac ata gca acg ttg ggt ccg ttg att ctt ccg tta    1056
Thr Val Lys Lys Asn Ile Ala Thr Leu Gly Pro Leu Ile Leu Pro Leu
            340             345             350 agc gag aaa ctt ctt ttt ttc gtt acc ttc atg ggc aag aaa ctt ttc    1104
Ser Glu Lys Leu Leu Phe Phe Val Thr Phe Met Gly Lys Lys Leu Phe
        355             360             365 aaa gat aaa atc aaa cat tac tac gtc ccg gat ttc aaa ctt gct att    1152
Lys Asp Lys Ile Lys His Tyr Tyr Val Pro Asp Phe Lys Leu Ala Ile
370             375             380 gac cat ttt tgt ata cat gcc gga ggc aga gcc gtg att gat gtg cta    1200
Asp His Phe Cys Ile His Ala Gly Gly Arg Ala Val Ile Asp Val Leu
385             390             395             400 gag aag aac cta gcc cta gca ccg atc gat gta gag gca tca aga tca    1248
Glu Lys Asn Leu Ala Leu Ala Pro Ile Asp Val Glu Ala Ser Arg Ser
        405             410             415 acg tta cat aga ttt gga aac act tca tct agc tca ata tgg tat gag    1296
Thr Leu His Arg Phe Gly Asn Thr Ser Ser Ser Ser Ile Trp Tyr Glu
            420             425             430 ttg gca tac ata gaa gca aaa gga agg atg aag aaa ggt aat aaa gtt    1344
Leu Ala Tyr Ile Glu Ala Lys Gly Arg Met Lys Lys Gly Asn Lys Val
        435             440             445 tgg cag att gct tta ggg tca ggc ttt aag tgt aac agt gca gtt tgg    1392
Trp Gln Ile Ala Leu Gly Ser Gly Phe Lys Cys Asn Ser Ala Val Trp
450             455             460 gtg gct cta aac aat gtc aaa gct tcg aca aat agt cct tgg gaa cac    1440
Val Ala Leu Asn Asn Val Lys Ala Ser Thr Asn Ser Pro Trp Glu His
465             470             475             480 tgc atc gac aga tac ccg gtc aaa att gat tct gat tca ggt aag tca    1488
Cys Ile Asp Arg Tyr Pro Val Lys Ile Asp Ser Asp Ser Gly Lys Ser
        485             490             495 gag act cgt gtc caa aac ggt cgg tcc taa                            1518
Glu Thr Arg Val Gln Asn Gly Arg Ser
            500             505

<210> SEQ ID NO 18
<211> LENGTH: 505
<212> TYPE: PRT
<213> ORGANISM: Artificial Sequence
<220> FEATURE:
<223> OTHER INFORMATION: 5' 74 amino acids from A. thaliana FAE1 (SEQ
      ID NO:2) and 3' 431 amino acids from B. napus
      elongase KCS (SEQ ID NO:4) having a mutation at
      residue 306; designated At74 G306D; hypothetical

<400> SEQUENCE: 18

Met Thr Ser Val Asn Val Lys Leu Leu Tyr Arg Tyr Val Leu Thr Asn
1               5                   10                  15

Phe Phe Asn Leu Cys Leu Phe Pro Leu Thr Ala Phe Leu Ala Gly Lys
            20                  25                  30

Ala Ser Arg Leu Thr Ile Asn Asp Leu His Asn Phe Leu Ser Tyr Leu
        35                  40                  45

Gln His Asn Leu Ile Thr Val Thr Leu Leu Phe Ala Phe Thr Val Phe
    50                  55                  60

Gly Leu Val Leu Tyr Ile Val Thr Arg Pro Lys Pro Val Tyr Leu Val
65                  70                  75                  80

Glu Tyr Ser Cys Tyr Leu Pro Pro Thr His Cys Arg Ser Ser Ile Ser
            85                  90                  95

Lys Val Met Asp Ile Phe Tyr Gln Val Arg Lys Ala Asp Pro Ser Arg
            100                 105                 110

```
Asn Gly Thr Cys Asp Asp Ser Ser Trp Leu Asp Phe Leu Arg Lys Ile
            115                 120                 125

Gln Glu Arg Ser Gly Leu Gly Asp Glu Thr His Gly Pro Glu Gly Leu
        130                 135                 140

Leu Gln Val Pro Pro Arg Lys Thr Phe Ala Ala Ala Arg Glu Glu Thr
145                 150                 155                 160

Glu Gln Val Ile Ile Gly Ala Leu Glu Asn Leu Phe Lys Asn Thr Asn
                165                 170                 175

Val Asn Pro Lys Asp Ile Gly Ile Leu Val Val Asn Ser Ser Met Phe
            180                 185                 190

Asn Pro Thr Pro Ser Leu Ser Ala Met Val Val Asn Thr Phe Lys Leu
        195                 200                 205

Arg Ser Asn Val Arg Ser Phe Asn Leu Gly Gly Met Gly Cys Ser Ala
    210                 215                 220

Gly Val Ile Ala Ile Asp Leu Ala Lys Asp Leu Leu His Val His Lys
225                 230                 235                 240

Asn Thr Tyr Ala Leu Val Val Ser Thr Glu Asn Ile Thr Tyr Asn Ile
                245                 250                 255

Tyr Ala Gly Asp Asn Arg Ser Met Met Val Ser Asn Cys Leu Phe Arg
            260                 265                 270

Val Gly Gly Ala Ala Ile Leu Leu Ser Asn Lys Pro Gly Asp Arg Arg
        275                 280                 285

Arg Ser Lys Tyr Glu Leu Val His Thr Val Arg Thr His Thr Gly Ala
    290                 295                 300

Asp Asp Lys Ser Phe Arg Cys Val Gln Gln Gly Asp Glu Asn Gly
305                 310                 315                 320

Lys Ile Gly Val Ser Leu Ser Lys Asp Ile Thr Asp Val Ala Gly Arg
                325                 330                 335

Thr Val Lys Lys Asn Ile Ala Thr Leu Gly Pro Leu Ile Leu Pro Leu
            340                 345                 350

Ser Glu Lys Leu Leu Phe Phe Val Thr Phe Met Gly Lys Lys Leu Phe
        355                 360                 365

Lys Asp Lys Ile Lys His Tyr Tyr Val Pro Asp Phe Lys Leu Ala Ile
    370                 375                 380

Asp His Phe Cys Ile His Ala Gly Gly Arg Ala Val Ile Asp Val Leu
385                 390                 395                 400

Glu Lys Asn Leu Ala Leu Ala Pro Ile Asp Val Glu Ala Ser Arg Ser
                405                 410                 415

Thr Leu His Arg Phe Gly Asn Thr Ser Ser Ser Ile Trp Tyr Glu
            420                 425                 430

Leu Ala Tyr Ile Glu Ala Lys Gly Arg Met Lys Lys Gly Asn Lys Val
        435                 440                 445

Trp Gln Ile Ala Leu Gly Ser Gly Phe Lys Cys Asn Ser Ala Val Trp
    450                 455                 460

Val Ala Leu Asn Asn Val Lys Ala Ser Thr Asn Ser Pro Trp Glu His
465                 470                 475                 480

Cys Ile Asp Arg Tyr Pro Val Lys Ile Asp Ser Asp Ser Gly Lys Ser
                485                 490                 495

Glu Thr Arg Val Gln Asn Gly Arg Ser
            500                 505

<210> SEQ ID NO 19
<211> LENGTH: 1521
```

```
<212> TYPE: DNA
<213> ORGANISM: Artificial Sequence
<220> FEATURE:
<223> OTHER INFORMATION: 5' 342 bp from A. thaliana FAE1 (SEQ ID NO:1)
      and 3' 1179 bp from B. napus elongase KCS (SEQ ID
      NO:3) having mutations at positions 271, 272, 275
      and 920; designated At114 L91C K92R G307D;
      hypothetical
<221> NAME/KEY: CDS
<222> LOCATION: (1)...(1518)

<400> SEQUENCE: 19
```

| | | | | | | | | | | | | | | | | |
|---|---|---|---|---|---|---|---|---|---|---|---|---|---|---|---|---|
| atg | acg | tcc | gtt | aac | gtt | aag | ctc | ctt | tac | cgt | tat | gtc | tta | acc | aac | 48 |
| Met | Thr | Ser | Val | Asn | Val | Lys | Leu | Leu | Tyr | Arg | Tyr | Val | Leu | Thr | Asn | |
| 1 | | | | 5 | | | | | 10 | | | | | 15 | | |
| ttt | ttc | aac | ctc | tgt | ttg | ttc | ccg | tta | acg | gcg | ttc | ctc | gcc | gga | aaa | 96 |
| Phe | Phe | Asn | Leu | Cys | Leu | Phe | Pro | Leu | Thr | Ala | Phe | Leu | Ala | Gly | Lys | |
| | | | 20 | | | | | 25 | | | | | 30 | | | |
| gcc | tct | cgg | ctt | acc | ata | aac | gat | ctc | cac | aac | ttc | ctt | tcc | tat | ctc | 144 |
| Ala | Ser | Arg | Leu | Thr | Ile | Asn | Asp | Leu | His | Asn | Phe | Leu | Ser | Tyr | Leu | |
| | | 35 | | | | | 40 | | | | | 45 | | | | |
| caa | cac | aac | ctt | ata | aca | gta | act | tta | ctc | ttt | gct | ttc | act | gtt | ttc | 192 |
| Gln | His | Asn | Leu | Ile | Thr | Val | Thr | Leu | Leu | Phe | Ala | Phe | Thr | Val | Phe | |
| | 50 | | | | | 55 | | | | | 60 | | | | | |
| ggt | ttg | gtt | ctc | tac | atc | gta | acc | cga | ccc | aat | ccg | gtt | tat | ctc | gtt | 240 |
| Gly | Leu | Val | Leu | Tyr | Ile | Val | Thr | Arg | Pro | Asn | Pro | Val | Tyr | Leu | Val | |
| 65 | | | | | 70 | | | | | 75 | | | | | 80 | |
| gac | tac | tcg | tgt | tac | ctt | ccg | cca | ccg | cat | tgc | aga | gtt | agt | gtc | tct | 288 |
| Asp | Tyr | Ser | Cys | Tyr | Leu | Pro | Pro | Pro | His | Cys | Arg | Val | Ser | Val | Ser | |
| | | | | 85 | | | | | 90 | | | | | 95 | | |
| aaa | gtc | atg | gat | att | ttc | tac | caa | ata | aga | aaa | gct | gat | act | tct | tca | 336 |
| Lys | Val | Met | Asp | Ile | Phe | Tyr | Gln | Ile | Arg | Lys | Ala | Asp | Thr | Ser | Ser | |
| | | | 100 | | | | | 105 | | | | | 110 | | | |
| cgg | aac | ggc | acg | tgt | gat | aat | tcg | tcg | tgg | ctt | gac | ttc | ttg | agg | aag | 384 |
| Arg | Asn | Gly | Thr | Cys | Asp | Asn | Ser | Ser | Trp | Leu | Asp | Phe | Leu | Arg | Lys | |
| | | | 115 | | | | | 120 | | | | | 125 | | | |
| att | caa | gaa | cgt | tca | ggt | cta | ggc | gat | gaa | act | cac | ggg | ccc | gag | ggg | 432 |
| Ile | Gln | Glu | Arg | Ser | Gly | Leu | Gly | Asp | Glu | Thr | His | Gly | Pro | Glu | Gly | |
| | 130 | | | | | 135 | | | | | 140 | | | | | |
| ctg | ctt | cag | gtc | cct | ccc | cgg | aag | act | ttt | gcg | gcg | gcg | cgt | gaa | gag | 480 |
| Leu | Leu | Gln | Val | Pro | Pro | Arg | Lys | Thr | Phe | Ala | Ala | Ala | Arg | Glu | Glu | |
| 145 | | | | | 150 | | | | | 155 | | | | | 160 | |
| acg | gag | caa | gtt | atc | att | ggt | gcg | cta | gaa | aat | cta | ttc | aag | aac | acc | 528 |
| Thr | Glu | Gln | Val | Ile | Ile | Gly | Ala | Leu | Glu | Asn | Leu | Phe | Lys | Asn | Thr | |
| | | | | 165 | | | | | 170 | | | | | 175 | | |
| aac | gtt | aac | cct | aaa | gat | ata | ggt | ata | ctt | gtg | gtg | aac | tca | agc | atg | 576 |
| Asn | Val | Asn | Pro | Lys | Asp | Ile | Gly | Ile | Leu | Val | Val | Asn | Ser | Ser | Met | |
| | | | 180 | | | | | 185 | | | | | 190 | | | |
| ttt | aat | cca | act | cca | tcg | ctc | tcc | gcg | atg | gtc | gtt | aac | act | ttc | aag | 624 |
| Phe | Asn | Pro | Thr | Pro | Ser | Leu | Ser | Ala | Met | Val | Val | Asn | Thr | Phe | Lys | |
| | | 195 | | | | | 200 | | | | | 205 | | | | |
| ctc | cga | agc | aac | gta | aga | agc | ttt | aac | ctt | ggt | ggc | atg | ggt | tgt | agt | 672 |
| Leu | Arg | Ser | Asn | Val | Arg | Ser | Phe | Asn | Leu | Gly | Gly | Met | Gly | Cys | Ser | |
| | 210 | | | | | 215 | | | | | 220 | | | | | |
| gcc | ggc | gtt | ata | gcc | att | gat | cta | gca | aag | gac | ttg | ttg | cat | gtc | cat | 720 |
| Ala | Gly | Val | Ile | Ala | Ile | Asp | Leu | Ala | Lys | Asp | Leu | Leu | His | Val | His | |
| 225 | | | | | 230 | | | | | 235 | | | | | 240 | |
| aaa | aat | acg | tat | gct | ctt | gtg | gtg | agc | aca | gag | aac | atc | act | tat | aac | 768 |
| Lys | Asn | Thr | Tyr | Ala | Leu | Val | Val | Ser | Thr | Glu | Asn | Ile | Thr | Tyr | Asn | |
| | | | | 245 | | | | | 250 | | | | | 255 | | |
| att | tac | gct | ggt | gat | aat | agg | tcc | atg | atg | gtt | tca | aat | tgc | ttg | ttc | 816 |
| Ile | Tyr | Ala | Gly | Asp | Asn | Arg | Ser | Met | Met | Val | Ser | Asn | Cys | Leu | Phe | |

```
cgt gtt ggt ggg gcc gct att ttg ctc tcc aac aag cct gga gat cgt        864
Arg Val Gly Gly Ala Ala Ile Leu Leu Ser Asn Lys Pro Gly Asp Arg
            275                 280                 285 aga cgg tcc aag tac gag cta gtt cac acg gtt cga acg cat acc gga        912
Arg Arg Ser Lys Tyr Glu Leu Val His Thr Val Arg Thr His Thr Gly
        290                 295                 300 gct gac gac aag tct ttt cgt tgc gtg caa caa gga gac gat gag aac        960
Ala Asp Asp Lys Ser Phe Arg Cys Val Gln Gln Gly Asp Asp Glu Asn
305                 310                 315                 320 ggc aaa atc gga gtg agt ttg tcc aag gac ata acc gat gtt gct ggt       1008
Gly Lys Ile Gly Val Ser Leu Ser Lys Asp Ile Thr Asp Val Ala Gly
            325                 330                 335 cga acg gtt aag aaa aac ata gca acg ttg ggt ccg ttg att ctt ccg       1056
Arg Thr Val Lys Lys Asn Ile Ala Thr Leu Gly Pro Leu Ile Leu Pro
            340                 345                 350 tta agc gag aaa ctt ctt ttt ttc gtt acc ttc atg ggc aag aaa ctt       1104
Leu Ser Glu Lys Leu Leu Phe Phe Val Thr Phe Met Gly Lys Lys Leu
        355                 360                 365 ttc aaa gat aaa atc aaa cat tac tac gtc ccg gat ttc aaa ctt gct       1152
Phe Lys Asp Lys Ile Lys His Tyr Tyr Val Pro Asp Phe Lys Leu Ala
370                 375                 380 att gac cat ttt tgt ata cat gcc gga ggc aga gcc gtg att gat gtg       1200
Ile Asp His Phe Cys Ile His Ala Gly Gly Arg Ala Val Ile Asp Val
385                 390                 395                 400 cta gag aag aac cta gcc cta gca ccg atc gat gta gag gca tca aga       1248
Leu Glu Lys Asn Leu Ala Leu Ala Pro Ile Asp Val Glu Ala Ser Arg
            405                 410                 415 tca acg tta cat aga ttt gga aac act tca tct agc tca ata tgg tat       1296
Ser Thr Leu His Arg Phe Gly Asn Thr Ser Ser Ser Ser Ile Trp Tyr
            420                 425                 430 gag ttg gca tac ata gaa gca aaa gga agg atg aag aaa ggt aat aaa       1344
Glu Leu Ala Tyr Ile Glu Ala Lys Gly Arg Met Lys Lys Gly Asn Lys
            435                 440                 445 gtt tgg cag att gct tta ggg tca ggc ttt aag tgt aac agt gca gtt       1392
Val Trp Gln Ile Ala Leu Gly Ser Gly Phe Lys Cys Asn Ser Ala Val
    450                 455                 460 tgg gtg gct cta aac aat gtc aaa gct tcg aca aat agt cct tgg gaa       1440
Trp Val Ala Leu Asn Asn Val Lys Ala Ser Thr Asn Ser Pro Trp Glu
465                 470                 475                 480 cac tgc atc gac aga tac ccg gtc aaa att gat tct gat tca ggt aag       1488
His Cys Ile Asp Arg Tyr Pro Val Lys Ile Asp Ser Asp Ser Gly Lys
                485                 490                 495 tca gag act cgt gtc caa aac ggt cgg tcc taa                           1521
Ser Glu Thr Arg Val Gln Asn Gly Arg Ser
                500                 505
```

<210> SEQ ID NO 20
<211> LENGTH: 506
<212> TYPE: PRT
<213> ORGANISM: Artificial Sequence
<220> FEATURE:
<223> OTHER INFORMATION: 5' 114 amino acids from A. thaliana FAE1 (SEQ
      ID NO:2) and 3' 392 amino acids from B. napus
      elongase KCS (SEQ ID NO:4) having mutations at
      positions 91, 92 and 307; designated At114 L91C
      K92R G307D; hypothetical

<400> SEQUENCE: 20

Met Thr Ser Val Asn Val Lys Leu Leu Tyr Arg Tyr Val Leu Thr Asn
1               5                   10                  15

-continued

```
Phe Phe Asn Leu Cys Leu Phe Pro Leu Thr Ala Phe Leu Ala Gly Lys
         20                  25                  30

Ala Ser Arg Leu Thr Ile Asn Asp Leu His Asn Phe Leu Ser Tyr Leu
         35                  40                  45

Gln His Asn Leu Ile Thr Val Thr Leu Leu Phe Ala Phe Thr Val Phe
         50                  55                  60

Gly Leu Val Leu Tyr Ile Val Thr Arg Pro Asn Pro Val Tyr Leu Val
 65                  70                  75                  80

Asp Tyr Ser Cys Tyr Leu Pro Pro His Cys Arg Val Ser Val Ser
                 85                  90                  95

Lys Val Met Asp Ile Phe Tyr Gln Ile Arg Lys Ala Asp Thr Ser Ser
                100                 105                 110

Arg Asn Gly Thr Cys Asp Asn Ser Ser Trp Leu Asp Phe Leu Arg Lys
                115                 120                 125

Ile Gln Glu Arg Ser Gly Leu Gly Asp Glu Thr His Gly Pro Glu Gly
                130                 135                 140

Leu Leu Gln Val Pro Pro Arg Lys Thr Phe Ala Ala Arg Glu Glu
145                 150                 155                 160

Thr Glu Gln Val Ile Ile Gly Ala Leu Glu Asn Leu Phe Lys Asn Thr
                165                 170                 175

Asn Val Asn Pro Lys Asp Ile Gly Ile Leu Val Val Asn Ser Ser Met
                180                 185                 190

Phe Asn Pro Thr Pro Ser Leu Ser Ala Met Val Val Asn Thr Phe Lys
                195                 200                 205

Leu Arg Ser Asn Val Arg Ser Phe Asn Leu Gly Gly Met Gly Cys Ser
                210                 215                 220

Ala Gly Val Ile Ala Ile Asp Leu Ala Lys Asp Leu Leu His Val His
225                 230                 235                 240

Lys Asn Thr Tyr Ala Leu Val Val Ser Thr Glu Asn Ile Thr Tyr Asn
                245                 250                 255

Ile Tyr Ala Gly Asp Asn Arg Ser Met Met Val Ser Asn Cys Leu Phe
                260                 265                 270

Arg Val Gly Gly Ala Ala Ile Leu Leu Ser Asn Lys Pro Gly Asp Arg
                275                 280                 285

Arg Arg Ser Lys Tyr Glu Leu Val His Thr Val Arg Thr His Thr Gly
                290                 295                 300

Ala Asp Asp Lys Ser Phe Arg Cys Val Gln Gln Gly Asp Asp Glu Asn
305                 310                 315                 320

Gly Lys Ile Gly Val Ser Leu Ser Lys Asp Ile Thr Asp Val Ala Gly
                325                 330                 335

Arg Thr Val Lys Lys Asn Ile Ala Thr Leu Gly Pro Leu Ile Leu Pro
                340                 345                 350

Leu Ser Glu Lys Leu Leu Phe Phe Val Thr Phe Met Gly Lys Lys Leu
                355                 360                 365

Phe Lys Asp Lys Ile Lys His Tyr Tyr Val Pro Asp Phe Lys Leu Ala
                370                 375                 380

Ile Asp His Phe Cys Ile His Ala Gly Gly Arg Ala Val Ile Asp Val
385                 390                 395                 400

Leu Glu Lys Asn Leu Ala Leu Ala Pro Ile Asp Val Glu Ala Ser Arg
                405                 410                 415

Ser Thr Leu His Arg Phe Gly Asn Thr Ser Ser Ser Ile Trp Tyr
                420                 425                 430

Glu Leu Ala Tyr Ile Glu Ala Lys Gly Arg Met Lys Lys Gly Asn Lys
```

```
                        435                 440                 445
        Val Trp Gln Ile Ala Leu Gly Ser Gly Phe Lys Cys Asn Ser Ala Val
            450                 455                 460

Trp Val Ala Leu Asn Asn Val Lys Ala Ser Thr Asn Ser Pro Trp Glu
        465                 470                 475                 480

His Cys Ile Asp Arg Tyr Pro Val Lys Ile Asp Ser Asp Ser Gly Lys
                        485                 490                 495

Ser Glu Thr Arg Val Gln Asn Gly Arg Ser
                    500                 505

<210> SEQ ID NO 21
<211> LENGTH: 1521
<212> TYPE: DNA
<213> ORGANISM: Artificial Sequence
<220> FEATURE:
<223> OTHER INFORMATION: 5' 342 bp from A. thaliana FAE1 (SEQ ID NO:1)
      and 3' 1179 bp from B. napus elongase KCS (SEQ ID
      NO:3) having mutations at positions 275 and 920;
      designated At114 K92R G307D; hypothetical
<221> NAME/KEY: CDS
<222> LOCATION: (1)...(1518)

<400> SEQUENCE: 21 atg acg tcc gtt aac gtt aag ctc ctt tac cgt tat gtc tta acc aac         48
Met Thr Ser Val Asn Val Lys Leu Leu Tyr Arg Tyr Val Leu Thr Asn
 1               5                  10                  15 ttt ttc aac ctc tgt ttg ttc ccg tta acg gcg ttc ctc gcc gga aaa         96
Phe Phe Asn Leu Cys Leu Phe Pro Leu Thr Ala Phe Leu Ala Gly Lys
                20                  25                  30 gcc tct cgg ctt acc ata aac gat ctc cac aac ttc ctt tcc tat ctc        144
Ala Ser Arg Leu Thr Ile Asn Asp Leu His Asn Phe Leu Ser Tyr Leu
            35                  40                  45 caa cac aac ctt ata aca gta act tta ctc ttt gct ttc act gtt ttc        192
Gln His Asn Leu Ile Thr Val Thr Leu Leu Phe Ala Phe Thr Val Phe
        50                  55                  60 ggt ttg gtt ctc tac atc gta acc cga ccc aat ccg gtt tat ctc gtt        240
Gly Leu Val Leu Tyr Ile Val Thr Arg Pro Asn Pro Val Tyr Leu Val
 65                  70                  75                  80 gac tac tcg tgt tac ctt ccg cca ccg cat ctc aga gtt agt gtc tct        288
Asp Tyr Ser Cys Tyr Leu Pro Pro Pro His Leu Arg Val Ser Val Ser
                85                  90                  95 aaa gtc atg gat att ttc tac caa ata aga aaa gct gat act tct tca        336
Lys Val Met Asp Ile Phe Tyr Gln Ile Arg Lys Ala Asp Thr Ser Ser
                100                 105                 110 cgg aac ggc acg tgt gat gat tcg tcg tgg ctt gac ttc ttg agg aag        384
Arg Asn Gly Thr Cys Asp Asp Ser Ser Trp Leu Asp Phe Leu Arg Lys
            115                 120                 125 att caa gaa cgt tca ggt cta ggc gat gaa act cac ggg ccc gag ggg        432
Ile Gln Glu Arg Ser Gly Leu Gly Asp Glu Thr His Gly Pro Glu Gly
        130                 135                 140 ctg ctt cag gtc cct ccc cgg aag act ttt gcg gcg gcg cgt gaa gag        480
Leu Leu Gln Val Pro Pro Arg Lys Thr Phe Ala Ala Ala Arg Glu Glu
145                 150                 155                 160 acg gag caa gtt atc att ggt gcg cta gaa aat cta ttc aag aac acc        528
Thr Glu Gln Val Ile Ile Gly Ala Leu Glu Asn Leu Phe Lys Asn Thr
                165                 170                 175 aac gtt aac cct aaa gat ata ggt ata ctt gtg gtg aac tca agc atg        576
Asn Val Asn Pro Lys Asp Ile Gly Ile Leu Val Val Asn Ser Ser Met
            180                 185                 190 ttt aat cca act cca tcg ctc tcc gcg atg gtc gtt aac act ttc aag        624
Phe Asn Pro Thr Pro Ser Leu Ser Ala Met Val Val Asn Thr Phe Lys
```

```
                    195                 200                 205
ctc cga agc aac gta aga agc ttt aac ctt ggt ggc atg ggt tgt agt         672
Leu Arg Ser Asn Val Arg Ser Phe Asn Leu Gly Gly Met Gly Cys Ser
    210                 215                 220 gcc ggc gtt ata gcc att gat cta gca aag gac ttg ttg cat gtc cat         720
Ala Gly Val Ile Ala Ile Asp Leu Ala Lys Asp Leu Leu His Val His
225                 230                 235                 240 aaa aat acg tat gct ctt gtg gtg agc aca gag aac atc act tat aac         768
Lys Asn Thr Tyr Ala Leu Val Val Ser Thr Glu Asn Ile Thr Tyr Asn
                245                 250                 255 att tac gct ggt gat aat agg tcc atg atg gtt tca aat tgc ttg ttc         816
Ile Tyr Ala Gly Asp Asn Arg Ser Met Met Val Ser Asn Cys Leu Phe
            260                 265                 270 cgt gtt ggt ggg gcc gct att ttg ctc tcc aac aag cct gga gat cgt         864
Arg Val Gly Gly Ala Ala Ile Leu Leu Ser Asn Lys Pro Gly Asp Arg
        275                 280                 285 aga cgg tcc aag tac gag cta gtt cac acg gtt cga acg cat acc gga         912
Arg Arg Ser Lys Tyr Glu Leu Val His Thr Val Arg Thr His Thr Gly
    290                 295                 300 gct gac gac aag tct ttt cgt tgc gtg caa caa gga gac gat gag aac         960
Ala Asp Asp Lys Ser Phe Arg Cys Val Gln Gln Gly Asp Asp Glu Asn
305                 310                 315                 320 ggc aaa atc gga gtg agt ttg tcc aag gac ata acc gat gtt gct ggt        1008
Gly Lys Ile Gly Val Ser Leu Ser Lys Asp Ile Thr Asp Val Ala Gly
                325                 330                 335 cga acg gtt aag aaa aac ata gca acg ttg ggt ccg ttg att ctt ccg        1056
Arg Thr Val Lys Lys Asn Ile Ala Thr Leu Gly Pro Leu Ile Leu Pro
            340                 345                 350 tta agc gag aaa ctt ctt ttt ttc gtt acc ttc atg ggc aag aaa ctt        1104
Leu Ser Glu Lys Leu Leu Phe Phe Val Thr Phe Met Gly Lys Lys Leu
        355                 360                 365 ttc aaa gat aaa atc aaa cat tac tac gtc ccg gat ttc aaa ctt gct        1152
Phe Lys Asp Lys Ile Lys His Tyr Tyr Val Pro Asp Phe Lys Leu Ala
    370                 375                 380 att gac cat ttt tgt ata cat gcc gga ggc aga gcc gtg att gat gtg        1200
Ile Asp His Phe Cys Ile His Ala Gly Gly Arg Ala Val Ile Asp Val
385                 390                 395                 400 cta gag aag aac cta gcc cta gca ccg atc gat gta gag gca tca aga        1248
Leu Glu Lys Asn Leu Ala Leu Ala Pro Ile Asp Val Glu Ala Ser Arg
                405                 410                 415 tca acg tta cat aga ttt gga aac act tca tct agc tca ata tgg tat        1296
Ser Thr Leu His Arg Phe Gly Asn Thr Ser Ser Ser Ser Ile Trp Tyr
            420                 425                 430 gag ttg gca tac ata gaa gca aaa gga agg atg aag aaa ggt aat aaa        1344
Glu Leu Ala Tyr Ile Glu Ala Lys Gly Arg Met Lys Lys Gly Asn Lys
        435                 440                 445 gtt tgg cag att gct tta ggg tca ggc ttt aag tgt aac agt gca gtt        1392
Val Trp Gln Ile Ala Leu Gly Ser Gly Phe Lys Cys Asn Ser Ala Val
    450                 455                 460 tgg gtg gct cta aac aat gtc aaa gct tcg aca aat agt cct tgg gaa        1440
Trp Val Ala Leu Asn Asn Val Lys Ala Ser Thr Asn Ser Pro Trp Glu
465                 470                 475                 480 cac tgc atc gac aga tac ccg gtc aaa att gat tct gat tca ggt aag        1488
His Cys Ile Asp Arg Tyr Pro Val Lys Ile Asp Ser Asp Ser Gly Lys
                485                 490                 495 tca gag act cgt gtc caa aac ggt cgg tcc taa                            1521
Ser Glu Thr Arg Val Gln Asn Gly Arg Ser
            500                 505
```

<210> SEQ ID NO 22
<211> LENGTH: 506
<212> TYPE: PRT
<213> ORGANISM: Artificial Sequence
<220> FEATURE:
<223> OTHER INFORMATION: 5' 114 amino acids from A. thaliana FAE1 (SEQ
ID NO:2) and 3' 392 amino acids from B. napus
elongase KCS (SEQ ID NO:4) having mutations at
positions 92 and 307; designated At114 K92R G307D;
hypothetical

<400> SEQUENCE: 22

```
Met Thr Ser Val Asn Val Lys Leu Leu Tyr Arg Tyr Val Leu Thr Asn
  1               5                  10                  15

Phe Phe Asn Leu Cys Leu Phe Pro Leu Thr Ala Phe Leu Ala Gly Lys
             20                  25                  30

Ala Ser Arg Leu Thr Ile Asn Asp Leu His Asn Phe Leu Ser Tyr Leu
         35                  40                  45

Gln His Asn Leu Ile Thr Val Thr Leu Leu Phe Ala Phe Thr Val Phe
     50                  55                  60

Gly Leu Val Leu Tyr Ile Val Thr Arg Pro Asn Pro Val Tyr Leu Val
 65                  70                  75                  80

Asp Tyr Ser Cys Tyr Leu Pro Pro Pro His Leu Arg Val Ser Val Ser
                 85                  90                  95

Lys Val Met Asp Ile Phe Tyr Gln Ile Arg Lys Ala Asp Thr Ser Ser
            100                 105                 110

Arg Asn Gly Thr Cys Asp Asp Ser Ser Trp Leu Asp Phe Leu Arg Lys
        115                 120                 125

Ile Gln Glu Arg Ser Gly Leu Gly Asp Glu Thr His Gly Pro Glu Gly
    130                 135                 140

Leu Leu Gln Val Pro Pro Arg Lys Thr Phe Ala Ala Ala Arg Glu Glu
145                 150                 155                 160

Thr Glu Gln Val Ile Ile Gly Ala Leu Glu Asn Leu Phe Lys Asn Thr
                165                 170                 175

Asn Val Asn Pro Lys Asp Ile Gly Ile Leu Val Val Asn Ser Ser Met
            180                 185                 190

Phe Asn Pro Thr Pro Ser Leu Ser Ala Met Val Val Asn Thr Phe Lys
        195                 200                 205

Leu Arg Ser Asn Val Arg Ser Phe Asn Leu Gly Gly Met Gly Cys Ser
    210                 215                 220

Ala Gly Val Ile Ala Ile Asp Leu Ala Lys Asp Leu Leu His Val His
225                 230                 235                 240

Lys Asn Thr Tyr Ala Leu Val Val Ser Thr Glu Asn Ile Thr Tyr Asn
                245                 250                 255

Ile Tyr Ala Gly Asp Asn Arg Ser Met Met Val Ser Asn Cys Leu Phe
            260                 265                 270

Arg Val Gly Gly Ala Ala Ile Leu Leu Ser Asn Lys Pro Gly Asp Arg
        275                 280                 285

Arg Arg Ser Lys Tyr Glu Leu Val His Thr Val Arg Thr His Thr Gly
    290                 295                 300

Ala Asp Asp Lys Ser Phe Arg Cys Val Gln Gln Gly Asp Asp Glu Asn
305                 310                 315                 320

Gly Lys Ile Gly Val Ser Leu Ser Lys Asp Ile Thr Asp Val Ala Gly
                325                 330                 335

Arg Thr Val Lys Lys Asn Ile Ala Thr Leu Gly Pro Leu Ile Leu Pro
            340                 345                 350
```

```
Leu Ser Glu Lys Leu Leu Phe Phe Val Thr Phe Met Gly Lys Lys Leu
            355                 360                 365

Phe Lys Asp Lys Ile Lys His Tyr Tyr Val Pro Asp Phe Lys Leu Ala
        370                 375                 380

Ile Asp His Phe Cys Ile His Ala Gly Gly Arg Ala Val Ile Asp Val
385                 390                 395                 400

Leu Glu Lys Asn Leu Ala Leu Ala Pro Ile Asp Val Glu Ala Ser Arg
                405                 410                 415

Ser Thr Leu His Arg Phe Gly Asn Thr Ser Ser Ser Ile Trp Tyr
            420                 425                 430

Glu Leu Ala Tyr Ile Glu Ala Lys Gly Arg Met Lys Lys Gly Asn Lys
        435                 440                 445

Val Trp Gln Ile Ala Leu Gly Ser Gly Phe Lys Cys Asn Ser Ala Val
    450                 455                 460

Trp Val Ala Leu Asn Asn Val Lys Ala Ser Thr Asn Ser Pro Trp Glu
465                 470                 475                 480

His Cys Ile Asp Arg Tyr Pro Val Lys Ile Asp Ser Asp Ser Gly Lys
            485                 490                 495

Ser Glu Thr Arg Val Gln Asn Gly Arg Ser
            500                 505

<210> SEQ ID NO 23
<211> LENGTH: 1521
<212> TYPE: DNA
<213> ORGANISM: Artificial Sequence
<220> FEATURE:
<223> OTHER INFORMATION: 5' 762 bp from A. thaliana FAE1 (SEQ ID NO:1)
      and 3' 759 bp from B. napus elongase KCS (SEQ ID
      NO:3); designated At254
<221> NAME/KEY: CDS
<222> LOCATION: (1)...(1518)

<400> SEQUENCE: 23 atg acg tcc gtt aac gtt aag ctc ctt tac cgt tac gtc tta acc aac      48
Met Thr Ser Val Asn Val Lys Leu Leu Tyr Arg Tyr Val Leu Thr Asn
1               5                   10                  15 ttt ttc aac ctc tgt ttg ttc ccg tta acg gcg ttc ctc gcc gga aaa      96
Phe Phe Asn Leu Cys Leu Phe Pro Leu Thr Ala Phe Leu Ala Gly Lys
            20                  25                  30 gcc tct cgg ctt acc ata aac gat ctc cac aac ctc ctt tcc tat ctc     144
Ala Ser Arg Leu Thr Ile Asn Asp Leu His Asn Leu Leu Ser Tyr Leu
        35                  40                  45 caa cac aac ctt ata aca gta act tta ctc ttt gct ttc act gtt ttc     192
Gln His Asn Leu Ile Thr Val Thr Leu Leu Phe Ala Phe Thr Val Phe
    50                  55                  60 ggt ttg gtt ctc tac atc gta acc cga ccc aat ccg gtt tat ctc gtt     240
Gly Leu Val Leu Tyr Ile Val Thr Arg Pro Asn Pro Val Tyr Leu Val
65                  70                  75                  80 gac tac tcg tgt tac ctt cca cca ccg cat ctc aaa gtt agt gtc tct     288
Asp Tyr Ser Cys Tyr Leu Pro Pro Pro His Leu Lys Val Ser Val Ser
                85                  90                  95 aaa gtc atg gat att ttc tac caa ata aga aaa gct gat act tct tca     336
Lys Val Met Asp Ile Phe Tyr Gln Ile Arg Lys Ala Asp Thr Ser Ser
            100                 105                 110 cgg aac gtg gca tgt gat gat ccg tcc tcg ctc gat ttc ctg agg aag     384
Arg Asn Val Ala Cys Asp Asp Pro Ser Ser Leu Asp Phe Leu Arg Lys
        115                 120                 125 att caa gag cgt tca ggt cta ggt gat gag acg tac agt cct gag gga     432
Ile Gln Glu Arg Ser Gly Leu Gly Asp Glu Thr Tyr Ser Pro Glu Gly
    130                 135                 140
```

```
ctc att cac gta cca ccg cgg aag act ttt gca gcg tca cgt gaa gag    480
Leu Ile His Val Pro Pro Arg Lys Thr Phe Ala Ala Ser Arg Glu Glu
145             150                 155                 160 aca gag aag gtt atc atc ggt gcg ctc gaa aat cta ttc gag aac acc    528
Thr Glu Lys Val Ile Ile Gly Ala Leu Glu Asn Leu Phe Glu Asn Thr
                165                 170                 175 aaa gtt aac cct aga gag att ggt ata ctt gtg gtg aac tca agc atg    576
Lys Val Asn Pro Arg Glu Ile Gly Ile Leu Val Val Asn Ser Ser Met
            180                 185                 190 ttt aat cca act cct tcg cta tcc gct atg gtc gtt aat act ttc aag    624
Phe Asn Pro Thr Pro Ser Leu Ser Ala Met Val Val Asn Thr Phe Lys
        195                 200                 205 ctc cga agc aac atc aaa agc ttt aat cta gga gga atg ggt tgt agt    672
Leu Arg Ser Asn Ile Lys Ser Phe Asn Leu Gly Gly Met Gly Cys Ser
    210                 215                 220 gct ggt gtt att gcc att gat ttg gct aaa gac ttg ttg cat gtt cat    720
Ala Gly Val Ile Ala Ile Asp Leu Ala Lys Asp Leu Leu His Val His
225                 230                 235                 240 aaa aac act tat gct ctc gtg gtg agc aca gag aac atc act tat aac    768
Lys Asn Thr Tyr Ala Leu Val Val Ser Thr Glu Asn Ile Thr Tyr Asn
                245                 250                 255 att tac gct ggt gat aat agg tcc atg atg gtt tca aat tgc ttg ttc    816
Ile Tyr Ala Gly Asp Asn Arg Ser Met Met Val Ser Asn Cys Leu Phe
            260                 265                 270 cgt gtt ggt ggg gcc gct att ttg ctc tcc aac aag cct gga gat cgt    864
Arg Val Gly Gly Ala Ala Ile Leu Leu Ser Asn Lys Pro Gly Asp Arg
        275                 280                 285 aga cgg tcc aag tac gag cta gtt cac acg gtt cga acg cat acc gga    912
Arg Arg Ser Lys Tyr Glu Leu Val His Thr Val Arg Thr His Thr Gly
    290                 295                 300 gct gac ggc aag tct ttt cgt tgc gtg caa caa gga gac gat gag aac    960
Ala Asp Gly Lys Ser Phe Arg Cys Val Gln Gln Gly Asp Asp Glu Asn
305                 310                 315                 320 ggc aaa atc gga gtg agt ttg tcc aag gac ata acc gat gtt gct ggt   1008
Gly Lys Ile Gly Val Ser Leu Ser Lys Asp Ile Thr Asp Val Ala Gly
                325                 330                 335 cga acg gtt aag aaa aac ata gca acg ttg ggt ccg ttg att ctt ccg   1056
Arg Thr Val Lys Lys Asn Ile Ala Thr Leu Gly Pro Leu Ile Leu Pro
            340                 345                 350 tta agc gag aaa ctt ctt ttt ttc gtt acc ttc atg ggc aag aaa ctt   1104
Leu Ser Glu Lys Leu Leu Phe Phe Val Thr Phe Met Gly Lys Lys Leu
        355                 360                 365 ttc aaa gat aaa atc aaa cat tac tac gtc ccg gat ttc aaa ctt gct   1152
Phe Lys Asp Lys Ile Lys His Tyr Tyr Val Pro Asp Phe Lys Leu Ala
    370                 375                 380 att gac cat ttt tgt ata cat gcc gga ggc aga gcc gtg att gat gtg   1200
Ile Asp His Phe Cys Ile His Ala Gly Gly Arg Ala Val Ile Asp Val
385                 390                 395                 400 cta gag aag aac cta gcc cta gca ccg atc gat gta gag gca tca aga   1248
Leu Glu Lys Asn Leu Ala Leu Ala Pro Ile Asp Val Glu Ala Ser Arg
                405                 410                 415 tca acg tta cat aga ttt gga aac act tca tct agc tca ata tgg tat   1296
Ser Thr Leu His Arg Phe Gly Asn Thr Ser Ser Ser Ser Ile Trp Tyr
            420                 425                 430 gag ttg gca tac ata gaa gca aaa gga agg atg aag aaa ggt aat aaa   1344
Glu Leu Ala Tyr Ile Glu Ala Lys Gly Arg Met Lys Lys Gly Asn Lys
        435                 440                 445 gtt tgg cag att gct tta ggg tca ggc ttt aag tgt aac agt gca gtt   1392
Val Trp Gln Ile Ala Leu Gly Ser Gly Phe Lys Cys Asn Ser Ala Val
```

```
                450                 455                 460
tgg gtg gct cta aac aat gtc aaa gct tcg aca aat agt cct tgg gaa    1440
Trp Val Ala Leu Asn Asn Val Lys Ala Ser Thr Asn Ser Pro Trp Glu
465                 470                 475                 480 cac tgc atc gac aga tac ccg gtc aaa att gat tct gat tca ggt aag    1488
His Cys Ile Asp Arg Tyr Pro Val Lys Ile Asp Ser Asp Ser Gly Lys
                485                 490                 495 tca gag act cgt gtc cca aac ggt cgg tcc taa                        1521
Ser Glu Thr Arg Val Pro Asn Gly Arg Ser
                500                 505
```

<210> SEQ ID NO 24
<211> LENGTH: 506
<212> TYPE: PRT
<213> ORGANISM: Artificial Sequence
<220> FEATURE:
<223> OTHER INFORMATION: 5' 254 amino acids from A. thaliana FAE1 (SEQ
      ID NO:2) and 3' 252 amino acids from B. napus
      elongase KCS (SEQ ID NO:4); designated At254

<400> SEQUENCE: 24

```
Met Thr Ser Val Asn Val Lys Leu Leu Tyr Arg Tyr Val Leu Thr Asn
1               5                   10                  15

Phe Phe Asn Leu Cys Leu Phe Pro Leu Thr Ala Phe Leu Ala Gly Lys
                20                  25                  30

Ala Ser Arg Leu Thr Ile Asn Asp Leu His Asn Leu Leu Ser Tyr Leu
            35                  40                  45

Gln His Asn Leu Ile Thr Val Thr Leu Leu Phe Ala Phe Thr Val Phe
        50                  55                  60

Gly Leu Val Leu Tyr Ile Val Thr Arg Pro Asn Pro Val Tyr Leu Val
65                  70                  75                  80

Asp Tyr Ser Cys Tyr Leu Pro Pro His Leu Lys Val Ser Val Ser
                85                  90                  95

Lys Val Met Asp Ile Phe Tyr Gln Ile Arg Lys Ala Asp Thr Ser Ser
                100                 105                 110

Arg Asn Val Ala Cys Asp Asp Pro Ser Ser Leu Asp Phe Leu Arg Lys
            115                 120                 125

Ile Gln Glu Arg Ser Gly Leu Gly Asp Glu Thr Tyr Ser Pro Glu Gly
        130                 135                 140

Leu Ile His Val Pro Pro Arg Lys Thr Phe Ala Ala Ser Arg Glu Glu
145                 150                 155                 160

Thr Glu Lys Val Ile Ile Gly Ala Leu Glu Asn Leu Phe Glu Asn Thr
                165                 170                 175

Lys Val Asn Pro Arg Glu Ile Gly Ile Leu Val Val Asn Ser Ser Met
                180                 185                 190

Phe Asn Pro Thr Pro Ser Leu Ser Ala Met Val Val Asn Thr Phe Lys
            195                 200                 205

Leu Arg Ser Asn Ile Lys Ser Phe Asn Leu Gly Gly Met Gly Cys Ser
        210                 215                 220

Ala Gly Val Ile Ala Ile Asp Leu Ala Lys Asp Leu Leu His Val His
225                 230                 235                 240

Lys Asn Thr Tyr Ala Leu Val Val Ser Thr Glu Asn Ile Thr Tyr Asn
                245                 250                 255

Ile Tyr Ala Gly Asp Asn Arg Ser Met Met Val Ser Asn Cys Leu Phe
                260                 265                 270

Arg Val Gly Gly Ala Ala Ile Leu Leu Ser Asn Lys Pro Gly Asp Arg
            275                 280                 285
```

```
Arg Arg Ser Lys Tyr Glu Leu Val His Thr Val Arg Thr His Thr Gly
    290                 295                 300

Ala Asp Gly Lys Ser Phe Arg Cys Val Gln Gln Gly Asp Asp Glu Asn
305                 310                 315                 320

Gly Lys Ile Gly Val Ser Leu Ser Lys Asp Ile Thr Asp Val Ala Gly
                325                 330                 335

Arg Thr Val Lys Lys Asn Ile Ala Thr Leu Gly Pro Leu Ile Leu Pro
                340                 345                 350

Leu Ser Glu Lys Leu Leu Phe Phe Val Thr Phe Met Gly Lys Lys Leu
            355                 360                 365

Phe Lys Asp Lys Ile Lys His Tyr Tyr Val Pro Asp Phe Lys Leu Ala
370                 375                 380

Ile Asp His Phe Cys Ile His Ala Gly Gly Arg Ala Val Ile Asp Val
385                 390                 395                 400

Leu Glu Lys Asn Leu Ala Leu Ala Pro Ile Asp Val Glu Ala Ser Arg
                405                 410                 415

Ser Thr Leu His Arg Phe Gly Asn Thr Ser Ser Ser Ile Trp Tyr
            420                 425                 430

Glu Leu Ala Tyr Ile Glu Ala Lys Gly Arg Met Lys Lys Gly Asn Lys
            435                 440                 445

Val Trp Gln Ile Ala Leu Gly Ser Gly Phe Lys Cys Asn Ser Ala Val
        450                 455                 460

Trp Val Ala Leu Asn Asn Val Lys Ala Ser Thr Asn Ser Pro Trp Glu
465                 470                 475                 480

His Cys Ile Asp Arg Tyr Pro Val Lys Ile Asp Ser Asp Ser Gly Lys
                485                 490                 495

Ser Glu Thr Arg Val Pro Asn Gly Arg Ser
                500                 505

<210> SEQ ID NO 25
<211> LENGTH: 1521
<212> TYPE: DNA
<213> ORGANISM: Artificial Sequence
<220> FEATURE:
<223> OTHER INFORMATION: 5' 519 bp from A. thaliana FAE1 (SEQ ID NO:1)
      and 3' 1002 bp from B. napus elongase KCS (SEQ ID
      NO:3); designated At173
<221> NAME/KEY: CDS
<222> LOCATION: (1)...(1518)

<400> SEQUENCE: 25 atg acg tcc gtt aac gtt aag ctc ctt tac cgt tac gtc tta acc aac        48
Met Thr Ser Val Asn Val Lys Leu Leu Tyr Arg Tyr Val Leu Thr Asn
1               5                   10                  15 ttt ttc aac ctc tgt ttg ttc ccg tta acg gcg ttc ctc gcc gga aaa        96
Phe Phe Asn Leu Cys Leu Phe Pro Leu Thr Ala Phe Leu Ala Gly Lys
            20                  25                  30 gcc tct cgg ctt acc ata aac gat ctc cac aac ttc ctt tcc tat ctc       144
Ala Ser Arg Leu Thr Ile Asn Asp Leu His Asn Phe Leu Ser Tyr Leu
        35                  40                  45 caa cac aac ctt ata aca gta act tta ctc ttt gct ttc act gtt ttc       192
Gln His Asn Leu Ile Thr Val Thr Leu Leu Phe Ala Phe Thr Val Phe
    50                  55                  60 ggt ttg gtt ctc tac atc gta acc cga ccc aat ccg gtt tat ctc gtt       240
Gly Leu Val Leu Tyr Ile Val Thr Arg Pro Asn Pro Val Tyr Leu Val
65                  70                  75                  80 gac tac tcg tgt tac ctt cca cca ccg cat ctc aaa gtt agt gtc tct       288
Asp Tyr Ser Cys Tyr Leu Pro Pro Pro His Leu Lys Val Ser Val Ser
```

-continued

| | | | | | | | | | | | | | | | |
|---|---|---|---|---|---|---|---|---|---|---|---|---|---|---|---|
| | | | | 85 | | | | 90 | | | | | 95 | | |
| aaa | gtc | atg | gat | att | ttc | tac | caa | ata | aga | aaa | gct | gat | act | tct | tca | 336 |
| Lys | Val | Met | Asp | Ile | Phe | Tyr | Gln | Ile | Arg | Lys | Ala | Asp | Thr | Ser | Ser | |
| | | | 100 | | | | | 105 | | | | 110 | | | | |
| cgg | aac | gtg | gca | tgt | gat | gat | ccg | tcc | tcg | ctc | gat | ttc | ctg | agg | aag | 384 |
| Arg | Asn | Val | Ala | Cys | Asp | Asp | Pro | Ser | Ser | Leu | Asp | Phe | Leu | Arg | Lys | |
| | | | 115 | | | | | 120 | | | | | 125 | | | |
| att | caa | gag | cgt | tca | ggt | cta | ggt | gat | gag | acg | tac | agt | cct | gag | gga | 432 |
| Ile | Gln | Glu | Arg | Ser | Gly | Leu | Gly | Asp | Glu | Thr | Tyr | Ser | Pro | Glu | Gly | |
| | | 130 | | | | | 135 | | | | | 140 | | | | |
| ctc | att | cac | gta | cca | ccg | cgg | aag | act | ttt | gca | gcg | tca | cgt | gaa | gag | 480 |
| Leu | Ile | His | Val | Pro | Pro | Arg | Lys | Thr | Phe | Ala | Ala | Ser | Arg | Glu | Glu | |
| 145 | | | | | 150 | | | | | 155 | | | | | 160 | |
| aca | gag | aag | gtt | atc | atc | ggt | gcg | ctc | gaa | aat | cta | ttc | aag | aac | acc | 528 |
| Thr | Glu | Lys | Val | Ile | Ile | Gly | Ala | Leu | Glu | Asn | Leu | Phe | Lys | Asn | Thr | |
| | | | | 165 | | | | | 170 | | | | | 175 | | |
| aac | gtt | aac | cct | aaa | gat | ata | ggt | ata | ctt | gtg | gtg | aac | tca | agc | atg | 576 |
| Asn | Val | Asn | Pro | Lys | Asp | Ile | Gly | Ile | Leu | Val | Val | Asn | Ser | Ser | Met | |
| | | | 180 | | | | | 185 | | | | | 190 | | | |
| ttt | aat | cca | act | cca | tcg | ctc | tcc | gcg | atg | gtc | gtt | aac | act | ttc | aag | 624 |
| Phe | Asn | Pro | Thr | Pro | Ser | Leu | Ser | Ala | Met | Val | Val | Asn | Thr | Phe | Lys | |
| | | 195 | | | | | 200 | | | | | 205 | | | | |
| ctc | cga | agc | aac | gta | aga | agc | ttt | aac | ctt | ggt | ggc | atg | ggt | tgt | agt | 672 |
| Leu | Arg | Ser | Asn | Val | Arg | Ser | Phe | Asn | Leu | Gly | Gly | Met | Gly | Cys | Ser | |
| | 210 | | | | | 215 | | | | | 220 | | | | | |
| gcc | ggc | gtt | ata | gcc | att | gat | cta | gca | aag | gac | ttg | ttg | cat | gtc | cat | 720 |
| Ala | Gly | Val | Ile | Ala | Ile | Asp | Leu | Ala | Lys | Asp | Leu | Leu | His | Val | His | |
| 225 | | | | | 230 | | | | | 235 | | | | | 240 | |
| aaa | aat | acg | tat | gct | ctt | gtg | gtg | agc | aca | gag | aac | atc | act | tat | aac | 768 |
| Lys | Asn | Thr | Tyr | Ala | Leu | Val | Val | Ser | Thr | Glu | Asn | Ile | Thr | Tyr | Asn | |
| | | | | 245 | | | | | 250 | | | | | 255 | | |
| att | tac | gct | ggt | gat | aat | agg | tcc | atg | atg | gtt | tca | aat | tgc | ttg | ttc | 816 |
| Ile | Tyr | Ala | Gly | Asp | Asn | Arg | Ser | Met | Met | Val | Ser | Asn | Cys | Leu | Phe | |
| | | | 260 | | | | | 265 | | | | | 270 | | | |
| cgt | gtt | ggt | ggg | gcc | gct | att | ttg | ctc | tcc | aac | aag | cct | gga | gat | cgt | 864 |
| Arg | Val | Gly | Gly | Ala | Ala | Ile | Leu | Leu | Ser | Asn | Lys | Pro | Gly | Asp | Arg | |
| | | 275 | | | | | 280 | | | | | 285 | | | | |
| aga | cgg | tcc | aag | tac | gag | cta | gtt | cac | acg | gtt | cga | acg | cat | acc | gga | 912 |
| Arg | Arg | Ser | Lys | Tyr | Glu | Leu | Val | His | Thr | Val | Arg | Thr | His | Thr | Gly | |
| | 290 | | | | | 295 | | | | | 300 | | | | | |
| gct | gac | ggc | aag | tct | ttt | cgt | tgc | gtg | caa | caa | gga | gac | gat | gag | aac | 960 |
| Ala | Asp | Gly | Lys | Ser | Phe | Arg | Cys | Val | Gln | Gln | Gly | Asp | Asp | Glu | Asn | |
| 305 | | | | | 310 | | | | | 315 | | | | | 320 | |
| ggc | aaa | atc | gga | gtg | agt | ttg | tcc | aag | gac | ata | acc | gat | gtt | gct | ggt | 1008 |
| Gly | Lys | Ile | Gly | Val | Ser | Leu | Ser | Lys | Asp | Ile | Thr | Asp | Val | Ala | Gly | |
| | | | | 325 | | | | | 330 | | | | | 335 | | |
| cga | acg | gtt | aag | aaa | aac | ata | gca | acg | ttg | ggt | ccg | ttg | att | ctt | ccg | 1056 |
| Arg | Thr | Val | Lys | Lys | Asn | Ile | Ala | Thr | Leu | Gly | Pro | Leu | Ile | Leu | Pro | |
| | | | 340 | | | | | 345 | | | | | 350 | | | |
| tta | agc | gag | aaa | ctt | ctt | ttt | ttc | gtt | acc | ttc | atg | ggc | aag | aaa | ctt | 1104 |
| Leu | Ser | Glu | Lys | Leu | Leu | Phe | Phe | Val | Thr | Phe | Met | Gly | Lys | Lys | Leu | |
| | | 355 | | | | | 360 | | | | | 365 | | | | |
| ttc | aaa | gat | aaa | atc | aaa | cat | tac | tac | gtc | ccg | gat | ttc | aaa | ctt | gct | 1152 |
| Phe | Lys | Asp | Lys | Ile | Lys | His | Tyr | Tyr | Val | Pro | Asp | Phe | Lys | Leu | Ala | |
| | 370 | | | | | 375 | | | | | 380 | | | | | |
| att | gac | cat | ttt | tgt | ata | cat | gcc | gga | ggc | aga | gcc | gtg | att | gat | gtg | 1200 |
| Ile | Asp | His | Phe | Cys | Ile | His | Ala | Gly | Gly | Arg | Ala | Val | Ile | Asp | Val | |
| 385 | | | | | 390 | | | | | 395 | | | | | 400 | |
| cta | gag | aag | aac | cta | gcc | cta | gca | ccg | atc | gat | gta | gag | gca | tca | aga | 1248 |

```
Leu Glu Lys Asn Leu Ala Leu Ala Pro Ile Asp Val Glu Ala Ser Arg
                405                 410                 415 tca acg tta cat aga ttt gga aac act tca tct agc tca ata tgg tat        1296
Ser Thr Leu His Arg Phe Gly Asn Thr Ser Ser Ser Ser Ile Trp Tyr
            420                 425                 430 gag ttg gca tac ata gaa gca aaa gga agg atg aag aaa ggt aat aaa        1344
Glu Leu Ala Tyr Ile Glu Ala Lys Gly Arg Met Lys Lys Gly Asn Lys
            435                 440                 445 gtt tgg cag att gct tta ggg tca ggc ttt aag tgt aac agt gca gtt        1392
Val Trp Gln Ile Ala Leu Gly Ser Gly Phe Lys Cys Asn Ser Ala Val
450                 455                 460 tgg gtg gct cta aac aat gtc aaa gct tcg aca aat agt cct tgg gaa        1440
Trp Val Ala Leu Asn Asn Val Lys Ala Ser Thr Asn Ser Pro Trp Glu
465                 470                 475                 480 cac tgc atc gac aga tac ccg gtc aaa att gat tct gat tca ggt aag        1488
His Cys Ile Asp Arg Tyr Pro Val Lys Ile Asp Ser Asp Ser Gly Lys
                485                 490                 495 tca gag act cgt gtc cma aac ggt cgg tcc taa                            1521
Ser Glu Thr Arg Val Xaa Asn Gly Arg Ser
                500                 505
```

<210> SEQ ID NO 26
<211> LENGTH: 506
<212> TYPE: PRT
<213> ORGANISM: Artificial Sequence
<220> FEATURE:
<223> OTHER INFORMATION: 5' 173 amino acids from A. thaliana FAE1 (SEQ
      ID NO:2) and 3' 333 amino acids from B. napus
      elongase KCS (SEQ ID NO:4); designated At173
<221> NAME/KEY: VARIANT
<222> LOCATION: (0)...(0)
<223> OTHER INFORMATION: Xaa = Pro or Gln

<400> SEQUENCE: 26

```
Met Thr Ser Val Asn Val Lys Leu Leu Tyr Arg Tyr Val Leu Thr Asn
1               5                   10                  15

Phe Phe Asn Leu Cys Leu Phe Pro Leu Thr Ala Phe Leu Ala Gly Lys
                20                  25                  30

Ala Ser Arg Leu Thr Ile Asn Asp Leu His Asn Phe Leu Ser Tyr Leu
            35                  40                  45

Gln His Asn Leu Ile Thr Val Thr Leu Leu Phe Ala Phe Thr Val Phe
        50                  55                  60

Gly Leu Val Leu Tyr Ile Val Thr Arg Pro Asn Pro Val Tyr Leu Val
65                  70                  75                  80

Asp Tyr Ser Cys Tyr Leu Pro Pro His Leu Lys Val Ser Val Ser
                85                  90                  95

Lys Val Met Asp Ile Phe Tyr Gln Ile Arg Lys Ala Asp Thr Ser Ser
                100                 105                 110

Arg Asn Val Ala Cys Asp Asp Pro Ser Ser Leu Asp Phe Leu Arg Lys
            115                 120                 125

Ile Gln Glu Arg Ser Gly Leu Gly Asp Glu Thr Tyr Ser Pro Glu Gly
        130                 135                 140

Leu Ile His Val Pro Pro Arg Lys Thr Phe Ala Ala Ser Arg Glu Glu
145                 150                 155                 160

Thr Glu Lys Val Ile Ile Gly Ala Leu Glu Asn Leu Phe Lys Asn Thr
                165                 170                 175

Asn Val Asn Pro Lys Asp Ile Gly Ile Leu Val Val Asn Ser Ser Met
            180                 185                 190

Phe Asn Pro Thr Pro Ser Leu Ser Ala Met Val Val Asn Thr Phe Lys
```

```
                195                 200                 205
Leu Arg Ser Asn Val Arg Ser Phe Asn Leu Gly Gly Met Gly Cys Ser
    210                 215                 220

Ala Gly Val Ile Ala Ile Asp Leu Ala Lys Asp Leu Leu His Val His
225                 230                 235                 240

Lys Asn Thr Tyr Ala Leu Val Val Ser Thr Glu Asn Ile Thr Tyr Asn
                245                 250                 255

Ile Tyr Ala Gly Asp Asn Arg Ser Met Met Val Ser Asn Cys Leu Phe
            260                 265                 270

Arg Val Gly Gly Ala Ala Ile Leu Leu Ser Asn Lys Pro Gly Asp Arg
        275                 280                 285

Arg Arg Ser Lys Tyr Glu Leu Val His Thr Val Arg Thr His Thr Gly
290                 295                 300

Ala Asp Gly Lys Ser Phe Arg Cys Val Gln Gln Gly Asp Asp Glu Asn
305                 310                 315                 320

Gly Lys Ile Gly Val Ser Leu Ser Lys Asp Ile Thr Asp Val Ala Gly
                325                 330                 335

Arg Thr Val Lys Lys Asn Ile Ala Thr Leu Gly Pro Leu Ile Leu Pro
            340                 345                 350

Leu Ser Glu Lys Leu Leu Phe Phe Val Thr Phe Met Gly Lys Lys Leu
        355                 360                 365

Phe Lys Asp Lys Ile Lys His Tyr Tyr Val Pro Asp Phe Lys Leu Ala
370                 375                 380

Ile Asp His Phe Cys Ile His Ala Gly Gly Arg Ala Val Ile Asp Val
385                 390                 395                 400

Leu Glu Lys Asn Leu Ala Leu Ala Pro Ile Asp Val Glu Ala Ser Arg
                405                 410                 415

Ser Thr Leu His Arg Phe Gly Asn Thr Ser Ser Ser Ile Trp Tyr
            420                 425                 430

Glu Leu Ala Tyr Ile Glu Ala Lys Gly Arg Met Lys Lys Gly Asn Lys
        435                 440                 445

Val Trp Gln Ile Ala Leu Gly Ser Gly Phe Lys Cys Asn Ser Ala Val
    450                 455                 460

Trp Val Ala Leu Asn Asn Val Lys Ala Ser Thr Asn Ser Pro Trp Glu
465                 470                 475                 480

His Cys Ile Asp Arg Tyr Pro Val Lys Ile Asp Ser Asp Ser Gly Lys
                485                 490                 495

Ser Glu Thr Arg Val Xaa Asn Gly Arg Ser
            500                 505

<210> SEQ ID NO 27
<211> LENGTH: 1521
<212> TYPE: DNA
<213> ORGANISM: Artificial Sequence
<220> FEATURE:
<223> OTHER INFORMATION: 5' 528 bp from B. napus elongase KCS (SEQ ID
      NO:3) and 3' 993 bp from A. thaliana FAE (SEQ ID NO:1);
      designated Bn176
<221> NAME/KEY: CDS
<222> LOCATION: (1)...(1518)

<400> SEQUENCE: 27 atg acg tcc att aac gta aag ctc ctt tac cat tac gtc ata acc aac        48
Met Thr Ser Ile Asn Val Lys Leu Leu Tyr His Tyr Val Ile Thr Asn
 1               5                  10                  15 ctt ttc aac ctt tgc ttc ttt ccg tta acg gcg atc gtc gcc gga aaa        96
Leu Phe Asn Leu Cys Phe Phe Pro Leu Thr Ala Ile Val Ala Gly Lys
```

-continued

```
             20                  25                  30
gcc tat cgg ctt acc ata gac gat ctt cac cac tta tac tat tcc tat       144
Ala Tyr Arg Leu Thr Ile Asp Asp Leu His His Leu Tyr Tyr Ser Tyr
         35                  40                  45 ctc caa cac aac ctc ata acc atc gct cca ctc ttt gcc ttc acc gtt       192
Leu Gln His Asn Leu Ile Thr Ile Ala Pro Leu Phe Ala Phe Thr Val
     50                  55                  60 ttc ggt tcg gtt ctc tac atc gca acc cgg ccc aaa ccg gtt tac ctc       240
Phe Gly Ser Val Leu Tyr Ile Ala Thr Arg Pro Lys Pro Val Tyr Leu
 65                  70                  75                  80 gtt gag tac tca tgc tac ctt cca cca acg cat tgt aga tca agt atc       288
Val Glu Tyr Ser Cys Tyr Leu Pro Pro Thr His Cys Arg Ser Ser Ile
                     85                  90                  95 tcc aag gtc atg gat atc ttt tat caa gta aga aaa gct gat cct tct       336
Ser Lys Val Met Asp Ile Phe Tyr Gln Val Arg Lys Ala Asp Pro Ser
                 100                 105                 110 cgg aac ggc acg tgc gat gac tcg tcg tgg ctt gac ttc ttg agg aag       384
Arg Asn Gly Thr Cys Asp Asp Ser Ser Trp Leu Asp Phe Leu Arg Lys
             115                 120                 125 att caa gaa cgt tca ggt cta ggc gat gaa act cac ggg ccc gag ggg       432
Ile Gln Glu Arg Ser Gly Leu Gly Asp Glu Thr His Gly Pro Glu Gly
     130                 135                 140 ctg ctt cag gtc cct ccc cgg aag act ttt gcg gcg gcg cgt gaa gag       480
Leu Leu Gln Val Pro Pro Arg Lys Thr Phe Ala Ala Ala Arg Glu Glu
145                 150                 155                 160 acg gag caa gtt atc att ggt gcg cta gaa aat cta ttc aag aac acc       528
Thr Glu Gln Val Ile Ile Gly Ala Leu Glu Asn Leu Phe Lys Asn Thr
                 165                 170                 175 aaa gtt aac cct aga gag att ggt ata ctt gtg gtg aac tca agc atg       576
Lys Val Asn Pro Arg Glu Ile Gly Ile Leu Val Val Asn Ser Ser Met
             180                 185                 190 ttt aat cca act cct tcg cta tcc gct atg gtc gtt aat act ttc aag       624
Phe Asn Pro Thr Pro Ser Leu Ser Ala Met Val Val Asn Thr Phe Lys
         195                 200                 205 ctc cga agc aac atc aaa agc ttt aat cta gga gga atg ggt tgt agt       672
Leu Arg Ser Asn Ile Lys Ser Phe Asn Leu Gly Gly Met Gly Cys Ser
     210                 215                 220 gct ggt gtt att gcc att gat ttg gct aaa gac ttg ttg cat gtt cat       720
Ala Gly Val Ile Ala Ile Asp Leu Ala Lys Asp Leu Leu His Val His
225                 230                 235                 240 aaa aac act tat gct ctt gtg gtg agc act gag aac atc aca caa ggc       768
Lys Asn Thr Tyr Ala Leu Val Val Ser Thr Glu Asn Ile Thr Gln Gly
                 245                 250                 255 att tat gct gga gaa aat aga tca atg atg gtt agc aat tgc ttg ttt       816
Ile Tyr Ala Gly Glu Asn Arg Ser Met Met Val Ser Asn Cys Leu Phe
             260                 265                 270 cgt gtt ggt ggg gcc gcg att ttg ctc tct aac aag tcg gga gac cgg       864
Arg Val Gly Gly Ala Ala Ile Leu Leu Ser Asn Lys Ser Gly Asp Arg
         275                 280                 285 aga cgg tcc aag tac aag cta gtt cac acg gtc cga acg cat act gga       912
Arg Arg Ser Lys Tyr Lys Leu Val His Thr Val Arg Thr His Thr Gly
     290                 295                 300 gct gat gac aag tct ttt cga tgt gtg caa caa gaa gat gat gag agc       960
Ala Asp Asp Lys Ser Phe Arg Cys Val Gln Gln Glu Asp Asp Glu Ser
305                 310                 315                 320 ggc aaa atc gga gtt tgt ctg tca aag gac ata acc aat gtt gcg ggg      1008
Gly Lys Ile Gly Val Cys Leu Ser Lys Asp Ile Thr Asn Val Ala Gly
                 325                 330                 335 aca aca ctt acg aaa aat ata gca aca ttg ggt ccg ttg att ctt cct      1056
```

```
Thr Thr Leu Thr Lys Asn Ile Ala Thr Leu Gly Pro Leu Ile Leu Pro
            340                 345                 350 tta agc gaa aag ttt ctt ttt ttc gct acc ttc gtc gcc aag aaa ctt      1104
Leu Ser Glu Lys Phe Leu Phe Phe Ala Thr Phe Val Ala Lys Lys Leu
            355                 360                 365 cta aag gat aaa atc aag cat tac tat gtt ccg gat ttc aag ctt gct      1152
Leu Lys Asp Lys Ile Lys His Tyr Tyr Val Pro Asp Phe Lys Leu Ala
        370                 375                 380 gtt gac cat ttc tgt att cat gcc gga ggc aga gcc gtg atc gat gag      1200
Val Asp His Phe Cys Ile His Ala Gly Gly Arg Ala Val Ile Asp Glu
385                 390                 395                 400 cta gag aag aac tta gga cta tcg ccg atc gat gtg gag gca tct aga      1248
Leu Glu Lys Asn Leu Gly Leu Ser Pro Ile Asp Val Glu Ala Ser Arg
                405                 410                 415 tca acg tta cat aga ttt ggg aat act tca tct agc tca att tgg tat      1296
Ser Thr Leu His Arg Phe Gly Asn Thr Ser Ser Ser Ser Ile Trp Tyr
            420                 425                 430 gaa tta gca tac ata gag gca aag gga aga atg aag aaa ggg aat aaa      1344
Glu Leu Ala Tyr Ile Glu Ala Lys Gly Arg Met Lys Lys Gly Asn Lys
            435                 440                 445 gct tgg cag att gct tta gga tca ggg ttt aag tgt aat agt gcg gtt      1392
Ala Trp Gln Ile Ala Leu Gly Ser Gly Phe Lys Cys Asn Ser Ala Val
        450                 455                 460 tgg gtg gct cta cgc aat gtc aag gca tcg gca aat agt cct tgg caa      1440
Trp Val Ala Leu Arg Asn Val Lys Ala Ser Ala Asn Ser Pro Trp Gln
465                 470                 475                 480 cat tgc atc gat aga tat ccg gtt aaa att gat tct gat ttg tca aag      1488
His Cys Ile Asp Arg Tyr Pro Val Lys Ile Asp Ser Asp Leu Ser Lys
                485                 490                 495 tca aag act cat gtc caa aac ggt cgg tcc taa                          1521
Ser Lys Thr His Val Gln Asn Gly Arg Ser
            500                 505

<210> SEQ ID NO 28
<211> LENGTH: 506
<212> TYPE: PRT
<213> ORGANISM: Artificial Sequence
<220> FEATURE:
<223> OTHER INFORMATION: 5' 176 amino acids from B. napus elongase KCS
      (SEQ ID NO:4) and 3' 330 amino acids from A. thaliana
      FAE1 (SEQ ID NO:2); designated Bn176

<400> SEQUENCE: 28

Met Thr Ser Ile Asn Val Lys Leu Leu Tyr His Tyr Val Ile Thr Asn
1               5                   10                  15

Leu Phe Asn Leu Cys Phe Phe Pro Leu Thr Ala Ile Val Ala Gly Lys
            20                  25                  30

Ala Tyr Arg Leu Thr Ile Asp Asp Leu His His Leu Tyr Tyr Ser Tyr
        35                  40                  45

Leu Gln His Asn Leu Ile Thr Ile Ala Pro Leu Phe Ala Phe Thr Val
    50                  55                  60

Phe Gly Ser Val Leu Tyr Ile Ala Thr Arg Pro Lys Pro Val Tyr Leu
65                  70                  75                  80

Val Glu Tyr Ser Cys Tyr Leu Pro Pro Thr His Cys Arg Ser Ser Ile
                85                  90                  95

Ser Lys Val Met Asp Ile Phe Tyr Gln Val Arg Lys Ala Asp Pro Ser
            100                 105                 110

Arg Asn Gly Thr Cys Asp Asp Ser Ser Trp Leu Asp Phe Leu Arg Lys
        115                 120                 125
```

-continued

```
Ile Gln Glu Arg Ser Gly Leu Gly Asp Glu Thr His Gly Pro Glu Gly
    130                 135                 140

Leu Leu Gln Val Pro Pro Arg Lys Thr Phe Ala Ala Arg Glu Glu
145                 150                 155                 160

Thr Glu Gln Val Ile Ile Gly Ala Leu Glu Asn Leu Phe Lys Asn Thr
                    165                 170                 175

Lys Val Asn Pro Arg Glu Ile Gly Ile Leu Val Val Asn Ser Ser Met
                180                 185                 190

Phe Asn Pro Thr Pro Ser Leu Ser Ala Met Val Val Asn Thr Phe Lys
            195                 200                 205

Leu Arg Ser Asn Ile Lys Ser Phe Asn Leu Gly Gly Met Gly Cys Ser
    210                 215                 220

Ala Gly Val Ile Ala Ile Asp Leu Ala Lys Asp Leu Leu His Val His
225                 230                 235                 240

Lys Asn Thr Tyr Ala Leu Val Val Ser Thr Glu Asn Ile Thr Gln Gly
                    245                 250                 255

Ile Tyr Ala Gly Glu Asn Arg Ser Met Met Val Ser Asn Cys Leu Phe
                260                 265                 270

Arg Val Gly Gly Ala Ala Ile Leu Leu Ser Asn Lys Ser Gly Asp Arg
            275                 280                 285

Arg Arg Ser Lys Tyr Lys Leu Val His Thr Val Arg Thr His Thr Gly
    290                 295                 300

Ala Asp Asp Lys Ser Phe Arg Cys Val Gln Gln Glu Asp Asp Glu Ser
305                 310                 315                 320

Gly Lys Ile Gly Val Cys Leu Ser Lys Asp Ile Thr Asn Val Ala Gly
                    325                 330                 335

Thr Thr Leu Thr Lys Asn Ile Ala Thr Leu Gly Pro Leu Ile Leu Pro
                340                 345                 350

Leu Ser Glu Lys Phe Leu Phe Phe Ala Thr Phe Val Ala Lys Lys Leu
            355                 360                 365

Leu Lys Asp Lys Ile Lys His Tyr Tyr Val Pro Asp Phe Lys Leu Ala
    370                 375                 380

Val Asp His Phe Cys Ile His Ala Gly Gly Arg Ala Val Ile Asp Glu
385                 390                 395                 400

Leu Glu Lys Asn Leu Gly Leu Ser Pro Ile Asp Val Glu Ala Ser Arg
                    405                 410                 415

Ser Thr Leu His Arg Phe Gly Asn Thr Ser Ser Ser Ile Trp Tyr
                420                 425                 430

Glu Leu Ala Tyr Ile Glu Ala Lys Gly Arg Met Lys Lys Gly Asn Lys
            435                 440                 445

Ala Trp Gln Ile Ala Leu Gly Ser Gly Phe Lys Cys Asn Ser Ala Val
    450                 455                 460

Trp Val Ala Leu Arg Asn Val Lys Ala Ser Ala Asn Ser Pro Trp Gln
465                 470                 475                 480

His Cys Ile Asp Arg Tyr Pro Val Lys Ile Asp Ser Asp Leu Ser Lys
                    485                 490                 495

Ser Lys Thr His Val Gln Asn Gly Arg Ser
                500                 505
```

<210> SEQ ID NO 29
<211> LENGTH: 1521
<212> TYPE: DNA
<213> ORGANISM: Artificial Sequence
<220> FEATURE:
<223> OTHER INFORMATION: 5' 1197 bp from A. thaliana FAE1 (SEQ ID NO:1)

and 3' 324 bp from B. napus elongase KCS (SEQ ID
NO:3); designated At399
<221> NAME/KEY: CDS
<222> LOCATION: (1)...(1518)

<400> SEQUENCE: 29

| | | | | | | | | | | | | | | | | |
|---|---|---|---|---|---|---|---|---|---|---|---|---|---|---|---|---|
| atg | acg | tcc | gtt | aac | gtt | aag | ctc | ctt | tac | cgt | tac | gtc | tta | acc | aac | 48 |
| Met | Thr | Ser | Val | Asn | Val | Lys | Leu | Leu | Tyr | Arg | Tyr | Val | Leu | Thr | Asn | |
| 1 | | | | 5 | | | | | 10 | | | | | 15 | | |

| ttt | ttc | aac | ctc | tgt | ttg | ttc | ccg | tta | acg | gcg | ttc | ctc | gcc | gga | aaa | 96 |
|---|---|---|---|---|---|---|---|---|---|---|---|---|---|---|---|---|
| Phe | Phe | Asn | Leu | Cys | Leu | Phe | Pro | Leu | Thr | Ala | Phe | Leu | Ala | Gly | Lys | |
| | | | 20 | | | | | 25 | | | | | 30 | | | |

| gcc | tct | cgg | ctt | acc | ata | aac | gat | ctc | cac | aac | ttc | ctt | tcc | tat | ctc | 144 |
|---|---|---|---|---|---|---|---|---|---|---|---|---|---|---|---|---|
| Ala | Ser | Arg | Leu | Thr | Ile | Asn | Asp | Leu | His | Asn | Phe | Leu | Ser | Tyr | Leu | |
| | | 35 | | | | | 40 | | | | | 45 | | | | |

| caa | cac | aac | ctt | ata | aca | gta | act | tta | ctc | ttt | gct | ttc | act | gtt | ttc | 192 |
|---|---|---|---|---|---|---|---|---|---|---|---|---|---|---|---|---|
| Gln | His | Asn | Leu | Ile | Thr | Val | Thr | Leu | Leu | Phe | Ala | Phe | Thr | Val | Phe | |
| 50 | | | | | 55 | | | | | 60 | | | | | | |

| ggt | ttg | gtt | ctc | tac | atc | gta | acc | cga | ccc | aat | ccg | gtt | tat | ctc | gtt | 240 |
|---|---|---|---|---|---|---|---|---|---|---|---|---|---|---|---|---|
| Gly | Leu | Val | Leu | Tyr | Ile | Val | Thr | Arg | Pro | Asn | Pro | Val | Tyr | Leu | Val | |
| 65 | | | | | 70 | | | | | 75 | | | | | 80 | |

| gac | tac | tcg | tgt | tac | ctt | cca | cca | ccg | cat | ctc | aaa | gtt | agt | gtc | tct | 288 |
|---|---|---|---|---|---|---|---|---|---|---|---|---|---|---|---|---|
| Asp | Tyr | Ser | Cys | Tyr | Leu | Pro | Pro | Pro | His | Leu | Lys | Val | Ser | Val | Ser | |
| | | | | 85 | | | | | 90 | | | | | 95 | | |

| aaa | gtc | atg | gat | att | ttc | tac | caa | ata | aga | aaa | gct | gat | act | tct | tca | 336 |
|---|---|---|---|---|---|---|---|---|---|---|---|---|---|---|---|---|
| Lys | Val | Met | Asp | Ile | Phe | Tyr | Gln | Ile | Arg | Lys | Ala | Asp | Thr | Ser | Ser | |
| | | | 100 | | | | | 105 | | | | | 110 | | | |

| cgg | aac | gtg | gca | tgt | gat | gat | ccg | tcc | tcg | ctc | gat | ttc | ctg | agg | aag | 384 |
|---|---|---|---|---|---|---|---|---|---|---|---|---|---|---|---|---|
| Arg | Asn | Val | Ala | Cys | Asp | Asp | Pro | Ser | Ser | Leu | Asp | Phe | Leu | Arg | Lys | |
| | | 115 | | | | | 120 | | | | | 125 | | | | |

| att | caa | gag | cgt | tca | ggt | cta | ggt | gat | gag | acg | tac | agt | cct | gag | gga | 432 |
|---|---|---|---|---|---|---|---|---|---|---|---|---|---|---|---|---|
| Ile | Gln | Glu | Arg | Ser | Gly | Leu | Gly | Asp | Glu | Thr | Tyr | Ser | Pro | Glu | Gly | |
| 130 | | | | | 135 | | | | | 140 | | | | | | |

| ctc | att | cac | gta | cca | ccg | cgg | aag | act | ttt | gca | gcg | tca | cgt | gaa | gag | 480 |
|---|---|---|---|---|---|---|---|---|---|---|---|---|---|---|---|---|
| Leu | Ile | His | Val | Pro | Pro | Arg | Lys | Thr | Phe | Ala | Ala | Ser | Arg | Glu | Glu | |
| 145 | | | | | 150 | | | | | 155 | | | | | 160 | |

| aca | gag | aag | gtt | atc | atc | ggt | gcg | ctc | gaa | aat | cta | ttc | gag | aac | acc | 528 |
|---|---|---|---|---|---|---|---|---|---|---|---|---|---|---|---|---|
| Thr | Glu | Lys | Val | Ile | Ile | Gly | Ala | Leu | Glu | Asn | Leu | Phe | Glu | Asn | Thr | |
| | | | | 165 | | | | | 170 | | | | | 175 | | |

| aaa | gtt | aac | cct | aga | gag | att | ggt | ata | ctt | gtg | gtg | aac | tca | agc | atg | 576 |
|---|---|---|---|---|---|---|---|---|---|---|---|---|---|---|---|---|
| Lys | Val | Asn | Pro | Arg | Glu | Ile | Gly | Ile | Leu | Val | Val | Asn | Ser | Ser | Met | |
| | | | 180 | | | | | 185 | | | | | 190 | | | |

| ttt | aat | cca | act | cct | tcg | cta | tcc | gct | atg | gtc | gtt | aat | act | ttc | aag | 624 |
|---|---|---|---|---|---|---|---|---|---|---|---|---|---|---|---|---|
| Phe | Asn | Pro | Thr | Pro | Ser | Leu | Ser | Ala | Met | Val | Val | Asn | Thr | Phe | Lys | |
| | | 195 | | | | | 200 | | | | | 205 | | | | |

| ctc | cga | agc | aac | atc | aaa | agc | ttt | aat | cta | gga | gga | atg | ggt | tgt | agt | 672 |
|---|---|---|---|---|---|---|---|---|---|---|---|---|---|---|---|---|
| Leu | Arg | Ser | Asn | Ile | Lys | Ser | Phe | Asn | Leu | Gly | Gly | Met | Gly | Cys | Ser | |
| 210 | | | | | 215 | | | | | 220 | | | | | | |

| gct | ggt | gtt | att | gcc | att | gat | ttg | gct | aaa | gac | ttg | ttg | cat | gtt | cat | 720 |
|---|---|---|---|---|---|---|---|---|---|---|---|---|---|---|---|---|
| Ala | Gly | Val | Ile | Ala | Ile | Asp | Leu | Ala | Lys | Asp | Leu | Leu | His | Val | His | |
| 225 | | | | | 230 | | | | | 235 | | | | | 240 | |

| aaa | aac | act | tat | gct | ctt | gtg | gtg | agc | act | gag | aac | atc | aca | caa | ggc | 768 |
|---|---|---|---|---|---|---|---|---|---|---|---|---|---|---|---|---|
| Lys | Asn | Thr | Tyr | Ala | Leu | Val | Val | Ser | Thr | Glu | Asn | Ile | Thr | Gln | Gly | |
| | | | | 245 | | | | | 250 | | | | | 255 | | |

| att | tat | gct | gga | gaa | aat | aga | tca | atg | atg | gtt | agc | aat | tgc | ttg | ttt | 816 |
|---|---|---|---|---|---|---|---|---|---|---|---|---|---|---|---|---|
| Ile | Tyr | Ala | Gly | Glu | Asn | Arg | Ser | Met | Met | Val | Ser | Asn | Cys | Leu | Phe | |
| | | | 260 | | | | | 265 | | | | | 270 | | | |

| cgt | gtt | ggt | ggg | gcc | gcg | att | ttg | ctc | tct | aac | aag | tcg | gga | gac | cgg | 864 |
|---|---|---|---|---|---|---|---|---|---|---|---|---|---|---|---|---|
| Arg | Val | Gly | Gly | Ala | Ala | Ile | Leu | Leu | Ser | Asn | Lys | Ser | Gly | Asp | Arg | |
| | | 275 | | | | | 280 | | | | | 285 | | | | |

```
aga cgg tcc aag tac aag cta gtt cac acg gtc cga acg cat act gga        912
Arg Arg Ser Lys Tyr Lys Leu Val His Thr Val Arg Thr His Thr Gly
    290                 295                 300 gct gat gac aag tct ttt cga tgt gtg caa caa gaa gac gat gag agc        960
Ala Asp Asp Lys Ser Phe Arg Cys Val Gln Gln Glu Asp Asp Glu Ser
305                 310                 315                 320 ggc aaa atc gga gtt tgt ctg tca aag gac ata acc aat gtt gcg ggg       1008
Gly Lys Ile Gly Val Cys Leu Ser Lys Asp Ile Thr Asn Val Ala Gly
                325                 330                 335 aca aca ctt acg aaa aat ata gca aca ttg ggt ccg ttg att ctt cct       1056
Thr Thr Leu Thr Lys Asn Ile Ala Thr Leu Gly Pro Leu Ile Leu Pro
            340                 345                 350 tta agc gaa aag ttt ctt ttt ttc gct acc ttc gtc gcc aag aaa ctt       1104
Leu Ser Glu Lys Phe Leu Phe Phe Ala Thr Phe Val Ala Lys Lys Leu
        355                 360                 365 cta aag gat aaa atc aag cat tac tat gtt ccg gat ttc aag ctt gct       1152
Leu Lys Asp Lys Ile Lys His Tyr Tyr Val Pro Asp Phe Lys Leu Ala
    370                 375                 380 gtt gac cat ttc tgt att cat gcc gga ggc aga gcc gtg atc gat gtg       1200
Val Asp His Phe Cys Ile His Ala Gly Gly Arg Ala Val Ile Asp Val
385                 390                 395                 400 cta gag aag aac cta gcc cta gca ccg atc gat gta gag gca tca aga       1248
Leu Glu Lys Asn Leu Ala Leu Ala Pro Ile Asp Val Glu Ala Ser Arg
                405                 410                 415 tca acg tta cat aga ttt gga aac act tca tct agc tca ata tgg tat       1296
Ser Thr Leu His Arg Phe Gly Asn Thr Ser Ser Ser Ser Ile Trp Tyr
            420                 425                 430 gag ttg gca tac ata gaa gca aaa gga agg atg aag aaa ggt aat aaa       1344
Glu Leu Ala Tyr Ile Glu Ala Lys Gly Arg Met Lys Lys Gly Asn Lys
        435                 440                 445 gtt tgg cag att gct tta ggg tca ggc ttt aag tgt aac agt gca gtt       1392
Val Trp Gln Ile Ala Leu Gly Ser Gly Phe Lys Cys Asn Ser Ala Val
    450                 455                 460 tgg gtg gct cta aac aat gtc aaa gct tcg aca aat agt cct tgg gaa       1440
Trp Val Ala Leu Asn Asn Val Lys Ala Ser Thr Asn Ser Pro Trp Glu
465                 470                 475                 480 cac tgc atc gac aga tac ccg gtc aaa att gat tct gat tca ggt aag       1488
His Cys Ile Asp Arg Tyr Pro Val Lys Ile Asp Ser Asp Ser Gly Lys
                485                 490                 495 tca gag act cgt gtc cma aac ggt cgg tcc taa                           1521
Ser Glu Thr Arg Val Xaa Asn Gly Arg Ser
            500                 505

<210> SEQ ID NO 30
<211> LENGTH: 506
<212> TYPE: PRT
<213> ORGANISM: Artificial Sequence
<220> FEATURE:
<223> OTHER INFORMATION: 5' 399 amino acids from A. thaliana FAE1 (SEQ
      ID NO:2) and 3' 107 amino acids from B. napus
      elongase KCS (SEQ ID NO:4); designated At399
<221> NAME/KEY: VARIANT
<222> LOCATION: (0)...(0)
<223> OTHER INFORMATION: Xaa = Pro or Gln

<400> SEQUENCE: 30

Met Thr Ser Val Asn Val Lys Leu Leu Tyr Arg Tyr Val Leu Thr Asn
1               5                   10                  15

Phe Phe Asn Leu Cys Leu Phe Pro Leu Thr Ala Phe Leu Ala Gly Lys
            20                  25                  30

Ala Ser Arg Leu Thr Ile Asn Asp Leu His Asn Phe Leu Ser Tyr Leu
        35                  40                  45
```

-continued

```
Gln His Asn Leu Ile Thr Val Thr Leu Leu Phe Ala Phe Thr Val Phe
 50                  55                  60

Gly Leu Val Leu Tyr Ile Val Thr Arg Pro Asn Pro Val Tyr Leu Val
 65                  70                  75                  80

Asp Tyr Ser Cys Tyr Leu Pro Pro His Leu Lys Val Ser Val Ser
                 85                  90                  95

Lys Val Met Asp Ile Phe Tyr Gln Ile Arg Lys Ala Asp Thr Ser Ser
            100                 105                 110

Arg Asn Val Ala Cys Asp Asp Pro Ser Ser Leu Asp Phe Leu Arg Lys
                115                 120                 125

Ile Gln Glu Arg Ser Gly Leu Gly Asp Glu Thr Tyr Ser Pro Glu Gly
130                 135                 140

Leu Ile His Val Pro Pro Arg Lys Thr Phe Ala Ala Ser Arg Glu Glu
145                 150                 155                 160

Thr Glu Lys Val Ile Ile Gly Ala Leu Glu Asn Leu Phe Glu Asn Thr
                165                 170                 175

Lys Val Asn Pro Arg Glu Ile Gly Ile Leu Val Val Asn Ser Ser Met
            180                 185                 190

Phe Asn Pro Thr Pro Ser Leu Ser Ala Met Val Val Asn Thr Phe Lys
        195                 200                 205

Leu Arg Ser Asn Ile Lys Ser Phe Asn Leu Gly Gly Met Gly Cys Ser
210                 215                 220

Ala Gly Val Ile Ala Ile Asp Leu Ala Lys Asp Leu Leu His Val His
225                 230                 235                 240

Lys Asn Thr Tyr Ala Leu Val Val Ser Thr Glu Asn Ile Thr Gln Gly
                245                 250                 255

Ile Tyr Ala Gly Glu Asn Arg Ser Met Met Val Ser Asn Cys Leu Phe
            260                 265                 270

Arg Val Gly Gly Ala Ala Ile Leu Leu Ser Asn Lys Ser Gly Asp Arg
        275                 280                 285

Arg Arg Ser Lys Tyr Lys Leu Val His Thr Val Arg Thr His Thr Gly
290                 295                 300

Ala Asp Asp Lys Ser Phe Arg Cys Val Gln Gln Glu Asp Asp Glu Ser
305                 310                 315                 320

Gly Lys Ile Gly Val Cys Leu Ser Lys Asp Ile Thr Asn Val Ala Gly
                325                 330                 335

Thr Thr Leu Thr Lys Asn Ile Ala Thr Leu Gly Pro Leu Ile Leu Pro
            340                 345                 350

Leu Ser Glu Lys Phe Leu Phe Phe Ala Thr Phe Val Ala Lys Lys Leu
        355                 360                 365

Leu Lys Asp Lys Ile Lys His Tyr Tyr Val Pro Asp Phe Lys Leu Ala
370                 375                 380

Val Asp His Phe Cys Ile His Ala Gly Gly Arg Ala Val Ile Asp Val
385                 390                 395                 400

Leu Glu Lys Asn Leu Ala Leu Ala Pro Ile Asp Val Glu Ala Ser Arg
                405                 410                 415

Ser Thr Leu His Arg Phe Gly Asn Thr Ser Ser Ser Ile Trp Tyr
            420                 425                 430

Glu Leu Ala Tyr Ile Glu Ala Lys Gly Arg Met Lys Lys Gly Asn Lys
        435                 440                 445

Val Trp Gln Ile Ala Leu Gly Ser Gly Phe Lys Cys Asn Ser Ala Val
450                 455                 460
```

```
Trp Val Ala Leu Asn Asn Val Lys Ala Ser Thr Asn Ser Pro Trp Glu
465                 470                 475                 480

His Cys Ile Asp Arg Tyr Pro Val Lys Ile Asp Ser Asp Ser Gly Lys
            485                 490                 495

Ser Glu Thr Arg Val Xaa Asn Gly Arg Ser
            500                 505

<210> SEQ ID NO 31
<211> LENGTH: 1521
<212> TYPE: DNA
<213> ORGANISM: Artificial Sequence
<220> FEATURE:
<223> OTHER INFORMATION: 5' 1197 bp from B. napus elongase KCS (SEQ ID
      NO:3) and 3' 324 bp from A. thaliana FAE1 (SEQ ID
      NO:1); designated Bn399
<221> NAME/KEY: CDS
<222> LOCATION: (1)...(1518)

<400> SEQUENCE: 31 atg acg tcc att aac gtt aag ctc ctt tac cat tac gtc ata acc aac      48
Met Thr Ser Ile Asn Val Lys Leu Leu Tyr His Tyr Val Ile Thr Asn
1               5                   10                  15 ctt ttc aac ctt tgc ttc ttt ccg tta acg gcg atc gtc gcc gga aaa     96
Leu Phe Asn Leu Cys Phe Phe Pro Leu Thr Ala Ile Val Ala Gly Lys
                20                  25                  30 gcc tat cgg ctt acc ata gac gat ctt cac cac tta tac tat tcc tat    144
Ala Tyr Arg Leu Thr Ile Asp Asp Leu His His Leu Tyr Tyr Ser Tyr
            35                  40                  45 ctc caa cac aac ctc ata acc atc gct cca ctc ttt gcc ttc acc gtt    192
Leu Gln His Asn Leu Ile Thr Ile Ala Pro Leu Phe Ala Phe Thr Val
        50                  55                  60 ttc ggt tcg gtt ctc tac atc gca acc cgg ccc aaa ccg gtt tac ctc    240
Phe Gly Ser Val Leu Tyr Ile Ala Thr Arg Pro Lys Pro Val Tyr Leu
65                  70                  75                  80 gtt gag tac tca tgc tac ctt cca cca acg cat tgt aga tca agt atc    288
Val Glu Tyr Ser Cys Tyr Leu Pro Pro Thr His Cys Arg Ser Ser Ile
                85                  90                  95 tcc aag gtc atg gat atc ttt tat caa gta aga aaa gct gat cct tct    336
Ser Lys Val Met Asp Ile Phe Tyr Gln Val Arg Lys Ala Asp Pro Ser
            100                 105                 110 cgg aac ggc acg tgc gat gac tcg tcg tgg ctt gac ttc ttg agg aag    384
Arg Asn Gly Thr Cys Asp Asp Ser Ser Trp Leu Asp Phe Leu Arg Lys
        115                 120                 125 att caa gaa cgt tca ggt cta ggc gat gaa act cac ggg ccc gag ggg    432
Ile Gln Glu Arg Ser Gly Leu Gly Asp Glu Thr His Gly Pro Glu Gly
    130                 135                 140 ctg ctt cag gtc cct ccc cgg aag act ttt gcg gcg gcg cgt gaa gag    480
Leu Leu Gln Val Pro Pro Arg Lys Thr Phe Ala Ala Ala Arg Glu Glu
145                 150                 155                 160 acg gag caa gtt atc att ggt gcg cta gaa aat cta ttc aag aac acc    528
Thr Glu Gln Val Ile Ile Gly Ala Leu Glu Asn Leu Phe Lys Asn Thr
                165                 170                 175 aac gtt aac cct aaa gat ata ggt ata ctt gtg gtg aac tca agc atg    576
Asn Val Asn Pro Lys Asp Ile Gly Ile Leu Val Val Asn Ser Ser Met
            180                 185                 190 ttt aat cca act cca tcg ctc tcc gcg atg gtc gtt aac act ttc aag    624
Phe Asn Pro Thr Pro Ser Leu Ser Ala Met Val Val Asn Thr Phe Lys
        195                 200                 205 ctc cga agc aac gta aga agc ttt aac ctt ggt ggc atg ggt tgt agt    672
Leu Arg Ser Asn Val Arg Ser Phe Asn Leu Gly Gly Met Gly Cys Ser
    210                 215                 220
```

```
gcc ggc gtt ata gcc att gat cta gca aag gac ttg ttg cat gtc cat    720
Ala Gly Val Ile Ala Ile Asp Leu Ala Lys Asp Leu Leu His Val His
225                 230                 235                 240 aaa aat acg tat gct ctt gtg gtg agc aca gag aac atc act tat aac    768
Lys Asn Thr Tyr Ala Leu Val Val Ser Thr Glu Asn Ile Thr Tyr Asn
                245                 250                 255 att tac gct ggt gat aat agg tcc atg atg gtt tca aat tgc ttg ttc    816
Ile Tyr Ala Gly Asp Asn Arg Ser Met Met Val Ser Asn Cys Leu Phe
            260                 265                 270 cgt gtt ggt ggg gcc gct att ttg ctc tcc aac aag cct gga gat cgt    864
Arg Val Gly Gly Ala Ala Ile Leu Leu Ser Asn Lys Pro Gly Asp Arg
        275                 280                 285 aga cgg tcc aag tac gag cta gtt cac acg gtt cga acg cat acc gga    912
Arg Arg Ser Lys Tyr Glu Leu Val His Thr Val Arg Thr His Thr Gly
    290                 295                 300 gct gac ggc aag tct ttt cgt tgc gtg caa caa gga gac gat gag aac    960
Ala Asp Gly Lys Ser Phe Arg Cys Val Gln Gln Gly Asp Asp Glu Asn
305                 310                 315                 320 ggc aaa atc gga gtg agt ttg tcc aag gac ata acc gat gtt gct ggt   1008
Gly Lys Ile Gly Val Ser Leu Ser Lys Asp Ile Thr Asp Val Ala Gly
                325                 330                 335 cga acg gtt aag aaa aac ata gca acg ttg ggt ccg ttg att ctt ccg   1056
Arg Thr Val Lys Lys Asn Ile Ala Thr Leu Gly Pro Leu Ile Leu Pro
            340                 345                 350 tta agc gag aaa ctt ctt ttt ttc gtt acc ttc atg ggc aag aaa ctt   1104
Leu Ser Glu Lys Leu Leu Phe Phe Val Thr Phe Met Gly Lys Lys Leu
        355                 360                 365 ttc aaa gat aaa atc aaa cat tac tac gtc ccg gat ttc aaa ctt gct   1152
Phe Lys Asp Lys Ile Lys His Tyr Tyr Val Pro Asp Phe Lys Leu Ala
    370                 375                 380 att gac cat ttt tgt ata cat gcc gga ggc aga gcc gtg atc gat gag   1200
Ile Asp His Phe Cys Ile His Ala Gly Gly Arg Ala Val Ile Asp Glu
385                 390                 395                 400 cta gag aag aac tta gga cta tcg ccg atc gat gtg gag gca tct aga   1248
Leu Glu Lys Asn Leu Gly Leu Ser Pro Ile Asp Val Glu Ala Ser Arg
                405                 410                 415 tca acg tta cat aga ttt ggg aat act tca tct agc tca att tgg tat   1296
Ser Thr Leu His Arg Phe Gly Asn Thr Ser Ser Ser Ser Ile Trp Tyr
            420                 425                 430 gaa tta gca tac ata gag gca aag gga aga atg aag aaa ggg aat aaa   1344
Glu Leu Ala Tyr Ile Glu Ala Lys Gly Arg Met Lys Lys Gly Asn Lys
        435                 440                 445 gct tgg cag att gct tta gga tca ggg ttt aag tgt aat agt gcg gtt   1392
Ala Trp Gln Ile Ala Leu Gly Ser Gly Phe Lys Cys Asn Ser Ala Val
    450                 455                 460 tgg gtg gct cta cgc aat gtc aag gca tcg gca aat agt cct tgg caa   1440
Trp Val Ala Leu Arg Asn Val Lys Ala Ser Ala Asn Ser Pro Trp Gln
465                 470                 475                 480 cat tgc atc gat aga tat ccg gtt aaa att gat tct gat ttg tca aag   1488
His Cys Ile Asp Arg Tyr Pro Val Lys Ile Asp Ser Asp Leu Ser Lys
                485                 490                 495 tca aag act cat gtc caa aac ggt cgg tcc taa                       1521
Ser Lys Thr His Val Gln Asn Gly Arg Ser
            500                 505
```

<210> SEQ ID NO 32
<211> LENGTH: 506
<212> TYPE: PRT
<213> ORGANISM: Artificial Sequence
<220> FEATURE:
<223> OTHER INFORMATION: 5' 399 amino acids from B. napus elongase KCS (SEQ ID NO:3) and 3' 107 amino acids from A. thaliana
FAE1 (SEQ ID NO:1); designated Bn399

<400> SEQUENCE: 32

```
Met Thr Ser Ile Asn Val Lys Leu Leu Tyr His Tyr Val Ile Thr Asn
 1               5                  10                  15

Leu Phe Asn Leu Cys Phe Phe Pro Leu Thr Ala Ile Val Ala Gly Lys
            20                  25                  30

Ala Tyr Arg Leu Thr Ile Asp Asp Leu His His Leu Tyr Tyr Ser Tyr
        35                  40                  45

Leu Gln His Asn Leu Ile Thr Ile Ala Pro Leu Phe Ala Phe Thr Val
    50                  55                  60

Phe Gly Ser Val Leu Tyr Ile Ala Thr Arg Pro Lys Pro Val Tyr Leu
65                  70                  75                  80

Val Glu Tyr Ser Cys Tyr Leu Pro Pro Thr His Cys Arg Ser Ser Ile
                85                  90                  95

Ser Lys Val Met Asp Ile Phe Tyr Gln Val Arg Lys Ala Asp Pro Ser
            100                 105                 110

Arg Asn Gly Thr Cys Asp Asp Ser Ser Trp Leu Asp Phe Leu Arg Lys
        115                 120                 125

Ile Gln Glu Arg Ser Gly Leu Gly Asp Glu Thr His Gly Pro Glu Gly
    130                 135                 140

Leu Leu Gln Val Pro Pro Arg Lys Thr Phe Ala Ala Arg Glu Glu
145                 150                 155                 160

Thr Glu Gln Val Ile Ile Gly Ala Leu Glu Asn Leu Phe Lys Asn Thr
                165                 170                 175

Asn Val Asn Pro Lys Asp Ile Gly Ile Leu Val Val Asn Ser Ser Met
            180                 185                 190

Phe Asn Pro Thr Pro Ser Leu Ser Ala Met Val Val Asn Thr Phe Lys
        195                 200                 205

Leu Arg Ser Asn Val Arg Ser Phe Asn Leu Gly Gly Met Gly Cys Ser
    210                 215                 220

Ala Gly Val Ile Ala Ile Asp Leu Ala Lys Asp Leu Leu His Val His
225                 230                 235                 240

Lys Asn Thr Tyr Ala Leu Val Val Ser Thr Glu Asn Ile Thr Tyr Asn
                245                 250                 255

Ile Tyr Ala Gly Asp Asn Arg Ser Met Met Val Ser Asn Cys Leu Phe
            260                 265                 270

Arg Val Gly Gly Ala Ala Ile Leu Leu Ser Asn Lys Pro Gly Asp Arg
        275                 280                 285

Arg Arg Ser Lys Tyr Glu Leu Val His Thr Val Arg Thr His Thr Gly
    290                 295                 300

Ala Asp Gly Lys Ser Phe Arg Cys Val Gln Gln Gly Asp Asp Glu Asn
305                 310                 315                 320

Gly Lys Ile Gly Val Ser Leu Ser Lys Asp Ile Thr Asp Val Ala Gly
                325                 330                 335

Arg Thr Val Lys Lys Asn Ile Ala Thr Leu Gly Pro Leu Ile Leu Pro
            340                 345                 350

Leu Ser Glu Lys Leu Leu Phe Phe Val Thr Phe Met Gly Lys Lys Leu
        355                 360                 365

Phe Lys Asp Lys Ile Lys His Tyr Tyr Val Pro Asp Phe Lys Leu Ala
    370                 375                 380

Ile Asp His Phe Cys Ile His Ala Gly Gly Arg Ala Val Ile Asp Glu
385                 390                 395                 400
```

```
Leu Glu Lys Asn Leu Gly Leu Ser Pro Ile Asp Val Glu Ala Ser Arg
            405                 410                 415

Ser Thr Leu His Arg Phe Gly Asn Thr Ser Ser Ser Ile Trp Tyr
        420                 425                 430

Glu Leu Ala Tyr Ile Glu Ala Lys Gly Arg Met Lys Lys Gly Asn Lys
            435                 440                 445

Ala Trp Gln Ile Ala Leu Gly Ser Gly Phe Lys Cys Asn Ser Ala Val
        450                 455                 460

Trp Val Ala Leu Arg Asn Val Lys Ala Ser Ala Asn Ser Pro Trp Gln
465                 470                 475                 480

His Cys Ile Asp Arg Tyr Pro Val Lys Ile Asp Ser Asp Leu Ser Lys
            485                 490                 495

Ser Lys Thr His Val Gln Asn Gly Arg Ser
        500                 505
```

<210> SEQ ID NO 33
<211> LENGTH: 1524
<212> TYPE: DNA
<213> ORGANISM: Artificial Sequence
<220> FEATURE:
<223> OTHER INFORMATION: 1524 bp from B. napus elongase KCS (SEQ ID NO:3) having a mutation at position 920; designated Bn G307D; hypothetical
<221> NAME/KEY: CDS
<222> LOCATION: (1)...(1518)

<400> SEQUENCE: 33

```
atg acg tcc att aac gta aag ctc ctt tac cat tac gtc ata acc aac     48
Met Thr Ser Ile Asn Val Lys Leu Leu Tyr His Tyr Val Ile Thr Asn
1               5                   10                  15 ctt ttc aac ctt tgc ttc ttt ccg tta acg gcg atc gtc gcc gga aaa    96
Leu Phe Asn Leu Cys Phe Phe Pro Leu Thr Ala Ile Val Ala Gly Lys
                20                  25                  30 gcc tat cgg ctt acc ata gac gat ctt cac cac tta tac tat tcc tat   144
Ala Tyr Arg Leu Thr Ile Asp Asp Leu His His Leu Tyr Tyr Ser Tyr
            35                  40                  45 ctc caa cac aac ctc ata acc atc gct cca ctc ttt gcc ttc acc gtt   192
Leu Gln His Asn Leu Ile Thr Ile Ala Pro Leu Phe Ala Phe Thr Val
        50                  55                  60 ttc ggt tcg gtt ctc tac atc gca acc cgg ccc aaa ccg gtt tac ctc   240
Phe Gly Ser Val Leu Tyr Ile Ala Thr Arg Pro Lys Pro Val Tyr Leu
65                  70                  75                  80 gtt gag tac tca tgc tac ctt cca cca acg cat tgt aga tca agt atc   288
Val Glu Tyr Ser Cys Tyr Leu Pro Pro Thr His Cys Arg Ser Ser Ile
                85                  90                  95 tcc aag gtc atg gat atc ttt tat caa gta aga aaa gct gat cct tct   336
Ser Lys Val Met Asp Ile Phe Tyr Gln Val Arg Lys Ala Asp Pro Ser
                100                 105                 110 cgg aac ggc acg tgc gat gac tcg tcg tgg ctt gac ttc ttg agg aag   384
Arg Asn Gly Thr Cys Asp Asp Ser Ser Trp Leu Asp Phe Leu Arg Lys
            115                 120                 125 att caa gaa cgt tca ggt cta ggc gat gaa act cac ggg ccc gag ggg   432
Ile Gln Glu Arg Ser Gly Leu Gly Asp Glu Thr His Gly Pro Glu Gly
        130                 135                 140 ctg ctt cag gtc cct ccc cgg aag act ttt gcg gcg gcg cgt gaa gag   480
Leu Leu Gln Val Pro Pro Arg Lys Thr Phe Ala Ala Ala Arg Glu Glu
145                 150                 155                 160 acg gag caa gtt atc att ggt gcg cta gaa aat cta ttc aag aac acc   528
Thr Glu Gln Val Ile Ile Gly Ala Leu Glu Asn Leu Phe Lys Asn Thr
                165                 170                 175
```

```
aac gtt aac cct aaa gat ata ggt ata ctt gtg gtg aac tca agc atg      576
Asn Val Asn Pro Lys Asp Ile Gly Ile Leu Val Val Asn Ser Ser Met
            180                 185                 190 ttt aat cca act cca tcg ctc tcc gcg atg gtc gtt aac act ttc aag      624
Phe Asn Pro Thr Pro Ser Leu Ser Ala Met Val Val Asn Thr Phe Lys
            195                 200                 205 ctc cga agc aac gta aga agc ttt aac ctt ggt ggc atg ggt tgt agt      672
Leu Arg Ser Asn Val Arg Ser Phe Asn Leu Gly Gly Met Gly Cys Ser
            210                 215                 220 gcc ggc gtt ata gcc att gat cta gca aag gac ttg ttg cat gtc cat      720
Ala Gly Val Ile Ala Ile Asp Leu Ala Lys Asp Leu Leu His Val His
225                 230                 235                 240 aaa aat acg tat gct ctt gtg gtg agc aca gag aac atc act tat aac      768
Lys Asn Thr Tyr Ala Leu Val Val Ser Thr Glu Asn Ile Thr Tyr Asn
            245                 250                 255 att tac gct ggt gat aat agg tcc atg atg gtt tca aat tgc ttg ttc      816
Ile Tyr Ala Gly Asp Asn Arg Ser Met Met Val Ser Asn Cys Leu Phe
            260                 265                 270 cgt gtt ggt ggg gcc gct att ttg ctc tcc aac aag cct gga gat cgt      864
Arg Val Gly Gly Ala Ala Ile Leu Leu Ser Asn Lys Pro Gly Asp Arg
            275                 280                 285 aga cgg tcc aag tac gag cta gtt cac acg gtt cga acg cat acc gga      912
Arg Arg Ser Lys Tyr Glu Leu Val His Thr Val Arg Thr His Thr Gly
            290                 295                 300 gct gac gac aag tct ttt cgt tgc gtg caa caa gga gac gat gag aac      960
Ala Asp Asp Lys Ser Phe Arg Cys Val Gln Gln Gly Asp Asp Glu Asn
305                 310                 315                 320 ggc aaa atc gga gtg agt ttg tcc aag gac ata acc gat gtt gct ggt     1008
Gly Lys Ile Gly Val Ser Leu Ser Lys Asp Ile Thr Asp Val Ala Gly
            325                 330                 335 cga acg gtt aag aaa aac ata gca acg ttg ggt ccg ttg att ctt ccg     1056
Arg Thr Val Lys Lys Asn Ile Ala Thr Leu Gly Pro Leu Ile Leu Pro
            340                 345                 350 tta agc gag aaa ctt ctt ttt ttc gtt acc ttc atg ggc aag aaa ctt     1104
Leu Ser Glu Lys Leu Leu Phe Phe Val Thr Phe Met Gly Lys Lys Leu
            355                 360                 365 ttc aaa gat aaa atc aaa cat tac tac gtc ccg gat ttc aaa ctt gct     1152
Phe Lys Asp Lys Ile Lys His Tyr Tyr Val Pro Asp Phe Lys Leu Ala
370                 375                 380 att gac cat ttt tgt ata cat gcc gga ggc aga gcc gtg att gat gtg     1200
Ile Asp His Phe Cys Ile His Ala Gly Gly Arg Ala Val Ile Asp Val
385                 390                 395                 400 cta gag aag aac cta gcc cta gca ccg atc gat gta gag gca tca aga     1248
Leu Glu Lys Asn Leu Ala Leu Ala Pro Ile Asp Val Glu Ala Ser Arg
            405                 410                 415 tca acg tta cat aga ttt gga aac act tca tct agc tca ata tgg tat     1296
Ser Thr Leu His Arg Phe Gly Asn Thr Ser Ser Ser Ser Ile Trp Tyr
            420                 425                 430 gag ttg gca tac ata gaa gca aaa gga agg atg aag aaa ggt aat aaa     1344
Glu Leu Ala Tyr Ile Glu Ala Lys Gly Arg Met Lys Lys Gly Asn Lys
            435                 440                 445 gtt tgg cag att gct tta ggg tca ggc ttt aag tgt aac agt gca gtt     1392
Val Trp Gln Ile Ala Leu Gly Ser Gly Phe Lys Cys Asn Ser Ala Val
450                 455                 460 tgg gtg gct cta aac aat gtc aaa gct tcg aca aat agt cct tgg gaa     1440
Trp Val Ala Leu Asn Asn Val Lys Ala Ser Thr Asn Ser Pro Trp Glu
465                 470                 475                 480 cac tgc atc gac aga tac ccg gtc aaa att gat tct gat tca ggt aag     1488
His Cys Ile Asp Arg Tyr Pro Val Lys Ile Asp Ser Asp Ser Gly Lys
```

```
                      485                 490                 495
tca gag act cgt gtc caa aac ggt cgg tcc taataa                              1524
Ser Glu Thr Arg Val Gln Asn Gly Arg Ser
            500                 505
```

<210> SEQ ID NO 34
<211> LENGTH: 506
<212> TYPE: PRT
<213> ORGANISM: Artificial Sequence
<220> FEATURE:
<223> OTHER INFORMATION: 506 amino acids from B. napus elongase KCS
      (SEQ ID NO:4) having a mutation at residue 307; designated
      Bn G307D; hypothetical

<400> SEQUENCE: 34

```
Met Thr Ser Ile Asn Val Lys Leu Leu Tyr His Tyr Val Ile Thr Asn
 1               5                  10                  15

Leu Phe Asn Leu Cys Phe Phe Pro Leu Thr Ala Ile Val Ala Gly Lys
             20                  25                  30

Ala Tyr Arg Leu Thr Ile Asp Asp Leu His His Leu Tyr Tyr Ser Tyr
         35                  40                  45

Leu Gln His Asn Leu Ile Thr Ile Ala Pro Leu Phe Ala Phe Thr Val
     50                  55                  60

Phe Gly Ser Val Leu Tyr Ile Ala Thr Arg Pro Lys Pro Val Tyr Leu
 65                  70                  75                  80

Val Glu Tyr Ser Cys Tyr Leu Pro Pro Thr His Cys Arg Ser Ser Ile
                 85                  90                  95

Ser Lys Val Met Asp Ile Phe Tyr Gln Val Arg Lys Ala Asp Pro Ser
            100                 105                 110

Arg Asn Gly Thr Cys Asp Asp Ser Ser Trp Leu Asp Phe Leu Arg Lys
        115                 120                 125

Ile Gln Glu Arg Ser Gly Leu Gly Asp Glu Thr His Gly Pro Glu Gly
    130                 135                 140

Leu Leu Gln Val Pro Pro Arg Lys Thr Phe Ala Ala Ala Arg Glu Glu
145                 150                 155                 160

Thr Glu Gln Val Ile Ile Gly Ala Leu Glu Asn Leu Phe Lys Asn Thr
                165                 170                 175

Asn Val Asn Pro Lys Asp Ile Gly Ile Leu Val Val Asn Ser Ser Met
            180                 185                 190

Phe Asn Pro Thr Pro Ser Leu Ser Ala Met Val Val Asn Thr Phe Lys
        195                 200                 205

Leu Arg Ser Asn Val Arg Ser Phe Asn Leu Gly Gly Met Gly Cys Ser
    210                 215                 220

Ala Gly Val Ile Ala Ile Asp Leu Ala Lys Asp Leu Leu His Val His
225                 230                 235                 240

Lys Asn Thr Tyr Ala Leu Val Val Ser Thr Glu Asn Ile Thr Tyr Asn
                245                 250                 255

Ile Tyr Ala Gly Asp Asn Arg Ser Met Met Val Ser Asn Cys Leu Phe
            260                 265                 270

Arg Val Gly Gly Ala Ala Ile Leu Leu Ser Asn Lys Pro Gly Asp Arg
        275                 280                 285

Arg Arg Ser Lys Tyr Glu Leu Val His Thr Val Arg Thr His Thr Gly
    290                 295                 300

Ala Asp Asp Lys Ser Phe Arg Cys Val Gln Gln Gly Asp Asp Glu Asn
305                 310                 315                 320

Gly Lys Ile Gly Val Ser Leu Ser Lys Asp Ile Thr Asp Val Ala Gly
```

```
                    325                 330                 335
Arg Thr Val Lys Lys Asn Ile Ala Thr Leu Gly Pro Leu Ile Leu Pro
                340                 345                 350

Leu Ser Glu Lys Leu Leu Phe Phe Val Thr Phe Met Gly Lys Lys Leu
            355                 360                 365

Phe Lys Asp Lys Ile Lys His Tyr Tyr Val Pro Asp Phe Lys Leu Ala
        370                 375                 380

Ile Asp His Phe Cys Ile His Ala Gly Gly Arg Ala Val Ile Asp Val
385                 390                 395                 400

Leu Glu Lys Asn Leu Ala Leu Ala Pro Ile Asp Val Glu Ala Ser Arg
                405                 410                 415

Ser Thr Leu His Arg Phe Gly Asn Thr Ser Ser Ser Ile Trp Tyr
            420                 425                 430

Glu Leu Ala Tyr Ile Glu Ala Lys Gly Arg Met Lys Lys Gly Asn Lys
        435                 440                 445

Val Trp Gln Ile Ala Leu Gly Ser Gly Phe Lys Cys Asn Ser Ala Val
    450                 455                 460

Trp Val Ala Leu Asn Asn Val Lys Ala Ser Thr Asn Ser Pro Trp Glu
465                 470                 475                 480

His Cys Ile Asp Arg Tyr Pro Val Lys Ile Asp Ser Asp Ser Gly Lys
                485                 490                 495

Ser Glu Thr Arg Val Gln Asn Gly Arg Ser
            500                 505

<210> SEQ ID NO 35
<211> LENGTH: 1709
<212> TYPE: DNA
<213> ORGANISM: Artificial Sequence
<220> FEATURE:
<223> OTHER INFORMATION: 1709 bp from A. thaliana FAE1 (SEQ ID NO:1)
      having a mutation at position 275; designated At K92R;
      hypothetical
<221> NAME/KEY: CDS
<222> LOCATION: (1)...(1518)

<400> SEQUENCE: 35 atg acg tcc gtt aac gtt aag ctc ctt tac cgt tac gtc tta acc aac        48
Met Thr Ser Val Asn Val Lys Leu Leu Tyr Arg Tyr Val Leu Thr Asn
 1               5                  10                  15 ttt ttc aac ctc tgt ttg ttc ccg tta acg gcg ttc ctc gcc gga aaa        96
Phe Phe Asn Leu Cys Leu Phe Pro Leu Thr Ala Phe Leu Ala Gly Lys
                20                  25                  30 gcc tct cgg ctt acc ata aac gat ctc cac aac ttc ctt tcc tat ctc       144
Ala Ser Arg Leu Thr Ile Asn Asp Leu His Asn Phe Leu Ser Tyr Leu
             35                  40                  45 caa cac aac ctt ata aca gta act tta ctc ttt gct ttc act gtt ttc       192
Gln His Asn Leu Ile Thr Val Thr Leu Leu Phe Ala Phe Thr Val Phe
         50                  55                  60 ggt ttg gtt ctc tac atc gta acc cga ccc aat ccg gtt tat ctc gtt       240
Gly Leu Val Leu Tyr Ile Val Thr Arg Pro Asn Pro Val Tyr Leu Val
 65                  70                  75                  80 gac tac tcg tgt tac ctt cca cca ccg cat ctc aga gtt agt gtc tct       288
Asp Tyr Ser Cys Tyr Leu Pro Pro Pro His Leu Arg Val Ser Val Ser
                 85                  90                  95 aaa gtc atg gat att ttc tac caa ata aga aaa gct gat act tct tca       336
Lys Val Met Asp Ile Phe Tyr Gln Ile Arg Lys Ala Asp Thr Ser Ser
                100                 105                 110 cgg aac gtg gca tgt gat gat ccg tcc tcg ctc gat ttc ctg agg aag       384
Arg Asn Val Ala Cys Asp Asp Pro Ser Ser Leu Asp Phe Leu Arg Lys
```

|  |  |  |  |  | 115 |  |  |  |  | 120 |  |  |  |  | 125 |  |
|---|---|---|---|---|---|---|---|---|---|---|---|---|---|---|---|---|
| att | caa | gag | cgt | tca | ggt | cta | ggt | gat | gag | acg | tac | agt | cct | gag | gga | 432 |
| Ile | Gln | Glu | Arg | Ser | Gly | Leu | Gly | Asp | Glu | Thr | Tyr | Ser | Pro | Glu | Gly |  |
|  | 130 |  |  |  | 135 |  |  |  |  | 140 |  |  |  |  |  |  |
| ctc | att | cac | gta | cca | ccg | cgg | aag | act | ttt | gca | gcg | tca | cgt | gaa | gag | 480 |
| Leu | Ile | His | Val | Pro | Pro | Arg | Lys | Thr | Phe | Ala | Ala | Ser | Arg | Glu | Glu |  |
| 145 |  |  |  |  | 150 |  |  |  |  | 155 |  |  |  |  | 160 |  |
| aca | gag | aag | gtt | atc | atc | ggt | gcg | ctc | gaa | aat | cta | ttc | gag | aac | acc | 528 |
| Thr | Glu | Lys | Val | Ile | Ile | Gly | Ala | Leu | Glu | Asn | Leu | Phe | Glu | Asn | Thr |  |
|  |  |  |  |  | 165 |  |  |  |  | 170 |  |  |  |  | 175 |  |
| aaa | gtt | aac | cct | aga | gag | att | ggt | ata | ctt | gtg | gtg | aac | tca | agc | atg | 576 |
| Lys | Val | Asn | Pro | Arg | Glu | Ile | Gly | Ile | Leu | Val | Val | Asn | Ser | Ser | Met |  |
|  |  |  | 180 |  |  |  |  | 185 |  |  |  |  | 190 |  |  |  |
| ttt | aat | cca | act | cct | tcg | cta | tcc | gct | atg | gtc | gtt | aat | act | ttc | aag | 624 |
| Phe | Asn | Pro | Thr | Pro | Ser | Leu | Ser | Ala | Met | Val | Val | Asn | Thr | Phe | Lys |  |
|  |  | 195 |  |  |  |  | 200 |  |  |  |  | 205 |  |  |  |  |
| ctc | cga | agc | aac | atc | aaa | agc | ttt | aat | cta | gga | gga | atg | ggt | tgt | agt | 672 |
| Leu | Arg | Ser | Asn | Ile | Lys | Ser | Phe | Asn | Leu | Gly | Gly | Met | Gly | Cys | Ser |  |
|  | 210 |  |  |  |  | 215 |  |  |  |  | 220 |  |  |  |  |  |
| gct | ggt | gtt | att | gcc | att | gat | ttg | gct | aaa | gac | ttg | ttg | cat | gtt | cat | 720 |
| Ala | Gly | Val | Ile | Ala | Ile | Asp | Leu | Ala | Lys | Asp | Leu | Leu | His | Val | His |  |
| 225 |  |  |  |  | 230 |  |  |  |  | 235 |  |  |  |  | 240 |  |
| aaa | aac | act | tat | gct | ctt | gtg | gtg | agc | act | gag | aac | atc | aca | caa | ggc | 768 |
| Lys | Asn | Thr | Tyr | Ala | Leu | Val | Val | Ser | Thr | Glu | Asn | Ile | Thr | Gln | Gly |  |
|  |  |  |  |  | 245 |  |  |  |  | 250 |  |  |  |  | 255 |  |
| att | tat | gct | gga | gaa | aat | aga | tca | atg | atg | gtt | agc | aat | tgc | ttg | ttt | 816 |
| Ile | Tyr | Ala | Gly | Glu | Asn | Arg | Ser | Met | Met | Val | Ser | Asn | Cys | Leu | Phe |  |
|  |  |  | 260 |  |  |  |  | 265 |  |  |  |  | 270 |  |  |  |
| cgt | gtt | ggt | ggg | gcc | gcg | att | ttg | ctc | tct | aac | aag | tcg | gga | gac | cgg | 864 |
| Arg | Val | Gly | Gly | Ala | Ala | Ile | Leu | Leu | Ser | Asn | Lys | Ser | Gly | Asp | Arg |  |
|  |  | 275 |  |  |  |  | 280 |  |  |  |  | 285 |  |  |  |  |
| aga | cgg | tcc | aag | tac | aag | cta | gtt | cac | acg | gtc | cga | acg | cat | act | gga | 912 |
| Arg | Arg | Ser | Lys | Tyr | Lys | Leu | Val | His | Thr | Val | Arg | Thr | His | Thr | Gly |  |
|  | 290 |  |  |  |  | 295 |  |  |  |  | 300 |  |  |  |  |  |
| gct | gat | gac | aag | tct | ttt | cga | tgt | gtg | caa | caa | gaa | gac | gat | gag | agc | 960 |
| Ala | Asp | Asp | Lys | Ser | Phe | Arg | Cys | Val | Gln | Gln | Glu | Asp | Asp | Glu | Ser |  |
| 305 |  |  |  |  | 310 |  |  |  |  | 315 |  |  |  |  | 320 |  |
| ggc | aaa | atc | gga | gtt | tgt | ctg | tca | aag | gac | ata | acc | aat | gtt | gcg | ggg | 1008 |
| Gly | Lys | Ile | Gly | Val | Cys | Leu | Ser | Lys | Asp | Ile | Thr | Asn | Val | Ala | Gly |  |
|  |  |  | 325 |  |  |  |  | 330 |  |  |  |  | 335 |  |  |  |
| aca | aca | ctt | acg | aaa | aat | ata | gca | aca | ttg | ggt | ccg | ttg | att | ctt | cct | 1056 |
| Thr | Thr | Leu | Thr | Lys | Asn | Ile | Ala | Thr | Leu | Gly | Pro | Leu | Ile | Leu | Pro |  |
|  |  |  | 340 |  |  |  |  | 345 |  |  |  |  | 350 |  |  |  |
| tta | agc | gaa | aag | ttt | ctt | ttt | ttc | gct | acc | ttc | gtc | gcc | aag | aaa | ctt | 1104 |
| Leu | Ser | Glu | Lys | Phe | Leu | Phe | Phe | Ala | Thr | Phe | Val | Ala | Lys | Lys | Leu |  |
|  |  | 355 |  |  |  |  | 360 |  |  |  |  | 365 |  |  |  |  |
| cta | aag | gat | aaa | atc | aag | cat | tac | tat | gtt | ccg | gat | ttc | aag | ctt | gct | 1152 |
| Leu | Lys | Asp | Lys | Ile | Lys | His | Tyr | Tyr | Val | Pro | Asp | Phe | Lys | Leu | Ala |  |
|  | 370 |  |  |  |  | 375 |  |  |  |  | 380 |  |  |  |  |  |
| gtt | gac | cat | ttc | tgt | att | cat | gcc | gga | ggc | aga | gcc | gtg | atc | gat | gag | 1200 |
| Val | Asp | His | Phe | Cys | Ile | His | Ala | Gly | Gly | Arg | Ala | Val | Ile | Asp | Glu |  |
| 385 |  |  |  |  | 390 |  |  |  |  | 395 |  |  |  |  | 400 |  |
| cta | gag | aag | aac | tta | gga | cta | tcg | ccg | atc | gat | gtg | gag | gca | tct | aga | 1248 |
| Leu | Glu | Lys | Asn | Leu | Gly | Leu | Ser | Pro | Ile | Asp | Val | Glu | Ala | Ser | Arg |  |
|  |  |  |  | 405 |  |  |  |  | 410 |  |  |  |  | 415 |  |  |
| tca | acg | tta | cat | aga | ttt | ggg | aat | act | tca | tct | agc | tca | att | tgg | tat | 1296 |
| Ser | Thr | Leu | His | Arg | Phe | Gly | Asn | Thr | Ser | Ser | Ser | Ser | Ile | Trp | Tyr |  |
|  |  |  | 420 |  |  |  |  | 425 |  |  |  |  | 430 |  |  |  |
| gaa | tta | gca | tac | ata | gag | gca | aag | gga | aga | atg | aag | aaa | ggg | aat | aaa | 1344 |

```
                                                       1392
gct tgg cag att gct tta gga tca ggg ttt aag tgt aat agt gcg gtt
Ala Trp Gln Ile Ala Leu Gly Ser Gly Phe Lys Cys Asn Ser Ala Val
450                 455                 460

1440
tgg gtg gct cta cgc aat gtc aag gca tcg gca aat agt cct tgg caa
Trp Val Ala Leu Arg Asn Val Lys Ala Ser Ala Asn Ser Pro Trp Gln
465                 470                 475                 480

1488
cat tgc atc gat aga tat ccg gtt aaa att gat tct gat ttg tca aag
His Cys Ile Asp Arg Tyr Pro Val Lys Ile Asp Ser Asp Leu Ser Lys
            485                 490                 495

1538
tca aag act cat gtc caa aac ggt cgg tcc taatttgatg tatctgagtg
Ser Lys Thr His Val Gln Asn Gly Arg Ser
                500                 505 ccaacgttta ctttgtcttt cctttctttt attggttatg aattagatgt ttactaatgt    1598
tcctctcttt ttcgttataa ataaagaagt tcaattcttc ctatagtttc aaacgcgatt    1658
ttaagcgttt ctatttaggt ttacatgaat ttcttttaca aaccatcttt t             1709

<210> SEQ ID NO 36
<211> LENGTH: 506
<212> TYPE: PRT
<213> ORGANISM: Artificial Sequence
<220> FEATURE:
<223> OTHER INFORMATION: 506 amino acids from A. thaliana FAE1 (SEQ ID
      NO:2) having a mutation at residue 92; designated
      At K92R; hypothetical

<400> SEQUENCE: 36

Met Thr Ser Val Asn Val Lys Leu Leu Tyr Arg Tyr Val Leu Thr Asn
1               5                   10                  15

Phe Phe Asn Leu Cys Leu Phe Pro Leu Thr Ala Phe Leu Ala Gly Lys
                20                  25                  30

Ala Ser Arg Leu Thr Ile Asn Asp Leu His Asn Phe Leu Ser Tyr Leu
            35                  40                  45

Gln His Asn Leu Ile Thr Val Thr Leu Leu Phe Ala Phe Thr Val Phe
        50                  55                  60

Gly Leu Val Leu Tyr Ile Val Thr Arg Pro Asn Pro Val Tyr Leu Val
65                  70                  75                  80

Asp Tyr Ser Cys Tyr Leu Pro Pro Pro His Leu Arg Val Ser Val Ser
                85                  90                  95

Lys Val Met Asp Ile Phe Tyr Gln Ile Arg Lys Ala Asp Thr Ser Ser
                100                 105                 110

Arg Asn Val Ala Cys Asp Asp Pro Ser Ser Leu Asp Phe Leu Arg Lys
            115                 120                 125

Ile Gln Glu Arg Ser Gly Leu Gly Asp Glu Thr Tyr Ser Pro Glu Gly
        130                 135                 140

Leu Ile His Val Pro Pro Arg Lys Thr Phe Ala Ala Ser Arg Glu Glu
145                 150                 155                 160

Thr Glu Lys Val Ile Ile Gly Ala Leu Glu Asn Leu Phe Glu Asn Thr
                165                 170                 175

Lys Val Asn Pro Arg Glu Ile Gly Ile Leu Val Val Asn Ser Ser Met
            180                 185                 190

Phe Asn Pro Thr Pro Ser Leu Ser Ala Met Val Val Asn Thr Phe Lys
        195                 200                 205

Leu Arg Ser Asn Ile Lys Ser Phe Asn Leu Gly Gly Met Gly Cys Ser
210                 215                 220
```

```
Glu Leu Ala Tyr Ile Glu Ala Lys Gly Arg Met Lys Lys Gly Asn Lys
            435                 440                 445
```

```
Ala Gly Val Ile Ala Ile Asp Leu Ala Lys Asp Leu Leu His Val His
225                 230                 235                 240

Lys Asn Thr Tyr Ala Leu Val Val Ser Thr Glu Asn Ile Thr Gln Gly
                245                 250                 255

Ile Tyr Ala Gly Glu Asn Arg Ser Met Met Val Ser Asn Cys Leu Phe
            260                 265                 270

Arg Val Gly Gly Ala Ala Ile Leu Leu Ser Asn Lys Ser Gly Asp Arg
        275                 280                 285

Arg Ser Lys Tyr Lys Leu Val His Thr Val Arg Thr His Thr Gly
    290                 295                 300

Ala Asp Asp Lys Ser Phe Arg Cys Val Gln Gln Asp Asp Glu Ser
305                 310                 315                 320

Gly Lys Ile Gly Val Cys Leu Ser Lys Asp Ile Thr Asn Val Ala Gly
                325                 330                 335

Thr Thr Leu Thr Lys Asn Ile Ala Thr Leu Gly Pro Leu Ile Leu Pro
            340                 345                 350

Leu Ser Glu Lys Phe Leu Phe Phe Ala Thr Phe Val Ala Lys Lys Leu
        355                 360                 365

Leu Lys Asp Lys Ile Lys His Tyr Tyr Val Pro Asp Phe Lys Leu Ala
370                 375                 380

Val Asp His Phe Cys Ile His Ala Gly Arg Ala Val Ile Asp Glu
385                 390                 395                 400

Leu Glu Lys Asn Leu Gly Leu Ser Pro Ile Asp Val Glu Ala Ser Arg
                405                 410                 415

Ser Thr Leu His Arg Phe Gly Asn Thr Ser Ser Ser Ile Trp Tyr
            420                 425                 430

Glu Leu Ala Tyr Ile Glu Ala Lys Gly Arg Met Lys Lys Gly Asn Lys
        435                 440                 445

Ala Trp Gln Ile Ala Leu Gly Ser Gly Phe Lys Cys Asn Ser Ala Val
450                 455                 460

Trp Val Ala Leu Arg Asn Val Lys Ala Ser Ala Asn Ser Pro Trp Gln
465                 470                 475                 480

His Cys Ile Asp Arg Tyr Pro Val Lys Ile Asp Ser Asp Leu Ser Lys
                485                 490                 495

Ser Lys Thr His Val Gln Asn Gly Arg Ser
            500                 505

<210> SEQ ID NO 37
<211> LENGTH: 1521
<212> TYPE: DNA
<213> ORGANISM: Artificial Sequence
<220> FEATURE:
<223> OTHER INFORMATION: 5' 762 bp from A. thaliana FAE1 (SEQ ID NO:1)
      and 3' 759 bp from B. napus elongase KCS (SEQ ID NO:3)
      and having a mutation at position 920; designated
      At254 G307D; hypothetical
<221> NAME/KEY: CDS
<222> LOCATION: (1)...(1518)

<400> SEQUENCE: 37 atg acg tcc gtt aac gtt aag ctc ctt tac cgt tac gtc tta acc aac        48
Met Thr Ser Val Asn Val Lys Leu Leu Tyr Arg Tyr Val Leu Thr Asn
 1               5                  10                  15 ttt ttc aac ctc tgt ttg ttc ccg tta acg gcg ttc ctc gcc gga aaa        96
Phe Phe Asn Leu Cys Leu Phe Pro Leu Thr Ala Phe Leu Ala Gly Lys
                20                  25                  30 gcc tct cgg ctt acc ata aac gat ctc cac aac ttc ctt tcc tat ctc       144
Ala Ser Arg Leu Thr Ile Asn Asp Leu His Asn Phe Leu Ser Tyr Leu
```

```
                 35                  40                  45
caa cac aac ctt ata aca gta act tta ctc ttt gct ttc act gtt ttc      192
Gln His Asn Leu Ile Thr Val Thr Leu Leu Phe Ala Phe Thr Val Phe
         50                  55                  60 ggt ttg gtt ctc tac atc gta acc cga ccc aat ccg gtt tat ctc gtt      240
Gly Leu Val Leu Tyr Ile Val Thr Arg Pro Asn Pro Val Tyr Leu Val
 65                  70                  75                  80 gac tac tcg tgt tac ctt cca cca ccg cat ctc aaa gtt agt gtc tct      288
Asp Tyr Ser Cys Tyr Leu Pro Pro Pro His Leu Lys Val Ser Val Ser
                 85                  90                  95 aaa gtc atg gat att ttc tac caa ata aga aaa gct gat act tct tca      336
Lys Val Met Asp Ile Phe Tyr Gln Ile Arg Lys Ala Asp Thr Ser Ser
            100                 105                 110 cgg aac gtg gca tgt gat gat ccg tcc tcg ctc gat ttc ctg agg aag      384
Arg Asn Val Ala Cys Asp Asp Pro Ser Ser Leu Asp Phe Leu Arg Lys
             115                 120                 125 att caa gag cgt tca ggt cta ggt gat gag acg tac agt cct gag gga      432
Ile Gln Glu Arg Ser Gly Leu Gly Asp Glu Thr Tyr Ser Pro Glu Gly
    130                 135                 140 ctc att cac gta cca ccg cgg aag act ttt gca gcg tca cgt gaa gag      480
Leu Ile His Val Pro Pro Arg Lys Thr Phe Ala Ala Ser Arg Glu Glu
145                 150                 155                 160 aca gag aag gtt atc atc ggt gcg ctc gaa aat cta ttc gag aac acc      528
Thr Glu Lys Val Ile Ile Gly Ala Leu Glu Asn Leu Phe Glu Asn Thr
                 165                 170                 175 aaa gtt aac cct aga gag att ggt ata ctt gtg gtg aac tca agc atg      576
Lys Val Asn Pro Arg Glu Ile Gly Ile Leu Val Val Asn Ser Ser Met
             180                 185                 190 ttt aat cca act cct tcg cta tcc gct atg gtc gtt aat act ttc aag      624
Phe Asn Pro Thr Pro Ser Leu Ser Ala Met Val Val Asn Thr Phe Lys
     195                 200                 205 ctc cga agc aac atc aaa agc ttt aat cta gga gga atg ggt tgt agt      672
Leu Arg Ser Asn Ile Lys Ser Phe Asn Leu Gly Gly Met Gly Cys Ser
    210                 215                 220 gct ggt gtt att gcc att gat ttg gct aaa gac ttg ttg cat gtt cat      720
Ala Gly Val Ile Ala Ile Asp Leu Ala Lys Asp Leu Leu His Val His
225                 230                 235                 240 aaa aac act tat gct ctc gtg gtg agc aca gag aac atc act tat aac      768
Lys Asn Thr Tyr Ala Leu Val Val Ser Thr Glu Asn Ile Thr Tyr Asn
                 245                 250                 255 att tac gct ggt gat aat agg tcc atg atg gtt tca aat tgc ttg ttc      816
Ile Tyr Ala Gly Asp Asn Arg Ser Met Met Val Ser Asn Cys Leu Phe
             260                 265                 270 cgt gtt ggt ggg gcc gct att ttg ctc tcc aac aag cct gga gat cgt      864
Arg Val Gly Gly Ala Ala Ile Leu Leu Ser Asn Lys Pro Gly Asp Arg
     275                 280                 285 aga cgg tcc aag tac gag cta gtt cac acg gtt cga acg cat acc gga      912
Arg Arg Ser Lys Tyr Glu Leu Val His Thr Val Arg Thr His Thr Gly
    290                 295                 300 gct gac gac aag tct ttt cgt tgc gtg caa caa gga gac gat gag aac      960
Ala Asp Asp Lys Ser Phe Arg Cys Val Gln Gln Gly Asp Asp Glu Asn
305                 310                 315                 320 ggc aaa atc gga gtg agt ttg tcc aag gac ata acc gat gtt gct ggt     1008
Gly Lys Ile Gly Val Ser Leu Ser Lys Asp Ile Thr Asp Val Ala Gly
                 325                 330                 335 cga acg gtt aag aaa aac ata gca acg ttg ggt ccg ttg att ctt ccg     1056
Arg Thr Val Lys Lys Asn Ile Ala Thr Leu Gly Pro Leu Ile Leu Pro
             340                 345                 350 tta agc gag aaa ctt ctt ttt ttc gtt acc ttc atg ggc aag aaa ctt     1104
```

-continued

```
Leu Ser Glu Lys Leu Leu Phe Phe Val Thr Phe Met Gly Lys Lys Leu
        355                 360                 365 ttc aaa gat aaa atc aaa cat tac tac gtc ccg gat ttc aaa ctt gct      1152
Phe Lys Asp Lys Ile Lys His Tyr Tyr Val Pro Asp Phe Lys Leu Ala
370                 375                 380 att gac cat ttt tgt ata cat gcc gga ggc aga gcc gtg att gat gtg      1200
Ile Asp His Phe Cys Ile His Ala Gly Gly Arg Ala Val Ile Asp Val
385                 390                 395                 400 cta gag aag aac cta gcc cta gca ccg atc gat gta gag gca tca aga      1248
Leu Glu Lys Asn Leu Ala Leu Ala Pro Ile Asp Val Glu Ala Ser Arg
        405                 410                 415 tca acg tta cat aga ttt gga aac act tca tct agc tca ata tgg tat      1296
Ser Thr Leu His Arg Phe Gly Asn Thr Ser Ser Ser Ser Ile Trp Tyr
        420                 425                 430 gag ttg gca tac ata gaa gca aaa gga agg atg aag aaa ggt aat aaa      1344
Glu Leu Ala Tyr Ile Glu Ala Lys Gly Arg Met Lys Lys Gly Asn Lys
        435                 440                 445 gtt tgg cag att gct tta ggg tca ggc ttt aag tgt aac agt gca gtt      1392
Val Trp Gln Ile Ala Leu Gly Ser Gly Phe Lys Cys Asn Ser Ala Val
450                 455                 460 tgg gtg gct cta aac aat gtc aaa gct tcg aca aat agt cct tgg gaa      1440
Trp Val Ala Leu Asn Asn Val Lys Ala Ser Thr Asn Ser Pro Trp Glu
465                 470                 475                 480 cac tgc atc gac aga tac ccg gtc aaa att gat tct gat tca ggt aag      1488
His Cys Ile Asp Arg Tyr Pro Val Lys Ile Asp Ser Asp Ser Gly Lys
                485                 490                 495 tca gag act cgt gtc caa aac ggt cgg tcc taa                          1521
Ser Glu Thr Arg Val Gln Asn Gly Arg Ser
                500                 505
```

<210> SEQ ID NO 38
<211> LENGTH: 506
<212> TYPE: PRT
<213> ORGANISM: Artificial Sequence
<220> FEATURE:
<223> OTHER INFORMATION: 5' 254 amino acids from A. thaliana FAE1 (SEQ
      ID NO:2) and 3' 252 amino acids from B. napus
      elongase KCS (SEQ ID NO:4) having a mutation at
      residue 307; designated At254 G307D; hypothetical

<400> SEQUENCE: 38

```
Met Thr Ser Val Asn Val Lys Leu Leu Tyr Arg Tyr Val Leu Thr Asn
1               5                   10                  15

Phe Phe Asn Leu Cys Leu Phe Pro Leu Thr Ala Phe Leu Ala Gly Lys
                20                  25                  30

Ala Ser Arg Leu Thr Ile Asn Asp Leu His Asn Phe Leu Ser Tyr Leu
        35                  40                  45

Gln His Asn Leu Ile Thr Val Thr Leu Leu Phe Ala Phe Thr Val Phe
    50                  55                  60

Gly Leu Val Leu Tyr Ile Val Thr Arg Pro Asn Pro Val Tyr Leu Val
65                  70                  75                  80

Asp Tyr Ser Cys Tyr Leu Pro Pro His Leu Lys Val Ser Val Ser
                85                  90                  95

Lys Val Met Asp Ile Phe Tyr Gln Ile Arg Lys Ala Asp Thr Ser Ser
                100                 105                 110

Arg Asn Val Ala Cys Asp Asp Pro Ser Ser Leu Asp Phe Leu Arg Lys
        115                 120                 125

Ile Gln Glu Arg Ser Gly Leu Gly Asp Glu Thr Tyr Ser Pro Glu Gly
    130                 135                 140
```

```
Leu Ile His Val Pro Pro Arg Lys Thr Phe Ala Ala Ser Arg Glu Glu
145                 150                 155                 160

Thr Glu Lys Val Ile Ile Gly Ala Leu Glu Asn Leu Phe Glu Asn Thr
                165                 170                 175

Lys Val Asn Pro Arg Glu Ile Gly Ile Leu Val Val Asn Ser Ser Met
            180                 185                 190

Phe Asn Pro Thr Pro Ser Leu Ser Ala Met Val Val Asn Thr Phe Lys
        195                 200                 205

Leu Arg Ser Asn Ile Lys Ser Phe Asn Leu Gly Gly Met Gly Cys Ser
210                 215                 220

Ala Gly Val Ile Ala Ile Asp Leu Ala Lys Asp Leu Leu His Val His
225                 230                 235                 240

Lys Asn Thr Tyr Ala Leu Val Val Ser Thr Glu Asn Ile Thr Tyr Asn
                245                 250                 255

Ile Tyr Ala Gly Asp Asn Arg Ser Met Met Val Ser Asn Cys Leu Phe
            260                 265                 270

Arg Val Gly Gly Ala Ala Ile Leu Leu Ser Asn Lys Pro Gly Asp Arg
        275                 280                 285

Arg Arg Ser Lys Tyr Glu Leu Val His Thr Val Arg Thr His Thr Gly
290                 295                 300

Ala Asp Asp Lys Ser Phe Arg Cys Val Gln Gln Gly Asp Asp Glu Asn
305                 310                 315                 320

Gly Lys Ile Gly Val Ser Leu Ser Lys Asp Ile Thr Asp Val Ala Gly
                325                 330                 335

Arg Thr Val Lys Lys Asn Ile Ala Thr Leu Gly Pro Leu Ile Leu Pro
            340                 345                 350

Leu Ser Glu Lys Leu Leu Phe Phe Val Thr Phe Met Gly Lys Lys Leu
        355                 360                 365

Phe Lys Asp Lys Ile Lys His Tyr Tyr Val Pro Asp Phe Lys Leu Ala
370                 375                 380

Ile Asp His Phe Cys Ile His Ala Gly Gly Arg Ala Val Ile Asp Val
385                 390                 395                 400

Leu Glu Lys Asn Leu Ala Leu Ala Pro Ile Asp Val Glu Ala Ser Arg
                405                 410                 415

Ser Thr Leu His Arg Phe Gly Asn Thr Ser Ser Ser Ile Trp Tyr
            420                 425                 430

Glu Leu Ala Tyr Ile Glu Ala Lys Gly Arg Met Lys Lys Gly Asn Lys
        435                 440                 445

Val Trp Gln Ile Ala Leu Gly Ser Gly Phe Lys Cys Asn Ser Ala Val
450                 455                 460

Trp Val Ala Leu Asn Asn Val Lys Ala Ser Thr Asn Ser Pro Trp Glu
465                 470                 475                 480

His Cys Ile Asp Arg Tyr Pro Val Lys Ile Asp Ser Asp Ser Gly Lys
                485                 490                 495

Ser Glu Thr Arg Val Gln Asn Gly Arg Ser
            500                 505

<210> SEQ ID NO 39
<211> LENGTH: 1521
<212> TYPE: DNA
<213> ORGANISM: Artificial Sequence
<220> FEATURE:
<223> OTHER INFORMATION: 5' 519 bp from A. thaliana FAE1 (SEQ ID NO:1)
      and 3' 1002 bp from B. napus elongase KCS (SEQ ID
      NO:3) and having a mutation at position 920;
      designated At173 G307D
```

```
<221> NAME/KEY: CDS
<222> LOCATION: (1)...(1518)

<400> SEQUENCE: 39 atg acg tcc gtt aac gtt aag ctc ctt tac cgt tac gtc tta acc aac      48
Met Thr Ser Val Asn Val Lys Leu Leu Tyr Arg Tyr Val Leu Thr Asn
 1               5                  10                  15 ttt ttc aac ctc tgt ttg ttc ccg tta acg gcg ttc ctc gcc gga aaa      96
Phe Phe Asn Leu Cys Leu Phe Pro Leu Thr Ala Phe Leu Ala Gly Lys
             20                  25                  30 gcc tct cgg ctt acc ata aac gat ctc cac aac ttc ctt tcc tat ctc     144
Ala Ser Arg Leu Thr Ile Asn Asp Leu His Asn Phe Leu Ser Tyr Leu
         35                  40                  45 caa cac aac ctt ata aca gta act tta ctc ttt gct ttc act gtt ttc     192
Gln His Asn Leu Ile Thr Val Thr Leu Leu Phe Ala Phe Thr Val Phe
     50                  55                  60 ggt ttg gtt ctc tac atc gta acc cga ccc aat ccg gtt tat ctc gtt     240
Gly Leu Val Leu Tyr Ile Val Thr Arg Pro Asn Pro Val Tyr Leu Val
 65                  70                  75                  80 gac tac tcg tgt tac ctt cca cca ccg cat ctc aaa gtt agt gtc tct     288
Asp Tyr Ser Cys Tyr Leu Pro Pro Pro His Leu Lys Val Ser Val Ser
                 85                  90                  95 aaa gtc atg gat att ttc tac caa ata aga aaa gct gat act tct tca     336
Lys Val Met Asp Ile Phe Tyr Gln Ile Arg Lys Ala Asp Thr Ser Ser
            100                 105                 110 cgg aac gtg gca tgt gat gat ccg tcc tcg ctc gat ttc ctg agg aag     384
Arg Asn Val Ala Cys Asp Asp Pro Ser Ser Leu Asp Phe Leu Arg Lys
        115                 120                 125 att caa gag cgt tca ggt cta ggt gat gag acg tac agt cct gag gga     432
Ile Gln Glu Arg Ser Gly Leu Gly Asp Glu Thr Tyr Ser Pro Glu Gly
    130                 135                 140 ctc att cac gta cca ccg cgg aag act ttt gca gcg tca cgt gaa gag     480
Leu Ile His Val Pro Pro Arg Lys Thr Phe Ala Ala Ser Arg Glu Glu
145                 150                 155                 160 aca gag aag gtt atc atc ggt gcg ctc gaa aat cta ttc aag aac acc     528
Thr Glu Lys Val Ile Ile Gly Ala Leu Glu Asn Leu Phe Lys Asn Thr
                165                 170                 175 aac gtt aac cct aaa gat ata ggt ata ctt gtg gtg aac tca agc atg     576
Asn Val Asn Pro Lys Asp Ile Gly Ile Leu Val Val Asn Ser Ser Met
            180                 185                 190 ttt aat cca act cca tcg ctc tcc gcg atg gtc gtt aac act ttc aag     624
Phe Asn Pro Thr Pro Ser Leu Ser Ala Met Val Val Asn Thr Phe Lys
        195                 200                 205 ctc cga agc aac gta aga agc ttt aac ctt ggt ggc atg ggt tgt agt     672
Leu Arg Ser Asn Val Arg Ser Phe Asn Leu Gly Gly Met Gly Cys Ser
    210                 215                 220 gcc ggc gtt ata gcc att gat cta gca aag gac ttg ttg cat gtc cat     720
Ala Gly Val Ile Ala Ile Asp Leu Ala Lys Asp Leu Leu His Val His
225                 230                 235                 240 aaa aat acg tat gct ctt gtg gtg agc aca gag aac atc act tat aac     768
Lys Asn Thr Tyr Ala Leu Val Val Ser Thr Glu Asn Ile Thr Tyr Asn
                245                 250                 255 att tac gct ggt gat aat agg tcc atg atg gtt tca aat tgc ttg ttc     816
Ile Tyr Ala Gly Asp Asn Arg Ser Met Met Val Ser Asn Cys Leu Phe
            260                 265                 270 cgt gtt ggt ggg gcc gct att ttg ctc tcc aac aag cct gga gat cgt     864
Arg Val Gly Gly Ala Ala Ile Leu Leu Ser Asn Lys Pro Gly Asp Arg
        275                 280                 285 aga cgg tcc aag tac gag cta gtt cac acg gtt cga acg cat acc gga     912
Arg Arg Ser Lys Tyr Glu Leu Val His Thr Val Arg Thr His Thr Gly
```

```
            290                 295                 300
gct gac gac aag tct ttt cgt tgc gtg caa caa gga gac gat gag aac      960
Ala Asp Asp Lys Ser Phe Arg Cys Val Gln Gln Gly Asp Asp Glu Asn
305                 310                 315                 320 ggc aaa atc gga gtg agt ttg tcc aag gac ata acc gat gtt gct ggt     1008
Gly Lys Ile Gly Val Ser Leu Ser Lys Asp Ile Thr Asp Val Ala Gly
                325                 330                 335 cga acg gtt aag aaa aac ata gca acg ttg ggt ccg ttg att ctt ccg     1056
Arg Thr Val Lys Lys Asn Ile Ala Thr Leu Gly Pro Leu Ile Leu Pro
            340                 345                 350 tta agc gag aaa ctt ctt ttt ttc gtt acc ttc atg ggc aag aaa ctt     1104
Leu Ser Glu Lys Leu Leu Phe Phe Val Thr Phe Met Gly Lys Lys Leu
        355                 360                 365 ttc aaa gat aaa atc aaa cat tac tac gtc ccg gat ttc aaa ctt gct     1152
Phe Lys Asp Lys Ile Lys His Tyr Tyr Val Pro Asp Phe Lys Leu Ala
370                 375                 380 att gac cat ttt tgt ata cat gcc gga ggc aga gcc gtg att gat gtg     1200
Ile Asp His Phe Cys Ile His Ala Gly Gly Arg Ala Val Ile Asp Val
385                 390                 395                 400 cta gag aag aac cta gcc cta gca ccg atc gat gta gag gca tca aga     1248
Leu Glu Lys Asn Leu Ala Leu Ala Pro Ile Asp Val Glu Ala Ser Arg
                405                 410                 415 tca acg tta cat aga ttt gga aac act tca tct agc tca ata tgg tat     1296
Ser Thr Leu His Arg Phe Gly Asn Thr Ser Ser Ser Ser Ile Trp Tyr
            420                 425                 430 gag ttg gca tac ata gaa gca aaa gga agg atg aag aaa ggt aat aaa     1344
Glu Leu Ala Tyr Ile Glu Ala Lys Gly Arg Met Lys Lys Gly Asn Lys
        435                 440                 445 gtt tgg cag att gct tta ggg tca ggc ttt aag tgt aac agt gca gtt     1392
Val Trp Gln Ile Ala Leu Gly Ser Gly Phe Lys Cys Asn Ser Ala Val
450                 455                 460 tgg gtg gct cta aac aat gtc aaa gct tcg aca aat agt cct tgg gaa     1440
Trp Val Ala Leu Asn Asn Val Lys Ala Ser Thr Asn Ser Pro Trp Glu
465                 470                 475                 480 cac tgc atc gac aga tac ccg gtc aaa att gat tct gat tca ggt aag     1488
His Cys Ile Asp Arg Tyr Pro Val Lys Ile Asp Ser Asp Ser Gly Lys
                485                 490                 495 tca gag act cgt gtc caa aac ggt cgg tcc taa                         1521
Ser Glu Thr Arg Val Gln Asn Gly Arg Ser
            500                 505
```

<210> SEQ ID NO 40
<211> LENGTH: 506
<212> TYPE: PRT
<213> ORGANISM: Artificial Sequence
<220> FEATURE:
<223> OTHER INFORMATION: 5' 173 amino acids from A. thaliana FAE1 (SEQ
      ID NO:2) and 3' 333 amino acids from B. napus
      elongase KCS (SEQ ID NO:4) having a mutation at
      residue 307; designated At173 G307D; hypothetical

<400> SEQUENCE: 40

```
Met Thr Ser Val Asn Val Lys Leu Leu Tyr Arg Tyr Val Leu Thr Asn
 1               5                  10                  15

Phe Phe Asn Leu Cys Leu Phe Pro Leu Thr Ala Phe Leu Ala Gly Lys
             20                  25                  30

Ala Ser Arg Leu Thr Ile Asn Asp Leu His Asn Phe Leu Ser Tyr Leu
         35                  40                  45

Gln His Asn Leu Ile Thr Val Thr Leu Leu Phe Ala Phe Thr Val Phe
     50                  55                  60
```

-continued

```
Gly Leu Val Leu Tyr Ile Val Thr Arg Pro Asn Pro Val Tyr Leu Val
 65                  70                  75                  80

Asp Tyr Ser Cys Tyr Leu Pro Pro His Leu Lys Val Ser Val Ser
                 85                  90                  95

Lys Val Met Asp Ile Phe Tyr Gln Ile Arg Lys Ala Asp Thr Ser Ser
            100                 105                 110

Arg Asn Val Ala Cys Asp Asp Pro Ser Ser Leu Asp Phe Leu Arg Lys
        115                 120                 125

Ile Gln Glu Arg Ser Gly Leu Gly Asp Glu Thr Tyr Ser Pro Glu Gly
130                 135                 140

Leu Ile His Val Pro Pro Arg Lys Thr Phe Ala Ala Ser Arg Glu Glu
145                 150                 155                 160

Thr Glu Lys Val Ile Ile Gly Ala Leu Glu Asn Leu Phe Lys Asn Thr
                165                 170                 175

Asn Val Asn Pro Lys Asp Ile Gly Ile Leu Val Val Asn Ser Ser Met
            180                 185                 190

Phe Asn Pro Thr Pro Ser Leu Ser Ala Met Val Val Asn Thr Phe Lys
        195                 200                 205

Leu Arg Ser Asn Val Arg Ser Phe Asn Leu Gly Gly Met Gly Cys Ser
210                 215                 220

Ala Gly Val Ile Ala Ile Asp Leu Ala Lys Asp Leu Leu His Val His
225                 230                 235                 240

Lys Asn Thr Tyr Ala Leu Val Val Ser Thr Glu Asn Ile Thr Tyr Asn
                245                 250                 255

Ile Tyr Ala Gly Asp Asn Arg Ser Met Met Val Ser Asn Cys Leu Phe
            260                 265                 270

Arg Val Gly Gly Ala Ala Ile Leu Leu Ser Asn Lys Pro Gly Asp Arg
        275                 280                 285

Arg Arg Ser Lys Tyr Glu Leu Val His Thr Val Arg Thr His Thr Gly
290                 295                 300

Ala Asp Asp Lys Ser Phe Arg Cys Val Gln Gln Gly Asp Asp Glu Asn
305                 310                 315                 320

Gly Lys Ile Gly Val Ser Leu Ser Lys Asp Ile Thr Asp Val Ala Gly
                325                 330                 335

Arg Thr Val Lys Lys Asn Ile Ala Thr Leu Gly Pro Leu Ile Leu Pro
            340                 345                 350

Leu Ser Glu Lys Leu Leu Phe Phe Val Thr Phe Met Gly Lys Lys Leu
        355                 360                 365

Phe Lys Asp Lys Ile Lys His Tyr Tyr Val Pro Asp Phe Lys Leu Ala
370                 375                 380

Ile Asp His Phe Cys Ile His Ala Gly Gly Arg Ala Val Ile Asp Val
385                 390                 395                 400

Leu Glu Lys Asn Leu Ala Leu Ala Pro Ile Asp Val Glu Ala Ser Arg
                405                 410                 415

Ser Thr Leu His Arg Phe Gly Asn Thr Ser Ser Ser Ile Trp Tyr
            420                 425                 430

Glu Leu Ala Tyr Ile Glu Ala Lys Gly Arg Met Lys Lys Gly Asn Lys
        435                 440                 445

Val Trp Gln Ile Ala Leu Gly Ser Gly Phe Lys Cys Asn Ser Ala Val
450                 455                 460

Trp Val Ala Leu Asn Asn Val Lys Ala Ser Thr Asn Ser Pro Trp Glu
465                 470                 475                 480

His Cys Ile Asp Arg Tyr Pro Val Lys Ile Asp Ser Asp Ser Gly Lys
```

<210> SEQ ID NO 41
<211> LENGTH: 1521
<212> TYPE: DNA
<213> ORGANISM: Artificial Sequence
<220> FEATURE:
<223> OTHER INFORMATION: 5' 1197 bp from B. napus elongase KCS (SEQ ID
     NO:3) and 3' 324 bp from A. thaliana FAE1 (SEQ ID
     NO:1) and having a mutation at nucleotide position
     920; designated Bn399 G307D; hypothetical
<221> NAME/KEY: CDS
<222> LOCATION: (1)...(1518)

<400> SEQUENCE: 41

| | | | | | | | | | | | | | | | | |
|---|---|---|---|---|---|---|---|---|---|---|---|---|---|---|---|---|
| atg | acg | tcc | att | aac | gtt | aag | ctc | ctt | tac | cat | tac | gtc | ata | acc | aac | 48 |
| Met | Thr | Ser | Ile | Asn | Val | Lys | Leu | Leu | Tyr | His | Tyr | Val | Ile | Thr | Asn | |
| 1 | | | | 5 | | | | | 10 | | | | | 15 | | |
| ctt | ttc | aac | ctt | tgc | ttc | ttt | ccg | tta | acg | gcg | atc | gtc | gcc | gga | aaa | 96 |
| Leu | Phe | Asn | Leu | Cys | Phe | Phe | Pro | Leu | Thr | Ala | Ile | Val | Ala | Gly | Lys | |
| | | | 20 | | | | | 25 | | | | | 30 | | | |
| gcc | tat | cgg | ctt | acc | ata | gac | gat | ctt | cac | cac | tta | tac | tat | tcc | tat | 144 |
| Ala | Tyr | Arg | Leu | Thr | Ile | Asp | Asp | Leu | His | His | Leu | Tyr | Tyr | Ser | Tyr | |
| | | 35 | | | | | 40 | | | | | 45 | | | | |
| ctc | caa | cac | aac | ctc | ata | acc | atc | gct | cca | ctc | ttt | gcc | ttc | acc | gtt | 192 |
| Leu | Gln | His | Asn | Leu | Ile | Thr | Ile | Ala | Pro | Leu | Phe | Ala | Phe | Thr | Val | |
| | 50 | | | | | 55 | | | | | 60 | | | | | |
| ttc | ggt | tcg | gtt | ctc | tac | atc | gca | acc | cgg | ccc | aaa | ccg | gtt | tac | ctc | 240 |
| Phe | Gly | Ser | Val | Leu | Tyr | Ile | Ala | Thr | Arg | Pro | Lys | Pro | Val | Tyr | Leu | |
| 65 | | | | | 70 | | | | | 75 | | | | | 80 | |
| gtt | gag | tac | tca | tgc | tac | ctt | cca | cca | acg | cat | tgt | aga | tca | agt | atc | 288 |
| Val | Glu | Tyr | Ser | Cys | Tyr | Leu | Pro | Pro | Thr | His | Cys | Arg | Ser | Ser | Ile | |
| | | | | 85 | | | | | 90 | | | | | 95 | | |
| tcc | aag | gtc | atg | gat | atc | ttt | tat | caa | gta | aga | aaa | gct | gat | cct | tct | 336 |
| Ser | Lys | Val | Met | Asp | Ile | Phe | Tyr | Gln | Val | Arg | Lys | Ala | Asp | Pro | Ser | |
| | | | 100 | | | | | 105 | | | | | 110 | | | |
| cgg | aac | ggc | acg | tgc | gat | gac | tcg | tcg | tgg | ctt | gac | ttc | ttg | agg | aag | 384 |
| Arg | Asn | Gly | Thr | Cys | Asp | Asp | Ser | Ser | Trp | Leu | Asp | Phe | Leu | Arg | Lys | |
| | | 115 | | | | | 120 | | | | | 125 | | | | |
| att | caa | gaa | cgt | tca | ggt | cta | ggc | gat | gaa | act | cac | ggg | ccc | gag | ggg | 432 |
| Ile | Gln | Glu | Arg | Ser | Gly | Leu | Gly | Asp | Glu | Thr | His | Gly | Pro | Glu | Gly | |
| | 130 | | | | | 135 | | | | | 140 | | | | | |
| ctg | ctt | cag | gtc | cct | ccc | cgg | aag | act | ttt | gcg | gcg | gcg | cgt | gaa | gag | 480 |
| Leu | Leu | Gln | Val | Pro | Pro | Arg | Lys | Thr | Phe | Ala | Ala | Ala | Arg | Glu | Glu | |
| 145 | | | | | 150 | | | | | 155 | | | | | 160 | |
| acg | gag | caa | gtt | atc | att | ggt | gcg | cta | gaa | aat | cta | ttc | aag | aac | acc | 528 |
| Thr | Glu | Gln | Val | Ile | Ile | Gly | Ala | Leu | Glu | Asn | Leu | Phe | Lys | Asn | Thr | |
| | | | | 165 | | | | | 170 | | | | | 175 | | |
| aac | gtt | aac | cct | aaa | gat | ata | ggt | ata | ctt | gtg | gtg | aac | tca | agc | atg | 576 |
| Asn | Val | Asn | Pro | Lys | Asp | Ile | Gly | Ile | Leu | Val | Val | Asn | Ser | Ser | Met | |
| | | | 180 | | | | | 185 | | | | | 190 | | | |
| ttt | aat | cca | act | cca | tcg | ctc | tcc | gcg | atg | gtc | gtt | aac | act | ttc | aag | 624 |
| Phe | Asn | Pro | Thr | Pro | Ser | Leu | Ser | Ala | Met | Val | Val | Asn | Thr | Phe | Lys | |
| | | 195 | | | | | 200 | | | | | 205 | | | | |
| ctc | cga | agc | aac | gta | aga | agc | ttt | aac | ctt | ggt | ggc | atg | ggt | tgt | agt | 672 |
| Leu | Arg | Ser | Asn | Val | Arg | Ser | Phe | Asn | Leu | Gly | Gly | Met | Gly | Cys | Ser | |
| | 210 | | | | | 215 | | | | | 220 | | | | | |
| gcc | ggc | gtt | ata | gcc | att | gat | cta | gca | aag | gac | ttg | ttg | cat | gtc | cat | 720 |
| Ala | Gly | Val | Ile | Ala | Ile | Asp | Leu | Ala | Lys | Asp | Leu | Leu | His | Val | His | |
| 225 | | | | | 230 | | | | | 235 | | | | | 240 | |

```
aaa aat acg tat gct ctt gtg gtg agc aca gag aac atc act tat aac      768
Lys Asn Thr Tyr Ala Leu Val Val Ser Thr Glu Asn Ile Thr Tyr Asn
            245                 250                 255 att tac gct ggt gat aat agg tcc atg atg gtt tca aat tgc ttg ttc      816
Ile Tyr Ala Gly Asp Asn Arg Ser Met Met Val Ser Asn Cys Leu Phe
            260                 265                 270 cgt gtt ggt ggg gcc gct att ttg ctc tcc aac aag cct gga gat cgt      864
Arg Val Gly Gly Ala Ala Ile Leu Leu Ser Asn Lys Pro Gly Asp Arg
            275                 280                 285 aga cgg tcc aag tac gag cta gtt cac acg gtt cga acg cat acc gga      912
Arg Arg Ser Lys Tyr Glu Leu Val His Thr Val Arg Thr His Thr Gly
        290                 295                 300 gct gac gac aag tct ttt cgt tgc gtg caa caa gga gac gat gag aac      960
Ala Asp Asp Lys Ser Phe Arg Cys Val Gln Gln Gly Asp Asp Glu Asn
305                 310                 315                 320 ggc aaa atc gga gtg agt ttg tcc aag gac ata acc gat gtt gct ggt     1008
Gly Lys Ile Gly Val Ser Leu Ser Lys Asp Ile Thr Asp Val Ala Gly
            325                 330                 335 cga acg gtt aag aaa aac ata gca acg ttg ggt ccg ttg att ctt ccg     1056
Arg Thr Val Lys Lys Asn Ile Ala Thr Leu Gly Pro Leu Ile Leu Pro
            340                 345                 350 tta agc gag aaa ctt ctt ttt ttc gtt acc ttc atg ggc aag aaa ctt     1104
Leu Ser Glu Lys Leu Leu Phe Phe Val Thr Phe Met Gly Lys Lys Leu
            355                 360                 365 ttc aaa gat aaa atc aaa cat tac tac gtc ccg gat ttc aaa ctt gct     1152
Phe Lys Asp Lys Ile Lys His Tyr Tyr Val Pro Asp Phe Lys Leu Ala
            370                 375                 380 att gac cat ttt tgt ata cat gcc gga ggc aga gcc gtg atc gat gag     1200
Ile Asp His Phe Cys Ile His Ala Gly Gly Arg Ala Val Ile Asp Glu
385                 390                 395                 400 cta gag aag aac tta gga cta tcg ccg atc gat gtg gag gca tct aga     1248
Leu Glu Lys Asn Leu Gly Leu Ser Pro Ile Asp Val Glu Ala Ser Arg
            405                 410                 415 tca acg tta cat aga ttt ggg aat act tca tct agc tca att tgg tat     1296
Ser Thr Leu His Arg Phe Gly Asn Thr Ser Ser Ser Ser Ile Trp Tyr
            420                 425                 430 gaa tta gca tac ata gag gca aag gga aga atg aag aaa ggg aat aaa     1344
Glu Leu Ala Tyr Ile Glu Ala Lys Gly Arg Met Lys Lys Gly Asn Lys
            435                 440                 445 gct tgg cag att gct tta gga tca ggg ttt aag tgt aat agt gcg gtt     1392
Ala Trp Gln Ile Ala Leu Gly Ser Gly Phe Lys Cys Asn Ser Ala Val
450                 455                 460 tgg gtg gct cta cgc aat gtc aag gca tcg gca aat agt cct tgg caa     1440
Trp Val Ala Leu Arg Asn Val Lys Ala Ser Ala Asn Ser Pro Trp Gln
465                 470                 475                 480 cat tgc atc gat aga tat ccg gtt aaa att gat tct gat ttg tca aag     1488
His Cys Ile Asp Arg Tyr Pro Val Lys Ile Asp Ser Asp Leu Ser Lys
            485                 490                 495 tca aag act cat gtc caa aac ggt cgg tcc taa                         1521
Ser Lys Thr His Val Gln Asn Gly Arg Ser
            500                 505
```

<210> SEQ ID NO 42
<211> LENGTH: 506
<212> TYPE: PRT
<213> ORGANISM: Artificial Sequence
<220> FEATURE:
<223> OTHER INFORMATION: 5' 399 amino acids from B. napus elongase KCS
      (SEQ ID NO:3) and 3' 107 amino acids from A. thaliana
      FAE1 (SEQ ID NO:1) having a mutation at residue
      306; designated Bn399 G307D; hypothetical -continued

```
<400> SEQUENCE: 42

Met Thr Ser Ile Asn Val Lys Leu Leu Tyr His Tyr Val Ile Thr Asn
  1               5                  10                  15

Leu Phe Asn Leu Cys Phe Phe Pro Leu Thr Ala Ile Val Ala Gly Lys
             20                  25                  30

Ala Tyr Arg Leu Thr Ile Asp Asp Leu His His Leu Tyr Tyr Ser Tyr
         35                  40                  45

Leu Gln His Asn Leu Ile Thr Ile Ala Pro Leu Phe Ala Phe Thr Val
     50                  55                  60

Phe Gly Ser Val Leu Tyr Ile Ala Thr Arg Pro Lys Pro Val Tyr Leu
 65                  70                  75                  80

Val Glu Tyr Ser Cys Tyr Leu Pro Pro Thr His Cys Arg Ser Ser Ile
                 85                  90                  95

Ser Lys Val Met Asp Ile Phe Tyr Gln Val Arg Lys Ala Asp Pro Ser
            100                 105                 110

Arg Asn Gly Thr Cys Asp Asp Ser Ser Trp Leu Asp Phe Leu Arg Lys
            115                 120                 125

Ile Gln Glu Arg Ser Gly Leu Gly Asp Glu Thr His Gly Pro Glu Gly
        130                 135                 140

Leu Leu Gln Val Pro Pro Arg Lys Thr Phe Ala Ala Arg Glu Glu
145                 150                 155                 160

Thr Glu Gln Val Ile Ile Gly Ala Leu Glu Asn Leu Phe Lys Asn Thr
                165                 170                 175

Asn Val Asn Pro Lys Asp Ile Gly Ile Leu Val Val Asn Ser Ser Met
            180                 185                 190

Phe Asn Pro Thr Pro Ser Leu Ser Ala Met Val Val Asn Thr Phe Lys
        195                 200                 205

Leu Arg Ser Asn Val Arg Ser Phe Asn Leu Gly Gly Met Gly Cys Ser
210                 215                 220

Ala Gly Val Ile Ala Ile Asp Leu Ala Lys Asp Leu Leu His Val His
225                 230                 235                 240

Lys Asn Thr Tyr Ala Leu Val Val Ser Thr Glu Asn Ile Thr Tyr Asn
                245                 250                 255

Ile Tyr Ala Gly Asp Asn Arg Ser Met Met Val Ser Asn Cys Leu Phe
            260                 265                 270

Arg Val Gly Gly Ala Ala Ile Leu Leu Ser Asn Lys Pro Gly Asp Arg
        275                 280                 285

Arg Arg Ser Lys Tyr Glu Leu Val His Thr Val Arg Thr His Thr Gly
    290                 295                 300

Ala Asp Asp Lys Ser Phe Arg Cys Val Gln Gln Gly Asp Asp Glu Asn
305                 310                 315                 320

Gly Lys Ile Gly Val Ser Leu Ser Lys Asp Ile Thr Asp Val Ala Gly
                325                 330                 335

Arg Thr Val Lys Lys Asn Ile Ala Thr Leu Gly Pro Leu Ile Leu Pro
            340                 345                 350

Leu Ser Glu Lys Leu Leu Phe Val Thr Phe Met Gly Lys Lys Leu
        355                 360                 365

Phe Lys Asp Lys Ile Lys His Tyr Tyr Val Pro Asp Phe Lys Leu Ala
    370                 375                 380

Ile Asp His Phe Cys Ile His Ala Gly Gly Arg Ala Val Ile Asp Glu
385                 390                 395                 400

Leu Glu Lys Asn Leu Gly Leu Ser Pro Ile Asp Val Glu Ala Ser Arg
```

```
                    405                 410                 415
Ser Thr Leu His Arg Phe Gly Asn Thr Ser Ser Ser Ile Trp Tyr
            420                 425                 430

Glu Leu Ala Tyr Ile Glu Ala Lys Gly Arg Met Lys Lys Gly Asn Lys
                435                 440                 445

Ala Trp Gln Ile Ala Leu Gly Ser Gly Phe Lys Cys Asn Ser Ala Val
    450                 455                 460

Trp Val Ala Leu Arg Asn Val Lys Ala Ser Ala Asn Ser Pro Trp Gln
465                 470                 475                 480

His Cys Ile Asp Arg Tyr Pro Val Lys Ile Asp Ser Asp Leu Ser Lys
                485                 490                 495

Ser Lys Thr His Val Gln Asn Gly Arg Ser
            500                 505

<210> SEQ ID NO 43
<211> LENGTH: 25
<212> TYPE: DNA
<213> ORGANISM: Artificial Sequence
<220> FEATURE:
<223> OTHER INFORMATION: primer for PCR

<400> SEQUENCE: 43
gcgctcgaaa atctattcaa gaaca                                      25

<210> SEQ ID NO 44
<211> LENGTH: 33
<212> TYPE: DNA
<213> ORGANISM: Artificial Sequence
<220> FEATURE:
<223> OTHER INFORMATION: primer for PCR

<400> SEQUENCE: 44
gttcttgaat agattttcga gcgcaccgat gat                             33

<210> SEQ ID NO 45
<211> LENGTH: 28
<212> TYPE: DNA
<213> ORGANISM: Artificial Sequence
<220> FEATURE:
<223> OTHER INFORMATION: primer for PCR

<400> SEQUENCE: 45
cggaacggca cgtgtgatga ttcgtcct                                   28

<210> SEQ ID NO 46
<211> LENGTH: 28
<212> TYPE: DNA
<213> ORGANISM: Artificial Sequence
<220> FEATURE:
<223> OTHER INFORMATION: primer for PCR

<400> SEQUENCE: 46
aggacggatc atcacacgcg acgttccg                                   28

<210> SEQ ID NO 47
<211> LENGTH: 23
<212> TYPE: DNA
<213> ORGANISM: Artificial Sequence
<220> FEATURE:
<223> OTHER INFORMATION: primer for PCR

<400> SEQUENCE: 47
cccaaaccgg tttacctcgt tga                                        23
```

<210> SEQ ID NO 48
<211> LENGTH: 23
<212> TYPE: DNA
<213> ORGANISM: Artificial Sequence
<220> FEATURE:
<223> OTHER INFORMATION: primer for PCR

<400> SEQUENCE: 48
tcaacgaggt aaaccggatt ggg                                            23

<210> SEQ ID NO 49
<211> LENGTH: 27
<212> TYPE: DNA
<213> ORGANISM: Artificial Sequence
<220> FEATURE:
<223> OTHER INFORMATION: primer for PCR

<400> SEQUENCE: 49
ccgcattgca gagttagtgt ctctaaa                                        27

<210> SEQ ID NO 50
<211> LENGTH: 27
<212> TYPE: DNA
<213> ORGANISM: Artificial Sequence
<220> FEATURE:
<223> OTHER INFORMATION: primer for PCR

<400> SEQUENCE: 50
tttagagaca ctaactctgc aatgcgg                                        27

<210> SEQ ID NO 51
<211> LENGTH: 27
<212> TYPE: DNA
<213> ORGANISM: Artificial Sequence
<220> FEATURE:
<223> OTHER INFORMATION: primer for PCR

<400> SEQUENCE: 51
ccaccgcatc tcagagttag tgtctct                                        27

<210> SEQ ID NO 52
<211> LENGTH: 27
<212> TYPE: DNA
<213> ORGANISM: Artificial Sequence
<220> FEATURE:
<223> OTHER INFORMATION: primer for PCR

<400> SEQUENCE: 52
agagacacta actctgagat gcggtgg                                        27

<210> SEQ ID NO 53
<211> LENGTH: 33
<212> TYPE: DNA
<213> ORGANISM: Artificial Sequence
<220> FEATURE:
<223> OTHER INFORMATION: primer for PCR

<400> SEQUENCE: 53
ggggatccat gacgtccgtt aacgttaagc tcc                                 33

<210> SEQ ID NO 54
<211> LENGTH: 31
<212> TYPE: DNA
<213> ORGANISM: Artificial Sequence
<220> FEATURE:

-continued

```
<223> OTHER INFORMATION: primer for PCR

<400> SEQUENCE: 54
ccgaattctt aggaccgacc gttttggaca c                              31

<210> SEQ ID NO 55
<211> LENGTH: 33
<212> TYPE: DNA
<213> ORGANISM: Artificial Sequence
<220> FEATURE:
<223> OTHER INFORMATION: primer for PCR

<400> SEQUENCE: 55
ggggatccat gacgtccatt aacgtaaagc tcc                            33

<210> SEQ ID NO 56
<211> LENGTH: 38
<212> TYPE: DNA
<213> ORGANISM: Artificial Sequence
<220> FEATURE:
<223> OTHER INFORMATION: primer for PCR

<400> SEQUENCE: 56
ccgaattctt aggaccgacc gttttggaca tgagtctt                       38
```